US010898507B2

(12) United States Patent
Donohue et al.

(10) Patent No.: US 10,898,507 B2
(45) Date of Patent: Jan. 26, 2021

(54) CONTROL OF COLEOPTERAN PESTS USING RNA MOLECULES

(71) Applicant: SYNGENTA PARTICIPATIONS AG, Basel (CH)

(72) Inventors: Kevin V. Donohue, Research Triangle Park, NC (US); Yann Naudet, Ghent (BE); Pascale Feldmann, Ghent (BE); Lies Degrave, Ghent (BE); Isabelle Maillet, Ghent (BE)

(73) Assignee: SYNGENTA PARTICIPATIONS AG, Basel (CH)

(*) Notice: Subject to any disclaimer, the term of this patent is extended or adjusted under 35 U.S.C. 154(b) by 129 days.

(21) Appl. No.: 15/746,449

(22) PCT Filed: Aug. 1, 2017

(86) PCT No.: PCT/US2017/044831
§ 371 (c)(1),
(2) Date: Jan. 22, 2018

(87) PCT Pub. No.: WO2018/026773
PCT Pub. Date: Feb. 8, 2018

(65) Prior Publication Data

US 2018/0200281 A1 Jul. 19, 2018

Related U.S. Application Data

(60) Provisional application No. 62/371,261, filed on Aug. 5, 2016.

(51) Int. Cl.

| | |
|---|---|
| ***C12N 15/11*** | (2006.01) |
| ***A61K 31/713*** | (2006.01) |
| ***A61K 45/06*** | (2006.01) |
| ***C12N 15/113*** | (2010.01) |
| ***C12N 15/82*** | (2006.01) |
| ***A01N 63/10*** | (2020.01) |
| ***A01C 1/06*** | (2006.01) |
| ***C12N 15/87*** | (2006.01) |

(52) U.S. Cl.
CPC .............. *A61K 31/713* (2013.01); *A01C 1/06* (2013.01); *A01N 63/10* (2020.01); *A61K 45/06* (2013.01); *C12N 15/113* (2013.01); *C12N 15/8218* (2013.01); *C12N 15/8286* (2013.01); *C12N 15/87* (2013.01); *C12N 2310/14* (2013.01); *Y02A 40/146* (2018.01)

(58) Field of Classification Search
None
See application file for complete search history.

(56) References Cited

U.S. PATENT DOCUMENTS

| | | | | |
|---|---|---|---|---|
| 8,759,611 | B2 | 6/2014 | Baum et al. | |
| 2005/0246794 | A1* | 11/2005 | Khvorova | A61K 31/713 800/286 |
| 2013/0291188 | A1 | 10/2013 | Bogaert et al. | |
| 2015/0337305 | A1 | 11/2015 | Bennett et al. | |
| 2016/0230186 | A1* | 8/2016 | Baum | C12N 15/8286 |

FOREIGN PATENT DOCUMENTS

| | | | |
|---|---|---|---|
| WO | 0134815 | A1 | 5/2001 |
| WO | 2016/105696 | A1 | 6/2016 |
| WO | 2017/218207 | A1 | 12/2017 |

OTHER PUBLICATIONS

Fishilevich et al., Insect Biochemistry and Molecular Biology, Apr. 2016, vol. 71, pp. 58-71.
International Search Report for International Application No. PCT/US2017/044831 dated Jan. 2, 2018.
Supplementary Partial European Search Report for EP Application No. 17837510.1 dated Dec. 12, 2019.
Thais Barros Rodrigues et al: Management of Insect Pest by RNAi—A New Tool for Crop Protection; RNA Interference; Apr. 6, 2016 (XP55648658).
Lincoln Fishilevich et al: University of Nebraska—RNAi as a management tool for the western corn rootworm, Diabrotica virgifera virgifera; Jan. 1, 2016 (XP55648663).

* cited by examiner

*Primary Examiner* — Ekaterina Poliakova-Georgantas
(74) *Attorney, Agent, or Firm* — Baker & Hostetler LLP; Toni-Junell Herbert

(57) ABSTRACT

Disclosed are double stranded RNA molecules that are toxic to coleopteran insects. In particular, interfering RNA molecules capable of interfering with pest target genes and that are toxic to the target pest are provided. Further, methods of making and using the interfering RNA, for example in transgenic plants or as the active ingredient in a composition, to confer protection from insect damage are disclosed.

17 Claims, No Drawings

Specification includes a Sequence Listing.

CONTROL OF COLEOPTERAN PESTS USING RNA MOLECULES

RELATED APPLICATION INFORMATION

This application is a 371 of International Application No. PCT/US2017/044831, filed Aug. 1, 2017, which claims priority to U.S. Provisional Application No. 62/371,261, filed Aug. 5, 2016, the contents of which are incorporated by reference herein.

SEQUENCE LISTING

A Sequence Listing in ASCII text format, submitted under 37 C.F.R. § 1.821, entitled "81040_ST25.txt", 467 kilobytes in size, generated on Jun. 22, 2017 and filed via EFS-Web is provided in lieu of a paper copy. This Sequence Listing is hereby incorporated by reference into the specification for its disclosures.

FIELD OF THE INVENTION

The invention relates generally to the control of pests that cause damage to crop plants by their feeding activities, and more particularly to the control of coleopteran pests by compositions comprising interfering RNA molecules. The invention further relates to the compositions and to methods of using such compositions comprising the interfering RNA molecules.

BACKGROUND

Insect species in the genus *Diabrotica* (corn rootworms and cucumber beetles) are considered some of the most important pests to crop plants. For example, species of corn rootworm, including *Diabrotica virgifera virgifera*, the western corn rootworm (WCR), *D. barberi*, the northern corn rootworm (NCR), *D. undecimpunctata howardi*, the southern corn rootworm (SCR), and *D. virgifera zeae*, the Mexican corn rootworm (MCR), are the most destructive corn pests in North America causing an estimated loss of over $1 billion annually. The western corn rootworm has also invaded Europe and causes an estimated 0.5 billion euros in damage each year. *Diabrotica speciosa* (common names include, among others, leaf beetle, little Brazilian beetle, cucurbit beetle and chrysanthemum beetle) is an important pest of corn, soybean and peanuts, in South America.

Most of the damage in corn is caused by larval rootworm feeding. Newly hatched rootworm larvae locate corn roots in the soil and initially begin feeding on the fine root hairs and burrow into root tips of the corn plant. As larvae grow larger, they feed on and tunnel into primary roots. When rootworms are abundant, larval feeding and deterioration of injured roots by root rot pathogens can result in roots being pruned to the base of the stalk. Severe root injury interferes with the roots' ability to transport water and nutrients into the plant, reduces plant growth, and results in reduced grain production. Severe root injury also may result in lodging of corn plants, making mechanical harvest more difficult or impossible. Corn rootworm adults feed primarily on corn silk, pollen, and kernels on exposed ear tips. If corn rootworm adults begin emerging before corn reproductive tissues are present, adults may feed on leaf tissue, scraping away the green surface tissue and leaving a window-pane appearance. Silk feeding by adults can result in pruning of silks at the ear tip, commonly called silk clipping. In field corn, beetle populations may reach a level high enough to cause severe silk clipping during pollen shed, which may interfere with pollination and reduce yield. Thus, unlike lepidopteran pests of corn in which only the larval stages cause damage, both the larval and adult stages of corn rootworm are capable of causing economic damage to corn.

*Diabrotica* insect pests are mainly controlled by intensive applications of chemical pesticides, which may be active against both larval and adult stages, through inhibition of insect growth, prevention of insect feeding or reproduction, or cause death. Good insect control can thus be reached, but these chemicals can sometimes also affect other, beneficial insects. Additional problems occur in areas of high insecticide use where populations of corn rootworm beetles have become resistant to certain insecticides. This has been partially alleviated by various resistance management practices, but there is an increasing need for alternative pest control agents.

Several native Cry proteins from *Bacillus thuringiensis*, or engineered Cry proteins, have been expressed in transgenic crop plants and exploited commercially to control certain lepidopteran and coleopteran insect pests. For example, starting in 2003, transgenic corn hybrids that control corn rootworm by expressing a Cry3Bb1, Cry34Ab1/Cry35Ab1 or modified Cry3A (mCry3A) or Cry3Ab (eCry3.1Ab) protein have been available commercially in the US.

The seed industry, university researchers and the US Environmental Protection Agency have worked together to develop management plans to help mitigate the onset of insect resistance to transgenic plants expressing insecticidal proteins. They are based primarily on a high dose and refuge strategy. A high dose strategy for corn is to use corn hybrids that express high enough levels of an insecticidal protein such as a Cry protein to kill even partially resistant insects. The underlying hypothesis is that killing partially resistant insects and preventing their mating greatly delays the development of resistance. The success of a high dose strategy depends in part on the specific activity of the insecticidal protein to the particular insect species and how much of that insecticidal protein can be expressed in the transgenic corn plant. The higher the specific activity of an insecticidal protein to a pest, the less amount of the insecticidal protein is required to be expressed in a transgenic plant to achieve a high dose strategy. For example, corn hybrids expressing the lepidopteran-active Cry protein, Cry1Ab, are considered high-dose against the primary target pest European corn borer (*Ostrinia nubilalis*). Because Cry1Ab is very toxic to European corn borer larvae with an LC50<10 ng/cm$^2$ (i.e. high specific activity), levels of expression of Cry1Ab that are achievable in transgenic plants easily places such corn hybrids in a high dose category. However, unlike the lepidopteran-active products, current rootworm products are not considered high-dose. The proteins they express are not active against adults and have limited activity against late instar larvae. Therefore, the current transgenic rootworm products allow some rootworm larvae to survive and emerge as adults.

Thus, economic levels of silk clipping by corn rootworm adults may still occur even in portions of fields planted to a transgenic corn rootworm hybrid. For example, densities of western corn rootworm adults may exceed economic levels in portions of fields planted to transgenic corn rootworm hybrids due to immigration of beetles as well as direct emergence of adults from transgenic root systems. There have been many reports that confirm western corn rootworm adult emergence from certain corn transgenic rootworm hybrids (Crowder et al. (2005) J. Econ. Entomol. 98:534-551). Another publication suggests that western corn rootworm adults will exhibit similar feeding behaviors when encountering some transgenic corn plants or non-transgenic corn plants in the field and that it is unlikely that certain insecticidal proteins in transgenic plants will have significant effects on adults that might impact resistance management.

Therefore, identifying alternative insect control agents with new modes of action would be beneficial. Particularly useful would be new insect control agents that may be toxic to multiple life stages of the target insect pest. Such insect control agents may include those that target genetic elements, such as genes that are essential to the growth and survival of a target insect pest.

RNA interference (RNAi) occurs when an organism recognizes double-stranded RNA (dsRNA) molecules and hydrolyzes them. The resulting hydrolysis products are small RNA fragments of about 19-24 nucleotides in length, called small interfering RNAs (siRNAs). The siRNAs then diffuse or are carried throughout the organism, including across cellular membranes, where they hybridize to mRNAs (or other RNAs) and cause hydrolysis of the RNA. Interfering RNAs are recognized by the RNA interference silencing complex (RISC) into which an effector strand (or "guide strand") of the RNA is loaded. This guide strand acts as a template for the recognition and destruction of the duplex sequences. This process is repeated each time the siRNA hybridizes to its complementary-RNA target, effectively preventing those mRNAs from being translated, and thus "silencing" the expression of specific genes from which the mRNAs were transcribed. Most plant microRNAs (miRNAs) show extensive base pairing to, and guide cleavage of, their target mRNAs (Jones-Rhoades et al. (2006) *Annu. Rev. Plant Biol.* 57, 19-53; Llave et al. (2002) *Proc. Natl. Acad. Sci. USA* 97, 13401-13406). In other instances, interfering RNAs may bind to target RNA molecules having imperfect complementarity, causing translational repression without mRNA degradation. The majority of the animal miRNAs studied so far appear to function in this manner.

RNAi has been found to be useful for insect control of certain insect pests. RNAi strategies typically employ a synthesized, non-naturally occurring "interfering RNA", or "interfering RNA molecule" which typically comprises at least a RNA fragment against a target gene, a spacer sequence, and a second RNA fragment which is complementary to the first, so that a double-stranded RNA structure can be formed. This non-naturally double-stranded RNA takes advantage of the native RNAi pathways in the insect to trigger down-regulation of target genes that may lead to the cessation of feeding and/or growth and may result in the death of the insect pest.

Although it is known in the literature that RNAi strategies focused on target genes can lead to an insecticidal effect in *Diabrotica* species, it is also known that not every target sequence is successful, and that an insecticidal effect cannot be predicted. The overwhelming majority of sequences complementary to corn rootworm DNAs are not lethal in species of corn rootworm when used as dsRNA or siRNA. For example, Baum et al. ((2007) Nature Biotechnology 25:1322-1326), describe the effects of inhibiting several WCR gene targets by RNAi. These authors reported that the 8 of 26 target genes they tested were not able to provide experimentally significant coleopteran pest mortality, even at a very high iRNA (e.g., dsRNA) concentration of more than 520 ng/$cm^2$. Additionally, target genes against which a dsRNA molecule is known to give a strong RNAi effect in one insect species may not be a good target for different insect species. Whyard et al. ((2009) *Insect Biochemistry and Molecular Biology* 39: 824-832) report nearly 100-fold differences in efficacy when testing conspecific dsRNA molecules against a V-ATPase gene in four different insect species.

There is an ongoing need for compositions containing insecticidal active ingredients, and for methods of using such compositions, for instance for use in crop protection or insect-mediated disease control. Novel compositions are required to overcome the problem of resistance to existing insecticides and/or to help mitigate the development of resistance to existing transgenic plant approaches. Ideally such compositions have a high toxicity and are effective when ingested orally by the target pest and have applicability for use against both the larval and adult stages of the pest insect. Thus any invention which provided compositions in which any of these properties was enhanced would represent a step forward in the art.

SUMMARY

The needs outlined above are met by the invention which, in various embodiments, provides new methods of controlling economically important insect pests. The invention in part comprises a method of inhibiting expression of one or more target genes and proteins in coleopteran insect pests. Specifically, the invention comprises methods of modulating expression of one or more target genes in *Diabrotica* species, such as *Diabrotica virgifera virgifera* (western corn rootworm), *Diabrotica barberi* (northern corn rootworm), *Diabrotica undecimpunctata howardi* (southern corn rootworm), *Diabrotica virgifera zeae* (Mexican corn rootworm), *Diabrotica speciosa* (chrysanthemum beetle), and related species, that causes cessation of feeding, growth, development and reproduction, and eventually results in the death of the insect. The method comprises introduction of an interfering RNA molecule comprising a double-stranded RNA (dsRNA) or its modified forms such as small interfering RNA (siRNA) sequences, into cells or into the extracellular environment, such as the midgut, within a pest insect body wherein the dsRNA or siRNA enters the cells and inhibits expression of at least one or more target genes and wherein inhibition of the one or more target genes exerts a deleterious effect upon the pest insect. The interfering RNA molecule is non-naturally occurring. It is specifically contemplated that the methods and compositions of the invention will be useful in limiting or eliminating pest insect infestation in or on any plant by providing one or more compositions comprising interfering RNA molecules comprising dsRNA or siRNA molecules in the diet of the pest. The invention also provides interfering RNA molecules that when delivered to an insect pest inhibits, through a toxic effect, the ability of the insect pest to survive, grow, feed and/or reproduce, or to limit pest related damage or loss to crop plants. Such delivery may be through production of the interfering RNA in a transgenic plant, for example corn, or by topically applying a composition comprising the interfering RNA to a plant or plant seed, such as a corn plant or corn seed. Delivery may further be through contacting the insect with the interfering RNA, such as when the insect feeds on plant material comprising the interfering RNA, either because the plant material is expressing the interfering RNA through a transgenic approach, or because the plant material is coated with a composition comprising the interfering RNA. The interfering RNA may also be provided in an artificial insect diet which the insect then contacts by feeding. The interfering RNA molecule comprises a nucleotide sequence that is complementary to a nucleotide sequence of a mRNA transcribable from a target gene or a portion of a nucleotide sequence of a mRNA transcribable from a target gene of the pest insect and therefore inhibits expression of the target gene, which causes cessation of feeding, growth, development, reproduction and eventually results in death of the pest insect. The invention is further drawn to nucleic acid constructs, nucleic acid molecules and recombinant vectors that comprise or encode at least a fragment of one strand of an interfering RNA molecule of the invention. The invention also provides chimeric nucleic acid molecules comprising an antisense strand of a dsRNA of the interfering RNA operably associated with a plant microRNA precursor molecule. The invention also provides artificial plant microRNA precursors comprising an antisense strand of a dsRNA of an interfering RNA of the invention.

The invention further provides an interfering ribonucleic acid (RNA) molecule wherein the RNA comprises at least one dsRNA wherein the dsRNA is a region of double-stranded RNA comprising annealed complementary strands, one strand of which comprises a sequence of at least 19 contiguous nucleotides which is at least partially complementary to a target nucleotide sequence within a *Diabrotica* spp target gene, and (i) is at least 85% identical to at least a 19 contiguous nucleotide fragment of SEQ ID NO: 121-210, SEQ ID NO: 274-276, SEQ ID NO: 280-282, SEQ ID NO: 304-324, or the complement thereof; or (ii) comprises at least a 19 contiguous nucleotide fragment of SEQ ID NO: 121-210 or, SEQ ID NO: 274-276, SEQ ID NO: 280-282, SEQ ID NO: 304-324, or the complement thereof; or (iii) comprises at least a 19 contiguous nucleotide fragment of a nucleotide sequence encoding an amino acid sequence encoded by SEQ ID NO: 121-210, SEQ ID NO: 274-276, SEQ ID NO: 280-282, SEQ ID NO: 304-324, or the complement thereof, wherein the interfering RNA molecule has insecticidal activity on a coleopteran plant pest. In some embodiments, the interfering molecule may comprise at least two dsRNAs, wherein each dsRNA comprises a sequence of nucleotides which is at least partially complementary to a target nucleotide sequence within the target gene. In further embodiments, each of the dsRNAs may comprise a different sequence of nucleotides which is complementary to a different target nucleotide sequence within the target gene.

The invention further provides compositions comprising one or more interfering RNA molecules comprising two or more of dsRNA molecules, wherein the two or more RNA molecules each comprise a different antisense strand, or comprising two or more nucleic acid constructs or nucleic acid molecules or artificial plant microRNA precursors of the invention.

The invention further provides insecticidal compositions for inhibiting the expression of a Coleopteran insect gene that comprises a dsRNA of the invention and an agriculturally acceptable carrier. In one embodiment, inhibition of the expression of a *Diabrotica* gene described here leads to cessation of feeding and growth and ultimately results in the death of the *Diabrotica* insect.

The invention is further drawn to transgenic plants which produce one or more interfering RNA molecules of the invention that are self-protected from insect feeding damage and to methods of using the plants alone or in combination with other insect control strategies to confer maximal insect control capabilities. Plants and/or plant parts producing one or more interfering RNA molecules of the invention or treated with a composition comprising one or more interfering RNA molecules of the invention are highly resistant to insect pest infestation. For example, economically important coleopteran pests can be controlled by a plant that produces an interfering RNA molecule of the invention or by a plant or plant seed that is treated with a composition comprising an interfering RNA molecule of the invention.

The invention also provides a method of controlling a Coleopteran insect plant pest comprising contacting the Coleopteran insect with a nucleic acid molecule that is or is capable of producing an interfering RNA of the invention for inhibiting expression of a gene in the Coleopteran insect thereby controlling the Coleopteran insect.

In other aspects, the invention provides a method of reducing a *Diabrotica* insect population on a transgenic plant expressing a second insecticidal agent, for example an insecticidal protein, in addition to an interfering RNA of the invention capable of inhibiting expression of an target gene in a *Diabrotica* insect, thereby reducing the *Diabrotica* insect population. The second insecticidal agent may be an insecticidal protein derived from *Bacillus thuringiensis*. A *B. thuringiensis* insecticidal protein can be any of a number of insecticidal proteins including but not limited to a Cry1 protein, a Cry3 protein, a Cry7 protein, a Cry8 protein, a Cry11 protein, a Cry22 protein, a Cry 23 protein, a Cry 36 protein, a Cry37 protein, a Cry34 protein together with a Cry35 protein, a binary insecticidal protein CryET33 and CryET34, a binary insecticidal protein TIC100 and TIC101, a binary insecticidal protein PS149B1, a VIP, a TIC900 or related protein, a TIC901, TIC1201, TIC407, TIC417, a modified Cry3A protein, or hybrid proteins or chimeras made from any of the preceding insecticidal proteins. In other embodiments, the *B. thuringiensis* insecticidal protein is selected from the group consisting of Cry3Bb1, Cry34Ab1 together with Cry35Ab1, mCry3A and eCry3.1Ab.

In other embodiments, the second insecticidal agent may be derived from sources other than *B. thuringiensis*. The second insecticidal agent can be an agent selected from the group comprising a patatin, a protease, a protease inhibitor, a urease, an alpha-amylase inhibitor, a pore-forming protein, a chitinase, a lectin, an engineered antibody or antibody fragment, a *Bacillus cereus* insecticidal protein, a *Xenorhabdus* spp. (such as *X. nematophila* or *X. bovienii*) insecticidal protein, a *Photorhabdus* spp. (such as *P. luminescens* or *P. asymobiotica*) insecticidal protein, a *Brevibacillus laterosporous* insecticidal protein, a *Lysinibacillus sphearicus* insecticidal protein, a *Chromobacterium* spp. insecticidal protein, a *Yersinia entomophaga* insecticidal protein, a *Paenibacillus popiliae* insecticidal protein, a *Clostridium* spp. (such as *C. bifermentans*) insecticidal protein, and a lignin. In other embodiments, the second agent may be at least one insecticidal protein derived from an insecticidal toxin complex (Tc) from *Photorhabdus, Xenorhabus, Serratia*, or *Yersinia*. In other embodiments, the insecticidal protein may be an ADP-ribosyltransferase derived from an insecticidal bacteria, such as *Photorhabdus* spp. In other embodiments, the insecticidal protein may be a VIP protein, such as VIP1 or VIP2 from *B. cereus*. In still other embodiments, the insecticidal protein may be a binary toxin derived from an insecticidal bacteria, such as ISP1A and ISP2A from *B. laterosporous* or BinA and BinB from *L. sphaericus*. In still other embodiments, the insecticidal protein may be engineered or may be a hybrid or chimera of any of the preceding insecticidal proteins.

In other aspects, the invention provides a method of reducing resistance development in a *Diabrotica* insect population to an interfering RNA of the invention, the method comprising expressing in a transgenic plant fed upon by the *Diabrotica* insect population an interfering RNA of the invention that is capable of inhibiting expression of a target gene in a larval and adult *Diabrotica* insect, thereby reducing resistance development in the *Diabrotica* insect population compared to a *Diabrotica* insect population exposed to an interfering RNA capable of inhibiting expression of a *Diabrotica* gene described herein in only the larval stage or adult stage of a *Diabrotica* insect.

In other aspects, the invention provides a method of reducing the level of a target RNA transcribable from a *Diabrotica* gene described herein in a *Diabrotica* insect comprising contacting the *Diabrotica* insect with a composition comprising an interfering RNA molecule of the invention, wherein the interfering RNA molecule reduces the level of the target RNA in a cell of the *Diabrotica* insect.

In still other aspects, the invention provides a method of conferring *Diabrotica* insect tolerance or Coleopteran plant pest tolerance to a plant, or part thereof, comprising introducing into the plant, or part thereof, an interfering RNA molecule, a dsRNA molecule, a nucleic acid construct, a chimeric nucleic acid molecule, an artificial plant microRNA precursor molecule and/or a composition of the invention, thereby conferring to the plant or part thereof tolerance to the *Diabrotica* insect or Coleopteran plant pest.

In further aspects, the invention provides a method of reducing root damage to a plant fed upon by a *Diabrotica* insect, comprising introducing into cells of the plant an interfering RNA molecule, a dsRNA, a nucleic acid molecule, a nucleic acid construct, a chimeric nucleic acid molecule, an artificial plant microRNA precursor molecule and/or a composition of the invention, thereby reducing root damage to the plant fed upon by a *Diabrotica* insect.

In other aspects, the invention provides a method of producing a transgenic plant cell having toxicity to a Coleopteran insect, comprising introducing into a plant cell an interfering RNA molecule, a dsRNA, a nucleic acid molecule, a nucleic acid construct, a chimeric nucleic acid molecule, an artificial plant microRNA precursor molecule and/or a composition of the invention, thereby producing the transgenic plant cell having toxicity to the Coleopteran insect compared to a control plant cell.

In further aspects, the invention provides a method of producing a transgenic plant having enhanced tolerance to Coleopteran insect feeding damage, comprising introducing into a plant an interfering RNA molecule, a dsRNA, a nucleic acid molecule, a nucleic acid construct, a chimeric nucleic acid molecule, an artificial plant microRNA precursor molecule and/or a composition of the invention, thereby producing a transgenic plant having enhanced tolerance to Coleopteran insect feeding damage compared to a control plant.

In other aspects, the invention provides a method of enhancing control of a Coleopteran insect population comprising providing a transgenic plant or transgenic seed of the invention and applying to the transgenic plant or the transgenic seed a chemical pesticide that is insecticidal to a Coleopteran insect, thereby enhancing control of the Coleopteran insect population.

In other aspects, the invention provides a method of providing a corn grower with a means of controlling a Coleopteran insect pest population below an economic threshold in a corn crop comprising (a) selling or providing to the grower transgenic corn seed comprising a dsRNA, a nucleic acid molecule, a nucleic acid construct, a chimeric nucleic acid molecule, an artificial plant microRNA precursor molecule and/or a composition of the invention; and (b) advertising to the grower that the transgenic corn seed produces transgenic corn plants capable of controlling a Coleopteran insect pest population.

In another aspect, the invention provides a method of identifying an orthologous target gene for using as a RNAi strategy for the control of a plant pest, said method comprising the steps of: a) producing a primer pair that will amplify a target selected from the group comprising or consisting of SEQ ID NO: 31-90, or a complement thereof; b) amplifying an orthologous target gene from a nucleic acid sample of the plant pest; c) identifying a sequence of an orthologous target gene; d) producing an interfering RNA molecule, wherein the RNA comprises at least one dsRNA, wherein the dsRNA is a region of double-stranded RNA comprising annealed complementary strands, one strand of which comprises a sequence of at least 19 contiguous nucleotides which is at least partially complementary to the orthologous target nucleotide sequence within the target gene; and e) determining if the interfering RNA molecule of step (d) has insecticidal activity on the plant pest. If the interfering RNA has insecticidal activity on the plant pest target gene, an orthologous target gene for using in the control of a plant pest has been identified.

These and other aspects of the invention are set forth in more detail in the description of the invention below.

BRIEF DESCRIPTION OF THE SEQUENCES IN THE SEQUENCE LISTING

SEQ ID NOs: 1-30 are fragments of DNA coding sequences used to synthesize interfering RNA molecules to test for insecticidal activity.

SEQ ID NOs: 31-90 are nucleic acid sequences of primers used to identify target genes from *Diabrotica* spp. for testing for insecticidal activity using a RNAi strategy.

SEQ ID NOs: 91-120 are complete DNA coding sequences of the 30 target genes identified in the RNAi-based screen for insecticidal activity.

SEQ ID NOs: 121-150 are RNA sequences of the fragments of the DNA coding sequences used to synthesize interfering RNA molecules to test for insecticidal activity.

SEQ ID NOs: 151-180 are RNA sequences of the complete DNA coding sequences of the 30 target genes identified in the RNAi-based screen for insecticidal activity.

SEQ ID NOs: 181-210 are complete mRNA sequences, including 5' and 3' UTRs, for the 30 target genes identified in the RNAi-based screen for insecticidal activity.

SEQ ID NOs: 211-240 are antisense RNA sequences of the complete DNA coding sequences of the 30 target genes identified in the RNAi-based screen for insecticidal activity.

SEQ ID NOs: 241-270 are amino acid sequences of the proteins encoded by the 30 target genes identified in the RNAi-based screen for insecticidal activity.

SEQ ID NOs: 271-273 are DNA coding sequences of NCR orthologs of three selected WCR target genes identified in the RNAi-based screen for insecticidal activity (BPA_2526, BPA_46378, and BPA_10976).

SEQ ID NOs: 274-276 are RNA sequences of the DNA coding sequences of the NCR orthologs of three selected WCR target genes identified in the RNAi-based screen for insecticidal activity (BPA_2526, BPA_46378, and BPA_10976).

SEQ ID NOs: 277-279 are DNA coding sequences of SCR orthologs of three selected WCR target genes identified in the RNAi-based screen for insecticidal activity (BPA_2526, BPA_46378, and BPA_10976).

SEQ ID NOs: 280-282 are RNA sequences of the DNA coding sequences of the SCR orthologs of three selected WCR target genes identified in the RNAi-based screen for insecticidal activity (BPA_2526, BPA_46378, and BPA_10976).

SEQ ID NOs: 283-289 are DNA sequences of fragments of the BPA_2526 target gene.

SEQ ID NOs: 290-297 are DNA sequences of fragments of the BPA_46378 target gene.

SEQ ID NOs: 298-303 are DNA sequences of fragments of the BPA_10976 target gene.

SEQ ID NOs: 304-310 are RNA sequences of fragments of the BPA_2526 target gene mRNA.

SEQ ID NOs: 311-318 are RNA sequences of fragments of the BPA_46378 target gene mRNA.

SEQ ID NOs: 319-324 are RNA sequences of fragments of the BPA_10976 target gene mRNA SEQ ID NOs: 325-326 are DNA sequences which each encode for a hairpin RNA structure to a target gene.

DETAILED DESCRIPTION

The following is a detailed description of the invention provided to aid those skilled in the art in practicing the invention. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments of the invention will be apparent to those skilled in the art in light of the instant disclosure, which do not depart from the invention. Hence, the following descriptions are intended to illustrate some particular embodiments of the invention, and not to exhaustively specify all permutations, combinations and variations thereof. Those of ordinary skill in the art will recognize that modifications and variations in the embodiments described herein may be made without departing from the spirit or scope of the invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

For clarity, certain terms used in the specification are defined and presented as follows:

As used herein, "a," "an" or "the" can mean one or more than one. For example, "a cell" can mean a single cell or a multiplicity of cells.

As used herein, "and/or" refers to and encompasses any and all possible combinations of one or more of the associated listed items, as well as the lack of combinations when interpreted in the alternative (or).

Further, the term "about," as used herein when referring to a measurable value such as an amount of a compound or agent, dose, time, temperature, and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising." A "coding sequence" is a nucleic acid sequence that is transcribed into RNA such as mRNA, rRNA, tRNA, snRNA, sense RNA or antisense RNA. Preferably the RNA is then translated in an organism to produce a protein.

The terms "sequence similarity" or "sequence identity" of nucleotide or amino acid sequences mean a degree of identity or similarity of two or more sequences and may be determined conventionally by using known software or computer programs such as the Best-Fit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2:482-489 (1981), to find the best segment of identity or similarity between two sequences. Sequence comparison between two or more polynucleotides or polypeptides is generally performed by comparing portions of the two sequences over a comparison window to identify and compare local regions of sequence similarity. The comparison window is generally from about 20 to 200 contiguous nucleotides. Gap performs global alignments: all of one sequence with all of another similar sequence using the method of Needleman and Wunsch, J. Mol. Biol. 48:443-453 (1970). When using a sequence alignment program such as BestFit to determine the degree of DNA sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

The phrase "substantially identical," in the context of two nucleic acids or two amino acid sequences, refers to two or more sequences or subsequences that have at least about 50% nucleotide or amino acid residue identity when compared and aligned for maximum correspondence as measured using one of the following sequence comparison algorithms or by visual inspection. In certain embodiments, substantially identical sequences have at least about 60%, or at least about 70%, or at least about 80%, or even at least about 90% or 95% nucleotide or amino acid residue identity. In certain embodiments, substantial identity exists over a region of the sequences that is at least about 50 residues in length, or over a region of at least about 100 residues, or the sequences are substantially identical over at least about 150 residues. In further embodiments, the sequences are substantially identical when they are identical over the entire length of the coding regions.

The term "homology" in the context of the invention refers to the level of similarity between nucleic acid or amino acid sequences in terms of nucleotide or amino acid identity or similarity, respectively, i.e., sequence similarity or identity. Homology, homologue, and homologous also refers to the concept of similar functional properties among different nucleic acids or proteins. Homologues include genes that are orthologous and paralogous. Homologues can be determined by using the coding sequence for a gene, disclosed herein or found in appropriate database (such as that at NCBI or others) in one or more of the following ways.

For an amino acid sequence, the sequences should be compared using algorithms (for instance see section on "identity" and "substantial identity"). For nucleotide sequences the sequence of one DNA molecule can be compared to the sequence of a known or putative homologue in much the same way. Homologues are at least 20% identical, or at least 30% identical, or at least 40% identical, or at least 50% identical, or at least 60% identical, or at least 70% identical, or at least 80% identical, or at least 88% identical, or at least 90% identical, or at least 92% identical, or at least 95% identical, across any substantial region of the molecule (DNA, RNA, or protein molecule).

Optimal alignment of sequences for comparison can be conducted, e.g., by the local homology algorithm of Smith & Waterman, *Adv. Appl. Math.* 2: 482 (1981), by the homology alignment algorithm of Needleman & Wunsch, *J. Mol. Biol.* 48: 443 (1970), by the search for similarity method of Pearson & Lipman, *Proc. Nat'l. Acad. Sci. USA* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., *J. Mol. Biol.* 215: 403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another widely used and accepted computer program for performing sequence alignments is CLUSTALW v1.6 (Thompson, et al. Nuc. Acids Res., 22: 4673-4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there were 100 matched amino acids between a 200 and a 400 amino acid proteins, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity.

Two nucleotide sequences can also be considered to be substantially identical when the two sequences hybridize to each other under stringent conditions. In representative embodiments, two nucleotide sequences considered to be substantially identical hybridize to each other under highly stringent conditions.

The terms "stringent conditions" or "stringent hybridization conditions" include reference to conditions under which a polynucleotide will hybridize to its target sequence to a detectably greater degree than other sequences (e.g., at least 2-fold over background). Stringent conditions are sequence-dependent and will be different in different circumstances. By controlling the stringency of the hybridization and/or washing conditions, target polynucleotides can be identified which are 100% complementary to the probe (homologous probing). Alternatively, stringency conditions can be adjusted to allow some mismatching in sequences so that lower degrees of similarity are detected (heterologous probing). Typically, stringent conditions will be those in which the salt concentration is less than approximately 1.5 M Na ion, typically about 0.01 to 1.0 M Na ion (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions also may be achieved with the addition of destabilizing agents such as formamide. Exemplary low stringency conditions include hybridization with a buffer solution of 30 to 35% formamide, 1 M NaCl, 1% SDS (w/v; sodium dodecyl sulphate) at 37° C., and a wash in 1× to 2×SSC (20×SSC=3.0 M NaCl/0.3 M trisodium citrate) at 50 to 55° C. Moderate stringency conditions detect sequences that share at least 80% sequence identity. Exemplary moderate stringency conditions include hybridization in 40 to 45% formamide, 1 M NaCl, 1% SDS at 37° C., and a wash in 0.5× to 1×SSC at 55 to 60° C. High stringency conditions detect sequences that share at least 90% sequence identity. Exemplary high stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the Tm can be approximated from the equation of Meinkoth and Wahl (Anal. Biochem., 138:267-284, 1984): Tm=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with approximately 90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution), it is preferred to increase the SSC concentration so that a higher temperature can be used. An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y. (1993); and Current Protocols in Molecular Biology, Chapter 2, Ausubel, et al., eds., Greene Publishing and Wiley-Interscience, New York (1995). Methods of stringent hybridization are known in the art which conditions can be calculated by means known in the art. This is disclosed in Sambrook et al., Molecular Cloning: A Laboratory Manual, 2nd Ed., Cold Spring Harbor Laboratory Press, 1989, Cold Spring Harbor, N.Y. and Current Protocols in Molecular Biology, Ausebel et al, eds., John Wiley and Sons, Inc., 2000. Methods of determining percent sequence identity are known in the art, an example of which is the GCG computer sequence analysis software (GCG, Inc, Madison Wis.).

Nucleic acids that do not hybridize to each other under stringent conditions are still substantially identical if the proteins that they encode are substantially identical (e.g., due to the degeneracy of the genetic code).

A further indication that two nucleic acids or proteins are substantially identical is that the protein encoded by the first nucleic acid is immunologically cross reactive with the protein encoded by the second nucleic acid. Thus, a protein is typically substantially identical to a second protein, for example, where the two proteins differ only by conservative substitutions.

A nucleic acid sequence is "isocoding with" a reference nucleic acid sequence when the nucleic acid sequence encodes a polypeptide having the same amino acid sequence as the polypeptide encoded by the reference nucleic acid sequence.

As used herein, "complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. For example, the sequence "A-G-T" binds to the complementary sequence "T-C-A." It is understood that two polynucleotides may hybridize to each other even if they are not completely complementary to each other, provided that each has at least one region that is substantially complementary to the other.

The terms "complementary" or "complementarity," refer to the natural binding of polynucleotides under permissive salt and temperature conditions by base-pairing. Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

As used herein, the terms "substantially complementary" or "partially complementary" mean that two nucleic acid sequences are complementary at least about 50%, 60%, 70%, 80% or 90% of their nucleotides. In some embodiments, the two nucleic acid sequences can be complementary at least at 85%, 90%, 95%, 96%, 97%, 98%, 99% or more of their nucleotides. The terms "substantially complementary" and "partially complementary" can also mean that two nucleic acid sequences can hybridize under high stringency conditions and such conditions are well known in the art.

As used herein, "dsRNA" or "RNAi" refers to a polyribonucleotide structure formed either by a single self-complementary RNA strand or at least by two complementary RNA strands. The degree of complementary, in other words the % identity, need not necessarily be 100%. Rather, it must be sufficient to allow the formation of a double-stranded structure under the conditions employed. As used herein, the term "fully complementary" means that all the bases of the nucleotide sequence of the dsRNA are complementary to or 'match' the bases of the target nucleotide sequence. The term "at least partially complementary" means that there is less than a 100% match between the bases of the dsRNA and the bases of the target nucleotide sequence. The skilled person will understand that the dsRNA need only be at least partially complementary to the target nucleotide sequence in order to mediate down-regulation of expression of the target gene. It is known in the art that RNA sequences with insertions, deletions and mismatches relative to the target sequence can still be effective at RNAi. According to the current invention, it is preferred that the dsRNA and the target nucleotide sequence of the target gene share at least 80% or 85% sequence identity, preferably at least 90% or 95% sequence identity, or more preferably at least 97% or 98% sequence identity and still more preferably at least 99% sequence identity. Alternatively, the dsRNA may comprise 1, 2 or 3 mismatches as compared with the target nucleotide sequence over every length of 24 partially complementary nucleotides. It will be appreciated by the person skilled in the art that the degree of complementarity shared between the dsRNA and the target nucleotide sequence may vary depending on the target gene to be down-regulated or depending on the insect pest species in which gene expression is to be controlled.

It will be appreciated that the dsRNA may comprise or consist of a region of double-stranded RNA comprising annealed complementary strands, one strand of which, the sense strand, comprises a sequence of nucleotides at least partially complementary to a target nucleotide sequence within a target gene.

The target nucleotide sequence may be selected from any suitable region or nucleotide sequence of the target gene or RNA transcript thereof. For example, the target nucleotide sequence may be located within the 5'UTR or 3'UTR of the target gene or RNA transcript or within exonic or intronic regions of the gene. The skilled person will be aware of methods of identifying the most suitable target nucleotide sequences within the context of the full-length target gene. For example, multiple dsRNAs targeting different regions of the target gene can be synthesised and tested. Alternatively, digestion of the RNA transcript with enzymes such as RNAse H can be used to determine sites on the RNA that are in a conformation susceptible to gene silencing. Target sites may also be identified using in silico approaches, for example, the use of computer algorithms designed to predict the efficacy of gene silencing based on targeting different sites within the full-length gene.

Preferably, the % identity of a polyribonucleotide is determined by GAP (Needleman and Wunsch, 1970) analysis (GCG program) using the default settings, wherein the query sequence is at least about 21 to about 23 nucleotides in length, and the GAP analysis aligns the two sequences over a region of at least about 21 nucleotides. In another embodiment, the query sequence is at least 150 nucleotides in length, and the GAP analysis aligns the two sequences over a region of at least 150 nucleotides. In a further embodiment, the query sequence is at least 300 nucleotides in length and the GAP analysis aligns the two sequences over a region of at least 300 nucleotides. In yet another embodiment, the query sequence corresponds to the full length of the target RNA, for example mRNA, and the GAP analysis aligns the two sequences over the full length of the target RNA.

Conveniently, the dsRNA can be produced from a single open reading frame in a recombinant host cell, wherein the sense and anti-sense sequences are flanked by an unrelated sequence which enables the sense and anti-sense sequences to hybridize to form the dsRNA molecule with the unrelated sequence forming a loop structure. Alternatively, the sense strand and antisense strand can be made without an open reading frame to ensure that no protein will be made in the transgenic host cell. The two strands can also be expressed separately as two transcripts, one encoding the sense strand and one encoding the antisense strand.

RNA duplex formation can be initiated either inside or outside the cell. The dsRNA can be partially or fully double-stranded. The RNA can be enzymatically or chemically synthesized, either in vitro or in vivo.

The dsRNA need not be full length relative to either the primary transcription product or fully processed RNA. It is well-known in the art that small dsRNA of about 19-23 bp in length can be used to trigger gene silencing of a target gene. Generally, higher identity can be used to compensate for the use of a shorter sequence. Furthermore, the dsRNA can comprise single stranded regions as well, e.g., the dsRNA can be partially or fully double stranded. The double stranded region of the dsRNA can have a length of at least about 19 to about 23 base pairs, optionally a sequence of about 19 to about 50 base pairs, optionally a sequence of about 50 to about 100 base pairs, optionally a sequence of about 100 to about 200 base pairs, optionally a sequence of about 200 to about 500, and optionally a sequence of about 500 to about 1000 or more base pairs, up to a molecule that is double stranded for its full length, corresponding in size to a full length target RNA molecule. Bolognesi et al (2012, *PLOS One,* 7(10): e47534, herein incorporated by reference) teach that dsRNAs greater than or equal to about 60 bp are required for biological activity in artificial diet bioassays with Southern Corn Rootworm (SCR; *Diabrotica undecimpunctata howardii*).

Mao et al (2007, *Nature Biotechnology,* 35(11): 1307-1313) teach a transgenic plant expressing a dsRNA construct against a target gene (CYP6AE14) of an insect pest (cotton bollworm, *Helicoverpa armigera*). Insects feeding on the transgenic plant have small RNAs of about 19-23 bp in size of the target gene in their midgut, with a corresponding reduction in CYP6AE14 transcripts and protein. This suggests that the small RNAs were efficacious in reducing expression of the target gene in the insect pest. Therefore, small RNAs of about 19 bp, about 20 bp, about 21 bp, about 22 bp, about 23 bp, about 24 bp, about 25 bp, about 26 bp, about 27 bp, about 28 bp, about 29 bp, or about 30 bp may be efficacious in reducing expression of the target gene in an insect pest.

Alternatively, the dsRNA may comprise a target dsRNA of at least 19 base pairs, and the target dsRNA may be within a dsRNA "carrier" or "filler" sequence. For example, Bolognesi et al (2012) show that a 240 bp dsRNA encompassing a target dsRNA, which comprised a 21 bp contiguous sequence with 100% identity to the target sequence, had biological activity in bioassays with Southern Corn Rootworm. The present application exemplifies a similar approach in bioassays with Western Corn Rootworm. The target dsRNA may have a length of at least 19 to about 25 base pairs, optionally a sequence of about 19 to about 50 base pairs, optionally a sequence of about 50 to about 100 base pairs, optionally a sequence of about 100 to about 200 base pairs, optionally a sequence of about 200 to about 500, and optionally a sequence of about 500 to about 1000 or more base pairs. Combined with the carrier dsRNA sequence, the dsRNA of the target sequence and the carrier dsRNA may have a total length of at least about 50 to about 100 base pairs, optionally a sequence of about 100 to about 200 base pairs, optionally a sequence of about 200 to about 500, and optionally a sequence of about 500 to about 1000 or more base pairs.

The dsRNA can contain known nucleotide analogs or modified backbone residues or linkages, which are synthetic, naturally occurring, and non-naturally occurring. Examples of such analogs include, without limitation, phosphorothioates, phosphoramidates, methyl phosphonates, chiralmethyl phosphonates and 2-O-methyl ribonucleotides.

As used herein, the term "specifically reduce the level of a target RNA and/or the production of a target protein encoded by the RNA", and variations thereof, refers to the sequence of a portion of one strand of the dsRNA being sufficiently identical to the target RNA such that the presence of the dsRNA in a cell reduces the steady state level and/or the production of said RNA. In many instances, the target RNA will be mRNA, and the presence of the dsRNA in a cell producing the mRNA will result in a reduction in the production of said protein. Preferably, this accumulation or production is reduced at least 10%, more preferably at least 50%, even more preferably at least 75%, yet even more preferably at least 95% and most preferably 100%, when compared to a wild-type cell.

The consequences of inhibition can be confirmed by examination of the outward properties of the cell or organism or by biochemical techniques such as, but not limited to, Northern hybridization, reverse transcription, gene expression monitoring with a microarray, antibody binding, enzyme linked immunosorbent assay (ELISA), Western blotting, radioimmunoassay (RIA), and other immunoassays.

The interfering RNAs of the current invention may comprise one dsRNA or multiple dsRNAs, wherein each dsRNA comprises or consists of a sequence of nucleotides which is at least partially complementary to a target nucleotide sequence within the target gene and that functions upon uptake by an insect pest species to down-regulate expression of said target gene. Concatemeric RNA constructs of this type are described in WO2006/046148 as incorporated herein by reference. In the context of the present invention, the term 'multiple' means at least two, at least three, at least four, etc and up to at least 10, 15, 20 or at least 30. In one embodiment, the interfering RNA comprises multiple copies of a single dsRNA i.e. repeats of a dsRNA that binds to a particular target nucleotide sequence within a specific target gene. In another embodiment, the dsRNAs within the interfering RNA comprise or consist of different sequences of nucleotides complementary to different target nucleotide sequences. It should be clear that combinations of multiple copies of the same dsRNA combined with dsRNAs binding to different target nucleotide sequences are within the scope of the current invention.

The dsRNAs may be arranged as one contiguous region of the interfering RNA or may be separated by the presence of linker sequences. The linker sequence may comprise a short random nucleotide sequence that is not complementary to any target nucleotide sequences or target genes. In one embodiment, the linker is a conditionally self-cleaving RNA sequence, preferably a pH-sensitive linker or a hydrophobic-sensitive linker. In one embodiment, the linker comprises a sequence of nucleotides equivalent to an intronic sequence. Linker sequences of the current invention may range in length from about 1 base pair to about 10000 base pairs, provided that the linker does not impair the ability of the interfering RNA to down-regulate the expression of target gene(s).

In addition to the dsRNA(s) and any linker sequences, the interfering RNA of the invention may comprise at least one additional polynucleotide sequence. In different embodiments of the invention, the additional sequence is chosen from (i) a sequence capable of protecting the interfering RNA against RNA processing, (ii) a sequence affecting the stability of the interfering RNA, (iii) a sequence allowing protein binding, for example to facilitate uptake of the interfering RNA by cells of the insect pest species, (iv) a sequence facilitating large-scale production of the interfering RNA, (v) a sequence which is an aptamer that binds to a receptor or to a molecule on the surface of the insect pest cells to facilitate uptake, or (v) a sequence that catalyses processing of the interfering RNA within the insect pest cells and thereby enhances the efficacy of the interfering RNA. Structures for enhancing the stability of RNA molecules are well known in the art and are described further in WO2006/046148 as incorporated herein by reference.

The interfering RNA may contain DNA bases, non-natural bases or non-natural backbone linkages or modifications of the sugar-phosphate backbone, for example to enhance stability during storage or enhance resistance to degradation by nucleases. Furthermore, the interfering RNA may be produced chemically or enzymatically by one skilled in the art through manual or automated reactions. Alternatively, the interfering RNA may be transcribed from a polynucleotide encoding the same. Thus, provided herein is an isolated polynucleotide encoding any of the interfering RNAs of the current invention.

MicroRNAs (miRNAs) are non-protein coding RNAs, generally of between about 18 to about 25 nucleotides in length (commonly about 20-24 nucleotides in length in plants). These miRNAs direct cleavage in trans of target transcripts, negatively regulating the expression of genes involved in various regulation and development pathways (Bartel, *Cell,* 116:281-297 (2004); Zhang et al. *Dev. Biol.* 289:3-16 (2006)). As such, miRNAs have been shown to be involved in different aspects of plant growth and development as well as in signal transduction and protein degradation. In addition, small endogenous mRNAs including miRNAs may also be involved in biotic stress responses such as pathogen attack. Since the first miRNAs were discovered in plants (Reinhart et al. *Genes Dev.* 16:1616-1626 (2002), Park et al. *Curr. Biol.* 12:1484-1495 (2002)) many hundreds have been identified. Furthermore, many plant miRNAs have been shown to be highly conserved across very divergent taxa. (Floyd et al. *Nature* 428:485-486 (2004); Zhang et al. *Plant J.* 46:243-259 (2006)). Many microRNA genes (MIR genes) have been identified and made publicly available in a database (miRBase, available via the world wide web). miRNAs are also described in U.S. Patent Publications 2005/0120415 and 2005/144669A1, the entire contents of which are incorporated by reference herein.

Genes encoding miRNAs yield primary miRNAs (termed a "pri-miRNA") of 70 to 300 bp in length that can form imperfect stem-loop structures. A single pri-miRNA may contain from one to several miRNA precursors. In animals, pri-miRNAs are processed in the nucleus into shorter hairpin RNAs of about 65 nt (pre-miRNAs) by the RNaseIII enzyme Drosha and its cofactor DGCR8/Pasha. The pre-miRNA is then exported to the cytoplasm, where it is further processed by another RNaseIII enzyme, Dicer, releasing a miRNA/miRNA* duplex of about 22 nt in size. In contrast to animals, in plants, the processing of pri-miRNAs into mature miRNAs occurs entirely in the nucleus using a single RNaseIII enzyme, DCL1 (Dicer-like 1). (Zhu. *Proc. Natl. Acad. Sci.* 105:9851-9852 (2008)). Many reviews on microRNA biogenesis and function are available, for example, see, Bartel *Cell* 116:281-297 (2004), Murchison et al. *Curr. Opin. Cell Biol.* 16:223-229 (2004), Dugas et al. *Curr. Opin. Plant Biol.* 7:512-520 (2004) and Kim *Nature Rev. Mol. Cell Biol.* 6:376-385 (2005).

The term "plant microRNA precursor molecule" as used herein describes a small (~70-300 nt) non-coding RNA sequence that is processed by plant enzymes to yield a ~19-24 nucleotide product known as a mature microRNA sequence. The mature sequences have regulatory roles through complementarity to messenger RNA (mRNA). The term "artificial plant microRNA precursor molecule" describes the non-coding miRNA precursor sequence prior to processing that is employed as a backbone sequence for the delivery of a siRNA molecule via substitution of the endogenous native miRNA/miRNA* duplex of the miRNA precursor molecule with that of a non-native, heterologous miRNA (amiRNA/amiRNA*; e.g. siRNA/siRNA*) that is then processed into the mature miRNA sequence with the siRNA sequence.

In the context of the invention, the term "toxic" used to describe a dsRNA of the invention means that the dsRNA molecules of the invention and combinations of such dsRNA molecules function as orally active insect control agents that have a negative effect on an insect. When a composition of the invention is delivered to the insect, the result is typically death of the insect, or the insect does not feed upon the source that makes the composition available to the insect. Such a composition may be a transgenic plant expressing the dsRNA of the invention.

To "control" or "controlling" insects means to inhibit, through a toxic effect, the ability of one or more insect pests to survive, grow, feed, and/or reproduce, or to limit insect-related damage or loss in crop plants. To "control" insects may or may not mean killing the insects, although it preferably means killing the insects. A composition that controls a target insect has insecticidal activity against the target insect.

To "deliver" or "delivering" a composition or dsRNA means that the composition or dsRNA comes in contact with an insect, resulting in a toxic effect and control of the insect. The composition or dsRNA can be delivered in many recognized ways, e.g., orally by ingestion by the insect via transgenic plant expression, formulated composition(s), sprayable composition(s), a bait matrix, or any other art-recognized toxicant delivery system.

The term "insect" as used herein includes any organism now known or later identified that is classified in the animal kingdom, phylum Arthropoda, class Insecta, including but not limited to insects in the orders Coleoptera (beetles), Lepidoptera (moths, butterflies), Diptera (flies), Protura, Collembola (springtails), Diplura, Microcoryphia (jumping bristletails), Thysanura (bristletails, silverfish), Ephemeroptera (mayflies), Odonata (dragonflies, damselflies), Orthoptera (grasshoppers, crickets, katydids), Phasmatodea (walkingsticks), Grylloblattodea (rock crawlers), Mantophasmatodea, Dermaptera (earwigs), Plecoptera (stoneflies), Embioptera (web spinners), Zoraptera, lsoptera (termites), Mantodea (mantids), Blattodea (cockroaches), Hemiptera (true bugs, cicadas, leafhoppers, aphids, scales), Thysanoptera (thrips), Psocoptera (book and bark lice), Phthiraptera (lice; including but not limited to suborders Amblycera, Ischnocera and Anoplura), Neuroptera (lacewings, owlflies, mantispids, antlions), Hymenoptera (bees, ants, wasps), Trichoptera (caddisflies), Siphonaptera (fleas), Mecoptera (scorpion flies), Strepsiptera (twisted-winged parasites), and any combination thereof.

As used herein, a "coleopteran insect" refers to any member of the Coleoptera order, including coleopteran plant pests. Insects in the order Coleoptera include but are not limited to any coleopteran insect now known or later identified including those in suborders Archostemata, Myxophaga, Adephaga and Polyphaga, and any combination thereof.

"*Diabrotica*" is a genus of beetles (from the Coleoptera order) commonly referred to as "corn rootworms" or "cucumber beetles." *Diabrotica* insects that are pests of crop plants, include without limitation, *Diabrotica barberi* (northern corn rootworm; NCR), *D. virgifera virgifera* (western corn rootworm; WCR), *D. undecimpunctata howardii* (southern corn rootworm; SCR), *D. virgifera zeae* (Mexican corn rootworm; MCR) and *D. speciosa*. In the context of the invention, the term "corn rootworm" or "cucumber beetle" is interchangeable with the term "*Diabrotica.*"

Other nonlimiting examples of coleopteran insect pests according to the present invention include *Leptinotarsa* spp. such as *L. decemlineata* (Colorado potato beetle); *Chrysomela* spp. such as *C. scripta* (cottonwood leaf beetle); *Hypothenemus* spp. such as *H. hampei* (coffee berry borer); *Sitophilus* spp. such as *S. zeamais* (maize weevil); *Epitrix* spp. such as *E. hirtipennis* (tobacco flea beetle) and *E. cucumeris* (potato flea beetle); *Phyllotreta* spp. such as *P. cruciferae* (crucifer flea beetle) and *P. pusilla* (western black flea beetle); *Anthonomus* spp. such as *A. eugenii* (pepper weevil); *Hemicrepidus* spp. such as *H. memnonius* (wireworms); *Melanotus* spp. such as *M. communis* (wireworm); *Ceutorhychus* spp. such as *C. assimilis* (cabbage seedpod weevil); *Phyllotreta* spp. such as *P. cruciferae* (crucifer flea beetle); *Aeolus* spp. such as *A. mellillus* (wireworm); *Aeolus* spp. such as *A. mancus* (wheat wireworm); *Horistonotus* spp. such as *H. uhlerii* (sand wireworm); *Sphenophorus* spp. such as *S. maidis* (maize billbug), *S. zeae* (timothy billbug), *S. parvulus* (bluegrass billbug), and *S. callosus* (southern corn billbug); *Phyllophaga* spp. (White grubs); *Chaetocnema* spp. such as *C. pulicaria* (corn flea beetle); *Popillia* spp. such as *P. japonica* (Japanese beetle); *Epilachna* spp. such as *E. varivestis* (Mexican bean beetle); *Cerotoma* spp. such as *C. trifurcate* (Bean leaf beetle); *Epicauta* spp. such as *E. pestifera* and *E. lemniscata* (Blister beetles); and any combination of the foregoing.

A "*Diabrotica* life stage" or "corn rootworm life stage" means the egg, larval, pupal or adult developmental form of a *Diabrotica* species.

"Effective insect-controlling amount" means that concentration of dsRNA that inhibits, through a toxic effect, the ability of insects to survive, grow, feed and/or reproduce, or to limit insect-related damage or loss in crop plants. "Effective insect-controlling amount" may or may not mean a concentration that kills the insects, although it preferably means that it kills the insects.

The term "agrochemically active ingredient" refers to chemicals and/or biological compositions, such as those described herein, which are effective in killing, preventing, or controlling the growth of undesirable pests, such as, plants, insects, mice, microorganism, algae, fungi, bacteria, and the like (such as pesticidally active ingredients). An interfering RNA molecule of the invention is an agrochemically active ingredient.

An "agriculturally acceptable carrier" includes adjuvants, mixers, enhancers, etc. beneficial for application of an active ingredient, such as an interfering RNA molecule of the invention. Suitable carriers should not be phytotoxic to valuable crops, particularly at the concentrations employed in applying the compositions in the presence of crops, and should not react chemically with the compounds of the active ingredient herein, namely an interfering RNA of the invention, or other composition ingredients. Such mixtures can be designed for application directly to crops, or can be concentrates or formulations which are normally diluted with additional carriers and adjuvants before application. They may include inert or active components and can be solids, such as, for example, dusts, granules, water dispersible granules, or wettable powders, or liquids, such as, for example, emulsifiable concentrates, solutions, emulsions or suspensions. Suitable agricultural carriers may include liquid carriers, for example water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates. Suitable solid carriers may include talc, pyrophyllite clay, silica, attapulgus clay, kieselguhr, chalk, diatomaceous earth, lime, calcium carbonate, bentonire clay, Fuller's earth, cotton seed hulls, wheat flour, soybean flour, pumice, wood flour, walnut shell flour, lignin, and the like.

For the present invention, an agriculturally acceptable carrier may also include non-pathogenic, attenuated strains of microorganisms, which carry the insect control agent, namely an interfering RNA molecule of the invention. In this case, the microorganisms carrying the interfering RNA may also be referred to as insect control agents. The microorganisms may be engineered to express a nucleotide sequence of a target gene to produce interfering RNA molecules comprising RNA sequences homologous or complementary to RNA sequences typically found within the cells of an insect. Exposure of the insects to the microorganisms result in ingestion of the microorganisms and down-regulation of expression of target genes mediated directly or indirectly by the interfering RNA molecules or fragments or derivatives thereof.

In another embodiment, the interfering RNA molecules may be encapsulated in a synthetic matrix such as a polymer and applied to the surface of a host such as a plant. Ingestion of the host cells by an insect permits delivery of the insect control agents to the insect and results in down-regulation of a target gene in the host.

A composition of the invention, for example a composition comprising an interfering RNA molecule of the invention and an agriculturally acceptable carrier, may be used in conventional agricultural methods. For example, the compositions of the invention may be mixed with water and/or fertilizers and may be applied preemergence and/or postemergence to a desired locus by any means, such as airplane spray tanks, irrigation equipment, direct injection spray equipment, knapsack spray tanks, cattle dipping vats, farm equipment used in ground spraying (e.g., boom sprayers, hand sprayers), and the like. The desired locus may be soil, plants, and the like.

A composition of the invention may be applied to a seed or plant propagule in any physiological state, at any time between harvest of the seed and sowing of the seed; during or after sowing; and/or after sprouting. It is preferred that the seed or plant propagule be in a sufficiently durable state that it incurs no or minimal damage, including physical damage or biological damage, during the treatment process. A formulation may be applied to the seeds or plant propagules using conventional coating techniques and machines, such as fluidized bed techniques, the roller mill method, rotostatic seed treaters, and drum coaters.

"Expression cassette" as used herein means a nucleic acid sequence capable of directing expression of a particular nucleic acid sequence in an appropriate host cell, comprising a promoter operably linked to the nucleic acid sequence of interest which is operably linked to termination signal sequences. It also typically comprises sequences required for proper translation of the nucleic acid sequence. The expression cassette comprising the nucleic acid sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event. The expression of the nucleic acid sequence in the expression cassette may be under the control of, for example, a constitutive promoter or of an inducible promoter that initiates transcription only when the host cell is exposed to some particular external stimulus. In the case of a multicellular organism, such as a plant, the promoter can also be specific to a particular tissue, or organ, or stage of development.

A "gene" is a defined region that is located within a genome and that, besides the aforementioned coding sequence, comprises other, primarily regulatory nucleic acid sequences responsible for the control of the expression, that is to say the transcription and translation, of the coding portion. A gene may also comprise other 5' and 3' untranslated sequences and termination sequences. Further elements that may be present are, for example, introns.

As used herein, the term "grower" means a person or entity that is engaged in agriculture, raising living organisms, such as crop plants, for example corn, for food, feed or raw materials.

A "heterologous" nucleic acid sequence is a nucleic acid sequence not naturally associated with a host cell into which it is introduced, including non-naturally occurring multiple copies of a naturally occurring nucleic acid sequence.

A "homologous" nucleic acid sequence is a nucleic acid sequence naturally associated with a host cell into which it is introduced.

"Insecticidal" is defined as a toxic biological activity capable of controlling insects, preferably by killing them.

An "isolated" nucleic acid molecule or nucleotide sequence or nucleic acid construct or dsRNA molecule or protein of the invention is generally exists apart from its native environment and is therefore not a product of nature. An isolated nucleic acid molecule or nucleotide sequence or nucleic acid construct or dsRNA molecule or protein may exist in a purified form or may exist in a non-native environment such as, for example, a recombinant host or host cell such as a transgenic plant or transgenic plant cell.

In the context of the invention, a number in front of the suffix "mer" indicates a specified number of subunits. When applied to RNA or DNA, this specifies the number of bases in the molecule. For example, a 19 nucleotide subsequence of an mRNA having the sequence ACUGGUCGCGUUGCAUGCU is a "19-mer."

A "plant" is any plant at any stage of development, particularly a seed plant.

A "plant cell" is a structural and physiological unit of a plant, comprising a protoplast and a cell wall. The plant cell may be in the form of an isolated single cell or a cultured cell, or as a part of a higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

A corn rootworm "transcriptome" is a collection of all or nearly all the ribonucleic acid (RNA) transcripts in a corn rootworm cell.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extra-chromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

The nomenclature used herein for DNA or RNA bases and amino acids is as set forth in 37 C.F.R. § 1.822.

The invention is based on the unexpected discovery that double stranded RNA (dsRNA) or small interfering RNAs (siRNA) designed to target a mRNA transcribable from the *Diabrotica* genes described herein are toxic to the *Diabrotica* insect pest and can be used to control *Diabrotica* or Coleopteran infestation of a plant and impart to a transgenic plant tolerance to a *Diabrotica* or Coleopteran infestation. Thus, in one embodiment, the invention provides a double stranded RNA (dsRNA) molecule comprising a sense strand and an antisense strand, wherein a nucleotide sequence of the antisense strand is complementary to a portion of a mRNA polynucleotide transcribable from a *Diabrotica* insect gene described in the present disclosure, wherein the dsRNA molecule is toxic to a *Diabrotica* insect or Coleopteran plant pest.

It is known in the art that dsRNA molecules that are not perfectly complementary to a target sequence (for example, having only 95% identity to the target gene) are effective to control coleopteran pests (see, for example, Narva et al., U.S. Pat. No. 9,012,722). The invention provides an interfering RNA molecule comprising at least one dsRNA, where the dsRNA is a region of double-stranded RNA comprising annealed at least partially complementary strands. One strand of the dsRNA comprises a sequence of at least 19, at least 20, at least 21, at least 22, at least 23, at least 24, at least 25, at least 26, at least 27, at least 28, at least 29, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 contiguous nucleotides which is at least partially complementary to a target nucleotide sequence within a *Diabrotica* spp target gene. The interfering RNA molecule (i) has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity, or 100% identity, to at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 contiguous nucleotide fragment of SEQ ID NO:121-210, SEQ ID NO: 274-276, SEQ ID NO: 280-282, SEQ ID NO: 304-324, or the complement thereof; (ii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 contiguous nucleotide fragment of SEQ ID NO:121-210, SEQ ID NO: 274-276, SEQ ID NO: 280-282, SEQ ID NO: 304-324, or the complement thereof; (iii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 contiguous nucleotide fragment of a nucleotide sequence encoding an amino acid sequence encoded by SEQ ID NO:121-210, SEQ ID NO: 274-276, SEQ ID NO: 280-282, SEQ ID NO: 304-324, or the complement thereof; or (iv) can hybridize under stringent conditions to a polynucleotide selected from the group consisting of SEQ ID NO:121-210, SEQ ID NO: 274-276, SEQ ID NO: 280-282, SEQ ID NO: 304-324, and the complements thereof, wherein the interfering RNA molecule has insecticidal activity on a coleopteran plant pest.

In some embodiments, the interfering RNA molecule comprises at least two dsRNAs, wherein each dsRNA comprises a sequence of nucleotides which is at least partially complementary to a target nucleotide sequence within the target gene. In some embodiments, each of the dsRNAs comprise a different sequence of nucleotides which is complementary to a different target nucleotide sequence within the target gene. In other embodiments, each of the dsRNAs comprise a different sequence of nucleotides which is complementary to a target nucleotide sequence within two different target genes.

In some embodiments, the interfering RNA molecule comprises a dsRNA that can comprise, consist essentially of or consist of from at least 18 to about 25 consecutive nucleotides (e.g. 18, 19, 20, 21, 22, 23, 24, 25, 26, 27, 28, or 29) to at least about 300 consecutive nucleotides. Additional nucleotides can be added at the 3' end, the 5' end or both the 3' and 5' ends to facilitate manipulation of the dsRNA molecule but that do not materially affect the basic characteristics or function of the dsRNA molecule in RNA interference (RNAi).

In some embodiments, the interfering RNA molecule comprises a dsRNA which comprises an antisense strand that is complementary to at least 19, at least 20, at least 21, at least 22, at least 23, at least 24, at least 25, at least 26, at least 27, at least 28, at least 29, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 consecutive nucleotides of SEQ ID NO:121-210, SEQ ID NO: 274-276, SEQ ID NO: 280-282, or SEQ ID NO: 304-324. In other embodiments, the portion of dsRNA comprises, consists essentially of or consists of at least from 19, 20 or 21 consecutive nucleotides to at least 19, at least 20, at least 21, at least 22, at least 23, at least 24, at least 25, at least 26, at least 27, at least 28, at least 29, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 consecutive nucleotides of SEQ ID NO:121-210, SEQ ID NO: 274-276, SEQ ID NO: 280-282, SEQ ID NO: 304-324, or the complement thereof.

In other embodiments, an interfering RNA molecule of the invention comprises a dsRNA which comprises, consists essentially of or consists of any 21-mer subsequence of SEQ ID NO: 181-210 consisting of N to N+20 nucleotides, or any complement thereof. For example, an interfering RNA molecule of the invention comprises a dsRNA which comprises, consist essentially of or consists of any 21-mer subsequence of SEQ ID NO: 181, wherein N is nucleotide 1 to nucleotide 776 of SEQ ID NO: 181, or any complement thereof. In other words, the portion of the mRNA that is targeted comprises any of the 776 21 consecutive nucleotide subsequences i.e. 21-mers) of SEQ ID NO: 181, or any of their complementing sequences. It will be recognized that these 776 21 consecutive nucleotide subsequences include all possible 21 consecutive nucleotide subsequences from SEQ ID NO: 121 and from SEQ ID NO: 151, and their complements, as SEQ ID NOs 121, 151, and 181 are all to the same target, namely BPA_15366. It will similarly be recognized that all 21-mer subsequences of SEQ ID NO: 181-210, and all complement subsequences thereof, include all possible 21 consecutive nucleotide subsequences of SEQ ID NOs: 121-180, and the complement subsequences thereof.

Similarly, an interfering RNA molecule of the invention comprises a dsRNA which comprises, consist essentially of or consists of any 21-mer subsequence of SEQ ID NO: 182, wherein N is nucleotide 1 to nucleotide 771 of SEQ ID NO: 182, or any complement thereof. Another interfering RNA molecule of the invention comprises a dsRNA which comprises, consist essentially of or consists of any 21-mer subsequence of SEQ ID NO: 183, wherein N is nucleotide 1 to nucleotide 2907 of SEQ ID NO: 183, or any complement thereof. Another interfering RNA molecule of the invention comprises a dsRNA which comprises, consist essentially of or consists of any 21-mer subsequence of SEQ ID NO: 184, wherein N is nucleotide 1 to nucleotide 1600 of SEQ ID NO: 184, or any complement thereof. Another interfering RNA molecule of the invention comprises a dsRNA which comprises, consist essentially of or consists of any 21-mer subsequence of SEQ ID NO: 185, wherein N is nucleotide 1 to nucleotide 2410 of SEQ ID NO: 185, or any complement thereof. Another interfering RNA molecule of the invention comprises a dsRNA which comprises, consist essentially of or consists of any 21-mer subsequence of SEQ ID NO: 186, wherein N is nucleotide 1 to nucleotide 2802 of SEQ ID NO: 186, or any complement thereof. Another interfering RNA molecule of the invention comprises a dsRNA which comprises, consist essentially of or consists of any 21-mer subsequence of SEQ ID NO: 187, wherein N is nucleotide 1 to nucleotide 3681 of SEQ ID NO: 187, or any complement thereof. Another interfering RNA molecule of the invention comprises a dsRNA which comprises, consist essentially of or consists of any 21-mer subsequence of SEQ ID NO: 188, wherein N is nucleotide 1 to nucleotide 651 of SEQ ID NO: 188, or any complement thereof. Another interfering RNA molecule of the invention comprises a dsRNA which comprises, consist essentially of or consists of any 21-mer subsequence of SEQ ID NO: 189, wherein N is nucleotide 1 to nucleotide 673 of SEQ ID NO: 189, or any complement thereof. Another interfering RNA molecule of the invention comprises a dsRNA which comprises, consist essentially of or consists of any 21-mer subsequence of SEQ ID NO: 190, wherein N is nucleotide 1 to nucleotide 2664 of SEQ ID NO: 190, or any complement thereof. Another interfering RNA molecule of the invention comprises a dsRNA which comprises, consist essentially of or consists of any 21-mer subsequence of SEQ ID NO: 191, wherein N is nucleotide 1 to nucleotide 438 of SEQ ID NO: 191, or any complement thereof. Another interfering RNA molecule of the invention comprises a dsRNA which comprises, consist essentially of or consists of any 21-mer subsequence of SEQ ID NO: 192, wherein N is nucleotide 1 to nucleotide 2458 of SEQ ID NO: 192, or any complement thereof. Another interfering RNA molecule of the invention comprises a dsRNA which comprises, consist essentially of or consists of any 21-mer subsequence of SEQ ID NO: 193, wherein N is nucleotide 1 to nucleotide 3254 of SEQ ID NO: 193, or any complement thereof. Another interfering RNA molecule of the invention comprises a dsRNA which comprises, consist essentially of or consists of any 21-mer subsequence of SEQ ID NO: 194, wherein N is nucleotide 1 to nucleotide 3632 of SEQ ID NO: 194, or any complement thereof. Another interfering RNA molecule of the invention comprises a dsRNA which comprises, consist essentially of or consists of any 21-mer subsequence of SEQ ID NO: 195, wherein N is nucleotide 1 to nucleotide 7611 of SEQ ID NO: 195, or any complement thereof. Another interfering RNA molecule of the invention comprises a dsRNA which comprises, consist essentially of or consists of any 21-mer subsequence of SEQ ID NO: 196, wherein N is nucleotide 1 to nucleotide 1008 of SEQ ID NO: 196, or any complement thereof. Another interfering RNA molecule of the invention comprises a dsRNA which comprises, consist essentially of or consists of any 21-mer subsequence of SEQ ID NO: 197, wherein N is nucleotide 1 to nucleotide 2992 of SEQ ID NO: 197, or any complement thereof. Another interfering RNA molecule of the invention comprises a dsRNA which comprises, consist essentially of or consists of any 21-mer subsequence of SEQ ID NO: 198, wherein N is nucleotide 1 to nucleotide 1192 of SEQ ID NO: 198, or any complement thereof. Another interfering RNA molecule of the invention comprises a dsRNA which comprises, consist essentially of or consists of any 21-mer subsequence of SEQ ID NO: 199, wherein N is nucleotide 1 to nucleotide 7626 of SEQ ID NO: 199, or any complement thereof. Another interfering RNA molecule of the invention comprises a dsRNA which comprises, consist essentially of or consists of any 21-mer subsequence of SEQ ID NO: 200, wherein N is nucleotide 1 to nucleotide 2580 of SEQ ID NO: 200, or any complement thereof. Another interfering RNA molecule of the invention comprises a dsRNA which comprises, consist essentially of or consists of any 21-mer subsequence of SEQ ID NO: 201, wherein N is nucleotide 1 to nucleotide 4628 of SEQ ID NO: 201, or any complement thereof. Another interfering RNA molecule of the invention comprises a dsRNA which comprises, consist essentially of or consists of any 21-mer subsequence of SEQ ID NO: 202, wherein N is nucleotide 1 to nucleotide 1557 of SEQ ID NO: 202, or any complement thereof. Another interfering RNA molecule of the invention comprises a dsRNA which comprises, consist essentially of or consists of any 21-mer subsequence of SEQ ID NO: 203, wherein N is nucleotide 1 to nucleotide 1019 of SEQ ID NO: 203, or any complement thereof. Another interfering RNA molecule of the invention comprises a dsRNA which comprises, consist essentially of or consists of any 21-mer subsequence of SEQ ID NO: 204, wherein N is nucleotide 1 to nucleotide 677 of SEQ ID NO: 204, or any complement thereof. Another interfering RNA molecule of the invention comprises a dsRNA which comprises, consist essentially of or consists of any 21-mer subsequence of SEQ ID NO: 205, wherein N is nucleotide 1 to nucleotide 764 of SEQ ID NO: 205, or any complement thereof. Another interfering RNA molecule of the invention comprises a dsRNA which comprises, consist essentially of or consists of any 21-mer subsequence of SEQ ID NO: 206, wherein N is nucleotide 1 to nucleotide 1830 of SEQ ID NO: 206, or any complement thereof. Another interfering RNA molecule of the invention comprises a dsRNA which comprises, consist essentially of or consists of any 21-mer subsequence of SEQ ID NO: 207, wherein N is nucleotide 1 to nucleotide 3225 of SEQ ID NO: 207, or any complement thereof. Another interfering RNA molecule of the invention comprises a dsRNA which comprises, consist essentially of or consists of any 21-mer subsequence of SEQ ID NO: 208, wherein N is nucleotide 1 to nucleotide 1003 of SEQ ID NO: 208, or any complement thereof. Another interfering RNA molecule of the invention comprises a dsRNA which comprises, consist essentially of or consists of any 21-mer subsequence of SEQ ID NO: 209, wherein N is nucleotide 1 to nucleotide 1419 of SEQ ID NO: 209, or any complement thereof. Another interfering RNA molecule of the invention comprises a dsRNA which comprises, consist essentially of or consists of any 21-mer subsequence of SEQ ID NO: 210, wherein N is nucleotide 1 to nucleotide 5206 of SEQ ID NO: 210, or any complement thereof.

In still other embodiments, the interfering RNA molecule of the invention comprises a dsRNA which comprises, consists essentially of or consists of SEQ ID NO:121-210, SEQ ID NO: 274-276, SEQ ID NO: 280-282, SEQ ID NO: 304-324, or the complement thereof.

In other embodiments of the interfering RNA molecule of the invention, the nucleotide sequence of the antisense strand of a dsRNA of the invention comprises, consists essentially of or consists of the nucleotide sequence of SEQ ID NO: 220, 224, 230. The nucleotide sequence of the antisense strand of a dsRNA of the invention can have one nucleotide at either the 3' or 5' end deleted or can have up to six nucleotides added at the 3' end, the 5' end or both, in any combination to achieve an antisense strand consisting essentially of any 19-mer, any 20-mer, or any 21-mer nucleotide sequence of SEQ ID NO: 211-240, as it would be understood that the deletion of the one nucleotide or the addition of up to the six nucleotides do not materially affect the basic characteristics or function of the double stranded RNA molecule of the invention. Such additional nucleotides can be nucleotides that extend the complementarity of the antisense strand along the target sequence and/or such nucleotides can be nucleotides that facilitate manipulation of the RNA molecule or a nucleic acid molecule encoding the RNA molecule, as would be known to one of ordinary skill in the art. For example, a TT overhang at the 3' end may be present, which is used to stabilize the siRNA duplex and does not affect the specificity of the siRNA.

In some embodiments of this invention, the antisense strand of the double stranded RNA of the interfering RNA molecule can be fully complementary to the target RNA polynucleotide or the antisense strand can be substantially complementary or partially complementary to the target RNA polynucleotide. The dsRNA of the interfering RNA molecule may comprise a dsRNA which is a region of double-stranded RNA comprising substantially complementary annealed strands, or which is a region of double-stranded RNA comprising fully complementary annealed strands. By substantially or partially complementary is meant that the antisense strand and the target RNA polynucleotide can be mismatched at about 1, 2, 3, 4, 5, 6, 7, 8, 9, or 10 nucleotide pairings. Such mismatches can be introduced into the antisense strand sequence, e.g., near the 3' end, to enhance processing of the double stranded RNA molecule by Dicer, to duplicate a pattern of mismatches in a siRNA molecule inserted into a chimeric nucleic acid molecule or artificial microRNA precursor molecule of this invention, and the like, as would be known to one of skill in the art. Such modification will weaken the base pairing at one end of the duplex and generate strand asymmetry, therefore enhancing the chance of the antisense strand, instead of the sense strand, being processed and silencing the intended gene (Geng and Ding "Double-mismatched siRNAs enhance selective gene silencing of a mutant ALS-causing Allele1" *Acta Pharmacol. Sin.* 29:211-216 (2008); Schwarz et al. "Asymmetry in the assembly of the RNAi enzyme complex" *Cell* 115:199-208 (2003)).

In some embodiments of this invention, the interfering RNA comprises a dsRNA which comprises a short hairpin RNA (shRNA) molecule. Expression of shRNA in cells is typically accomplished by delivery of plasmids or recombinant vectors, for example in transgenic plants such as transgenic corn.

The invention encompasses a nucleic acid construct comprising an interfering RNA of the invention. The invention further encompasses a nucleic acid molecule encoding at least one interfering molecule of the invention. The invention further encompasses a nucleic acid construct comprising at least one interfering molecule of the invention or comprising a nucleic acid molecule encoding the at least one interfering molecule of the invention. The invention further encompasses a nucleic acid construct wherein the nucleic acid construct is an expression vector. The invention further encompasses a recombinant vector comprising a regulatory sequence operably linked to a nucleotide sequence that encodes an interfering RNA molecule of the invention. A regulatory sequence may refer to a promoter, enhancer, transcription factor binding site, insulator, silencer, or any other DNA element involved in the expression of a gene.

The invention further encompasses chimeric nucleic acid molecules comprising an interfering RNA molecule with an antisense strand of a dsRNA operably linked with a plant microRNA precursor molecule. In some embodiments, the chimeric nucleic acid molecule comprises an antisense strand having the nucleotide sequence of any of the 21-mer subsequences of SEQ ID NOs: 181-210, or any complement thereof, operably linked with a plant microRNA precursor molecule. In some embodiments, the plant microRNA precursor molecule is a maize microRNA precursor.

In some embodiments, the invention encompasses an artificial plant microRNA precursor molecule comprising an antisense strand of a dsRNA of an interfering RNA molecule of the invention. In other embodiments, the artificial plant microRNA precursor molecule comprises an antisense strand having the nucleotide sequence of any of the 19-mer, 20-mer, or 21-mer subsequences of SEQ ID NOs: 211-240. The use of artificial plant microRNAs to deliver a nucleotide sequence of interest (e.g an artificial miRNA; siRNA/siRNA*) into a plant is known in the art (see, e.g., Schwab et al. 2006. The Plant Cell 18:1121-1133 and Examples section herein). In the invention, the artificial microRNAs are chimeric or hybrid molecules, having a plant microRNA precursor backbone and an insect siRNA sequence inserted therein. As would be understood by one of ordinary skill in the art, it is typically desirable to maintain mismatches that normally occur in the plant microRNA precursor sequence in any nucleotide sequence that is substituted into the plant microRNA precursor backbone. In still other embodiments, the artificial plant microRNA precursor comprises portions of a corn microRNA precursor molecule. Any corn microRNA (miRNA) precursor is suitable for the compositions and methods of the invention. Non-limiting examples include miR156, miR159, miR160, miR162, miR164, miR166, miR167, miR168, miR169, miR171, miR172, miR319, miR390, miR393, miR394, miR395, miR396, miR397, miR398, miR399, miR408, miR482, miR528, miR529, miR827, miR1432, as well as any other plant miRNA precursors now known or later identified.

In some embodiments, the invention encompasses interfering RNA molecules, nucleic acid constructs, nucleic acid molecules or recombinant vectors comprising at least one strand of a dsRNA of an interfering RNA molecule of the invention, or comprising a chimeric nucleic acid molecule of the invention, or comprising an artificial plant microRNA of the invention. In some embodiments the nucleic acid construct comprises a nucleic acid molecule of the invention. In other embodiments, the nucleic acid construct is a recombinant expression vector.

In some embodiments, the interfering RNA molecules of the invention have insecticidal activity on a *Diabrotica* insect. In some embodiments the *Diabrotica* insect selected from the group consisting of *Diabrotica barberi* (northern corn rootworm), *D. virgifera virgifera* (western corn rootworm), *D. undecimpunctata howardi* (southern corn rootworm), *D. balteata* (banded cucumber beetle), *D. undecimpunctata undecimpunctata* (western spotted cucumber beetle), *D. significata* (3-spotted leaf beetle), *D. speciosa* (chrysanthemum beetle), *D. virgifera zeae* (Mexican corn rootworm), *D. beniensis, D. cristata, D. curvipustulata, D. dissimilis, D. elegantula, D. emorsitans, D. graminea, D. hispanolae, D. lemniscata, D. linsleyi, D. milleri, D. nummularis, D. occlusa, D. porracea, D. scutellata, D. tibialis, D. trifasciata* and *D. viridula*. In further embodiments, the *Diabrotica* insect is *D. virgifera virgifera* (western corn rootworm), *D. undecimpunctata howardi* (southern corn rootworm) or *D. barberi* (northen corn rootworm). In some embodiments, the coding sequence of the target gene comprises a sequence selected from the group comprising SEQ ID NO: 91-120.

In some embodiments, the invention encompasses a composition comprising one or more or two or more of the interfering RNA molecules of the invention. In some embodiments, the interfering RNA molecules are present on the same nucleic acid construct, on different nucleic acid constructs, or any combination thereof. For example, one interfering RNA molecule of the invention may be present on a nucleic acid construct, and a second interfering RNA molecule of the invention may be present on the same nucleic acid construct or on a separate, second nucleic acid construct. The second interfering RNA molecule of the invention may be to the same target gene or to a different target gene.

In some embodiments, the invention encompasses a composition comprising an interfering RNA molecule which comprises at least one dsRNA wherein the dsRNA is a region of double-stranded RNA comprising annealed complementary strands. One strand of the dsRNA comprises a sequence of at least 19, at least 20, at least 21, at least 22, at least 23, at least 24, at least 25, at least 26, at least 27, at least 28, at least 29, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 contiguous nucleotides which is at least partially complementary to a target nucleotide sequence within a *Diabrotica* spp target gene. The interfering RNA molecule (i) has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity, or 100% identity, to at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 contiguous nucleotide fragment of SEQ ID NO:121-210, SEQ ID NO: 274-276, SEQ ID NO: 280-282, SEQ ID NO: 304-324, or the complement thereof; (ii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 contiguous nucleotide fragment of SEQ ID NO:121-210, SEQ ID NO: 274-276, SEQ ID NO: 280-282, SEQ ID NO: 304-324, or the complement thereof; (iii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 contiguous nucleotide fragment of a nucleotide sequence encoding an amino acid sequence encoded by SEQ ID NO:121-210, SEQ ID NO: 274-276, SEQ ID NO: 280-282, SEQ ID NO: 304-324, or the complement thereof; or (iv) can hybridize under stringent conditions to a polynucleotide selected from the group consisting of SEQ ID NO:121-210, SEQ ID NO: 274-276, SEQ ID NO: 280-282, SEQ ID NO: 304-324, and the complements thereof.

In some embodiments, the invention encompasses compositions comprising an interfering RNA molecule comprising two or more dsRNAs, wherein the two or more dsRNAs each comprise a different antisense strand. In some embodiments the invention encompasses compositions comprising at least two more interfering RNA molecules, wherein the two or more interfering RNA molecules each comprise a dsRNA comprising a different antisense strand. The two or more interfering RNAs may be present on the same nucleic acid construct, on different nucleic acid constructs or any combination thereof. In other embodiments, the composition comprises a RNA molecule comprising an antisense strand consisting essentially of a nucleotide sequence comprising at least a 19 contiguous nucleotide fragment of SEQ ID NO: 211-240, and in some embodiments may further comprise an RNA molecule comprising an antisense strand consisting essentially of a second nucleotide sequence comprising at least a 19 contiguous nucleotide fragment of SEQ ID NO: 211-240; and in some embodiments may further comprise an RNA molecule comprising an antisense strand consisting essentially of a third nucleotide sequence comprising at least a 19 contiguous nucleotide fragment of SEQ ID NO: 211-240, and in some embodiments may further comprise an RNA molecule comprising an antisense strand consisting essentially of a fourth nucleotide sequence comprising at least a 19 contiguous nucleotide fragment of SEQ ID NO: 211-240, and in some embodiments may further comprise an RNA molecule comprising an antisense strand consisting essentially of a fifth nucleotide sequence comprising at least a 19 contiguous nucleotide fragment of SEQ ID NO: 211-240, and in some embodiments may further comprise an RNA molecule comprising an antisense strand consisting essentially of a sixth nucleotide sequence comprising at least a 19 contiguous nucleotide fragment of SEQ ID NO: 211-240, and in some embodiments may further comprise an RNA molecule comprising an antisense strand consisting essentially of a seventh nucleotide sequence comprising at least a 19 contiguous nucleotide fragment of SEQ ID NO: 211-240. In other embodiments, the composition may comprise two or more of the nucleic acid molecules, wherein the two or more nucleic acid molecules each encode a different interfering RNA molecule. In other embodiments, the composition may comprise two or more of the nucleic acid constructs, wherein the two or more nucleic acid constructs each comprise a nucleic acid molecule encoding a different interfering RNA.

In other embodiments, the composition comprises two or more nucleic acid constructs, two or more nucleic acid molecules, two or more chimeric nucleic acid molecules, two or more artificial plant microRNA precursors of the invention, wherein the two or more nucleic acid constructs, two or more nucleic acid molecules, two or more chimeric nucleic acid molecules, or two or more artificial plant microRNA precursors, each comprise a different antisense strand.

In some embodiments, the invention encompasses an insecticidal composition for inhibiting the expression of a *Diabrotica* insect gene described herein, comprising an interfering RNA of the invention and an agriculturally acceptable carrier. In some embodiments, the acceptable agricultural carrier is a transgenic organism expressing an interfering RNA of the invention. In some embodiments the transgenic organism may be a transgenic plant expressing the interfering RNA of the invention that when fed upon by a target Coleopteran plant pest causes the target Coleopteran plant pest to stop feeding, growing or reproducing or causing death of the target Coleopteran plant pest. In other embodiments, the transgenic plant is a transgenic corn plant and the target pest is a *Diabrotica* insect pest. In still other embodiments, the *Diabrotica* insect pest is selected from the group consisting of *Diabrotica barberi* (northern corn rootworm), *D. virgifera virgifera* (western corn rootworm), *D. undecimpunctata howardi* (southern corn rootworm), *D. balteata* (banded cucumber beetle), *D. undecimpunctata undecimpunctata* (western spotted cucumber beetle), *D. significata* (3-spotted leaf beetle), *D. speciosa* (chrysanthemum beetle), *D. virgifera zeae* (Mexican corn rootworm).

In other embodiments, the transgenic organism is selected from, but not limited to, the group consisting of: yeast, fungi, algae, bacteria, virus or an arthropod expressing the interfering RNA molecule of the invention. In some embodiments, the transgenic organism is a virus, for example an insect baculovirus that expresses an interfering RNA molecule of the invention upon infection of an insect host. Such a baculovirus is likely more virulent against the target insect than the wildtype untransformed baculovirus. In other embodiments the transgenic organism is a transgenic bacterium that is applied to an environment where a target pest occurs or is known to have occurred. In some embodiments, non-pathogenic symbiotic bacteria, which are able to live and replicate within plant tissues, so-called endophytes, or non-pathogenic symbiotic bacteria, which are capable of colonizing the phyllosphere or the rhizosphere, so-called epiphytes, are used. Such bacteria include bacteria of the genera *Agrobacterium, Alcaligenes, Azospirillum, Azotobacter, Bacillus, Clavibacter, Enterobacter, Erwinia, Flavobacter, Klebsiella, Pseudomonas, Rhizobium, Serratia, Streptomyces* and *Xanthomonas*. Symbiotic fungi, such as *Trichoderma* and *Gliocladium* are also possible hosts for expression of the inventive interfering RNA molecule for the same purpose.

In some embodiments, an acceptable agricultural carrier is a formulation useful for applying the composition comprising the interfering RNA molecule to a plant or seed. In some embodiments, the interfering RNA molecules are stabilized against degradation because of their double stranded nature and the introduction of Dnase/Rnase inhibitors. For example, dsRNA or siRNA can be stabilized by including thymidine or uridine nucleotide 3' overhangs. The dsRNA or siRNA contained in the compositions of the invention can be chemically synthesized at industrial scale in large amounts. Methods available would be through chemical synthesis or through the use of a biological agent.

In other embodiments the formulation comprises a transfection promoting agent. In other embodiments, the transfection promoting agent is a lipid-containing compound. In further embodiments, the lipid-containing compound is selected from the group consisting of; Lipofectamine, Cellfectin, DMRIE-C, DOTAP and Lipofectin. In another embodiment, the lipid-containing compound is a Tris cationic lipid.

In some embodiments, the formulation further comprises a nucleic acid condensing agent. The nucleic acid condensing agent can be any such compound known in the art. Examples of nucleic acid condensing agents include, but are not limited to, spermidine (N-[3-aminopropyl]-1,4-butanediamine), protamine sulphate, poly-lysine as well as other positively charged peptides. In some embodiments, the nucleic acid condensing agent is spermidine or protamine sulfate.

In still further embodiments, the formulation further comprises buffered sucrose or phosphate buffered saline.

In some embodiments, the invention encompasses transgenic plants, or parts thereof, comprising an interfering RNA molecule, a nucleic acid construct, a chimeric nucleic acid molecule, a artificial plant microRNA precursor molecule and/or a composition of the invention, wherein the transgenic plant has enhanced resistance to a Coleopteran insect or *Diabrotica* insect as compared to a control plant. In other embodiments, the transgenic plant, or part thereof, is a transgenic corn plant, or part thereof. The invention further encompasses transgenic seed of the transgenic plants of the invention, wherein the transgenic seed comprises an interfering RNA molecule, a nucleic acid construct, a chimeric nucleic acid molecule, an artificial plant microRNA precursor molecule and/or a composition of the invention. In some embodiments the transgenic seed is a transgenic corn seed.

Transgenic plants expressing an interfering RNA of the invention are tolerant or resistant to attack by target insect pests. When the insect starts feeding on such a transgenic plant, it also ingests the expressed dsRNA or siRNA. This may deter the insect from further biting into the plant tissue or may even harm or kill the insect. A nucleic acid sequence encoding a dsRNA or siRNA of the invention is inserted into an expression cassette, which is then preferably stably integrated in the genome of the plant. The nucleic acid sequences of the expression cassette introduced into the genome of the plant are heterologous to the plant and non-naturally occurring. Plants transformed in accordance with the present invention may be monocots or dicots and include, but are not limited to, corn, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugar beet, sunflower, rapeseed, clover, tobacco, carrot, cotton, alfalfa, rice, potato, eggplant, cucumber, *Arabidopsis*, and woody plants such as coniferous and deciduous trees. In further embodiments, the transgenic plant is a transgenic corn plant.

Expression of the interfering RNA molecule in transgenic plants is driven by regulatory sequences comprising promoters that function in plants. The choice of promoter will vary depending on the temporal and spatial requirements for expression, and also depending on the insect target species. Thus, expression of the interfering RNAs of this invention in leaves, in stalks or stems, in ears, in inflorescences (e.g. spikes, panicles, cobs, etc.), in roots, and/or seedlings is contemplated. In many cases, however, protection against more than one type of insect pest is sought, and thus expression in multiple tissues is desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the dsRNA or siRNA in the desired cell.

Promoters useful with the invention include, but are not limited to, those that drive expression of a nucleotide sequence constitutively, those that drive expression when induced, and those that drive expression in a tissue- or developmentally-specific manner. These various types of promoters are known in the art.

In some embodiments, tissue-specific/tissue-preferred promoters can be used. Tissue-specific or tissue-preferred expression patterns include, but are not limited to, green tissue specific or preferred, root specific or preferred, stem specific or preferred, and flower specific or preferred. In addition, promoters functional in plastids can be used. In some embodiments of the invention, inducible promoters can be used. In further aspects, the nucleotide sequences of the invention can be operably associated with a promoter that is wound inducible or inducible by pest or pathogen infection (e.g., a insect or nematode plant pest)

In some embodiments of the present invention, a "minimal promoter" or "basal promoter" is used. A minimal promoter is capable of recruiting and binding RNA polymerase II complex and its accessory proteins to permit transcriptional initiation and elongation. In some embodiments, a minimal promoter is constructed to comprise only the nucleotides/nucleotide sequences from a selected promoter that are required for binding of the transcription factors and transcription of a nucleotide sequence of interest that is operably associated with the minimal promoter including but not limited to TATA box sequences. In other embodiments, the minimal promoter lacks cis sequences that recruit and bind transcription factors that modulate (e.g., enhance, repress, confer tissue specificity, confer inducibility or repressibility) transcription. A minimal promoter is generally placed upstream (i.e., 5') of a nucleotide sequence to be expressed. Thus, nucleotides/nucleotide sequences from any promoter useable with the present invention can be selected for use as a minimal promoter.

In some embodiments, a recombinant nucleic acid molecule of the invention can be an "expression cassette." As used herein, "expression cassette" means a recombinant nucleic acid molecule comprising a nucleotide sequence of interest (e.g., the nucleotide sequences of the invention), wherein the nucleotide sequence is operably associated with at least a control sequence (e.g., a promoter). Thus, some embodiments of the invention provide expression cassettes designed to express nucleotides sequences encoding the dsRNAs or siRNAs of the invention. In this manner, for example, one or more plant promoters operably associated with one or more nucleotide sequences of the invention are provided in expression cassettes for expression in a corn plant, plant part and/or plant cell.

An expression cassette comprising a nucleotide sequence of interest may be chimeric, meaning that at least one of its components is heterologous with respect to at least one of its other components. An expression cassette may also be one that comprises a native promoter driving its native gene, however it has been obtained in a recombinant form useful for heterologous expression. Such usage of an expression cassette makes it so it is not naturally occurring in the cell into which it has been introduced.

An expression cassette also can optionally include a transcriptional and/or translational termination region (i.e., termination region) that is functional in plants. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the plant host, or may be derived from another source (i.e., foreign or heterologous to the promoter, the nucleotide sequence of interest, the plant host, or any combination thereof). Appropriate transcriptional terminators include, but are not limited to, the CAMV 35S terminator, the tml terminator, the nopaline synthase terminator and/or the pea rbcs E9 terminator. These can be used in both monocotyledons and dicotyledons. In addition, a coding sequence's native transcription terminator can be used.

An expression cassette of the invention also can include a nucleotide sequence for a selectable marker, which can be used to select a transformed plant, plant part and/or plant cell. As used herein, "selectable marker" means a nucleotide sequence that when expressed imparts a distinct phenotype to the plant, plant part and/or plant cell expressing the marker and thus allows such transformed plants, plant parts and/or plant cells to be distinguished from those that do not have the marker. Such a nucleotide sequence may encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening (e.g., the R-locus trait). Of course, many examples of suitable selectable markers are known in the art and can be used in the expression cassettes described herein.

Examples of selectable markers include, but are not limited to, a nucleotide sequence encoding neo or nptII, which confers resistance to kanamycin, G418, and the like (Potrykus et al. (1985) *Mol. Gen. Genet.* 199:183-188); a nucleotide sequence encoding bar, which confers resistance to phosphinothricin; a nucleotide sequence encoding an altered 5-enolpyruvylshikimate-3-phosphate (EPSP) synthase, which confers resistance to glyphosate (Hinchee et al. (1988) *Biotech.* 6:915-922); a nucleotide sequence encoding a nitrilase such as bxn from *Klebsiella ozaenae* that confers resistance to bromoxynil (Stalker et al. (1988) *Science* 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) *J. Biol. Chem.* 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; and/or a nucleotide sequence encoding hph that confers resistance to hygromycin. One of skill in the art is capable of choosing a suitable selectable marker for use in an expression cassette of the invention.

An expression cassette of the invention also can include polynucleotides that encode other desired traits. Such desired traits can be other polynucleotides which confer insect resistance, or which confer nematode resistance, or other agriculturally desirable traits. Such polynucleotides can be stacked with any combination of nucleotide sequences to create plants, plant parts or plant cells having the desired phenotype. Stacked combinations can be created by any method including, but not limited to, cross breeding plants by any conventional methodology, or by genetic transformation. If stacked by genetically transforming the plants, nucleotide sequences encoding additional desired traits can be combined at any time and in any order. For example, a single transgene can comprise multiple expression cassettes, such that multiple expression cassettes are introduced into the genome of a transformed cell at a single genomic location. Alternatively, a transgenic plant comprising one or more desired traits can be used as the target to introduce further traits by subsequent transformation. The additional nucleotide sequences can be introduced simultaneously in a co-transformation protocol with a nucleotide sequence, nucleic acid molecule, nucleic acid construct, and/or other composition of the invention, provided by any combination of expression cassettes. For example, if two nucleotide sequences will be introduced, they can be incorporated in separate cassettes (trans) or can be incorporated on the same cassette (cis). Expression of the nucleotide sequences can be driven by the same promoter or by different promoters. It is further recognized that nucleotide sequences can be stacked at a desired genomic location using a site-specific recombination system. See, e.g., Int'l Patent Application Publication Nos. WO 99/25821; WO 99/25854; WO 99/25840; WO 99/25855 and WO 99/25853.

Thus, an expression cassette can include a coding sequence for one or more polypeptides for agronomic traits that primarily are of benefit to a seed company, grower or grain processor. A polypeptide of interest can be any polypeptide encoded by a polynucleotide sequence of interest. Non-limiting examples of polypeptides of interest that are suitable for production in plants include those resulting in agronomically important traits such as herbicide resistance (also sometimes referred to as "herbicide tolerance"), virus resistance, bacterial pathogen resistance, insect resistance, nematode resistance, and/or fungal resistance. See, e.g., U.S. Pat. Nos. 5,569,823; 5,304,730; 5,495,071; 6,329,504; and 6,337,431.

Vectors suitable for plant transformation are described elsewhere in this specification. For *Agrobacterium*-mediated transformation, binary vectors or vectors carrying at least one T-DNA border sequence are suitable, whereas for direct gene transfer any vector is suitable and linear DNA containing only the construct of interest may be preferred. In the case of direct gene transfer, transformation with a single DNA species or co-transformation can be used (Schocher et al. Biotechnology 4:1093-1096 (1986)). For both direct gene transfer and *Agrobacterium*-mediated transfer, transformation is usually (but not necessarily) undertaken with a selectable marker that may provide resistance to an antibiotic (kanamycin, hygromycin or methotrexate) or a herbicide (basta). Plant transformation vectors of the invention may also comprise other selectable marker genes, for example, phosphomannose isomerase (pmi), which provides for positive selection of the transgenic plants as disclosed in U.S. Pat. Nos. 5,767,378 and 5,994,629, herein incorporated by reference, or phosphinotricin acetyltransferase (pat), which provides tolerance to the herbicide phosphinotricin (glufosinate). The choice of selectable marker is not, however, critical to the invention.

In other embodiments, a nucleic acid sequence of the invention is directly transformed into the plastid genome. Plastid transformation technology is extensively described in U.S. Pat. Nos. 5,451,513, 5,545,817, and 5,545,818, in PCT application no. WO 95/16783, and in McBride et al. (1994) Proc. Natl. Acad. Sci. USA 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, Z., Hajdukiewicz, P., and Maliga, P. (1990) Proc. Natl. Acad. Sci. USA 87, 8526-8530; Staub, J. M., and Maliga, P. (1992) Plant Cell 4, 39-45). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P. (1993) EMBO J. 12, 601-606). Substantial increases in transformation frequency are obtained by replacement of the recessive rRNA or r-protein antibiotic resistance genes with a dominant selectable marker, the bacterial aadA gene encoding the spectinomycin-cletoxifying enzyme aminoglycoside-3'-adenyltransferase (Svab, Z., and Maliga, P. (1993) Proc. Natl. Acad. Sci. USA 90, 913-917). Previously, this marker had been used successfully for high-frequency transformation of the plastid genome of the green alga *Chlamydomonas reinhardtii* (Goldschmidt-Clermont, M. (1991) Nucl. Acids Res. 19:4083-4089). Other selectable markers useful for plastid transformation are known in the art and encompassed within the scope of the invention. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleic acid sequence of the present invention is inserted into a plastid-targeting vector and transformed into the plastid genome of a desired plant host. Plants homoplastic for plastid genomes containing a nucleic acid sequence of the present invention are obtained, and are preferentially capable of high expression of the nucleic acid sequence.

Transgenic plants or seed comprising an interfering RNA of the invention can also be treated with an insecticide or insecticidal seed coating as described in U. S. Pat. Nos. 5,849,320 and 5,876,739, herein incorporated by reference. Where both the insecticide or insecticidal seed coating and the transgenic plant or seed of the invention are active against the same target insect, for example a Coleopteran pest or a *Diabrotica* target pest, the combination is useful (i) in a method for further enhancing activity of the composition of the invention against the target insect, and (ii) in a method for preventing development of resistance to the composition of the invention by providing yet another mechanism of action against the target insect. Thus, the invention provides a method of enhancing control of a *Diabrotica* insect population comprising providing a transgenic plant or seed of the invention and applying to the plant or the seed an insecticide or insecticidal seed coating to a transgenic plant or seed of the invention. Examples of such insecticides and/or insecticidal seed coatings include, without limitation, a carbamate, a pyrethroid, an organophosphate, a friprole, a neonicotinoid, an organochloride, a nereistoxin, or a combination thereof. In another embodiment, the insecticide or insecticidal seed coating are selected from the group consisting of carbofuran, carbaryl, methomyl, bifenthrin, tefluthrin, permethrin, cyfluthrin, lambda-cyhalothrin, cypermethrin, deltamethrin, chlorpyrifos, chlorethoxyfos, dimethoate, ethoprophos, malathion, methyl-parathion, phorate, terbufos, tebupirimiphos, fipronil, acetamiprid, imidacloprid, thiacloprid, thiamethoxam, endosulfan, bensultap, and a combination thereof. Commercial products containing such insecticides and insecticidal seed coatings include, without limitation, Furadan® (carbofuran), Lanate® (methomyl, metomil, mesomile), Sevin® (carbaryl), Talstar® (bifenthrin), Force® (tefluthrin), Ammo® (cypermethrin), Cymbush® (cypermethrin), Delta Gold® (deltamethrin), Karate® (lambda-cyhalothrin), Ambush® (permethrin), Pounce® (permethrin), Brigade® (bifenthrin), Capture® (bifenthrin), ProShield® (tefluthrin), Warrior® (lambda-cyhalothrin), Dursban® (chlorphyrifos), Fortress® (chlorethoxyfos), Mocap® (ethoprop), Thimet® (phorate), AAstar® (phorate, flucythinate), Rampart® (phorate), Counter® (terbufos), Cygon® (dimethoate), Dicapthon, Regent® (fipronil), Cruiser® (thiamethoxam), Gaucho® (imidacloprid), Prescribe® (imidacloprid), Poncho® (clothianidin) and Aztec® (cyfluthrin, tebupirimphos).

The compositions of the invention can also be combined with other biological control agents to enhance control of a coleopteran insect or a *Diabrotica* insect populations. Thus, the invention provides a method of enhancing control of a Coleopteran insect population or a *Diabrotica* insect population by providing a transgenic plant that produces an interfering RNA of the invention and further comprises a polynucleotide that encodes a second insecticidal agent. The second insecticidal agent may be an insecticidal protein derived from *Bacillus thuringiensis*. A *B. thuringiensis* insecticidal protein can be any of a number of insecticidal proteins including but not limited to a Cry1 protein, a Cry3 protein, a Cry7 protein, a Cry8 protein, a Cry11 protein, a Cry22 protein, a Cry 23 protein, a Cry 36 protein, a Cry37 protein, a Cry34 protein together with a Cry35 protein, a binary insecticidal protein CryET33 and CryET34, a binary insecticidal protein TIC100 and TIC101, a binary insecticidal protein PS149B1, a VIP, a TIC900 or related protein, a TIC901, TIC1201, TIC407, TIC417, a modified Cry3A protein, or hybrid proteins or chimeras made from any of the preceding insecticidal proteins. In other embodiments, the *B. thuringiensis* insecticidal protein is selected from the group consisting of Cry3Bb1, Cry34Ab1 together with Cry35Ab1, mCry3A and eCry3.1Ab.

In other embodiments, the transgenic plant may produce an interfering RNA of the invention and a second insecticidal agent which is derived from sources other than *B. thuringiensis*. The second insecticidal agent can be an agent selected from the group comprising a patatin, a protease, a protease inhibitor, a chitinase, a urease, an alpha-amylase inhibitor, a pore-forming protein, a lectin, an engineered antibody or antibody fragment, a *Bacillus cereus* insecticidal protein, a *Xenorhabdus* spp. (such as *X. nematophila* or *X. bovienii*) insecticidal protein, a *Photorhabdus* spp. (such as *P. luminescens* or *P. asymobiotica*) insecticidal protein, a *Brevibacillus laterosporous* insecticidal protein, a *Lysinibacillus sphearicus* insecticidal protein, a *Chromobacterium* spp. insecticidal protein, a *Yersinia entomophaga* insecticidal protein, a *Paenibacillus popiliae* insecticidal protein, a *Clostridium* spp. (such as *C. bifermentans*) insecticidal protein, and a lignin. In other embodiments, the second agent may be at least one insecticidal protein derived from an insecticidal toxin complex (Tc) from *Photorhabdus, Xenorhabus, Serratia*, or *Yersinia*. In other embodiments, the insecticidal protein may be an ADP-ribosyltransferase derived from an insecticidal bacteria, such as *Photorhabdus* spp. In other embodiments, the insecticidal protein may be a VIP protein, such as VIP1 or VIP2 from *B. cereus*. In still other embodiments, the insecticidal protein may be a binary toxin derived from an insecticidal bacteria, such as ISP1A and ISP2A from *B. laterosporous* or BinA and BinB from *L. sphaericus*. In still other embodiments, the insecticidal protein may be engineered or may be a hybrid or chimera of any of the preceding insecticidal proteins.

In another embodiment, the transgenic plant and transgenic seed is a corn plant or corn seed. In another embodiment, the transgenic corn plant is provided by crossing a first transgenic corn plant comprising a dsRNA of the invention with a transgenic corn plant comprising a transgenic event selected from the group consisting of MIR604, Event 5307, DAS51922-7, MON863 and MON88017.

Even where the insecticide or insecticidal seed coating is active against a different insect, the insecticide or insecticidal seed coating is useful to expand the range of insect control, for example by adding an insecticide or insecticidal seed coating that has activity against lepidopteran insects to the transgenic plant or seed of the invention, which has activity against coleopteran insects, the treated plant or coated transgenic seed controls both lepidopteran and coleopteran insect pests.

In further embodiments, the invention encompasses a biological sample from a transgenic plant, seed, or parts thereof, of the invention, wherein the sample comprises a nucleic acid that is or encodes at least one strand of a dsRNA of the invention. In other embodiments, the invention encompasses a commodity product derived from a transgenic plant, seed, or parts thereof, of the invention. In some embodiments, the commodity product is selected from the group consisting of whole or processed seeds, beans, grains, kernels, hulls, meals, grits, flours, sugars, sugars, starches, protein concentrates, protein isolates, waxes, oils, extracts, juices, concentrates, liquids, syrups, feed, silage, fiber, paper or other food or product produced from plants. In other embodiments, the biological sample or commodity product is toxic to insects. In other embodiments, the transgenic plant is a transgenic corn plant.

The invention further encompasses a method of controlling a coleopteran insect or a *Diabrotica* insect comprising contacting the insect with a nucleic acid molecule that is or is capable of producing an interfering RNA molecule of the invention for inhibiting expression of a target gene in the insect thereby controlling the coleopteran insect or the *Diabrotica* insect. In some embodiments, the target gene comprises a coding sequence (i) having at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity, or 100% identity, to at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 contiguous nucleotide fragment of SEQ ID NO: 1-30, SEQ ID NO: 91-120, SEQ ID NO: 271-273, SEQ ID NO: 277-279, SEQ ID NO: 283-303; or (ii) comprising at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 contiguous nucleotide fragment of SEQ ID NO: 1-30, SEQ ID NO: 91-120, SEQ ID NO: 271-273, SEQ ID NO: 277-279, SEQ ID NO: 283-303; (iii) comprising at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 contiguous nucleotide fragment of a nucleotide sequence encoding an amino acid sequence encoded by SEQ ID NO: 1-30, SEQ ID NO: 91-120, SEQ ID NO: 271-273, SEQ ID NO: 277-279, or SEQ ID NO: 283-303; or (iv) can hybridize under stringent conditions to a polynucleotide selected from the group consisting of SEQ ID NO: 1-30, SEQ ID NO: 91-120, SEQ ID NO: 271-273, SEQ ID NO: 277-279, SEQ ID NO: 283-303, and the complements thereof. In some embodiments the target gene coding sequence comprises SEQ ID NO: 1-30, SEQ ID NO: 91-120, SEQ ID NO: 271-273, SEQ ID NO: 277-279, SEQ ID NO: 283-303, or the complement thereof. In other embodiments, the interfering RNA molecule of the invention is complementary to a portion of a mRNA polynucleotide transcribable from the *Diabrotica* target genes described herein.

In some embodiments of the method of controlling a coleopteran insect pest or a *Diabrotica* insect pest, the interfering RNA molecule of the invention comprises at least one dsRNA, wherein the dsRNA is a region of double-stranded RNA comprising annealed complementary strands, one strand of which comprises a sequence of at least 19 contiguous nucleotides which (i) has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity, or 100% identity, to at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 contiguous nucleotide fragment of SEQ ID NO: 121-210, SEQ ID NO: 274-276, SEQ ID NO: 280-282, SEQ ID NO: 304-324, or the complement thereof; (ii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 contiguous nucleotide fragment of SEQ ID NO: 121-210, SEQ ID NO: 274-276, SEQ ID NO: 280-282, SEQ ID NO: 304-324, or the complement thereof; (iii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 contiguous nucleotide fragment of a nucleotide sequence encoding an amino acid sequence encoded by SEQ ID NO: 121-210, SEQ ID NO: 274-276, SEQ ID NO: 280-282, SEQ ID NO: 304-324, or the complement thereof; or (iv) can hybridize under stringent conditions to a polynucleotide selected from the group consisting of SEQ ID NO: 1-30, SEQ ID NO: 91-120, SEQ ID NO: 271-273, SEQ ID NO: 277-279, SEQ ID NO: 283-303, and the complements thereof.

In some embodiments of the method of controlling a coleopteran insect pest or a *Diabrotica* insect pest, the interfering RNA molecule comprises, consists essentially of or consists of from 18, 19, 20 or 21 consecutive nucleotides to at least about 300 consecutive nucleotides of SEQ ID NO: 181-210. In other embodiments, the interfering RNA of the invention comprises, consists essentially of or consists of any 21-mer subsequence of SEQ ID NO: 181-210 consisting of N to N+20 nucleotides, or any complement thereof. For example, an interfering RNA molecule of the invention comprises a dsRNA which comprises, consist essentially of or consists of any 21-mer subsequence of SEQ ID NO: 181, wherein N is nucleotide 1 to nucleotide 776 of SEQ ID NO: 181, or any complement thereof. In other words, the portion of the mRNA that is targeted comprises any of the 776 21 consecutive nucleotide subsequences i.e. 21-mers) of SEQ ID NO: 181, or any of their complementing sequences. It will be recognized that these 776 21 consecutive nucleotide subsequences include all possible 21 consecutive nucleotide subsequences from SEQ ID NO: 121 and from SEQ ID NO: 151, and their complements, as SEQ ID NOs 121, 151, and 181 are all to the same target, namely BPA_15366. It will similarly be recognized that all 21-mer subsequences of SEQ ID NO: 181-210, and all complement subsequences thereof, include all possible 21 consecutive nucleotide subsequences of SEQ ID NOs: 121-180, and the complement subsequences thereof.

Similarly, an interfering RNA molecule of the invention comprises a dsRNA which comprises, consist essentially of or consists of any 21-mer subsequence of SEQ ID NO: 182, wherein N is nucleotide 1 to nucleotide 771 of SEQ ID NO: 182, or any complement thereof. Another interfering RNA molecule of the invention comprises a dsRNA which comprises, consist essentially of or consists of any 21-mer subsequence of SEQ ID NO: 183, wherein N is nucleotide 1 to nucleotide 2907 of SEQ ID NO: 183, or any complement thereof. Another interfering RNA molecule of the invention comprises a dsRNA which comprises, consist essentially of or consists of any 21-mer subsequence of SEQ ID NO: 184, wherein N is nucleotide 1 to nucleotide 1600 of SEQ ID NO: 184, or any complement thereof. Another interfering RNA molecule of the invention comprises a dsRNA which comprises, consist essentially of or consists of any 21-mer subsequence of SEQ ID NO: 185, wherein N is nucleotide 1 to nucleotide 2410 of SEQ ID NO: 185, or any complement thereof. Another interfering RNA molecule of the invention comprises a dsRNA which comprises, consist essentially of or consists of any 21-mer subsequence of SEQ ID NO: 186, wherein N is nucleotide 1 to nucleotide 2802 of SEQ ID NO: 186, or any complement thereof. Another interfering RNA molecule of the invention comprises a dsRNA which comprises, consist essentially of or consists of any 21-mer subsequence of SEQ ID NO: 187, wherein N is nucleotide 1 to nucleotide 3681 of SEQ ID NO: 187, or any complement thereof. Another interfering RNA molecule of the invention comprises a dsRNA which comprises, consist essentially of or consists of any 21-mer subsequence of SEQ ID NO: 188, wherein N is nucleotide 1 to nucleotide 651 of SEQ ID NO: 188, or any complement thereof. Another interfering RNA molecule of the invention comprises a dsRNA which comprises, consist essentially of or consists of any 21-mer subsequence of SEQ ID NO: 189, wherein N is nucleotide 1 to nucleotide 673 of SEQ ID NO: 189, or any complement thereof. Another interfering RNA molecule of the invention comprises a dsRNA which comprises, consist essentially of or consists of any 21-mer subsequence of SEQ ID NO: 190, wherein N is nucleotide 1 to nucleotide 2664 of SEQ ID NO: 190, or any complement thereof. Another interfering RNA molecule of the invention comprises a dsRNA which comprises, consist essentially of or consists of any 21-mer subsequence of SEQ ID NO: 191, wherein N is nucleotide 1 to nucleotide 438 of SEQ ID NO: 191, or any complement thereof. Another interfering RNA molecule of the invention comprises a dsRNA which comprises, consist essentially of or consists of any 21-mer subsequence of SEQ ID NO: 192, wherein N is nucleotide 1 to nucleotide 2458 of SEQ ID NO: 192, or any complement thereof. Another interfering RNA molecule of the invention comprises a dsRNA which comprises, consist essentially of or consists of any 21-mer subsequence of SEQ ID NO: 193, wherein N is nucleotide 1 to nucleotide 3254 of SEQ ID NO: 193, or any complement thereof. Another interfering RNA molecule of the invention comprises a dsRNA which comprises, consist essentially of or consists of any 21-mer subsequence of SEQ ID NO: 194, wherein N is nucleotide 1 to nucleotide 3632 of SEQ ID NO: 194, or any complement thereof. Another interfering RNA molecule of the invention comprises a dsRNA which comprises, consist essentially of or consists of any 21-mer subsequence of SEQ ID NO: 195, wherein N is nucleotide 1 to nucleotide 7611 of SEQ ID NO: 195, or any complement thereof. Another interfering RNA molecule of the invention comprises a dsRNA which comprises, consist essentially of or consists of any 21-mer subsequence of SEQ ID NO: 196, wherein N is nucleotide 1 to nucleotide 1008 of SEQ ID NO: 196, or any complement thereof. Another interfering RNA molecule of the invention comprises a dsRNA which comprises, consist essentially of or consists of any 21-mer subsequence of SEQ ID NO: 197, wherein N is nucleotide 1 to nucleotide 2992 of SEQ ID NO: 197, or any complement thereof. Another interfering RNA molecule of the invention comprises a dsRNA which comprises, consist essentially of or consists of any 21-mer subsequence of SEQ ID NO: 198, wherein N is nucleotide 1 to nucleotide 1192 of SEQ ID NO: 198, or any complement thereof. Another interfering RNA molecule of the invention comprises a dsRNA which comprises, consist essentially of or consists of any 21-mer subsequence of SEQ ID NO: 199, wherein N is nucleotide 1 to nucleotide 7626 of SEQ ID NO: 199, or any complement thereof. Another interfering RNA molecule of the invention comprises a dsRNA which comprises, consist essentially of or consists of any 21-mer subsequence of SEQ ID NO: 200, wherein N is nucleotide 1 to nucleotide 2580 of SEQ ID NO: 200, or any complement thereof. Another interfering RNA molecule of the invention comprises a dsRNA which comprises, consist essentially of or consists of any 21-mer subsequence of SEQ ID NO: 201, wherein N is nucleotide 1 to nucleotide 4628 of SEQ ID NO: 201, or any complement thereof. Another interfering RNA molecule of the invention comprises a dsRNA which comprises, consist essentially of or consists of any 21-mer subsequence of SEQ ID NO: 202, wherein N is nucleotide 1 to nucleotide 1557 of SEQ ID NO: 202, or any complement thereof. Another interfering RNA molecule of the invention comprises a dsRNA which comprises, consist essentially of or consists of any 21-mer subsequence of SEQ ID NO: 203, wherein N is nucleotide 1 to nucleotide 1019 of SEQ ID NO: 203, or any complement thereof. Another interfering RNA molecule of the invention comprises a dsRNA which comprises, consist essentially of or consists of any 21-mer subsequence of SEQ ID NO: 204, wherein N is nucleotide 1 to nucleotide 677 of SEQ ID NO: 204, or any complement thereof. Another interfering RNA molecule of the invention comprises a dsRNA which comprises, consist essentially of or consists of any 21-mer subsequence of SEQ ID NO: 205, wherein N is nucleotide 1 to nucleotide 764 of SEQ ID NO: 205, or any complement thereof. Another interfering RNA molecule of the invention comprises a dsRNA which comprises, consist essentially of or consists of any 21-mer subsequence of SEQ ID NO: 206, wherein N is nucleotide 1 to nucleotide 1830 of SEQ ID NO: 206, or any complement thereof. Another interfering RNA molecule of the invention comprises a dsRNA which comprises, consist essentially of or consists of any 21-mer subsequence of SEQ ID NO: 207, wherein N is nucleotide 1 to nucleotide 3225 of SEQ ID NO: 207, or any complement thereof. Another interfering RNA molecule of the invention comprises a dsRNA which comprises, consist essentially of or consists of any 21-mer subsequence of SEQ ID NO: 208, wherein N is nucleotide 1 to nucleotide 1003 of SEQ ID NO: 208, or any complement thereof. Another interfering RNA molecule of the invention comprises a dsRNA which comprises, consist essentially of or consists of any 21-mer subsequence of SEQ ID NO: 209, wherein N is nucleotide 1 to nucleotide 1419 of SEQ ID NO: 209, or any complement thereof. Another interfering RNA molecule of the invention comprises a dsRNA which comprises, consist essentially of or consists of any 21-mer subsequence of SEQ ID NO: 210, wherein N is nucleotide 1 to nucleotide 5206 of SEQ ID NO: 210, or any complement thereof.

In some embodiments of the method of controlling a *Diabrotica* insect pest, the *Diabrotica* insect is selected from the group consisting of *D. barberi* (northern corn rootworm), *D. virgifera virgifera* (western corn rootworm), *D. undecimpunctata howardi* (southern corn rootworm), *D. balteata* (banded cucumber beetle), *D. undecimpunctata undecimpunctata* (western spotted cucumber beetle), *D. significata* (3-spotted leaf beetle), *D. speciosa* (chrysanthemum beetle) and *D. virgifera zeae* (Mexican corn rootworm).

In other embodiments of the method of controlling a coleopteran insect pest or a *Diabrotica* insect pest, the contacting comprises (a) planting a transgenic seed capable of producing a transgenic plant that expresses the nucleic acid molecule, wherein the insect feeds on the transgenic plant, or part thereof; or (b) applying a composition comprising the nucleic acid molecule to a seed or plant, or part thereof, wherein the insect feeds on the seed, the plant, or a part thereof. In some embodiments, the transgenic seed and the transgenic plant is a corn seed or a corn plant. In other embodiments the seed or plant is a corn seed or a corn plant.

The invention also encompasses a method of controlling a *Diabrotica* insect comprising contacting the *Diabrotica* insect with a nucleic acid molecule that is or is capable of producing the interfering RNA molecule of the invention for inhibiting expression of a target gene in the *Diabrotica* insect, and also contacting the *Diabrotica* insect with at least a second insecticidal agent for controlling *Diabrotica*, wherein said second insecticidal agent comprises a *B. thuringiensis* insecticidal protein, thereby controlling the *Diabrotica* insect. The invention also encompasses a method for controlling *Diabrotica* insect pests on a plant, comprising topically applying to said plant a pesticide composition comprising an interfering RNA of the invention and at least a second insecticidal agent for controlling *Diabrotica*, wherein said second insecticidal agent does not comprise a *B. thuringiensis* insecticidal protein, and providing said plant in the diet of said *Diabrotica* insect. The invention also encompasses a method wherein the second insecticidal agent comprises a patatin, a protease, a protease inhibitor, a urease, an alpha-amylase inhibitor, a pore-forming protein, a lectin, an engineered antibody or antibody fragment, or a chitinase. The second insecticidal agent may also be a *Bacillus cereus* insecticidal protein, a *Xenorhabdus* spp. insecticidal protein, a *Photorhabdus* spp. insecticidal protein, a *Brevibacillus laterosporous* insecticidal protein, a *Lysinibacillus sphearicus* insecticidal protein, a *Chromobacterium* ssp. insecticidal protein, a *Yersinia entomophaga* insecticidal protein, a *Paenibacillus popiliae* insecticidal protein, or a *Clostridium* spp. insecticidal protein.

The invention also encompasses a method of reducing an adult coleopteran insect population or an adult *Diabrotica* insect population on a transgenic plant expressing a Cry protein, a hybrid Cry protein or modified Cry protein comprising expressing in the transgenic plant a nucleic acid molecule that is or is capable of producing an interfering RNA molecule of the invention capable of inhibiting expression of a target gene as described herein in an adult insect, thereby reducing the adult coleopteran insect population or adult *Diabrotica* insect population.

In some embodiments, the invention encompasses a method of reducing the level of a target mRNA transcribable from a target gene as described herein in a coleopteran insect or a *Diabrotica* insect comprising contacting the insect with a composition comprising the interfering RNA molecule of the invention, wherein the interfering RNA molecule reduces the level of the target mRNA in a cell of the insect. In some embodiments, the interfering RNA of the method comprises at least one dsRNA, wherein the dsRNA is a region of double-stranded RNA comprising annealed complementary strands, one strand of which comprises a sequence of at least 19 contiguous nucleotides which (i) has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity, or 100% identity, to at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 contiguous nucleotide fragment of SEQ ID NO: 121-210, SEQ ID NO: 274-276, SEQ ID NO: 280-282, SEQ ID NO: 304-324, or the complement thereof; (ii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 contiguous nucleotide fragment of SEQ ID NO: 121-210, SEQ ID NO: 274-276, SEQ ID NO: 280-282, SEQ ID NO: 304-324, or the complement thereof; (iii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 contiguous nucleotide fragment of a nucleotide sequence encoding an amino acid sequence encoded by SEQ ID NO: 121-210, SEQ ID NO: 274-276, SEQ ID NO: 280-282, SEQ ID NO: 304-324, or the complement thereof, or (iv) can hybridize under stringent conditions to a polynucleotide selected from the group consisting of SEQ ID NO: 121-210, SEQ ID NO: 274-276, SEQ ID NO: 280-282, SEQ ID NO: 304-324, and the complement thereof, wherein the interfering RNA molecule has insecticidal activity against the target coleopteran insect or a *Diabrotica* insect. In another embodiment, the contacting is achieved by the target insect feeding on the composition. In other embodiments, production of the protein encoded by the target mRNA is reduced. In other embodiments, the target protein comprises an amino acid having at least about 80%, at least about 85%, at least about 90%, at least about 91%, at least about 92%, at least about 93%, at least about 94%, at least about 95%, at least about 96%, at least about 97%, at least about 98% or at least about 99% identity to SEQ ID NO: 241-270. In other embodiments the target protein comprises SEQ ID NO:241-270. In other embodiments, the interfering RNA is contacted with a coleopteran insect or a *Diabrotica* insect through a transgenic organism expressing the interfering RNA. In other embodiments, the transgenic organism is a transgenic plant, a transgenic microorganism, a transgenic bacterium or a transgenic endophyte. In other embodiments, the interfering RNA is contacted with a coleopteran insect or a *Diabrotica* insect by topically applying an interfering RNA in an acceptable agricultural carrier to a plant or plant part on which the insect feeds. In some embodiments, the interfering RNA that reduces the level of a target mRNA transcribable from a target gene described herein is lethal to the coleopteran insect or *Diabrotica* insect. In some embodiments, the *Diabrotica* insect is selected from the group consisting of *D. barberi* (northern corn rootworm), *D. virgifera virgifera* (western corn rootworm), *D. undecimpunctata howardi* (southern corn rootworm), *D. balteata* (banded cucumber beetle), *D. undecimpunctata undecimpunctata* (western spotted cucumber beetle), *D. significata* (3-spotted leaf beetle), *D. speciosa* (chrysanthemum beetle) and *D. virgifera zeae* (Mexican corn rootworm).

In some embodiments, the invention encompasses a method of conferring coleopteran insect tolerance or *Diabrotica* insect tolerance to a plant, or part thereof, comprising introducing into the plant, or part thereof, an interfering RNA molecule, a dsRNA molecule, a nucleic acid construct, a chimeric nucleic acid molecule, an artificial plant microRNA precursor molecule and/or a composition of the invention, wherein the dsRNA molecule, nucleic acid construct, chimeric nucleic acid molecule, artificial plant microRNA precursor molecule and/or composition of the invention are toxic to the insect, thereby conferring tolerance of the plant or part thereof to the coleopteran insect or *Diabrotica* insect. In other embodiments, the introducing step is performed by transforming a plant cell and producing the transgenic plant from the transformed plant cell. In still other embodiments, the introducing step is performed by breeding two plants together.

In other embodiments, the invention encompasses a method of reducing root damage to a plant fed upon by a *Diabrotica* insect, comprising introducing into cells of the plant an interfering RNA molecule, a dsRNA, a nucleic acid molecule, a nucleic acid construct, a chimeric nucleic acid molecule, an artificial plant microRNA precursor molecule and/or a composition of the invention, wherein the dsRNA, nucleic acid molecule, nucleic acid construct, chimeric nucleic acid molecule, artificial plant microRNA precursor molecule and/or composition of the invention are toxic to the *Diabrotica* insect, thereby reducing root damage to the plant. In other embodiments, the introducing step is performed by transforming a plant cell and producing the transgenic plant from the transformed plant cell. In still other embodiments, the introducing step is performed by breeding two plants together.

In still other embodiments, the invention encompasses a method of producing a transgenic plant cell having toxicity to a coleopteran insect or *Diabrotica* insect, comprising introducing into a plant cell an interfering RNA molecule, a dsRNA, a nucleic acid molecule, a nucleic acid construct, a chimeric nucleic acid molecule, an artificial plant microRNA precursor molecule and/or a composition of the invention, thereby producing the transgenic plant cell having toxicity to the insect compared to a control plant cell. In some embodiments, the invention encompasses a plurality of transgenic plant cells produced by this method. In other embodiments, the plurality of transgenic plant cells is grown under conditions which include natural sunlight. In other embodiments, the introducing step is performed by transforming a plant cell and producing the transgenic plant from the transformed plant cell. In still other embodiments, the introducing step is performed by breeding two plants together.

In some embodiments, the invention encompasses a method of producing a transgenic plant having enhanced tolerance to coleopteran or *Diabrotica* insect feeding damage, comprising introducing into a plant an interfering RNA molecule, a dsRNA, a nucleic acid molecule, a nucleic acid construct, a chimeric nucleic acid molecule, an artificial plant microRNA precursor molecule and/or a composition of the invention, thereby producing a transgenic plant having enhanced tolerance to coleopteran or *Diabrotica* insect feeding damage compared to a control plant. In other embodiments, the introducing step is performed by transforming a plant cell and producing the transgenic plant from the transformed plant cell. In still other embodiments, the introducing step is performed by breeding two plants together.

In some embodiments, the invention encompasses a method of providing a corn grower with a means of controlling a coleopteran insect pest population or a *Diabrotica* insect pest population in a corn crop comprising (a) selling or providing to the grower transgenic corn seed that comprises an interfering RNA, a nucleic acid molecule, a nucleic acid construct, a chimeric nucleic acid molecule, an artificial plant microRNA precursor molecule and/or a composition of the invention; and (b) advertising to the grower that the transgenic corn seed produce transgenic corn plants that control a coleopteran or *Diabrotica* pest population.

In some embodiments, the invention encompasses a method of identifying a target gene for using as a RNAi strategy for the control of a plant pest for RNAi in a coleopteran plant pest, said method comprising the steps of a) producing a primer pair with sequences selected from the group comprising or consisting of SEQ ID NO: 31-90, or a complement thereof; b) amplifying an orthologous target from a nucleic acid sample of the plant pest; c) identifying a sequence of an orthologous target gene; d) producing an interfering RNA molecule, wherein the RNA comprises at least one dsRNA, wherein the dsRNA is a region of double-stranded RNA comprising annealed complementary strands, one strand of which comprises a sequence of at least 19 contiguous nucleotides which is at least partially complementary to a target nucleotide sequence within a coleopteran target gene, is obtained; and e) determining if the interfering RNA molecule has insecticidal activity on the plant pest. If the interfering RNA has insecticidal activity on the coleopteran pest, a target gene for using in the control of the plant pest has been identified. In some embodiments, the plant pest is a coleopteran plant pest.

EXAMPLES

The invention will be further described by reference to the following detailed examples. These examples are provided for the purposes of illustration only, and are not intended to be limiting unless otherwise specified.

Example 1. Identification of RNAi Gene Targets in *Diabrotica virgifera virgifera*

This example describes the cloning and sequencing of RNAi target genes and coding sequences from *Diabrotica* insects.

*Diabrotica virgifera virgifera* Pyrosequencing Library Preparation and Sequencing A whole-body neonate *Diabrotica virgifera virgifera* (Western Corn Rootworm (WCR)) transcriptome was sequenced by pyrosequencing on a 454 platform (454 Life Sciences, Branford, Conn.) essentially according to the manufacturer's instructions. The resulting reads (i.e., short fragments of nucleic acid sequence) were trimmed and assembled into contigs using a MIRA assembler (See, for example, Chevreux et al. 2004. Genome Res. 14:1147-1159, incorporated herein by reference).

Identification of Lead Target Genes from *Diabrotica* Spp.

Assembled contigs were compared via BLAST to known lethal genes and alleles in other organisms, which were identified based on published disclosures including those in the website wormbase (wormbase.org) and Boutros et al (2004, Science 303: 832-835). From this analysis, 4,608 target genes were identified. Each of these target genes is non-redundant and is known to possess an allele(s) which is lethal, or is known to result in lethality when targeted by RNAi, in either *C. elegans*, *Drosophila*, or both. Therefore, each of these targets were considered essential. It was expected that a significantly large percentage of these target genes would have an insecticidal effect in WCR. Surprisingly, that was not the case.

dsRNAs of the 4,608 targets were produced on an 384 well automated library synthesis platform. All the dsRNA samples tested were designed automatically using Primer3, a primer design tool, to synthetize a dsRNA fragment of around 500-600 bp based on the coding sequence of each target gene. Smaller fragments were designed if the size of the coding sequence did not allow a 500 bp fragment. These samples were screened in a 24-well WCR assay, at one concentration (100 ng dsRNA/$cm^2$, i.e. 190 ng dsRNA/well) with 10 L2 WCR larvae per well. The mortality was scored after 10 days. The cut-off for candidate hits was 69% mortality. Of the 4,608 candidate dsRNA targets, 183 target genes were identified. These results are surprising, as a person skilled in the art would have expected that a greater number of the 4,608 candidate targets would have conferred toxicity in the bioassays.

In a first assay, 7 targets were tested in laboratory bioassays in a 10-fold dilution series starting from 1 μg dsRNA/well. Bioassays were performed using an RNA-treated artificial diet method. Briefly, molten artificial diet, modified from the diet of Marrone et al. 1985 (J. Econ. Entomol. 78:290-293), was poured into each well of 48-well plates and allowed to solidify. dsRNA molecules were diluted to appropriate concentration so that 20 μl of solution was added to the surface of the diet in half of the wells of a 48-well plate, with a final overlay concentration of 1 μg, 0.1 μg, 0.01 μg and 0.001 μg per well. One or two WCR larvae were added to each well to have between 24 and 48 replicate larvae per concentration of dsRNA tested. Each 48-well plate was maintained at approximately 26° C. with a 16 hour:8 hour light:dark photoperiod. Mortality was recorded at 1, 2, 3, 4, 6 and 7 d post-infestation. dsRNA designed to target green fluorescent protein (GFP) was used in all bioassays as a negative control and dsRNA designed to target an ubiquitin gene of WCR was used as a positive control. From this assay, BPA_46378 (alpha-snap) was confirmed positive. Four candidates were not confirmed positive.

The other 176 target genes were tested simultaneously in a confirmation screen. dsRNA of the 176 targets, as well as positive and negative control dsRNAs, were produced on an automated library synthesis platform. BPA_46378 was also tested under this screen. Bioassays were performed using an RNA-treated artificial diet method. Briefly, molten artificial diet, modified from the diet of Marrone et al. 1985 (J. Econ. Entomol. 78:290-293), was poured into each well of 48-well plates and allowed to solidify. dsRNA molecules were diluted to appropriate concentration so that 20 μl of solution was added to the surface of the diet in half of the wells of a 48-well plate, with a final overlay concentration of 0.5 μg dsRNA per well. One or two WCR larvae were added to each well to have between 24 and 48 replicate larvae per dsRNA tested. Each 48-well plate was maintained at approximately 26° C. and 16:8 light:dark photoperiod. Mortality was recorded at 7 days after treatment.

The results, shown in Table 1, found 29 dsRNA molecules of the initial 176 dsRNA molecules identified were confirmed to be highly toxic to *Diabrotica virgifera virgifera* (western corn rootworm), in addition to the alpha-snap target which was re-confirmed. SEQ ID NOs: 1-30 are nucleotide sequences of the nucleic acid fragments of each toxic target gene identified in the screen. SEQ ID NOs: 31-90, or a complement thereof, are nucleotide sequences of the primer pairs used to synthesize the nucleic acid fragments of each target gene identified in the screen. SEQ ID NOs: 91-120 are nucleotide sequences of the full-length coding sequences of each target gene identified by this screen.

It has previously been suggested that certain genes of *Diabrotica* spp. may be exploited for RNAi-mediated insect control. See U.S. Patent Publication No. 2007/0124836, which discloses 906 sequences, and U.S. Pat. No. 7,612,194, which discloses 9,112 sequences. However, as demonstrated here, the ability of any given gene target to confer toxicity through an RNAi approach cannot be predicted, and can only be determined empirically. Similar conclusions have been reached by Narva et al. (U.S. Publication No. 2015/0322456). The present invention identifies 30 target genes which each provide surprising and unexpected superior control of *Diabrotica*.

TABLE 1

Activity of dsRNA against *Diabrotica virgifera virgifera* 7 d after treatment

| Target ID | Putative Dm orthologue | putative gene name or function | SEQ ID NO: | % mortality at d7 (0.5 μg/well) |
|---|---|---|---|---|
| BPA_15366 | CG7178 | troponin | 1 | 96.00 |
| BPA_16909 | CG12051 | actin 42A | 2 | 100.00 |
| BPA_45189 | CG6699 | beta'-coatomer | 3 | 100.00 |
| BPA_71902 | CG32744 | ubiquitin-5E | 4 | 90.91 |
| BPA_16014 | CG18290 | Actin 87E | 5 | 84.00 |
| BPA_41555 | CG1528 | gamma-coatomer | 6 | 97.14 |
| BPA_71568 | CG3664 | Rab5 | 7 | 100.00 |
| BPA_16830 | NA | unknown function | 8 | 92.00 |
| BPA_15330 | CG5271 | RpS27A | 9 | 85.29 |
| BPA_2526 | CG11415 | tetraspanin | 10 | 97.22 |
| BPA_11606 | CG33865 | histone2A | 11 | 93.94 |
| BPA_12879 | CG1664 | small bristles | 12 | 97.30 |
| BPA_2443 | CG6223 | beta-coatomer | 13 | 93.94 |
| BPA_10976 | CG8385 | ARF1 | 14 | 78.95 |
| BPA_875 | CG3722 | DE-cadherin | 15 | 76.47 |
| BPA_2184 | CG40127 | RNase K | 16 | 75.76 |
| BPA_7931 | CG11027 | ARF102F | 17 | 82.35 |
| BPA_17622 | CG7007 | Vacuolar H[+] ATPase PPA1 | 18 | 70.00 |
| BPA_450 | CG1554 | RNApol II | 19 | 78.05 |
| BPA_46378 | CG6625 | Alpha snap | 20 | 100.00 |
| BPA_71489 | CG3320 | Rab1 | 21 | 85.00 |
| BPA_4800 | CG7269 | helicase | 22 | 69.57 |
| BPA_880 | CG4775 | Tango14 | 23 | 63.64 |
| BPA_15751 | CG12775 | RpL21 | 24 | 65.79 |
| BPA_41770 | CG3948 | zeta-coatomer | 25 | 71.05 |
| BPA_9438 | CG8472 | calmodulin | 26 | 65.63 |
| BPA_16140 | CG7185 | RNA recognition motif domain | 27 | 54.80 |
| BPA_65371 | CG1519 | proteasome alpha | 28 | 52.50 |
| BPA_12351 | CG8186 | Vacuolar H[+] ATPase Vha36-1 | 29 | 42.60 |

TABLE 1-continued

Activity of dsRNA against *Diabrotica virgifera virgifera* 7 d after treatment

| Target ID | Putative Dm orthologue | putative gene name or function | SEQ ID NO: | % mortality at d7 (0.5 μg/well) |
|---|---|---|---|---|
| BPA_17046 | CG9311 | myopic | 30 | 47.40 |
| | | GFP repl1 | | 21.21 |
| | | GFP repl2 | | 11.76 |
| | | Dv ubiquitin control repl1 | | 100.00 |
| | | Dv ubiquitin control repl2 | | 100.00 |

Example 2. Activity of dsRNA Against *Diabrotica virgifera virgifera*-DRC 4 Concentrations This example describes testing dsRNAs of the invention for biological activity against *Diabrotica virgifera virgifera* (WCR).

The 30 dsRNA molecules described above were tested for toxicity against WCR in laboratory bioassays in a 10-fold dilution series starting from 1 μg dsRNA/well. Bioassays were performed using an RNA-treated artificial diet method. Briefly, molten artificial diet, modified from the diet of Marrone et al. 1985 (J. Econ. Entomol. 78:290-293), was poured into each well of 48-well plates and allowed to solidify. Synthesized dsRNA molecules were diluted to appropriate concentration so that 20 μl of solution was added to the surface of the diet in half of the wells of a 48-well plate, with a final overlay concentration of 1 μg, 0.1 μg, 0.01 μg and 0.001 μg per well. One or two WCR larvae were added to each well to have between 24 and 48 replicate larvae per concentration of dsRNA tested. Each 48-well plate was maintained at approximately 26° C. and 16:8 light:dark photoperiod. Mortality was recorded at 1, 2, 3, 4, 6 and 7 d post-infestation. dsRNA designed to target GFP was used as a negative control and dsRNA designed to target an ubiquitin gene of WCR was used as a positive control.

The results, shown in Table 2, show that the 30 dsRNA molecules designed to target mRNA transcribable from WCR genes are toxic to highly toxic to WCR. After correction for the control mortality on the GFP dsRNA, the estimated $LT_{50}$ and $LC_{50}$ were calculated by curve fitting analysis. $LT_{50}$ stands for the lethal time to obtain 50% of mortality in the test insects. $LC_{50}$ stands for the concentration of the dsRNA, which causes the death of 50% of the test insects. In Table 2, the % mortality at day 7 is based on 1 μg dsRNA/well. The $LT_{50}$ is based on using 1 μg dsRNA/day and is measured in days. The $LC_{50}$ was measured in μg dsRNA/well.

TABLE 2

Activity of dsRNA against *Diabrotica virgifera virgifera*, 7 d after treatment

| Target ID | SEQ ID NO: | % mortality at d7 (1 μg/well) | $LT_{50}$ (days) | $LC_{50}$ μg/(well) |
|---|---|---|---|---|
| BPA_15366 | 1 | 97.30 | 2.53 | 0.005 |
| BPA_16909 | 2 | 100.00 | 3.52 | 0.009 |
| BPA_45189 | 3 | 100.00 | 5.14 | 0.005 |
| BPA_71902 | 4 | 88.89 | 3.74 | 0.045 |
| BPA_16014 | 5 | 85.71 | 5.21 | 0.077 |
| BPA_41555 | 6 | 100.00 | 5.14 | <0.001 |

TABLE 2-continued

Activity of dsRNA against *Diabrotica virgifera virgifera*, 7 d after treatment

| Target ID | SEQ ID NO: | % mortality at d7 (1 μg/well) | $LT_{50}$ (days) | $LC_{50}$ μg/ (well) |
|---|---|---|---|---|
| BPA_71568 | 7 | 97.22 | 5.03 | 0.015 |
| BPA_16830 | 8 | 84.21 | 5.73 | 0.008 |
| BPA_15330 | 9 | 58.33 | 6.98 | 0.858 |
| BPA_2526 | 10 | 97.37 | 5.22 | 0.028 |
| BPA_11606 | 11 | 97.22 | 5.03 | 0.061 |
| BPA_12879 | 12 | 93.55 | 4.85 | 0.009 |
| BPA_2443 | 13 | 100.00 | 4.71 | 0.004 |
| BPA_10976 | 14 | 85.00 | 5.49 | 0.008 |
| BPA_875 | 15 | 94.29 | 4.84 | 0.084 |
| BPA_2184 | 16 | 64.44 | 6.71 | 0.763 |
| BPA_7931 | 17 | 90.32 | 5.38 | 0.081 |
| BPA_17622 | 18 | 70.73 | 6.60 | 0.649 |
| BPA_450 | 19 | 65.71 | 6.57 | 0.256 |
| BPA_46378 | 20 | 100.00 | 5.49 | 0.015 |
| BPA_71489 | 21 | 92.68 | 5.29 | 0.009 |
| BPA_4800 | 22 | 51.35 | NA | NA |
| BPA_880 | 23 | 53.13 | NA | NA |
| BPA_15751 | 24 | 85.29 | 5.74 | 0.058 |
| BPA_41770 | 25 | 62.16 | 6.71 | 0.090 |
| BPA_9438 | 26 | 51.35 | NA | NA |
| BPA_16140 | 27 | 76.67 | 6.56 | 0.201 |
| BPA_65371 | 28 | 34.29 | NA | NA |
| BPA_12351 | 29 | 35.29 | NA | NA |
| BPA_17046 | 30 | 51.43 | NA | NA |
| GFP repl1 | | 15.80 | NA | NA |
| GFP repl2 | | 20.00 | NA | NA |
| Dv ubiquitin | | 97.22 | 3.33 | 0.028 |

Based on these results, a sub-set of targets were prioritized for further investigation. The results of these targets are shown below.

Example 3. Activity of dsRNA Against *Diabrotica virgifera virgifera*

This example describes testing of a sub-set of the identified target dsRNAs of the invention for biological activity against *Diabrotica virgifera virgifera* (WCR).

The dsRNA molecules described above were tested for toxicity against WCR in laboratory bioassays in a 3-fold dilution series starting at 0.5 μg dsRNA/well. Bioassays were performed using an RNA-treated artificial diet method. Briefly, molten artificial diet, modified from the diet of Marrone et al. 1985 (J. Econ. Entomol. 78:290-293), was poured into each well of 48-well plates and allowed to solidify. dsRNA molecules were diluted to appropriate concentration so that 20 μl of solution was added to the surface of the diet in half of the wells of a 48-well plate, with a final overlay concentration of 0.5 μg, 0.16 μg, 0.05 μg, 0.02 μg, 0.006 μg, 0.002 μg, 0.0007 μg and 0.0002 μg per well. One or two WCR larvae were added to each well to have between 24 and 48 replicate larvae per concentration of dsRNA tested. Each 48-well plate was maintained at approximately 26° C. and 16:8 light:dark photoperiod. Mortality was recorded at 1, 2, 3, 4, 6 and 7 d post-infestation. dsRNA designed to target GFP was used as a negative control and dsRNA designed to target an ubiquitin gene of WCR was used as a positive control.

The results, shown in Table 3, show that the dsRNA molecules designed to target mRNA transcribable from WCR genes are toxic to highly toxic to WCR. After correction for the control mortality on the GFP dsRNA, the estimated $LT_{50}$ and $LC_{50}$ were calculated by curve fitting analysis. $LT_{50}$ stands for the lethal time to obtain 50% of mortality in the test insects. $LC_{50}$ stands for the concentration of the dsRNA, which causes the death of 50% of the test insects. In Table 3, the % mortality at day 7 is based on 0.5 μg dsRNA/well. The $LT_{50}$ is based on using 0.5 μg dsRNA/day and is measured in days. The $LC_{50}$ was measured in μg dsRNA/well. These results confirm the toxicity of the candidate targets.

TABLE 3

Activity of dsRNA against *Diabrotica virgifera virgifera*

| Target ID | SEQ ID NO: | % mortality at d7 (0.5 μg/well) | $LT_{50}$ (days) | $LC_{50}$ (μg/well) |
|---|---|---|---|---|
| BPA_2526 | 10 | 97.4 | 5.1 | 0.0024 |
| BPA_46378 | 20 | 100.0 | 5.1 | 0.0076 |
| BPA_10976 | 14 | 93.5 | 5.5 | 0.0019 |
| GFP | | 22.9 | NA | NA |
| Dv ubiquitin | | 100.0 | 3.7 | 0.0065 |

Example 4. Activity of dsRNA Against *Diabrotica undecimpunctata howardi*

This example describes testing dsRNAs of the invention for biological activity against *Diabrotica undecimpunctata howardi* (southern corn rootworm (SCR)).

The dsRNA molecules described above were tested for toxicity against SCR in laboratory bioassays in a 10-fold dilution series starting at 0.5 μg dsRNA/well. Bioassays were performed using an RNA-treated artificial diet method. Briefly, molten artificial diet, modified from the diet of Marrone et al. 1985 (J. Econ. Entomol. 78:290-293), was poured into each well of 48-well plates and allowed to solidify. Synthesized dsRNA molecules were diluted to appropriate concentrations so that 20 μl of solution was added to the surface of the diet in each well, with a final overlay concentration series of 8 concentrations going from 0.5 μg/well down to 0.00022 μg/well in steps of 3× dilution. One or two SCR larvae were added to each well to have between 24 and 48 replicate larvae per concentration of dsRNA tested. Each 48-well plate was maintained at approximately 26° C. and 16:8 light:dark photoperiod. Mortality was recorded at 1, 2, 3, 4, 5, 6, 7, 8, 9, 10, and 14 days post-infestation. dsRNA designed to target GFP was used as a negative control and dsRNA designed to target the *Diabrotica virgifera virgifera* (Dv) ubiquitin gene and the *Diabrotica undecimpunctata howardi* (Du) ubiquitin gene were used as positive controls.

After correction for the control mortality on the GFP dsRNA, the estimated $LT_{50}$ and $LC_{50}$ were calculated by curve fitting analysis. $LT_{50}$ stands for the lethal time to obtain 50% of mortality in the test insects. $LC_{50}$ stands for the concentration of the dsRNA, which causes the death of 50% of the test insects. In Table 4, the % mortality at day 14 is based on 0.5 μg dsRNA/well. The $LT_{50}$ is based on using 0.5 μg dsRNA/day and is measured in days. The $LC_{50}$ was measured in μg dsRNA/well. The results, shown in Table 4, show that the dsRNA molecules designed to target mRNA transcribable from *Diabrotica virgifera virgifera* (WCR) genes are also toxic to *Diabrotica undecimpunctata howardi* (SCR). This demonstrates that the targets of the invention are suitable targets for SCR as well, such that dsRNA molecules based on the native SCR mRNAs would be toxic to SCR and other *Diabrotica* spp. as well.

TABLE 4

| Activity of dsRNA against *Diabrotica undecimpunctata howardi* 14 d after treatment | | | | |
|---|---|---|---|---|
| Target ID | SEQ ID NO: | % mortality at d14 (0.5 μg/well) | $LT_{50}$ (days) | $LC_{50}$ (μg/well) |
| BPA_2526 | 10 | 97.22 | 6.56 | 0.0185 |
| BPA_46378 | 20 | 94.74 | 8.48 | 0.0092 |
| BPA_10976 | 14 | 100.00 | 8.00 | 0.0405 |
| GFP | | 8.33 | NA | NA |
| Dv ubiquitin | | 97.14 | 6.75 | 0.0123 |
| Du ubiquitin | | 100.00 | 5.57 | 0.0209 |

Example 5. Activity of dsRNA Against *Diabrotica barberi*

This example describes testing dsRNAs of the invention for biological activity against *Diabrotica barberi* (northern corn rootworm (NCR)).

The dsRNA molecules described above were tested for toxicity against NCR in laboratory bioassays. Bioassays were performed using an RNA-treated artificial diet method. Briefly, molten artificial diet, modified from the diet of Marrone et al. 1985 (J. Econ. Entomol. 78:290-293), was poured into each well of 48-well plates and allowed to solidify. Synthesized dsRNA molecules were diluted to appropriate concentration so that 20 μl of solution was added to the surface of the diet in half of the wells of a 48-well plate, with a final overlay concentration of 0.5 μg dsRNA per well. One or two NCR larvae were added to each well to have between 24 and 48 replicate larvae per dsRNA tested. Each 48-well plate was maintained at approximately 26° C. and 16:8 light:dark photoperiod. Mortality was recorded at 7 d post-infestation. dsRNA designed to target GFP was used in all bioassays as a negative control and dsRNA designed to target the *Diabrotica barberi* (Dr) ubiquitin gene was used as positive control.

The results, shown in Table 5, show that the dsRNA molecules designed to target mRNA transcribable from *Diabrotica virgifera* virgifera genes are also toxic to *Diabrotica barberi*. This demonstrates that the targets of the invention are suitable targets for NCR as well, such that dsRNA molecules based on the native NCR mRNAs would be toxic to NCR and other *Diabrotica* spp. as well.

TABLE 5

| Activity of dsRNA against *Diabrotica barberi* 7 d after treatment | | |
|---|---|---|
| target ID | SEQ ID NO: | % mortality at day 9 |
| BPA_2526 | 10 | 100.00 |
| BPA_46378 | 20 | N.D. |
| BPA_10976 | 14 | 100.00 |
| GFP repl1 | | 18.75 |
| GFP repl2 | | 22.00 |
| Dr ubiquitin repl1 | | 85.00 |
| Dr ubiquitin repl2 | | 86.00 |

Example 6. Fragment Size Assays in WCR

All dsRNA samples tested in the previous examples were designed automatically using Primer3, a primer design tool, to synthesize a dsRNA fragment of around 500 bp based on the coding sequence of each target gene. Smaller fragments were designed if the size of the coding sequence did not allow a 500 bp fragment.

In the big-to-small experiments, different dsRNA fragments were designed based on the complete coding sequence of each target gene. The complete coding sequence was tested as a whole if available and if not greater than 1000 bp. The coding sequence was also divided into fragments of approximately 200 bp, with some overlap of 25-30 bp between subsequent fragments. For each fragment new primers were designed and dsRNA was synthesized on the automated library synthesis platform. All dsRNA fragments were then tested in a WCR bioassay at two different concentrations (0.1 μg dsRNA and 0.01 μg dsRNA per well) and mortality was scored at day 7.

The dsRNA molecules described above were tested for toxicity against *Diabrotica virgifera virgifera* in laboratory bioassays. Bioassays were performed using an RNA-treated artificial diet method. Briefly, molten artificial diet, modified from the diet of Marrone et al. 1985 (J. Econ. Entomol. 78:290-293), was poured into each well of 48-well plates and allowed to solidify. Synthesized dsRNA molecules were diluted to appropriate concentration so that 20 μl of solution was added to the surface of the diet in half of the wells of a 48-well plate, with a final overlay concentration of 0.1 μg dsRNA or 0.01 μg dsRNA per well. One or two *Diabrotica virgifera virgifera* larvae were added to each well to have between 24 and 48 replicate larvae per dsRNA tested. Each 48-well plate was maintained at approximately 26° C. and 16:8 light:dark photoperiod. Mortality was recorded at 7 d post-infestation. dsRNA designed to target GFP was used in all bioassays as a negative control and dsRNA designed to target an ubiquitin gene of *Diabrotica virgifera virgifera* was used as a positive control.

The results, shown in Table 6, show that the dsRNA fragments designed to target mRNA transcribable from *Diabrotica virgifera virgifera* genes are toxic to highly toxic to *Diabrotica virgifera virgifera*.

TABLE 6

| Activity of dsRNA sub-fragments against *Diabrotica virgifera virgifera* 7 d after treatment | | | | |
|---|---|---|---|---|
| | SEQ ID | Fragment size | % mortality at d7 | |
| Target ID | NO: | (bp) | 0.01 μg | 0.1 μg |
| BPA_2526_screen | 283 | 524 | 51 | 83 |
| BPA_2526_1 | 284 | 744 | 43 | 91 |
| BPA_2526_2 | 285 | 197 | 45 | 93 |
| BPA_2526_3 | 286 | 220 | 54 | 91 |
| BPA_2526_4 | 287 | 213 | 18 | 93 |
| BPA_2526_5 | 288 | 198 | 58 | 51 |
| BPA_2526_6 | 289 | 169 | 67 | 100 |
| BPA_46378_screen | 290 | 564 | 94 | 97 |
| BPA_46378_1 | 291 | 873 | 86 | 97 |
| BPA_46378_2 | 292 | 197 | 68 | 95 |
| BPA_46378_3 | 293 | 236 | 79 | 92 |
| BPA_46378_4 | 294 | 197 | 90 | 95 |
| BPA_46378_5 | 295 | 199 | 66 | 97 |
| BPA_46378_6 | 296 | 197 | 47 | 97 |
| BPA_46378_7 | 297 | 122 | 76 | 89 |
| BPA_10976_screen | 298 | 458 | 78 | 95 |
| BPA_10976_1 | 299 | 546 | 74 | 97 |
| BPA_10976_2 | 300 | 200 | 37 | 89 |
| BPA_10976_3 | 301 | 200 | 67 | 89 |
| BPA_10976_4 | 302 | 198 | 72 | 89 |
| BPA_10976_5 | 303 | 95 | 66 | 77 |
| GFP | | | NA | 3 |
| GFP | | | NA | 24 |

TABLE 6-continued

Activity of dsRNA sub-fragments against *Diabrotica virgifera virgifera* 7 d after treatment

| Target ID | SEQ ID NO: | Fragment size (bp) | % mortality at d7 0.01 μg | 0.1 μg |
|---|---|---|---|---|
| positive control | | | 79 | 100 |
| positive control | | | 57 | 75 |

Example 7. Expression of an Interfering RNA Molecule Comprising Target dsRNA in Corn Plants This example describes introducing a construct that expresses an interfering RNA molecule into plant cells.

Vector Construction

Expression vectors designed to produce hairpin RNAs (hpRNA) consisted of a cassette containing a promoter, a sense strand, an intron functioning as a loop sequence, an antisense strand, and terminator. Binary vector 23160 comprises an expression cassette comprising a DNA sequence designed to produce a hpRNA targeting a 524 nucleotide fragment of BPA_2526 (SEQ ID NO: 325). Binary vector 23564 comprises an expression cassette comprising a DNA sequence designed to produce a hpRNA targeting a 197 nucleotide fragment of BPA_46378 (SEQ ID NO: 326). Each binary vector also contained a second cassette between the left and right borders, designed to express phosphomannose isomerase (PMI) which provides the ability to metabolize mannose (U.S. Pat. Nos. 5,767,378 and 5,994,629, which are incorporated by reference herein) as a selectable marker during plant transformation. The vectors also contained selectable markers for selection in bacteria.

*Agrobacterium* Mediated Transformation

Each resulting plasmid containing the hairpin cassette was transformed into *Agrobacterium tumefaciens* using standard molecular biology techniques known to those skilled in the art. The vectors described above were transformed into maize. *Agrobacterium* transformation of immature maize embryos was performed essentially as described in Negrotto et al., 2000, Plant Cell Reports 19: 798-803. For this example, all media constituents are essentially as described in Negrotto et al., supra. However, various media constituents known in the art may be substituted. Following transformation, selection, and regeneration, plants were tested for the presence of the pmi gene and the hairpin dsRNA interfering RNA molecule. Positive plants from the PCR assay were transferred to the greenhouse and tested for resistance to at least Western Corn Rootworm.

Transgenic Maize WCR Insecticidal Assay

Six F1 progeny of transgenic maize plants comprising the transgene of binary vector 23160 or binary vector 23564 were germinated and allowed to grow. A PMI ELISA strip test (Romer Labs SeedChek® PMI (#7000052)) was used to identify plants positive for the transgene and null, non-transgenic segregating sister plants. Each plant was infested with 10 neonate western corn rootworms at its base. Seven days after infestation, the survival and size of the rootworms were evaluated. Additionally, the corn roots from each of the plants were examined for feeding damage. This experiment was repeated eight times each for F1 progeny of transgenic maize plants comprising the transgene of binary vector 23160 or binary vector 23564, for a total of 48 F1 progeny evaluated per transgene.

Representative results are shown in Tables 7 and 8. Table 7 shows results for transgenic maize transformed with the transgene of binary vector 23160. Table 8 shows results for transgenic maize transformed with the transgene of binary vector 23564. For each transgene, the results from F1 progeny of two different transgenic events are shown. If an F1 progeny failed to germinate, it is noted in the table as "N/A" for all fields. For the BPA_2526 target, which is targeted by the RNAi construct of vector 23160, F1 progeny from transgenic events ID 1283 and 1610 were examined. For the BPA_46378 target, which is targeted by the RNAi construct of vector 23564, F1 progeny from transgenic events ID 4850 and 4853 were examined. The number of Western Corn Rootworms (WCR) recovered seven days after infestation is indicated (#WCR). Recovered rootworm were graded by size (WCR size), as medium (m), medium/big (mb), big (b), or very big (vb). Roots of the corn plants were also analyzed for feeding damage. "Minor" root damage indicates roots appear strong and healthy. "Noticeable" root damage indicates the roots were slightly weaker compared to controls. "Significant" root damage indicates that the smaller roots were damaged or missing. "Severe" root damage indicates only the largest roots remained attached to the plant.

TABLE 7

WCR tolerance in hpRNA BPA_2526 transgenic maize plants

| Plant ID | PMI? | # WCR | WCR size | Root Damage |
|---|---|---|---|---|
| 1283-1 | No | 7 | 7vb | significant |
| 1283-2 | N/A | N/A | N/A | N/A |
| 1283-3 | Yes | 5 | 3m, 3b, 1vb | minor |
| 1283-4 | No | 8 | 8vb | significant |
| 1283-5 | Yes | 5 | 1m, 2b, 2vb | minor |
| 1283-6 | No | 5 | 5vb | significant |
| 1610-1 | No | 6 | 6vb | noticeable |
| 1610-2 | Yes | 5 | 3vb, 2b | noticeable |
| 1610-3 | Yes | 7 | 5vb, 1b, 1m | noticeable |
| 1610-4 | N/A | N/A | N/A | N/A |
| 1610-5 | No | 7 | 7vb | significant |
| 1610-6 | No | 8 | 8vb | significant |

TABLE 8

WCR tolerance in hpRNA BPA_46378 transgenic maize plants

| Plant ID | PMI? | # WCR | WCR size | Root Damage |
|---|---|---|---|---|
| 4850-1 | No | 7 | 5vb, 1b, 1mb | noticable |
| 4850-2 | No | 9 | 9vb | minor |
| 4850-3 | No | 10 | 10vb | minor |
| 4850-4 | No | 9 | 7vb, 1b, 1mb | severe |
| 4850-5 | Yes | 4 | 2vb, 2mb | noticable |
| 4850-6 | Yes | 6 | 2vb, 4b | severe |
| 4853-1 | Yes | 4 | 4vb | noticeable |
| 4853-2 | Yes | 6 | 1m, 1b, 4vb | significant |
| 4853-3 | No | 10 | 9vb, 1b | severe |
| 4853-4 | No | 10 | 10vb | significant |
| 4853-5 | N/A | N/A | N/A | N/A |
| 4853-6 | No | 9 | 9vb | significant |

The data in Tables 7 and 8 indicate that the transgenic corn plants expressing dsRNAs that target insect genes BPA_2526 or BPA_46378 may suffer less root damage compared to the non-transgenic, negative control sister plants. Tables 7 and 8 show that a transgenic plant comprising an interfering RNA molecule of the invention has enhanced resistance to an insect pest as compared to a non-transgenic control plant.

Transgenic Maize CRW Root Assay

Transgenic maize expressing the transgene from binary vector 23160 were grown and brace roots or crown roots from the plant were removed. Root pieces were placed on a 2% agar plate and infested with 80 to 100 L1 WCR larvae. Following an incubation in the dark 26° C. for 24 to 48 hours, the L1 larvae were transferred to a 48-well WCR diet plate and incubated in the dark at 26° C. and scored daily for mortality of the WCR larvae, up to 7 days post-infestation. This experiment was performed on three different transgenic maize events, and on a non-transgenic control maize plant. Cumulative results are shown in Table 9. % Mortality indicates the total percent of WCR larvae which died.

TABLE 9

CRW Root Assay for hpRNA BPA_2526 Transgenic Maize

| Plant ID | % Mortality |
|---|---|
| Non-transgenic | 14 |
| Event 1 | 77 |
| Event 2 | 72 |
| Event 3 | 78 |

The data in Table 9 indicate that the transgenic corn plants expressing dsRNAs that target the insect gene BPA_2526 have an insecticidal effect on insect pests. This further shows that a transgenic plant comprising an interfering RNA molecule of the invention has enhanced resistance to an insect pest as compared to a non-transgenic control plant.

Example 8. Interfering RNA Molecules with a Second Insecticidal Agent Bioassays

This example illustrates the toxicity of interfering RNA molecules of the invention in combination with a second insecticidal agent.

Double stranded RNA molecules were produced against the BPA_15366 target. Additionally, a second insecticidal agent was prepared. Both the RNA and the second insecticidal agent were tested in combination for toxicity against WCR in laboratory bioassays.

It should be understood that the examples and embodiments described herein are for illustrative purposes only and that various modifications or changes in light thereof of the description will be suggested to persons skilled in the art and are to be included within the spirit and purview of this application and the scope of the appended claims.

All publications and patent applications mentioned in this specification are indicative of the level of skill of those skilled in the art that this invention pertains. All publications and patent applications are herein incorporated by reference to the same extent as if each individual publication or patent application was specifically and individually indicated to be incorporated by reference.

What is claimed is:

1. An interfering ribonucleic acid (RNA) molecule wherein the RNA comprises at least one dsRNA wherein the dsRNA is a region of double-stranded RNA comprising annealed complementary strands, one strand of which comprises a sequence of at least 19 contiguous nucleotides which is at least partially complementary to a target nucleotide sequence within a *Diabrotica* spp target gene, and (i) is at least 95% identical to at least a 19 contiguous nucleotide fragment of SEQ ID NO: 130, or the complement thereof; or (ii) comprises at least a 19 contiguous nucleotide fragment of SEQ ID NO: 130, or the complement thereof; or (iii) comprises at least a 19 contiguous nucleotide fragment of a nucleotide sequence encoding an amino acid sequence encoded by SEQ ID NO: 130, or the complement thereof, wherein the interfering RNA molecule has insecticidal activity on a *Diabrotica* insect plant pest.

2. An interfering RNA molecule of claim 1 wherein the RNA comprises at least two dsRNAs, wherein each dsRNA comprises a sequence of nucleotides which is at least partially complementary to a target nucleotide sequence within the target gene.

3. A nucleic acid molecule encoding the interfering RNA molecule of claim 1.

4. A recombinant vector comprising a regulatory sequence operably linked to a nucleotide sequence that encodes the interfering RNA molecule of claim 1.

5. A composition comprising the interfering RNA molecule of claim 1.

6. A composition comprising two or more interfering RNA molecules of claim 1, wherein the two or more interfering RNA molecules are present on the same nucleic acid construct, on different nucleic acid constructs, or any combination thereof.

7. A composition comprising two or more of the nucleic acid molecules of claim 3, wherein the two or more nucleic acid molecules each encode a different interfering RNA molecule.

8. An insecticidal composition for inhibiting the expression of a *Diabrotica* insect target gene, comprising the interfering RNA of claim 1 and an agriculturally acceptable carrier.

9. An insecticidal composition of claim 8 comprising at least a second insecticidal agent for controlling a *Diabrotica* insect.

10. A transgenic plant, or part thereof, comprising the nucleic acid molecule of claim 3, wherein the transgenic plant has enhanced resistance to a *Diabrotica* insect as compared to a control plant.

11. A transgenic plant, or part thereof, of claim 10, wherein the transgenic plant comprises at least a second insecticidal agent for controlling *Diabrotica* insects.

12. A transgenic plant, or part thereof, of claim 11, wherein the second insecticidal agent is a *Bacillus thuringiensis* insecticidal protein.

13. A transgenic plant, or part thereof, of claim 11, wherein the second insecticidal agent is not a *Bacillus thuringiensis* insecticidal protein.

14. A transgenic plant, or part thereof, of claim 10, wherein transgenic plant, or part thereof, is a maize plant or part thereof.

15. A method of controlling a *Diabrotica* insect comprising contacting the *Diabrotica* insect with a nucleic acid molecule that is or is capable of producing an interfering RNA molecule of claim 1 for inhibiting expression of a target gene in the *Diabrotica* insect thereby controlling the *Diabrotica* insect.

16. A method of controlling a *Diabrotica* insect comprising contacting the *Diabrotica* insect with a nucleic acid molecule that is or is capable of producing the interfering RNA molecule of claim 1 for inhibiting expression of a target gene in the *Diabrotica* insect, and contacting the *Diabrotica* insect with at least a second insecticidal agent for controlling *Diabrotica*.

17. The interfering RNA of claim 1, wherein one strand of the interfering RNA comprises at least a 19 contiguous nucleotide fragment of SEQ ID NO: 130, or the complement thereof.

* * * * *

SEQUENCE LISTING

```
<160> NUMBER OF SEQ ID NOS: 326

<210> SEQ ID NO 1
<211> LENGTH: 478
<212> TYPE: DNA
<213> ORGANISM: Diabrotica virgifera

<400> SEQUENCE: 1

ggtttcatga cccctgagag aaagaagaaa cttaggttac tgttgagaaa gaaagccgcc      60

gaagaattaa agaaagaaca agaacgcaaa gcagccgaaa ggaggcgtat cattgaagaa     120

aggtgcggta aacccaaact tgtcgatgac gcaaatgaag gcccattaaa acaagtatgt     180

gagggatatc acagacgtat tgtagaccta gaaaataaga aatttgacct cgaaaaagaa     240

gtggaattca gagattttca gatctccgaa ttgaacagcc aagtaaacga ccttagaggc     300

aaattcgtca aaccaacctt gaagaaggta tccaaatacg aaaacaaatt cgccaaactt     360

caaaagaagg cagctgaatt taacttccgt aaccaactca aagttgtcaa gaagaaagaa     420

ttcaccttag aagaagaaga caaagaaaag aaaccagact ggtcaaagaa gggagacg       478


<210> SEQ ID NO 2
<211> LENGTH: 529
<212> TYPE: DNA
<213> ORGANISM: Diabrotica virgifera

<400> SEQUENCE: 2

agaagttgcc gctttagtcg tagacaatgg atccggtatg tgcaaagctg gttttgctgg      60

ggatgatgca cctcgtgctg tattcccttc aattgttgga cgcccaagac atcagggtgt     120

gatggtagga atgggacaaa aagattccta tgtaggtgat gaagctcaaa gtaaaagagg     180

tatccttacc ttaaaatacc ccatcgagca cggaatagtc acaaactggg atgatatgga     240

gaaaatttgg catcatacat tctacaatga actcagagta gccccagaag aacaccctgt     300
```

```
tctgttgaca gaagctcctc tcaaccccaa ggccaacagg gaaaagatga cacaaataat    360

gtttgaaact ttcaacaccc cagccatgta tgttgccatc caggctgtac tctccttgta    420

tgcatctggt cgtacaactg gtattgtgtt ggattctggt gatggtgtat cccacactgt    480

cccaatctat gaaggttatg ctcttcctca tgcaatcctt cgtttggac                529


<210> SEQ ID NO 3
<211> LENGTH: 592
<212> TYPE: DNA
<213> ORGANISM: Diabrotica virgifera

<400> SEQUENCE: 3

accggccttt gtatgtcttg ggatatgtgc ctaaagacga tagattatac ctcgtagata     60

aagagttgcg cgtagtaagc taccaattac ttctttctgt tcttgaatat caaactgccg    120

tcatgagaag agactttcca acagcagaca gagtacttcc gtccattcct aaggagcaca    180

gaacgagagt ggcacatttc ttagaaaagc aaggcttcaa acagcaagct ttggccgtaa    240

gtacagatcc agagcacaga ttcgagctgg cagtagcatt agaggatctt aatatagcca    300

aaactctagc tcaagaagcg aacagtccgc aaaagtggaa tcaactagca gaattggcag    360

ctgctactaa taatgtaagc gtagccaagg aatgtatgca aaaagcgcaa gattatggag    420

gcttgttgct tcttgctacg agctccggtg atgaaaattt agtccgtact ctaggagaaa    480

cgacacaagc tgaaagcaaa cataacttag catttttgtc acacttgtta gtaggtgatt    540

taaacaaatg tctagacatt cttattaata ccggtagatt gccagaagct gc            592


<210> SEQ ID NO 4
<211> LENGTH: 594
<212> TYPE: DNA
<213> ORGANISM: Diabrotica virgifera

<400> SEQUENCE: 4

gaaagcagtt ggaagatggc cgtactctct cagactacaa cattcaaaaa gagtctaccc     60

tccatttggt acttcgtctt agaggaggta tgcagatttt tgttaaaact ttaactggaa    120

agaccatcac ccttgaagta gaaccttctg ataccatcga aaatgtcaaa gccaaaattc    180

aagacaaaga aggtattcca ccagatcaac aaagattaat ctttgccgga aagcaattgg    240

aagatggtcg tacactctca gactacaaca ttcaaaagga atctaccctc catttggtac    300

ttcgtcttag aggaggtatg caaatctttg taaaaacact cactggtaag accatcaccc    360

tcgaggttga accatcagat accatcgaga atgtcaaagc taaaattcaa gacaaagaag    420

gtattccacc agatcaacag agattaatct tcgctggaaa gcagttggaa gatggccgta    480

ctctctcaga ctacaatatt cagaaagagt ctaccctcca tttggtactt cgtcttagag    540

gaggtatgca aatctttgta aaaactctca ctggtaagac catcaccctc gagg          594


<210> SEQ ID NO 5
<211> LENGTH: 547
<212> TYPE: DNA
<213> ORGANISM: Diabrotica virgifera

<400> SEQUENCE: 5

taccccattg aacacggaat tatcactaac tgggacgata tggaaaagat ctggcatcac     60

accttctaca atgaacttag agtagccccc gaagaacatc ccattctttt gactgaagct    120

ccacttaacc caaaagccaa cagagaaaag atgactcaaa tcatgtttga aactttcaat    180
```

-continued

```
accccctgcca tgtatgttgc cattcaagct gtattgtctc tgtacgcttc cggtcgtacc    240

actggtattg tacttgattc tggagatggt gtatcccaca cagtacccat ctatgaaggt    300

tacgctctcc cacacgccat cttgcgtttg gacttggccg gtagagactt gactgactac    360

cttatgaaga tcttaaccga aagaggttac tctttcacca ccacagctga aagagaaata    420

gttcgtgaca tcaaggaaaa attgtgctat gtagctttgg acttcgaaca ggaaatggcc    480

acagcagcca gctccacctc cttagaaaag agttatgaac ttcctgacgg tcaagtcatc    540

accattg                                                              547


<210> SEQ ID NO 6
<211> LENGTH: 592
<212> TYPE: DNA
<213> ORGANISM: Diabrotica virgifera

<400> SEQUENCE: 6

aggaaaggaa ggacccaaga ccaaacaacc atcgagatac atccgtttta tctacaatcg     60

cgtcatattg gaatgtcctt ctgtaagagc tgctgcagtc tccgccatgg cacaattcgg    120

agcctcttgt cccgatttgt tagaaaatat ccaaatatta ctttcgaggt gtcagatgga    180

ttcagacgat gaagttaggg acagagctac atattatagt aatatactta acaaaaatga    240

taaaagttta tacaacaatt acattttgga ttctttgcag gtttcaattc cttcactaga    300

aagatcgctt agagaataca ttcaaaatcc aactgacgaa ccatttgaca ttaagtccgt    360

acctgtagca gcagtgccaa cagcagaaga acgagaagtt aaaaacaaat ctgaaggact    420

gctagtctct caaggtccag tccgacctcc tccggtgtct agagaagaaa acttcgccga    480

aaaacttagt aacgttccgg gtatacaaca gttaggacct ttgttcaaaa cttccgacgt    540

cgttgaactc actgaatctg aaacagagta ttttgtccgc tgtatcaagc ac            592


<210> SEQ ID NO 7
<211> LENGTH: 500
<212> TYPE: DNA
<213> ORGANISM: Diabrotica virgifera

<400> SEQUENCE: 7

tactaggcga aagtgccgtc ggtaagtcga gtttggtact gaggttcgtc aaaggacagt     60

tccacgaata ccaggagagt accataggag cagctttcct tacacaaacc atatgcctcg    120

acgatacaac tgttaaattt gaaatttggg acacagcggg tcaagaaagg taccacagtt    180

tagctcctat gtactatagg ggcgcacagg cagctatagt cgtctacgac ataaccaatc    240

aagacacatt cggcagggcg aaaacgtggg tgaaggaact tcaaaggcag gccagtccga    300

cgatcgtgat agctttggcc ggcaacaagc aagatttggc caacaaacgt atggtagaat    360

acgaagaggc gcagacgtat gctgacgaaa acggcttact ttttatggaa acttccgcaa    420

agacggcaat gaacgtcaac gatatatttt tagcaatagc taagaaactg cccaagaatg    480

aacaaaccac aggtcaaggc                                                500


<210> SEQ ID NO 8
<211> LENGTH: 189
<212> TYPE: DNA
<213> ORGANISM: Diabrotica virgifera

<400> SEQUENCE: 8

cgatgaggtt gaaggaagga gaaaaatttt gatggggcga aaaagcatta ccaggacata     60

tcttcgtgga aatgctgttc ctgcgtatgt gataataatc cttgtaggaa ttggtcaaat    120
```

catcctggga gggatattgt acgttgcatt gaggaagaag atcattgctg cacctgtaac 180
ggcatcata 189

<210> SEQ ID NO 9
<211> LENGTH: 393
<212> TYPE: DNA
<213> ORGANISM: Diabrotica virgifera

<400> SEQUENCE: 9
tgaggtcgag ccctcagata ctatcgaaaa tgtgaaagct aaaatccagg ataaagaagg 60
aattccccca gaccagcaac gtctcatctt cgctggaaaa caactcgaag atggtcgtac 120
cttgtctgac tataatattc aaaaagaatc aacccttcac ttggtgttga gattgagagg 180
aggtgctaag aaacgtaaga agaagaatta ctccaccccc aagaaaatca agcacaagaa 240
gaagaaggtt aagttagctg tattgaaatt ttataaggtt gacgaaaatg gtaaaatcca 300
ccgattgaga cgtgaatgcc ccgctgaaca atgtggagct ggtgtcttca tggcagccat 360
ggaagacagg cattactgtg gcaagtgcgg tta 393

<210> SEQ ID NO 10
<211> LENGTH: 524
<212> TYPE: DNA
<213> ORGANISM: Diabrotica virgifera

<400> SEQUENCE: 10
tctttgcctt tggctacgat tcgaggaggg cattcaagaa tggctccaga aattggattc 60
agaacaattt tacatcggag tatatgtact tatagtcgct tcactgatcg tcatgattgt 120
gtcctttata ggatgtatta gtgccctgca ggagagtacc atggcccttt tagtgtacat 180
cggcacccaa gtgctcagtt ttatattcgg tttatccggt tcggcggttc ttctggataa 240
cagcgccaga gattcccact tccaaccgag gatccgagag agtatgcgac gtcttatcat 300
gaatgctcat cacgaccaat ccagacaaac actagccatg attcaggaaa atgttggttg 360
ctgcggagct gatggcgcaa cagactacct ctctcttcag cagcccccttc caagtcagtg 420 cagagacacc gttactggaa acccattctt ccacggatgt gtagatgaac tcacctggtt 480
cttcgaagaa aaatgtggtt ggatagcagg tttagctatg gcga 524

<210> SEQ ID NO 11
<211> LENGTH: 267
<212> TYPE: DNA
<213> ORGANISM: Diabrotica virgifera

<400> SEQUENCE: 11
tcgtgctggt ttacaatttc ctgtaggtcg tattcatcgt ttattgagaa aaggaaatta 60
tgccgaaaga gttggtgctg gagctcctgt atacttggca gctgttatgg aatatttagc 120
tgctgaagtt ttggaattgg caggaaatgc agctagagat aacaaaaaga cccgtataat 180
tcctagacat ttacaattgg ccataagaaa tgacgaggaa ttgaacaaat tactgtcagg 240
agttaccatc gcccaaggtg gagtatt 267

<210> SEQ ID NO 12
<211> LENGTH: 558
<212> TYPE: DNA
<213> ORGANISM: Diabrotica virgifera

<400> SEQUENCE: 12

-continued

```
gtgcatgaag ttggatggtg tagatctgcc cccaccaatt agcttcgaca ttgcggaaga     60

gcaaccgtta ccaccttgcc aacagacgtt cttatgtaat ggtgatggag gatccatagt    120

gcgacagttt ctcgagctgt atttcgtaat atatgattca gataataggc agtcccttct    180

tcaggcatat cacgaaaaag ccacattttc aatgacaatg gcctacccgt acggctattc    240

caaagacagt aaaggagtat cgtggttgaa ttggtatgcc accgataata gaaatttatt    300

acgagttcaa gatccagaca gaagaaacaa gttgttaaga cagggacaag ttgctgtagt    360

ttcgttcttg caagatatgc cgcacacgaa gcacgatatt cacagtttta cagtagattt    420

gacagttttt acaccccaga tgttatgttt gacagtggct ggtatgttta aagaattgaa    480

aagtggccac aaagtacctc ctttaagata tttcttcaga acccttgtaa ttgtacctgc    540

tggatcaggt ttttgcat                                                  558
```

<210> SEQ ID NO 13
<211> LENGTH: 582
<212> TYPE: DNA
<213> ORGANISM: Diabrotica virgifera

<400> SEQUENCE: 13

```
gattcggagc cctacaatga aatgcaacta aaaatggatt tagaaaaggg tgaggttaaa     60

gtaaaaataa gagcattaga aaaaataatt cacatgattc tggcaggaga aaggttgccg    120

aatggatttc taatgaccat cataagaaac gttttacctt tacaagatca tttggcaaaa    180

aaactattat tgattttctg ggaaatagtt ccaaaaacaa atccagaagg taaactacta    240

caagagatga ttttggtatg tgatgcctat agaaaagatc tgcaacaccc aaatgaattt    300

ttgagaggtt ctacacttcg cttcttgtgc aaactgaagg aaccagaatt gttggaacca    360

ttaatgccca gtattagagc ttgtttggat cataggcaca gctatgtgag gaggaatgct    420

gtactggcaa tttttaccat ttacaaaaat tttgaagccc tcattccaga tgctcctgaa    480

ctgatctcca attatttgga tggtgagcaa gacatgtctt gtaaaagaaa tgcgttttta    540

atgcttcttc atgctgacca agaaagggcg ttgtcgtatt tg                       582
```

<210> SEQ ID NO 14
<211> LENGTH: 458
<212> TYPE: DNA
<213> ORGANISM: Diabrotica virgifera

<400> SEQUENCE: 14

```
ttggcaaaaa ggaaatgagg atattgatgg taggactcga tgcagctggt aaaaccacaa     60

ttttatataa acttaaatta ggagaaattg taacaactat tccaacaatt ggatttaatg    120

tggagactgt agaatataag aacattagtt ttacagtatg ggatgtaggt ggtcaagata    180

aaattaggcc attgtggaga cactatttcc aaaacacaca aggcctaatt ttcgtagtag    240

acagtaacga cagggaacgt atcactgagg ctaaagatga attaatgcgt atgttggccg    300

aagatgaact tagagatgcc gtacttctca ttttcgccaa caaacaagat ttgcccaatg    360

caatgaacgc tgcagaaatc accgacaaac tcggtctcca ttcactacgc aaccgcaact    420

ggtacattca agctacctgt gcaactagcg gagatggt                           458
```

<210> SEQ ID NO 15
<211> LENGTH: 592
<212> TYPE: DNA
<213> ORGANISM: Diabrotica virgifera

<400> SEQUENCE: 15

```
ggtcgcgaaa gaacagaaag attttttgac cgtatctgcc gatggatgcg tacaagtaac     60

aaaacctctc gaccgagatc cgcctttcgg tagcccaaca cgacaagtct tcatctatgc    120

tcgtgataat gatggaggca caaattcatt gttggccact gcagaaattg aaattatttt    180

aatagatata aacgataatg ctcccttttt aaatgttaca gaaattgttt attatgaaaa    240

ccaggatcca ggttttatag gtaacctaag tgccgatgat tacgatggtc ctgataatgg    300

acctccgttt gcttttcgat tatcagacac tgcttcagat agtattagat cgaaattttc    360

cattatcgga aaccagcttt tcgctttaga aatgtttgat agagaagagc aaaaatatta    420

tgacattgcc attgacatta cagatagtgg agtacctcca ctaacaggaa ctagtattct    480

tagagttata atcggagatg taaatgataa tccagctaca gacggaaaca gcacgatctt    540

tgtgtataag tacgtcaatg ggccagaaaa tttcatggaa atcggacgtg ta            592


<210> SEQ ID NO 16
<211> LENGTH: 214
<212> TYPE: DNA
<213> ORGANISM: Diabrotica virgifera

<400> SEQUENCE: 16

gcatggggta tcatccagtt gggtttcatg ggtgtattct attacattgg ggctgtggct     60

ttagcagaag atattccaga ggttgagttt aagggcgatt tagacaaatt ttatagcgac    120

gtcaacacgg gtttcacaca gaatgcttac aactgctgga ttgctgctct cctatacctg    180

ataacattag cagtatcagc tcaccaattc tggg                                214


<210> SEQ ID NO 17
<211> LENGTH: 459
<212> TYPE: DNA
<213> ORGANISM: Diabrotica virgifera

<400> SEQUENCE: 17

tagatgccgc aggtaaaacc acaatcttat acaaattgaa gcttggtgaa atcgtaacta     60

caataccaac catcggcttc aatgtagaaa ccgttgagta caagaatata tctttcacgg    120

tatgggatgt aggtggccag acgagaatca gaaaactctg gagacactat ttcgccaaca    180

ctgatggact catttttgtg gttgattcca acgaccgaga ccgtatcgcg gaagccgaag    240

aagaattgca caatatgtta ggagaggacg atttaagaga ctgcattttg ttaatattcg    300

ccaacaaaca agatttaccg aactcgatgt ccactgctga attgaccgat aagcttaagt    360

tgcacacttt gaagaatagg aggtggtaca tacaagccac atgtgctact caagggaatg    420

gtttgtacga aggactagat tggttgtcga atgaattgg                           459


<210> SEQ ID NO 18
<211> LENGTH: 536
<212> TYPE: DNA
<213> ORGANISM: Diabrotica virgifera

<400> SEQUENCE: 18

gctaccctag cgtccactgt aacactgatt tttgccctct actactgcct cacgggaaaa     60

ggagagcaag ttagtttagc atggttattg ttgaatgtgt ctccccacat gtgggcaggt    120

ctaggaattg gccttgctgt atcattatca gttgtaggag ctgctgcagg aattcacact    180

acaggagtca gtatcgtagg agctggtgtt aaagccccca gaatcaaaac caaaaattta    240

atttctatta ttttctgtga agctgtggct atctatgggt taattatggc tatagtactc    300
```

-continued

```
tgtggaagtt ggaagaattt cgatgtagac ctattcaacc tcaaaactca taactttgct    360

caaaaccatt atggatcaca tgttattttt ggatccggtt taactgttgg atttgtaaat    420

ctattatgtg gattttgtgt tggagtagtt ggttctggtg cagccatttc tgatgcagcc    480

aattcatcat tattcgtcaa aattttgatt attgagattt ttggaagtgc cattgg        536


<210> SEQ ID NO 19
<211> LENGTH: 547
<212> TYPE: DNA
<213> ORGANISM: Diabrotica virgifera

<400> SEQUENCE: 19

accttatggg aaagcgtgtg gacttttctg cacgtactgt catcacacca gatcccaatt     60

tacgtatcga ccaagtagga gtgcctagaa gtattgctca aaacatgacg tttccagaaa    120

tcgtcacacc tttcaatttt gacaaaatgt tggaattggt acagagaggt aattctcagt    180

atccaggagc taagtatatc atcagagaca atggagagag gattgattta cgtttccacc    240

caaaaccgtc agatttacat ttgcagtgtg gttataaggt agaaagacac atcagagacg    300

gcgatctagt aatcttcaac cgtcaaccaa ccctccacaa gatgagtatg atgggccaca    360

gagtcaaagt cttaccctgg tcgacgttcc gtatgaatct ctcgtgcacc tctccctaca    420

acgccgattt tgacggcgac gaaatgaacc tccatgtgcc ccaaagtatg gaaactcgag    480

ctgaagtcga aaacctccac atcactccca ggcaaatcat tactccgcaa gctaaccaac    540

ccgtcat                                                              547


<210> SEQ ID NO 20
<211> LENGTH: 564
<212> TYPE: DNA
<213> ORGANISM: Diabrotica virgifera

<400> SEQUENCE: 20

cggatctcta tttgggggat caagtcgtat tgaagatgca gtggaatgtt acacaagagc     60

tgcaaacctt tttaaaatgg ccaagagctg ggatgctgcc ggtaaagcct tttgtgaggc    120

tgctaatttg cattccagaa ctggtgctcg tcatgacgct gccactaatt atatagatgc    180

tgcaaattgt tacaaaaaag ccgatgtatt tgaggctgta aactgcttta taaaagctat    240

agacatttat accgaaatgg gtcgctttac aatggctgca aaacaccatc agactattgc    300

agaaatgtat gagactgatg ctgtggacat cgaaagggct gttcaacact atgaacaggc    360

ggctgattac ttcagaggag aagaaagcaa tgcttccgcc aataagtgtc ttcttaaagt    420

ggctcaatat gcagcccaac ttgaaaacta tgaaaaagca gtgggaattt atcaagaagt    480

ggcttatgca gctctggaaa gctctctttt aaaatacagt gcaaaggaat acttattcag    540

agctgccctt tgtcaccttt gtgt                                           564


<210> SEQ ID NO 21
<211> LENGTH: 564
<212> TYPE: DNA
<213> ORGANISM: Diabrotica virgifera

<400> SEQUENCE: 21

tgctgattgg agattcagga gtaggaaaat cttgtcttct actgagattt gcagatgata     60

cctacacaga aagctatatt agtaccattg gcgtagattt taaaatcagg acaatcgatt    120

tagatggaaa gacaattaaa ttgcaaattt gggatacagc aggtcaggaa aggtttagaa    180

cgattacatc aagttattac cgaggagcac atggtattat tgtagtgtac gattgcacag    240
```

-continued accaagattc attcaataac gttaaacagt ggctcgaaga aatcgaccgt tatgcgtgtg 300
acaatgtaaa caaattactg gtagggaata aaagcgattt gacaactaag aaagttgtcg 360
acttcactac agccaaggag tatgccgacc aattgggtat accatttttg gaaacctcag 420
ctaagaatgc aaccaatgta gaacaggcct ttatgactat ggccgctgaa ataaaaaata 480
gagtaggacc tccatcttct gcggtagacc aaggaaataa ggttaggttc gatcaaagtc 540
gcccagtcga aacaaccaaa tccg 564

<210> SEQ ID NO 22
<211> LENGTH: 502
<212> TYPE: DNA
<213> ORGANISM: Diabrotica virgifera

<400> SEQUENCE: 22
gagctatagt ggactgcggg ttcgaacatc cttcagaagt tcaacatgaa tgtattcctc 60
aagctgtcat tggcatggat attctgtgcc aagctaaatc cggtatggga aaaacggctg 120
tttttgtatt agctacactc caagtaatag atcctacaga aaatgttgta tatgttctcg 180
tcatgtgcca taccagagag ttagccttcc agataagcaa agagtacgaa cgtttcagta 240
aatatatgcc caatattaaa gtaggggtct tctttggtgg cttgcctatc cagaaagatg 300
aggaaacgtt aaaaaataat tgcccgcata tcgttgtggg tactccagga agaattttag 360
cattggtcag atcgaaaaaa cttaatctca aacatctaaa gcatttttatt ttggatgaat 420 gtgataaaat gttggagtta ttagacatga gacgtgatgt tcaagaaata tatcgtaaca 480
ctccccacga aaaacaagtc at 502

<210> SEQ ID NO 23
<211> LENGTH: 505
<212> TYPE: DNA
<213> ORGANISM: Diabrotica virgifera

<400> SEQUENCE: 23
tggtagattt ggctaacctc gtatattggt gtttaggtct taatattccg tacgttagtt 60
tctatgatta taaaggtaat ttaaaaaagc atgaagagaa gttgcaacaa attgtagaat 120
ccagaaaatc agagaatatc aacataattt ggcacaccca tgcagaacaa aggcataaaa 180
atggattttt gggtccaaaa atccacgtaa aagtgttaac acacgcggac ggaaagcaaa 240
gtatagtaaa tgttactaaa aaattagctc taaataaaga aaaagacatt agtaaagaaa 300
aaattagtga attactatta aggcagtatg aatttccaga tccagaaatg gctattattt 360
gtggaaagaa actgaacatt tataattatc ctccttggca gttaagactc acagaattct 420
ttaaagtcaa caaagtcaac aacatcacat tcccagtgtt tgtggaaaaa ttggaaaagt 480
acagcaaatg tgaacagagg gtggg 505

<210> SEQ ID NO 24
<211> LENGTH: 410
<212> TYPE: DNA
<213> ORGANISM: Diabrotica virgifera

<400> SEQUENCE: 24
aaccagggat ctatttgccc gcaagtttaa aaaacgtggt gtaattccac tttccacata 60
tttgagagtc tacaaagttg gagatattgt agatatcaag ggtaatggtg cagttcaaaa 120
gggtatgccc cacaaagtgt accatggtaa gacaggacgt gttttcaatg ttactgcaca 180

-continued tgcattaggt gtaattgtaa acaaaagggt tcgaggaaga atcatcccca aaagaatcaa 240
tctccgtatt gaacatgtaa accactccaa gtgtcgtcaa gacttcttgc aaagagtaaa 300
atccaacgaa aagctacgta aagaagctaa agaaaagaac attaaagtag aacttaggag 360
acaacctgcc caacctaggc cagcacatat tgttagcgga aaggttccag 410

<210> SEQ ID NO 25
<211> LENGTH: 467
<212> TYPE: DNA
<213> ORGANISM: Diabrotica virgifera

<400> SEQUENCE: 25
tgatggtaat agagtgctgg ctaaatacta cgataaagat atatttccta cagcaaaaga 60
gcagaaagct tttgagaaaa atttgttcaa taaaactcat agggcagacg cagaaattat 120
catgttggat ggtttaactt gtgtgtatag aagtaatgta gatttattct tttatgttat 180
gggcagttca catgaaaatg agctaatttt aatgagtgtt ttaaattgct tgtatgactc 240
agtaagtcaa atattgaaga aaaatatgca aaaacgagct gtcttggaat cactagatat 300
tgttatgctg gctatggatg aaattgttga tggaggaata attatagatt ctgattcaag 360
ttcagtagta tctagaatag cattaaggac tgatgatatt ccattaggag aacaaactgt 420
agctcaggta ttccaaacgg ccaaagaaca gctgaaatgg tcattgc 467

<210> SEQ ID NO 26
<211> LENGTH: 368
<212> TYPE: DNA
<213> ORGANISM: Diabrotica virgifera

<400> SEQUENCE: 26
caccgaagaa caaattgctg aattcaaaga agctttctca ctattcgata aagatggtga 60
tggtacaatt acgactaaag aattaggaac agtaatgaga tctctaggac aaaatccaac 120
agaggctgaa ttacaggata tgatcaatga agtagatgcc gatggtaacg gcacgatcga 180
tttcccagaa tttttaacga tgatggcacg taaaatgaaa gataccgata gtgaggaaga 240
aattcgtgaa gcattccgag tgttcgacaa agacggcaat ggtttcatct cagcagcaga 300
attgcgccac gtcatgacca acttgggtga aaaattgaca gacgaagaag tcgatgaaat 360
gattcggg 368

<210> SEQ ID NO 27
<211> LENGTH: 430
<212> TYPE: DNA
<213> ORGANISM: Diabrotica virgifera

<400> SEQUENCE: 27
ttcgcacaag atgactttgg tggtgaaaat gttgatctat atgacgatgt aatatccgct 60
cctcctggaa ataatgacaa cccaggtgat tcaaatcatc atgctcctcc tggtgctggt 120
gaagatggtg gaggtaattt tgttgggtca ggaggagcac ccaataatat aaattcttct 180
ggaagaagac atcagctgta tgttggaaat ctgacttggt ggacaactga tcaagatata 240
gaaaatgcag tgcatgatat aggggtaacc gacttccatg aagttaagtt ttttgaacac 300
agagcaaatg gtcaatccaa gggattctgt gtcatatctt tgggatctga gggaagcatg 360
agactctgcc tggaactcct atctaaaaaa gagatcaatg gccaaaatcc ccttgttacc 420
cttcccacaa 430

-continued

<210> SEQ ID NO 28
<211> LENGTH: 505
<212> TYPE: DNA
<213> ORGANISM: Diabrotica virgifera

<400> SEQUENCE: 28

```
taggaatggc attttcaggc ttaatagctg atgcaaggca aatcgttgag attgctagaa     60

aagaagcatc aaattataga catcaatatg gttcaaatat tcctcttaaa tacctaaatg    120

atagagtaag catgtacatg catgcataca ctttatacag tgctgttaga ccatttggtt    180

gcagtgtcat cttggccagt tatgaagata gtgacccatc tatgtatctg attgatccat    240

ctggagttag ctatggatac tttggatgtg ctacaggtaa agcaaaacag tctgcaaaga    300

ctgaaataga aaaattgaag atggggaatc taacatgcaa agaacttgtt aaagaagcag    360

ccaaaatcat ttatttggtc catgatgagc tgaaggataa gaattttgaa ctggaacttt    420

catgggtatg caaagatacg aatggtttac ataccaaagt gcctgaatca gtgtttgctg    480

atgcagaaaa agctgccaaa caagc                                          505
```

<210> SEQ ID NO 29
<211> LENGTH: 548
<212> TYPE: DNA
<213> ORGANISM: Diabrotica virgifera

<400> SEQUENCE: 29

```
tccatctaga ggagcccaaa tgatgatgaa atccaggcta aagggagccc aaaagggaca     60

tagtttatta aagaagaaag ctgatgcttt acaaatgaga tttagaatga ttttgaacaa    120

aattattgag accaaaactc tcatgggtga agtaatgaaa gaagctgcct tttctttagc    180

tgaagcaaag tttgcaactg gtgacttcaa tcaagttgtt cttcaaaatg tcaccaaggc    240

tcaaataaaa ataagaacta agaaagacaa cgttgctggt gttactttac cagtgtttga    300

atgctaccaa gatggtacag atacatatga gttggctggt ttggctaggg gaggtcaaca    360

attgacaaaa ctcaagaaga attatcaaag tgctgttaaa ctgttggttg aattagcctc    420

tttgcaaact tcttttgtaa ctcttgatga tgtaatcaaa ataacaaaca gaagagtcaa    480

tgccattgaa catgttatca ttccaagaat agagcgtact ttggcttaca tcatatccga    540

actggacg                                                             548
```

<210> SEQ ID NO 30
<211> LENGTH: 521
<212> TYPE: DNA
<213> ORGANISM: Diabrotica virgifera

<400> SEQUENCE: 30

```
gatctggaag cgctagttgc aaaagtagac gaaatgagaa cccaaagagc catgctatgg     60

gctcaacttc gagaatctat tcaccaagac gatattacaa gttcccttgt aacgaaacaa    120

ccaaatcagt cgctggaaca gctgttccag caagaacttc aaaagcatca aaatctgatt    180

tcgttgattg aacaaaacac ctcggcacaa gaaaacatta agagcgcctt agtcgattct    240

tacgcttacg ctgtaaattc aagaaaatac atccaagata tactccaaaa gagaaccaca    300

accataacgt cactgatagc atcgttcgac tcttacgaag acttattggc aaaagctaac    360

aaagggatag agttttactc aaaacttgaa acgaacgtat ccaagttact gcaaagaata    420

aggagtacct gcaaagttca acaagaagag cgagatcaga tgatgtcgac tgcgcaagtg    480

cctcaatggg agagtcatac gtcacttgcc gctcctaaac t                        521
```

<210> SEQ ID NO 31
<211> LENGTH: 20
<212> TYPE: DNA
<213> ORGANISM: Diabrotica virgifera

<400> SEQUENCE: 31
ggtttcatga cccctgagag 20

<210> SEQ ID NO 32
<211> LENGTH: 20
<212> TYPE: DNA
<213> ORGANISM: Diabrotica virgifera

<400> SEQUENCE: 32
cgtctccctt ctttgaccag 20

<210> SEQ ID NO 33
<211> LENGTH: 20
<212> TYPE: DNA
<213> ORGANISM: Diabrotica virgifera

<400> SEQUENCE: 33
agaagttgcc gctttagtcg 20

<210> SEQ ID NO 34
<211> LENGTH: 20
<212> TYPE: DNA
<213> ORGANISM: Diabrotica virgifera

<400> SEQUENCE: 34
gtccaaacga aggattgcat 20

<210> SEQ ID NO 35
<211> LENGTH: 20
<212> TYPE: DNA
<213> ORGANISM: Diabrotica virgifera

<400> SEQUENCE: 35
accggccttt gtatgtcttg 20

<210> SEQ ID NO 36
<211> LENGTH: 20
<212> TYPE: DNA
<213> ORGANISM: Diabrotica virgifera

<400> SEQUENCE: 36
gcagcttctg gcaatctacc 20

<210> SEQ ID NO 37
<211> LENGTH: 20
<212> TYPE: DNA
<213> ORGANISM: Diabrotica virgifera

<400> SEQUENCE: 37
gaaagcagtt ggaagatggc 20

<210> SEQ ID NO 38
<211> LENGTH: 20
<212> TYPE: DNA
<213> ORGANISM: Diabrotica virgifera

<400> SEQUENCE: 38
cctcgagggt gatggtctta 20

<210> SEQ ID NO 39
<211> LENGTH: 20
<212> TYPE: DNA
<213> ORGANISM: Diabrotica virgifera

<400> SEQUENCE: 39
taccccattg aacacggaat 20

<210> SEQ ID NO 40
<211> LENGTH: 20
<212> TYPE: DNA
<213> ORGANISM: Diabrotica virgifera

<400> SEQUENCE: 40
caatggtgat gacttgaccg 20

<210> SEQ ID NO 41
<211> LENGTH: 20
<212> TYPE: DNA
<213> ORGANISM: Diabrotica virgifera

<400> SEQUENCE: 41
aggaaaggaa ggacccaaga 20

<210> SEQ ID NO 42
<211> LENGTH: 20
<212> TYPE: DNA
<213> ORGANISM: Diabrotica virgifera

<400> SEQUENCE: 42
gtgcttgata cagcggacaa 20

<210> SEQ ID NO 43
<211> LENGTH: 20
<212> TYPE: DNA
<213> ORGANISM: Diabrotica virgifera

<400> SEQUENCE: 43
tactaggcga aagtgccgtc 20

<210> SEQ ID NO 44
<211> LENGTH: 20
<212> TYPE: DNA
<213> ORGANISM: Diabrotica virgifera

<400> SEQUENCE: 44
gccttgacct gtggtttgtt 20

<210> SEQ ID NO 45
<211> LENGTH: 20
<212> TYPE: DNA
<213> ORGANISM: Diabrotica virgifera

<400> SEQUENCE: 45
cgatgaggtt gaaggaagga 20

<210> SEQ ID NO 46
<211> LENGTH: 20
<212> TYPE: DNA
<213> ORGANISM: Diabrotica virgifera

<400> SEQUENCE: 46

-continued tatgatgccg ttacaggtgc 20

<210> SEQ ID NO 47
<211> LENGTH: 20
<212> TYPE: DNA
<213> ORGANISM: Diabrotica virgifera

<400> SEQUENCE: 47
tgaggtcgag ccctcagata 20

<210> SEQ ID NO 48
<211> LENGTH: 20
<212> TYPE: DNA
<213> ORGANISM: Diabrotica virgifera

<400> SEQUENCE: 48
taaccgcact tgccacagta 20

<210> SEQ ID NO 49
<211> LENGTH: 20
<212> TYPE: DNA
<213> ORGANISM: Diabrotica virgifera

<400> SEQUENCE: 49
tctttgcctt tggctacgat 20

<210> SEQ ID NO 50
<211> LENGTH: 20
<212> TYPE: DNA
<213> ORGANISM: Diabrotica virgifera

<400> SEQUENCE: 50
tcgccatagc taaacctgct 20

<210> SEQ ID NO 51
<211> LENGTH: 21
<212> TYPE: DNA
<213> ORGANISM: Diabrotica virgifera

<400> SEQUENCE: 51
tcgtgctggt ttacaatttc c 21

<210> SEQ ID NO 52
<211> LENGTH: 20
<212> TYPE: DNA
<213> ORGANISM: Diabrotica virgifera

<400> SEQUENCE: 52
aatactccac cttgggcgat 20

<210> SEQ ID NO 53
<211> LENGTH: 20
<212> TYPE: DNA
<213> ORGANISM: Diabrotica virgifera

<400> SEQUENCE: 53
gtgcatgaag ttggatggtg 20

<210> SEQ ID NO 54
<211> LENGTH: 20
<212> TYPE: DNA
<213> ORGANISM: Diabrotica virgifera

<400> SEQUENCE: 54
atgcaaaaac ctgatccagc 20

<210> SEQ ID NO 55
<211> LENGTH: 20
<212> TYPE: DNA
<213> ORGANISM: Diabrotica virgifera

<400> SEQUENCE: 55
gattcggagc cctacaatga 20

<210> SEQ ID NO 56
<211> LENGTH: 20
<212> TYPE: DNA
<213> ORGANISM: Diabrotica virgifera

<400> SEQUENCE: 56
caaatacgac aacgcccttt 20

<210> SEQ ID NO 57
<211> LENGTH: 20
<212> TYPE: DNA
<213> ORGANISM: Diabrotica virgifera

<400> SEQUENCE: 57
ttggcaaaaa ggaaatgagg 20

<210> SEQ ID NO 58
<211> LENGTH: 20
<212> TYPE: DNA
<213> ORGANISM: Diabrotica virgifera

<400> SEQUENCE: 58
accatctccg ctagttgcac 20

<210> SEQ ID NO 59
<211> LENGTH: 20
<212> TYPE: DNA
<213> ORGANISM: Diabrotica virgifera

<400> SEQUENCE: 59
ggtcgcgaaa gaacagaaag 20

<210> SEQ ID NO 60
<211> LENGTH: 20
<212> TYPE: DNA
<213> ORGANISM: Diabrotica virgifera

<400> SEQUENCE: 60
tacacgtccg atttccatga 20

<210> SEQ ID NO 61
<211> LENGTH: 20
<212> TYPE: DNA
<213> ORGANISM: Diabrotica virgifera

<400> SEQUENCE: 61
gcatggggta tcatccagtt 20

<210> SEQ ID NO 62
<211> LENGTH: 20
<212> TYPE: DNA
<213> ORGANISM: Diabrotica virgifera

<400> SEQUENCE: 62
cccagaattg gtgagctgat 20

<210> SEQ ID NO 63
<211> LENGTH: 20
<212> TYPE: DNA
<213> ORGANISM: Diabrotica virgifera

<400> SEQUENCE: 63
tagatgccgc aggtaaaacc 20

<210> SEQ ID NO 64
<211> LENGTH: 20
<212> TYPE: DNA
<213> ORGANISM: Diabrotica virgifera

<400> SEQUENCE: 64
ccaattcatt cgacaaccaa 20

<210> SEQ ID NO 65
<211> LENGTH: 20
<212> TYPE: DNA
<213> ORGANISM: Diabrotica virgifera

<400> SEQUENCE: 65
gctaccctag cgtccactgt 20

<210> SEQ ID NO 66
<211> LENGTH: 20
<212> TYPE: DNA
<213> ORGANISM: Diabrotica virgifera

<400> SEQUENCE: 66
ccaatggcac ttccaaaaat 20

<210> SEQ ID NO 67
<211> LENGTH: 20
<212> TYPE: DNA
<213> ORGANISM: Diabrotica virgifera

<400> SEQUENCE: 67
accttatggg aaagcgtgtg 20

<210> SEQ ID NO 68
<211> LENGTH: 20
<212> TYPE: DNA
<213> ORGANISM: Diabrotica virgifera

<400> SEQUENCE: 68
atgacgggtt ggttagcttg 20

<210> SEQ ID NO 69
<211> LENGTH: 20
<212> TYPE: DNA
<213> ORGANISM: Diabrotica virgifera

<400> SEQUENCE: 69
cggatctcta tttgggggat 20

<210> SEQ ID NO 70
<211> LENGTH: 20
<212> TYPE: DNA
<213> ORGANISM: Diabrotica virgifera

<400> SEQUENCE: 70
acacaaaggt gacaaagggc 20

<210> SEQ ID NO 71
<211> LENGTH: 21
<212> TYPE: DNA
<213> ORGANISM: Diabrotica virgifera

<400> SEQUENCE: 71
tgctgattgg agattcagga g 21

<210> SEQ ID NO 72
<211> LENGTH: 20
<212> TYPE: DNA
<213> ORGANISM: Diabrotica virgifera

<400> SEQUENCE: 72
cggatttggt tgtttcgact 20

<210> SEQ ID NO 73
<211> LENGTH: 20
<212> TYPE: DNA
<213> ORGANISM: Diabrotica virgifera

<400> SEQUENCE: 73
gagctatagt ggactgcggg 20

<210> SEQ ID NO 74
<211> LENGTH: 20
<212> TYPE: DNA
<213> ORGANISM: Diabrotica virgifera

<400> SEQUENCE: 74
atgacttgtt tttcgtgggg 20

<210> SEQ ID NO 75
<211> LENGTH: 21
<212> TYPE: DNA
<213> ORGANISM: Diabrotica virgifera

<400> SEQUENCE: 75
tggtagattt ggctaacctc g 21

<210> SEQ ID NO 76
<211> LENGTH: 20
<212> TYPE: DNA
<213> ORGANISM: Diabrotica virgifera

<400> SEQUENCE: 76
cccaccctct gttcacattt 20

<210> SEQ ID NO 77
<211> LENGTH: 20
<212> TYPE: DNA
<213> ORGANISM: Diabrotica virgifera

<400> SEQUENCE: 77
aaccagggat ctatttgccc 20

<210> SEQ ID NO 78
<211> LENGTH: 20
<212> TYPE: DNA

<213> ORGANISM: Diabrotica virgifera

<400> SEQUENCE: 78
ctggaacctt tccgctaaca 20

<210> SEQ ID NO 79
<211> LENGTH: 22
<212> TYPE: DNA
<213> ORGANISM: Diabrotica virgifera

<400> SEQUENCE: 79
tgatggtaat agagtgctgg ct 22

<210> SEQ ID NO 80
<211> LENGTH: 21
<212> TYPE: DNA
<213> ORGANISM: Diabrotica virgifera

<400> SEQUENCE: 80
gcaatgacca tttcagctgt t 21

<210> SEQ ID NO 81
<211> LENGTH: 20
<212> TYPE: DNA
<213> ORGANISM: Diabrotica virgifera

<400> SEQUENCE: 81
caccgaagaa caaattgctg 20

<210> SEQ ID NO 82
<211> LENGTH: 20
<212> TYPE: DNA
<213> ORGANISM: Diabrotica virgifera

<400> SEQUENCE: 82
cccgaatcat ttcatcgact 20

<210> SEQ ID NO 83
<211> LENGTH: 20
<212> TYPE: DNA
<213> ORGANISM: Diabrotica virgifera

<400> SEQUENCE: 83
ttcgcacaag atgactttgg 20

<210> SEQ ID NO 84
<211> LENGTH: 20
<212> TYPE: DNA
<213> ORGANISM: Diabrotica virgifera

<400> SEQUENCE: 84
ttgtgggaag ggtaacaagg 20

<210> SEQ ID NO 85
<211> LENGTH: 20
<212> TYPE: DNA
<213> ORGANISM: Diabrotica virgifera

<400> SEQUENCE: 85
taggaatggc attttcaggc 20

<210> SEQ ID NO 86
<211> LENGTH: 20

<212> TYPE: DNA
<213> ORGANISM: Diabrotica virgifera

<400> SEQUENCE: 86
gcttgtttgg cagctttttc 20

<210> SEQ ID NO 87
<211> LENGTH: 20
<212> TYPE: DNA
<213> ORGANISM: Diabrotica virgifera

<400> SEQUENCE: 87
tccatctaga ggagcccaaa 20

<210> SEQ ID NO 88
<211> LENGTH: 20
<212> TYPE: DNA
<213> ORGANISM: Diabrotica virgifera

<400> SEQUENCE: 88
cgtccagttc ggatatgatg 20

<210> SEQ ID NO 89
<211> LENGTH: 20
<212> TYPE: DNA
<213> ORGANISM: Diabrotica virgifera

<400> SEQUENCE: 89
gatctggaag cgctagttgc 20

<210> SEQ ID NO 90
<211> LENGTH: 20
<212> TYPE: DNA
<213> ORGANISM: Diabrotica virgifera

<400> SEQUENCE: 90
agtttaggag cggcaagtga 20

<210> SEQ ID NO 91
<211> LENGTH: 633
<212> TYPE: DNA
<213> ORGANISM: Diabrotica virgifera

<400> SEQUENCE: 91
atggcggacg atgagagaaa gaaactggag gaggaaaaga agaggaaaca ggccgaaatt 60
gaacgcaaaa gggccgaggt cagggctcgt atggaagagg cctcaaaagc caagaaggcc 120
aagaaaggtt tcatgacccc tgagagaaag aagaaactta ggttactgtt gagaaagaaa 180
gccgccgaag aattaaagaa agaacaagaa cgcaaagcag ccgaaaggag gcgtatcatt 240
gaagaaaggt gcggtaaacc caaacttgtc gatgacgcaa atgaaggccc attaaaacaa 300
gtatgtgagg gatatcacag acgtattgta gacctagaaa ataagaaatt tgacctcgaa 360
aaagaagtgg aattcagaga ttttcagatc tccgaattga acagccaagt aaacgacctt 420
agaggcaaat tcgtcaaacc aaccttgaag aaggtatcca aatacgaaaa caaattcgcc 480
aaacttcaaa agaaggcagc tgaatttaac ttccgtaacc aactcaaagt tgtcaagaag 540
aaagaattca ccttagaaga agaagacaaa gaaaagaaac cagactggtc aaagaaggga 600
gacgaaaaga aggtacaaga ggctgaagca tga 633

<210> SEQ ID NO 92

<211> LENGTH: 603
<212> TYPE: DNA
<213> ORGANISM: Diabrotica virgifera

<400> SEQUENCE: 92
atgtgtgaag aagaagttgc cgctttagtc gtagacaatg gatccggtat gtgcaaagct 60
ggttttgctg gggatgatgc acctcgtgct gtattccctt caattgttgg acgcccaaga 120
catcagggtg tgatggtagg aatgggacaa aaagattcct atgtaggtga tgaagctcaa 180
agtaaaagag gtatccttac cttaaaatac cccatcgagc acggaatagt cacaaactgg 240
gatgatatgg agaaaatttg gcatcataca ttctacaatg aactcagagt agccccagaa 300
gaacaccctg ttctgttgac agaagctcct ctcaacccca aggccaacag ggaaaagatg 360
acacaaataa tgtttgaaac tttcaacacc ccagccatgt atgttgccat ccaggctgta 420
ctctccttgt atgcatctgg tcgtacaact ggtattgtgt tggattctgg tgatggtgta 480
tcccacactg tcccaatcta tgaaggttat gctcttcctc atgcaatcct tcgtttggac 540
ttagctggta gagacttgac tgattacctc atgaaaattt tgactgaacg tggctactct 600
ttc 603

<210> SEQ ID NO 93
<211> LENGTH: 2742
<212> TYPE: DNA
<213> ORGANISM: Diabrotica virgifera

<400> SEQUENCE: 93
atgccacttc gattagatat aaaaagaaag ctaacagctc gctcagaccg ggtaaaatgt 60
gtggatcttc accctacaga accttggatg ctgtgttctc tttacagcgg aaatataaac 120
gtttggaaca ccgaaaatca gcaactggtt aagacttttg aagtatgtga tgtacctgtt 180
cggacagcta agtttttgcc caggaagaac tggatagtca gtgggtctga tgatatgcag 240
attcgagttt tcaattacaa taccttagat cgggtacatt cttttgaggc tcattcggat 300
tatgtgagat gtattgtcgt acaccctaca caaccttata tattaacaag tagtgatgat 360
atgcttatca agctttggaa ttgggaaaaa gcatgggctt gtcagcaagt tttcgaagga 420
cacactcatt atattatgca aatcgccata aatccaaaag acaacaacac atttgccagt 480
gcatccctag atagaacatt gaaagtatgg caattgggag cgtccacagc gaatttcaca 540
ctagaaggtc atgagaaagg cgttaactgt gtggactatt atcacggtgg agataaacct 600
tatttaatct caggcgctga tgatagatta gtaaaaatct gggattatca aaacaaaact 660
tgtgttcaaa ctttggaagg acatgctcaa aatgtaaccg ctgcatgttt ccatccagaa 720
cttcctgtag ctcttactgg aagtgaagat ggtactgtca gagtgtggca tgccaacacc 780
cataggttag aaagtagctt aaattatggc tttgaaagag tatggactat tttctgccta 840
aagggatcca ataacgtggc attgggttat gatgaaggta gcattttggt taaagttggt 900
agagaagaac cagctgttag tatggatgcc agtggaggca aaattatttg ggccagacac 960
tctgaacttc aacaggcaaa tctcaaggcg ttagctgaag gtgcggaaat aagagatgga 1020
gaacgccttc cagtttctgt aaaagatatg ggtgcttgcg agatataccc tcagacaatt 1080
caacacaatc ccaatggccg ttttgttgtt gtctgtgggg atggagaata cataatctac 1140
acagcaatgg ctttaagaaa caaagcgttt ggtagcgcac aagaatttgt gtgggctcaa 1200
gattccagcg aatatgccat cagagaatcc ggatctacta tcagaatttt taagaatttc 1260
aaagagaaga agaattttaa gtccgatttt ggagctgaag gtatatacgg tggatacctt 1320
ttgggagtca aatcggtttc tggtttgact ttctatgatt gggaaactct cgatttagtc 1380
agaagaatcg agatacaacc aaaagcagtt tactggtcag atagtggtaa attagtatgt 1440
ttggccacag aagatagcta ctttattctt tcttatgatt ctgatgaagt tcaaaaagcc 1500
agagataaca atcaggttgc ggatgatgga gtagaatcgg ctttcaatct tctaggtgaa 1560
ataaacgaat cagtgcgaac tggtctctgg gtaggcgact gttttatcta cacgaattct 1620
gttaatcgta tcaactactt cgttggaggt gaactggtta caattgctca tttggaccgg 1680
cctttgtatg tcttgggata tgtgcctaaa gacgatagat tatacctcgt agataaagag 1740
ttgcgcgtag taagctacca attacttctt tctgttcttg aatatcaaac tgccgtcatg 1800
agaagagact ttccaacagc agacagagta cttccgtcca ttcctaagga gcacagaacg 1860
agagtggcac atttcttaga aaagcaaggc ttcaaacagc aagctttggc cgtaagtaca 1920
gatccagagc acagattcga gctggcagta gcattagagg atcttaatat agccaaaact 1980
ctagctcaag aagcgaacag tccgcaaaag tggaatcaac tagcagaatt ggcagctgct 2040
actaataatg taagcgtagc caaggaatgt atgcaaaaag cgcaagatta tggaggcttg 2100
ttgcttcttg ctacgagctc cggtgatgaa aatttagtcc gtactctagg agaaacgaca 2160
caagctgaaa gcaaacataa cttagcattt ttgtcacact tgttagtagg tgatttaaac 2220
aaatgtctag acattcttat taataccggt agattgccag aagctgcatt tttcgccaga 2280
tcttaccttc ctgataagat tacagaagtc gtggaactgt ggaagactca gttatcttca 2340
gtcaatcaaa aagctggaca gagccttgcc gatcctaaaa actacgaaaa tctgttccct 2400
ggtttacaag aggcggtggt agctcagaaa tttttggaac agcagaataa aggtttagcg 2460
cccgcaagag ttgccaccac cattcctcct aatcacgaca ggaatgttgt agccgaagtt 2520
caagcacaat cgaaacacga tgtaccatca tttagttctt cgtttatttc atcagaaata 2580
gaagcacaaa caaggagttc tgctaaacct gaagaatctt caaacattat acagctggac 2640
caagatgacg acgatatcga tttagatttg gacggtgtaa atatcgatga gaacattgac 2700
acgacggata tcaacatcga tgatgatttg ctgagtgatt ga 2742

<210> SEQ ID NO 94
<211> LENGTH: 1146
<212> TYPE: DNA
<213> ORGANISM: Diabrotica virgifera

<400> SEQUENCE: 94
atgcagatct ttgtaaaaac actcactggt aaaaccatca ccctcgaggt tgaaccatca 60
gataccatcg agaatgtcaa agctaaaatt caagacaaag aaggtattcc accagatcaa 120
cagagattaa tctttgctgg aaagcagtta gaagatggcc gtactctctc agactacaac 180
attcagaaag aatctacact acacttagtg cttcgtctta gaggaggtat gcacatcttt 240
gtaaaaactc tcactggtaa gaccatcacc cttgaggttg aaccatcaga taccatcgag 300
aatgtcaaag ctaaaattca agacaaagaa ggtattccac cagatcaaca gagattaatc 360
tttgctggaa agcagttgga agatggccgt actctctcag actacaacat tcaaaaagag 420
tctaccctcc atttggtact tcgtcttaga ggaggtatgc agatttttgt taaaacttta 480
actggaaaga ccatcaccct tgaagtagaa ccttctgata ccatcgaaaa tgtcaaagcc 540
aaaattcaag acaaagaagg tattccacca gatcaacaaa gattaatctt tgccggaaag 600
caattggaag atggtcgtac actctcagac tacaacattc aaaaggaatc taccctccat 660

```
ttggtacttc gtcttagagg aggtatgcaa atctttgtaa aaacactcac tggtaagacc    720

atcaccctcg aggttgaacc atcagatacc atcgagaatg tcaaagctaa aattcaagac    780

aaagaaggta ttccaccaga tcaacagaga ttaatcttcg ctggaaagca gttggaagat    840

ggccgtactc tctcagacta caatattcag aaagagtcta ccctccattt ggtacttcgt    900

cttagaggag gtatgcaaat ctttgtaaaa actctcactg gtaagaccat caccctcgag    960

gttgaaccat cagataccat cgagaatgtc aaagctaaaa ttcaagacaa agaaggtatt   1020

ccaccagatc aacaaagatt aatctttgcc ggaaagcagt tggaagatgg ccgtactctc   1080

tcagactaca acattcaaaa agagtctacc cttcacttgg tacttcgttt aagaggagga   1140

aattaa                                                              1146
```

<210> SEQ ID NO 95
<211> LENGTH: 1131
<212> TYPE: DNA
<213> ORGANISM: Diabrotica virgifera

<400> SEQUENCE: 95

```
atgtgtgacg acgatgtagc ggctcttgtc gtcgacaatg gctccggaat gtgcaaagcc     60

ggtttcgccg gtgatgacgc ccctcgtgct gtctttccat ccatcgtagg tcgtcccaga    120

caccaaggtg tcatggtggg tatgggtcaa aaagactcct acgtaggaga cgaagcccaa    180

agcaaaagag gtatcctcac cttaaaatac cccattgaac acggaattat cactaactgg    240

gacgatatgg aaaagatctg gcatcacacc ttctacaatg aacttagagt agcccccgaa    300

gaacatccca ttcttttgac tgaagctcca cttaacccaa aagccaacag agaaaagatg    360

actcaaatca tgtttgaaac tttcaatacc cctgccatgt atgttgccat tcaagctgta    420

ttgtctctgt acgcttccgg tcgtaccact ggtattgtac ttgattctgg agatggtgta    480

tcccacacag tacccatcta tgaaggttac gctctcccac acgccatctt gcgtttggac    540

ttggccggta gagacttgac tgactacctt atgaagatct taaccgaaag aggttactct    600

ttcaccacca cagctgaaag agaaatagtt cgtgacatca aggaaaaatt gtgctatgta    660

gctttggact tcgaacagga aatggccaca gcagccagct ccacctcctt agaaaagagt    720

tatgaacttc ctgacggtca agtcatcacc attggtaatg aaaggttccg ttgccctgaa    780

gctctcttcc aaccttcctt cttgggtatg gaatcttgcg gtatccacga aactgtctac    840

aactccatca tgaagtgcga tgtcgacatc cgtaaagact tgtacgccaa cactgtcctt    900

tctggaggta ccacaatgta ccctggtatt gccgatcgta tgcaaaagga aatcactgcc    960

ttggctccat caaccatcaa aatcaagatc atcgctcccc cagaaagaaa gtactccgtt   1020

tggatcggtg gctccatctt ggcctccctc tccaccttcc aacagatgtg gatctccaaa   1080

caagaatacg acgaatccgg ccctggaatt gttcaccgca aatgcttcta a            1131
```

<210> SEQ ID NO 96
<211> LENGTH: 2640
<212> TYPE: DNA
<213> ORGANISM: Diabrotica virgifera

<400> SEQUENCE: 96

```
atgggtactt ttaaaagaga tactcatgat gaggacgggg gatcaagtgc ttttcaaaat     60

ctggagaaaa ctactgtttt gcaggaagct agagttttta atgaaactag tgtaaatcca    120

agaaaatgta caccgatact aacaaaactg ttgtacttat tgaaccaggg tgaaacttta    180

agtgccaaag aggccacaga tgttttcttt gccatgacca aactgttcca atcaaaagat    240
```

```
gtaatattga gaaggatggt ttatttggga attaaagaac tcagttctgt tgctgatgat    300
gtcattattg taacatccag tcttacaaaa gatatgactg gtaaagaaga catgtacaga    360
gcagctgcta taagagcatt atgcagtatt actgatgcta ctatgcttca agctatagaa    420
cgttatatga agcaagctat tgtagataga aacgcagctg tcagttcagc agcactaatt    480
agttcattac atatgagcaa attagctcca gatgtagtaa aaagatgggt aaatgaagct    540
caggaagcag taaatagtga taatgcaatg gtacagtatc acgcattagg tcttctatac    600
catattagga agactgataa gctagcagtg acaaaattga tttccaagct gaattcaatg    660
ggtttaaaga gcccttatgc tttgtgtatg ttgataagaa tcactgcaaa acttttagaa    720
gaagaggacc aagagtcact cctcaactcc ccatatacaa taatatttac aatgggctta    780
aggaacaaat ctgaaatggt ggtgtatgaa gctgcacatg ccatggttaa cctgaagttc    840
acgagtagta atgtgctagc acccgctata agtgttctac aactattttg tggatctcct    900
aaagccacac tcagatttgc tgctgttaga actttaaatc aagtggccac cacccaccct    960
gcgtcagtga cagcttgtaa tttggatcta gaaaatttga ttactgatcc taataggtca   1020
attgctacac tggccattac tactcttttg aaaacaggtg ccgaatcttc tgttgacaga   1080
ctaatgaaac aaatcgctac ttttgtatct gaaatcagtg atgaatttaa agtggttgtc   1140
attcaggcaa ttaaggtatt agctttgaaa tttccaagga aacatagcac gcttatgaat   1200
ttcctatccg ccatgttaag agatgaggga ggtttagaat ataaagcatc catagcagat   1260
accattataa ccctaatcga agataatccc gaagctaaag aatctggttt ggcgcatctt   1320
tgcgagttca ttgaagactg tgaacatgtt tctttggctg tgagaatctt gcatttgtta   1380
ggaaaggaag gacccaagac caaacaacca tcgagataca tccgttttat ctacaatcgc   1440
gtcatattgg aatgtccttc tgtaagagct gctgcagtct ccgccatggc acaattcgga   1500
gcctcttgtc ccgatttgtt agaaaatatc caaatattac tttcgaggtg tcagatggat   1560
tcagacgatg aagttaggga cagagctaca tattatagta atatacttaa caaaaatgat   1620
aaaagtttat acaacaatta cattttggat tctttgcagg tttcaattcc ttcactagaa   1680
agatcgctta gagaatacat tcaaaatcca actgacgaac catttgacat taagtccgta   1740
cctgtagcag cagtgccaac agcagaagaa cgagaagtta aaaacaaatc tgaaggactg   1800
ctagtctctc aaggtccagt ccgacctcct ccggtgtcta gagaagaaaa cttcgccgaa   1860
aaacttagta acgttccggg tatacaacag ttaggacctt tgttcaaaac ttccgacgtc   1920
gttgaactca ctgaatctga aacagagtat tttgtccgct gtatcaagca ctgtttcaaa   1980
catcacatcg tcctccaatt cgattgtctg aataccttgc cagaccagct tttagaaaac   2040
gttagagtgg agatagacgc cggtgaaacc ttcgaaattt tggcagaaat accttgtgaa   2100
aagttgcact ataacgaaac cggtaccaca tatgtagtag ttaagttgcc tgatgatgat   2160
ctccccaact ctgttggtac gtgtggagcc gtgttgaagt tcttagtgaa agattgtgat   2220
ccatcaacgg gaataccaga ttctgatgag ggttacgatg atgaatatac actggaagac   2280
atcgaaataa cattagggga ccaaattcaa aaagtaagca aagtaaattg ggctgcagcc   2340
tgggaagaag ctgcagctac ttatgtagaa aaagaggata catactcctt gaccatcaat   2400
acgctaagtg gcgctgttaa gaatattatt cagttcttgg gattacagcc tgcggaaagg   2460
actgacagag taccggaggg taaatctacg cacacattac ttcttgctgg tgtattcagg   2520
ggaggtattg acatactagt aagagcgaaa ctagctttgg gcgaatgtgt tacgatgcaa   2580
```

ctaacagtca ggtcgccaga tcctgacgtt gctgagctta taacttcaac tgtaggttaa 2640

<210> SEQ ID NO 97
<211> LENGTH: 651
<212> TYPE: DNA
<213> ORGANISM: Diabrotica virgifera

<400> SEQUENCE: 97
atggcggcaa acagaactgg acctgctcag agaccaaatg gcgctaccca aggaaagata 60
tgtcagttca aactggtcct actaggcgaa agtgccgtcg gtaagtcgag tttggtactg 120
aggttcgtca aaggacagtt ccacgaatac caggagagta ccataggagc agctttcctt 180
acacaaacca tatgcctcga cgatacaact gttaaatttg aaatttggga cacagcgggt 240
caagaaaggt accacagttt agctcctatg tactataggg gcgcacaggc agctatagtc 300
gtctacgaca taaccaatca agacacattc ggcagggcga aaacgtgggt gaaggaactt 360
caaaggcagg ccagtccgac gatcgtgata gctttggccg gcaacaagca agatttggcc 420
aacaaacgta tggtagaata cgaagaggcg cagacgtatg ctgacgaaaa cggcttactt 480
tttatggaaa cttccgcaaa gacggcaatg aacgtcaacg atatattttt agcaatagct 540
aagaaactgc ccaagaatga acaaaccaca ggtcaaggcg gcagtgccca aggcaggcgg 600
ctagcggagg gcgattcggg cgccaaggca cccggaaatt gttgcaagtg a 651

<210> SEQ ID NO 98
<211> LENGTH: 279
<212> TYPE: DNA
<213> ORGANISM: Diabrotica virgifera

<400> SEQUENCE: 98
atgaagtttt taagatcgac agtgtgctac attgccatct tggcaattct ctttaccctc 60
tgtgccgatg aggttgaagg aaggagaaaa attttgatgg ggcgaaaaag cattaccagg 120
acatatcttc gtggaaatgc tgttcctgcg tatgtgataa taatccttgt aggaattggt 180
caaatcatcc tgggagggat attgtacgtt gcattgagga agaagatcat tgctgcacct 240
gtaacggcat catatgcagt ggctagacaa gaaccataa 279

<210> SEQ ID NO 99
<211> LENGTH: 474
<212> TYPE: DNA
<213> ORGANISM: Diabrotica virgifera

<400> SEQUENCE: 99
atgcagatct tcgttaaaac cttaacgggt aagaccatca ctcttgaggt cgagccctca 60
gatactatcg aaaatgtgaa agctaaaatc caggataaag aaggaattcc cccagaccag 120
caacgtctca tcttcgctgg aaaacaactc gaagatggtc gtaccttgtc tgactataat 180
attcaaaaag aatcaaccct tcacttggtg ttgagattga gaggaggtgc taagaaacgt 240
aagaagaaga attactccac ccccaagaaa atcaagcaca agaagaagaa ggttaagtta 300
gctgtattga aattttataa ggttgacgaa aatggtaaaa tccaccgatt gagacgtgaa 360
tgccccgctg aacaatgtgg agctggtgtc ttcatggcag ccatggaaga caggcattac 420
tgtggcaagt gcggttacac tcttgtcttc tccaaaccag gagatgagaa atag 474

<210> SEQ ID NO 100
<211> LENGTH: 747
<212> TYPE: DNA
<213> ORGANISM: Diabrotica virgifera

<400> SEQUENCE: 100
atgatgtcca aagcagacac acaggaagat gcctccttcg ccaaattgga aaatcagatt 60
gctatcatca aatacgtaat actctttacc aacgttttgc aatgggctct cggtgcagca 120
atcttcgctc tttgcctttg gctacgattc gaggagggca ttcaagaatg gctccagaaa 180
ttggattcag aacaatttta catcggagta tatgtactta tagtcgcttc actgatcgtc 240
atgattgtgt cctttatagg atgtattagt gccctgcagg agagtaccat ggccctttta 300
gtgtacatcg gcacccaagt gctcagtttt atattcggtt tatccggttc ggcggttctt 360
ctggataaca gcgccagaga ttcccacttc caaccgagga tccgagagag tatgcgacgt 420
cttatcatga atgctcatca cgaccaatcc agacaaacac tagccatgat tcaggaaaat 480
gttggttgct gcggagctga tggcgcaaca gactacctct ctcttcagca gccccttcca 540
agtcagtgca gagacaccgt tactggaaac ccattcttcc acggatgtgt agatgaactc 600
acctggttct tcgaagaaaa atgtggttgg atagcaggtt tagctatggc gatatgcatg 660
attaacgtcc ttagtattgt tttatctacg gtactcatcc aggcattgaa aaaagaagaa 720
gaagcatccg attcatacag gagatag 747

<210> SEQ ID NO 101
<211> LENGTH: 375
<212> TYPE: DNA
<213> ORGANISM: Diabrotica virgifera

<400> SEQUENCE: 101
atgtctggac gtggcaaggg aggcaaagta aagggaaaag caaagtcccg atcaaatcgt 60
gctggtttac aatttcctgt aggtcgtatt catcgtttat tgagaaaagg aaattatgcc 120
gaaagagttg gtgctggagc tcctgtatac ttggcagctg ttatggaata tttagctgct 180
gaagttttgg aattggcagg aaatgcagct agagataaca aaaagacccg tataattcct 240
agacatttac aattggccat aagaaatgac gaggaattga acaaattact gtcaggagtt 300
accatcgccc aaggtggagt attgcctaat atacaagcag tactgttacc taaaaaaact 360
gaaaagaaag cttaa 375

<210> SEQ ID NO 102
<211> LENGTH: 864
<212> TYPE: DNA
<213> ORGANISM: Diabrotica virgifera

<400> SEQUENCE: 102
atgaagttgg atggtgtaga tctgcccccca ccaattagct tcgacattgc ggaagagcaa 60
ccgttaccac cttgccaaca gacgttctta tgtaatggtg atggaggatc catagtgcga 120
cagtttctcg agctgtattt cgtaatatat gattcagata ataggcagtc ccttcttcag 180
gcatatcacg aaaaagccac attttcaatg acaatggcct acccgtacgg ctattccaaa 240
gacagtaaag gagtatcgtg gttgaattgg tatgccaccg ataatagaaa tttattacga 300
gttcaagatc cagacagaag aaacaagttg ttaagacagg gacaagttgc tgtagtttcg 360
ttcttgcaag atatgccgca cacgaagcac gatattcaca gttttacagt agatttgaca 420
gtttttacac cccagatgtt atgtttgaca gtggctggta tgtttaaaga attgaaaagt 480
ggccacaaag tacctccttt aagatatttc ttcagaaccc ttgtaattgt acctgctgga 540
tcaggttttt gcatagcaaa tgaagaactt cacatatcca atgcaactcc ggaccaagca 600
aaagatgctt tcaagaccac cgttaatgta gctccggcac cagcccctgt gattacctct 660
cctggaccca gtataccaca acccgctgtg ccagatgatg ctacaaaaca agaaatggta 720
aaacagatgt ccgcagtatc cggaatgaat ctcgagtggt cgctacagtg tctcgaagaa 780
acacaatggg actaccagaa agccataatg gtattccaaa atttaaacgc acaaggtgtt 840
gtaccacaag cagcatttat taaa 864

<210> SEQ ID NO 103
<211> LENGTH: 2868
<212> TYPE: DNA
<213> ORGANISM: Diabrotica virgifera

<400> SEQUENCE: 103
atgactgcgg tagaacaacc ttgttacaca ctaataaact tgccaacaga ttcggagccc 60
tacaatgaaa tgcaactaaa aatggattta gaaaagggtg aggttaaagt aaaaataaga 120
gcattagaaa aaataattca catgattctg gcaggagaaa ggttgccgaa tggatttcta 180
atgaccatca taagaaacgt tttacccttta caagatcatt tggcaaaaaa actattattg 240
attttctggg aaatagttcc aaaaacaaat ccagaaggta aactactaca agagatgatt 300
ttggtatgtg atgcctatag aaaagatctg caacacccaa atgaattttt gagaggttct 360
acacttcgct tcttgtgcaa actgaaggaa ccagaattgt tggaaccatt aatgcccagt 420
attagagctt gtttggatca taggcacagc tatgtgagga ggaatgctgt actggcaatt 480
tttaccattt acaaaaattt tgaagccctc attccagatg ctcctgaact gatctccaat 540
tatttggatg gtgagcaaga catgtcttgt aaaagaaatg cgtttttaat gcttcttcat 600
gctgaccaag aaagggcgtt gtcgtatttg gcatcatgtt tagatcaagt aaattcattt 660
ggagatattc tacaactggt catcgttgag ttgatatata aggtgtgtca ttccaatcct 720
gcggaaagat ctagatttat tagatgtata tataacttgt tgaactcaag cagtcctgct 780
gtcaggtacg aagctgcagg aactttagtc accctctcca gtgccccgac tgccgttaaa 840
gctgctgcta gctgttacat tgagttaatt atcaaagaaa gtgacaacaa tgtaaaactc 900
atcgttttgg acaggctgat agcacttaag gagcttccta atcacgaaag aattctgcag 960
gatttagtta tggacatact gagagtactc tctgctcctg acttagaagt ccgcaagaag 1020
actttaagtc tagcccttga attagtctct tcacggaaca tagaagaaat ggtattagta 1080
ttaacaaagg aagtgagtaa aacggtagac agtgaacatg aggatacagg aaagtacagg 1140
caattgttag taaggactct acattcgtgt tccattaagt tcccagatat cgcacgtagt 1200
gttataccag tcttgattga atttttatcc gataataatg aactggctgc cacagatgta 1260
ttgctgttct taagggaagc catacagaag tttaaagaat tgcaaccgtt aattattgag 1320
aaactcatcg aaactttcaa agacattaaa ttggtcaaag tccatagagc agcaatttgg 1380
attttgggag aatacgcgag tactgcttcc gatatagaag ttatcgttgg agaaattaac 1440
agattgttgg gtgaaggatc cctcgttgaa gctgagcaga agttaatagc aggagatacg 1500
gaagagaatg ctcctgcacc tgctgcaggc gccaccactt tagttacttc cgatggaaca 1560
tatgctaccc aatcagcttt caacactgtc agccaaacca ctaaagaagc acgacctcct 1620
ctaagacaat acctcatgga tggtgatttt ttcatcggag cctctttggc atctacatta 1680
accaaactgt ctttgcggta tgaggacctc acctctcctg ctgctagcaa tggattcaat 1740
gccaaaatta tgcttattat ggctggaatt cttcacttgg gaaaatcagg acttcccaca 1800
aaatcaataa ccaacgacga taaagaccac attctgttct gtttacgagt cctatctgat 1860

```
cgttctccaa tcattgttga aattttcaaa aaattgtgcc gctcggcact aaatgagatg   1920

cttctagcta aggaatcggt agaagcgatc tcgcaaaaga gcaaagaaaa aaacaagcgt   1980

acgattcaaa ctgacgacgc tataagcttc ctgcaattag agacagataa aagtggagag   2040

ctaggagaaa acgtattcga gatgtcgctg tcacaagctt tagtaggagg tcgaacggga   2100

ggtggcgaat cagtattaag ttccaataaa ttagataaaa tcacacaact gactggtttt   2160

tccgatccag tttattccga agcatacgtt cacgtgaatc agtacgatat cgtgcttgat   2220

gtcttaatcg taaaccaaac taacgatact ttacaaaact gcacgctaga gctggctact   2280

ttaggcgatt tgaagttggt agagaagcca caacctgtcg tattggcgcc caaagacttt   2340

tgcaacatta aagctaacgt gaaagtggcc tcaactgaaa acggaattat atttggcaac   2400

attgtgtatg atgtcatagg agcggggtca gataggaatg ttgtagtttt gaatgatata   2460

cacatagata taatggacta tatagtgcct gctagttgta cagatagcga gtttatgaga   2520

atgtgggcgg aatttgaatg ggaaaataag gtaaccgtta acacacccct cacggaactt   2580

tcagaatacc tcgaacatct actcaaaagc acaaatttga aatgtttaac atcagaaaaa   2640

gctctgagcg ggcagtgtgg ttttatggca gccaatttat atgcaaaatc catttttgga   2700

gaagacgctt tggccaactt aagtatagag aaacctttta ataaacccga tgcgccagta   2760

agcggtcata ttagaataag ggccaaaagt cagggcatgg ccttaagttt aggagacaaa   2820

gtcaatatga cacagaagag cacacaacat aaagtagtag ctgcataa                2868
```

```
<210> SEQ ID NO 104
<211> LENGTH: 549
<212> TYPE: DNA
<213> ORGANISM: Diabrotica virgifera

<400> SEQUENCE: 104

atgggtaatg tgtttgcaaa tttattcaaa ggcctctttg gcaaaaagga aatgaggata     60

ttgatggtag gactcgatgc agctggtaaa accacaattt tatataaact taaattagga    120

gaaattgtaa caactattcc aacaattgga tttaatgtgg agactgtaga atataagaac    180

attagtttta cagtatggga tgtaggtggt caagataaaa ttaggccatt gtggagacac    240

tatttccaaa acacacaagg cctaattttc gtagtagaca gtaacgacag ggaacgtatc    300

actgaggcta aagatgaatt aatgcgtatg ttggccgaag atgaacttag agatgccgta    360

cttctcattt tcgccaacaa acaagatttg cccaatgcaa tgaacgctgc agaaatcacc    420

gacaaactcg gtctccattc actacgcaac cgcaactggt acattcaagc tacctgtgca    480

actagcggag atggtctcta tgaaggtctg gactggttgt ccaatcaatt aaagaacgcc    540

aatcgctag                                                            549
```

```
<210> SEQ ID NO 105
<211> LENGTH: 4425
<212> TYPE: DNA
<213> ORGANISM: Diabrotica virgifera

<400> SEQUENCE: 105

atgggacggt tgcactgttt attttgtatt ttcctatgtt ttaccgtcat caacacgcag     60

acaacgaata tacatggatt ctcggaaaat tccgtggata catttctatc acctcatggg    120

aaaagtgcaa aattcgtgca ccaaaatcac aaacccaaaa ttgaaaattg tcagaactac    180

aaaccctcgg tgaaagaaga acagccaggc ggaacgtacg taacaacggt taccgctatc    240
```

-continued

```
gatgacgatc ctagggaggg aggaggaaca attagttaca aactaattca tagagaagga    300
gaacatgttt tatttgacat agacaacgtt actggtgttt tgacaactat ccagccattt    360
gatcgggatg aaccagtaag gcagaaggaa ctttatgtaa ccgtacaagc ttcagacaac    420
ggcaggccac cattagcaga tgtctgtaca tttacagtta ccattaccga cattaatgat    480
aatgcgccac agcttgataa actgaaatac gatgcacaag tttctgaaga tttaaaagta    540
ggaagtgaag tgatgagagt ttttgcttac gacattgatg atggggaaaa ttcaagatta    600
tcgtataact tttcaaacga aaatgctcaa ttcacccagt atttcaggat agatcgagat    660
actggcgttg tgtatttaaa ggaagcttta acagacaaaa agaatactag atttaacagt    720
gctgtttatg tagccgataa tggcgttaac gatcaagaag gccaaaaaga ttcaaccgct    780
aagatatcta taacagtagt agggtctgat aaacagcctc ccagatttac tcaaaaaatg    840
cctgatggaa tcttggagat ccccgaagat tttaaagact tttctaaaca tattgtcaca    900
gtcgaagcaa cgtccaacat tgcggatcca caacttgctt ttgaattggt gaagggaaag    960
acatatcaaa ccaataaaga ccaaacgttt cttttggagg cagaaggaaa taaagcgcac   1020
ataaagctag tgcgtccact ggattatgaa acagtaacgg aatatactct aactattcga   1080
gtaaaaaaca aagatttaat ggattcttcc ataaaatatac caattaaagt attagatgtt   1140
aatgatgaaa ttcctaattt ccttgaattt cttaaaggta gtgtcgtgga aaatgacaag   1200
ccaggtgcac aagcgattca agtaagagca atcgataaag acggaactgc tgctaacaac   1260
attgtgagct atgaactcgt tgacaataca gatttgtttg caataaaccg atctacggga   1320
gtaattacgt cgagagtgga gtttgatcgt gaaactgtac ctctatatca cgtaaacgtt   1380
aaagcttatg ataactctcc gtctgctttg tataacacga cattgcctaa cattgtaatt   1440
cagacattcc aaatcagtat agaagatcaa aatgacaaca aacctgtatt tactcatcca   1500
atttatcagt tcagtaatat tactgagctt gctgataaat cgagtattgt tggtgaagtc   1560
aaagctttag ataatgacac ggcttcagtt ataagttata gtattacaaa tggaaatatt   1620
gacgatgcgt ttatgattga aaattctacc ggcagaataa gagttaatgg aaaactggat   1680
tacgagaaaa tcgaacaata caacttaacc gttcgcgcat ttgatggggc atttgaagat   1740
tttgcaattg ttttaatttc catacttaat gaaaatgacg aacctccagt ttttgacgac   1800
tatatcagag aaattcaaat taaagaggaa gaacctatga tatccggatg cgttgttaga   1860
gtgactgctc atgatccaga tattaaagac aggcatgctg atcaacacat agtatatgag   1920
gtcgcgaaag aacagaaaga ttttttgacc gtatctgccg atggatgcgt acaagtaaca   1980
aaacctctcg accgagatcc gcctttcggt agcccaacac gacaagtctt catctatgct   2040
cgtgataatg atggaggcac aaattcattg ttggccactg cagaaattga aattatttta   2100
atagatataa acgataatgc tcccttttta aatgttacag aaattgttta ttatgaaaac   2160
caggatccag gttttatagg taacctaagt gccgatgatt acgatggtcc tgataatgga   2220
cctccgtttg cttttcgatt atcagacact gcttcagata gtattagatc gaaattttcc   2280
attatcggaa accagctttt cgctttagaa atgtttgata gagaagagca aaaatattat   2340
gacattgcca ttgacattac agatagtgga gtacctccac taacaggaac tagtattctt   2400
agagttataa tcggagatgt aaatgataat ccagctacag acggaaacag cacgatcttt   2460
gtgtataagt acgtcaatgg gccagaaaat ttcatggaaa tcggacgtgt atatgttaca   2520
gacctagacg attgggattt aaatgacaaa gtctttgttc aagaagataa ctttgatgaa   2580
tttgtgttaa accagcataa caacggtatg attctgatga aaccaacaac ggctgaggga   2640
```

acttatgagg ttcattacag ggtcactgaa acccatgaac ccacaataca cgaacataca 2700
gttaatgcaa tagtcacgat tacagttaaa gtacttccag aggaagcggt tgtaaaatca 2760
ggatcaattc gattgagagg aacaactaag gaagaattca tagaaaattc attgaatgga 2820
aagagcaaaa gagacatatt acaccaagaa ctctccaaaa tattaaatac atctttagcg 2880
aatgttgatg tatttactgt tttaaattca ccccaccaga atagttcgtt tgtggatgtt 2940
cgattttctg ctcatggatc tccatattat gctccagaga aactcgaaaa caaagttaca 3000
gatcatcaaa tggagcttga acaaaaatta gatgtggaat tctacatgat caacgtaaac 3060
gagtgcctta acgaaacaac gtgtggagct gaaaactcat gtacgaacaa attaaacata 3120
acacgagaac cagctgtagt gtttactaac agaacatcct ttgtcggtgt aaatgcattt 3180
attgatcctg tgtgtgccgc tttaccaaga gatgttatgg aatgtttcaa cggaggcgtc 3240
cttatcgaaa acacagcgtg taattgtcct gcaggatttg aaggaccaca ttgtgaaatc 3300
ctagctatag gatttacagg aactggttgg gctatgtatc catcctttga cgctacaaac 3360
aggactgaga ttatactgca tattttatca caaactgata atggtttgat attttacaat 3420
ggacctttaa atataagaca aacttctttg tctaaagatt atatatcatt agaacttaaa 3480
gacggatatc cattacttca aatttgcacc ggctcaagca ctcaagaaat ttatctgaaa 3540
gagcgcattc acaaattgag cgatggatcg ttacacaaaa taaaaatagg atctggattt 3600
gacgatatat ccctggaagt agacgactgt ggaacaacgt gttcaatttg gactaataaa 3660
ctacataaag gtgttatccg agcaaatggc ccccttcaac tgggaggtat gaaaaacaga 3720
ttcaccgatc aagaattcaa acgaatttgg gaccatttgc caccgactgc cacccgtttc 3780
tctggttgta ttagaaattt gacgtataat gaattttact acaacctcgg tgcaccttct 3840
gatgcattcc aagcgtatcc cgactgtaac tatgcagtga tgcaagctgt gactttcggt 3900
atcgactcca atttcttggt tgctattctg gtttgtgtag caattttgat aattcttctt 3960
ctggcagtag ttgtacatag acgtaaacac gacaacttta acgaaaaaga aatcgatgat 4020
actcgcgaaa acattatcaa ctacgaagat gaaggtggcg gcgaatgtga caccaactac 4080
gacctgtctg ttttccatca gaacaacatt gtggacgaaa aaccattgat gagagacaac 4140
cccgatgtac ctgcagatat aagtggcttt ttagataaca agaaagacaa ctgtgataaa 4200
gaccccgata atttgcctta tgacgacgtt cgccattatg cctacgaggg agacggaaat 4260
agcaccggat ccttatcttc tctcgcttca tgtacggacg aaggagattt aaagttcaac 4320
tacttatcaa gttttggacc cagattcaga aagttagccg acatgtatgg agaagatcca 4380
agcgatgaag actcacacga tggaaacgaa gaatcctggt gctag 4425

<210> SEQ ID NO 106
<211> LENGTH: 291
<212> TYPE: DNA
<213> ORGANISM: Diabrotica virgifera

<400> SEQUENCE: 106
atgcctttct gtggtcccaa attgtccctc tgcggcctga ttatcagtgc atggggtatc 60
atccagttgg gtttcatggg tgtattctat tacattgggg ctgtggcttt agcagaagat 120
attccagagg ttgagtttaa gggcgattta gacaaatttt atagcgacgt caacacgggt 180
ttcacacaga atgcttacaa ctgctggatt gctgctctcc tatacctgat aacattagca 240
gtatcagctc accaattctg ggccaacaac agatcatcat tgaacgtcta a 291

<210> SEQ ID NO 107
<211> LENGTH: 540
<212> TYPE: DNA
<213> ORGANISM: Diabrotica virgifera

<400> SEQUENCE: 107
atgggtctta ccatatcagc agtgtttaat aggttgttta gtaaaaagcc tatgagaatt 60
ttaatggtag gattagatgc cgcaggtaaa accacaatct tatacaaatt gaagcttggt 120
gaaatcgtaa ctacaatacc aaccatcggc ttcaatgtag aaaccgttga gtacaagaat 180
atatctttca cggtatggga tgtaggtggc cagacgagaa tcagaaaact ctggagacac 240
tatttcgcca acactgatgg actcattttt gtggttgatt ccaacgaccg agaccgtatc 300
gcggaagccg aagaagaatt gcacaatatg ttaggagagg acgatttaag agactgcatt 360
ttgttaatat tcgccaacaa acaagattta ccgaactcga tgtccactgc tgaattgacc 420
gataagctta agttgcacac tttgaagaat aggaggtggt acatacaagc cacatgtgct 480
actcaaggga atggtttgta cgaaggacta gattggttgt cgaatgaatt ggccaagtga 540

<210> SEQ ID NO 108
<211> LENGTH: 618
<212> TYPE: DNA
<213> ORGANISM: Diabrotica virgifera

<400> SEQUENCE: 108
atgcggtaca ctttgagtta catcggtgct accctagcgt ccactgtaac actgattttt 60
gccctctact actgcctcac gggaaaagga gagcaagtta gtttagcatg gttattgttg 120
aatgtgtctc cccacatgtg ggcaggtcta ggaattggcc ttgctgtatc attatcagtt 180
gtaggagctg ctgcaggaat tcacactaca ggagtcagta tcgtaggagc tggtgttaaa 240
gcccccagaa tcaaaaccaa aaatttaatt tctattattt tctgtgaagc tgtggctatc 300
tatgggttaa ttatggctat agtactctgt ggaagttgga agaatttcga tgtagaccta 360
ttcaacctca aaactcataa ctttgctcaa aaccattatg gatcacatgt tatttttgga 420
tccggtttaa ctgttggatt tgtaaatcta ttatgtggat tttgtgttgg agtagttggt 480
tctggtgcag ccatttctga tgcagccaat tcatcattat tcgtcaaaat tttgattatt 540
gagatttttg gaagtgccat tggtctcttc ggtctgattg ttggagtata cttgacgtca 600
agaggctcta tggtttaa 618

<210> SEQ ID NO 109
<211> LENGTH: 5694
<212> TYPE: DNA
<213> ORGANISM: Diabrotica virgifera

<400> SEQUENCE: 109
atggctacca acgatagtaa agctccgttg aggacagtta aaagagtgca atttggaata 60
cttagtccag atgaaattag acgaatgtca gtcacagaag ggggcatccg cttcccagaa 120
accatggaag caggccgccc caaactatgc ggtcttatgg accccagaca aggtgtcata 180
gacagaagct caagatgcca gacatgtgcc ggaaatatga cagaatgtcc tggacatttc 240
ggacatatcg agctggcaaa accagttttc cacgtaggat tcgtaacaaa aacaataaag 300
atcttgagat gcgtttgctt cttttgcagt aaattattag tcagtccaaa taatccgaaa 360
attaaagaag ttgtaatgaa atcaaaggga cagccacgta aaagattagc tttcgtttat 420
gatctgtgta aaggtaaaaa tatttgtgaa ggtggagatg aaatggatgt gggtaaagaa 480

-continued

```
agcgaagatc ccaataaaaa agcaggccat ggtggttgtg gtcgatatca accaaatatc    540
agacgtgccg gtttagattt aacagcagaa tggaaacacg tcaatgaaga cacacaagaa    600
aagaaaatcg cactatctgc cgaacgtgtc tgggaaatcc taaaacatat cacagatgaa    660
gaatgtttca ttcttggtat ggatcccaaa tttgctagac cagattggat gatagtaacg    720
gtacttcctg ttcctcccct agcagtacga cctgctgtag ttatgcacgg atctgcaagg    780
aatcaggatg atatcactca caaattggcc gacattatca aggcgaataa cgaattacag    840
aagaacgagt ctgcaggtgc agccgctcat ataatcacag aaaatattaa gatgttgcaa    900
tttcacgtcg ccactttagt tgacaacgat atgccgggaa tgccgagagc aatgcaaaaa    960
tctggaaaac ccctaaaagc tatcaaagct cggctgaaag gtaaagaagg aaggattcga   1020
ggtaacctta tgggaaagcg tgtggacttt tctgcacgta ctgtcatcac accagatccc   1080
aatttacgta tcgaccaagt aggagtgcct agaagtattg ctcaaaacat gacgtttcca   1140
gaaatcgtca cacctttcaa ttttgacaaa atgttggaat tggtacagag aggtaattct   1200
cagtatccag gagctaagta tatcatcaga gacaatggag agaggattga tttacgtttc   1260
cacccaaaac cgtcagattt acatttgcag tgtggttata aggtagaaag acacatcaga   1320
gacggcgatc tagtaatctt caaccgtcaa ccaaccctcc acaagatgag tatgatgggc   1380
cacagagtca aagtcttacc ctggtcgacg ttccgtatga atctctcgtg cacctctccc   1440
tacaacgccg attttgacgg cgacgaaatg aacctccatg tgccccaaag tatggaaact   1500
cgagctgaag tcgaaaacct ccacatcact cccaggcaaa tcattactcc gcaagctaac   1560
caacccgtca tgggtattgt acaagatacg ttgacagctg ttaggaagat gacaaaaagg   1620
gatgtattca tcgagaagga acaaatgatg aatatattga tgttcttgcc aatttgggat   1680
ggtaaaatgc cccgtccagc catcctcaaa cccaaaccgt tgtggacagg aaaacagata   1740
ttttccctga tcattcctgg caatgtaaat atgatacgta cccattctac gcatccagac   1800
gacgaggacg acggtcccta taaatggata tcgccaggag atacgaaagt tatggtagaa   1860
catggagaat tggtcatggg tatattgtgt aagaaaagtc ttggaacatc agcaggttcc   1920
ctgctgcata tttgtatgtt ggaattagga cacgaagtgt gtggtagatt ttatggtaac   1980
attcaaactg taatcaacaa ctggttgttg ttagaaggtc acagcatcgg tattggagac   2040
accattgccg atcctcagac ttacacagaa attcagagag ccatcaggaa agccaaagaa   2100
gatgtaatag aagtcatcca gaaagctcac aacatggaac tggaaccgac tcccggtaat   2160
acgttgcgtc agactttcga aaatcaagta aacagaattc taaacgacgc tcgtgacaaa   2220
actggtggtt ccgctaagaa atctttgact gaatacaata acctaaaggc tatggtcgta   2280
tcgggatcca agggatccaa cattaatatt tcccaggtta ttgcttgcgt gggtcaacag   2340
aacgtagaag gtaaacgtat tccatttggc ttcagaaaac gcacgttgcc gcacttcatc   2400
aaggacgatt acggtcctga atccagaggt ttcgtagaaa attcgtatct tgccggtctc   2460
actccttcgg agttctattt ccacgctatg ggaggtcgtg aaggtcttat cgatactgct   2520
gtaaaaactg ccgaaactgg ttacatccag cgtcgtctga tcaaggctat ggagagtgta   2580
atggtacact acgacggtac cgtaagaaat tctgtaggac aacttatcca gttgagatac   2640
ggtgaggacg gactctgtgg agagatggta gagtttcaat atttagcaac ggtcaaatta   2700
agtaacaagg cgtttgagag aaaattcaga tttgatccga gtaatgaaag gtatttgaga   2760
agagttttca atgaagaagt tatcaagcaa ctgatgggtt caggggaagt catttccgaa   2820
```

-continued

```
cttgagagag aatgggaaca actccagaaa gacagagaag ccttaagaca aatcttccct   2880
agcggagaat ccaaagtagt actcccctgt aatttacaac gtatgatctg gaatgtacaa   2940
aaaattttcc acataaacaa acgagccccg acagacctgt ccccgttaag agttatccaa   3000
ggcgttcgag aattactcag gaaatgcgtc atcgtagctg gcgaggatcg tctgtccaaa   3060
caagccaacg aaaacgcaac gttactcttc cagtgtctag tcagatcgac cctctgcacc   3120
aaatgcgttt ctgaagaatt caggctcagc accgaagcct tcgagtggtt gataggagaa   3180
atcgagacga ggttccaaca agcccaagcc aatcctggag aaatggtggg cgctctggcc   3240
gcgcagtcac tgggagaacc cgctactcag atgacactga acactttcca ttttgctggt   3300
gtatcctcca agaacgtaac cctgggtgta cctagattaa aggaaattat taatatttcc   3360
aagaaaccca aggctccatc tctaaccgtg tttttaactg gtgcggctgc tagagatgcg   3420
gaaaaagcga agaatgtgtt atgcagactt gaacacacca ctcttcgtaa agtaaccgcc   3480
aacaccgcca tctattacga tcctgaccca caaaataccg tcattcctga ggatcaggag   3540
ttcgttaacg tctactatga aatgcccgat ttcgatccta cccgtatatc gccgtggttg   3600
cttcgtatcg aactggacag aaagagaatg acagataaga aactaactat ggaacaaatt   3660
gctgaaaaga tcaacgctgg gttcggggac gatttgaatt gtattttcaa cgacgacaat   3720
gctgaaaagt tggtgctgcg tatcagaatc atgaacagcg acgatggaaa attcggagaa   3780
ggtgctgatg aggacgtaga caaaatggat gacgacatgt tttgagatg catcgaagcg    3840
aacatgctga gcgatatgac cttgcaaggt atagaagcga tttccaaggt atacatgcac   3900
ttgccacaga ctgactcgaa aaaaaggatc gtcatcactg aaacaggcga atttaaggcc   3960
atcgcagaat ggctattgga aactgacggt accagcatga tgaaagtact gtcagaaaga   4020
gacgtcgatc cggtcaggac gttttctaac gacatttgtg aaatattttc ggtacttggt   4080
atcgaggctg tgcgtaagtc tgtagagaag gaaatgaacg ctgtcctttc gttctacggt   4140
ctgtatgtaa actatcgcca tcttgccttg ctttgtgacg taatgacagc caaaggtcac   4200
ttaatggcca tcacccgtca cggtatcaac agacaagaca ctggagctct gatgaggtgt   4260
tccttcgagg aaactgtaga tgtattgatg gacgctgcca gtcatgcgga ggtcgaccca   4320
atgagaggag tatctgaaaa cattatcctc ggtcaactac caagaatggg cacaggctgc   4380
ttcgatcttt tgctggacgc cgaaaaatgt aaaatgggaa ttgccatacc tcaagcgcac   4440
agcagcgatc taatggcttc aggaatgttc tttggattag ccgctacacc cagcagtatg   4500
agtccaggtg gtgctatgac cccatggaat caagcagcta caccatacgt tggcagtatc   4560
tggtctccac agaatttaat gggcagtgga atgacaccag gtggtgccgc tttctcccca   4620
tcagctgcgt cagatgcatc aggaatgtca ccagcttatg gcggttggtc accaacacca   4680
caatctcctg caatgtcgcc atatatggct tctccacatg gacaatcgcc ttcctacagt   4740
ccatcaagtc cagcgttcca acctacttca ccatccatga cgccgacctc tcctggatat   4800
tctcccagtt ctcctggtta ttcacctacc agtctcaatt acagtccaac gagtcccagt   4860
tattcaccca cttctcagag ttactcccca acctcaccta gttactcacc gacttctcca   4920
aattattcac ctacttcccc aagctacagt ccaacatccc ctaactattc accaacatct   4980
cccaactatt cacccacttc acctagttat ccttcaactt cgccaggtta cagccccact   5040
tcacgcagct actcacccac atctcctagt tactcaggaa cttcgccctc ttattcacca   5100
acttcgccaa gttactcccc tacttctcct agttattcgc cgtcgtctcc taattactct   5160
cccacttctc caaattacag tcccacttct cctaattact caccgtcctc tcctaggtac   5220
```

```
acgcccggtt ctcctagttt ttccccaagt tcgaacagtt actctcccac atctcctcaa   5280

tattctccaa catctccaag ttattcgcct tcttcgccca aatattcacc aacttccccc   5340

aattattcgc caacatctcc atcattttct ggaggaagtc cacaatattc acccacatca   5400

ccgaaatact ctccaacctc gcccaattac actctgtcga gtccgcagca cactccaaca   5460

ggtagcagtc gatattcacc gtcaacttcg agttattctc ctaattcgcc caattattca   5520

ccgacgtctc cacaatactc catccacagt acaaaatatt cccctgcaag tcctacattc   5580

acacccacca gtcctagttt ctctcccgct tcacccgcat attcgcctca acctatgtat   5640

tcaccttctt ctcctaatta ttctcccact agtcccagtc aagacactga ctaa         5694
```

<210> SEQ ID NO 110
<211> LENGTH: 876
<212> TYPE: DNA
<213> ORGANISM: Diabrotica virgifera

<400> SEQUENCE: 110

```
atgtcgtcaa atattcaaaa ggcccagcag ttgatggcgg atgcagaaaa gaaagtaaca     60

tctcgaggtt tcttcggatc tctatttggg ggatcaagtc gtattgaaga tgcagtggaa    120

tgttacacaa gagctgcaaa ccttttttaaa atggccaaga gctgggatgc tgccggtaaa    180

gccttttgtg aggctgctaa tttgcattcc agaactggtg ctcgtcatga cgctgccact    240

aattatatag atgctgcaaa ttgttacaaa aaagccgatg tatttgaggc tgtaaactgc    300

tttataaaag ctatagacat ttataccgaa atgggtcgct ttacaatggc tgcaaaacac    360

catcagacta ttgcagaaat gtatgagact gatgctgtgg acatcgaaag ggctgttcaa    420

cactatgaac aggcggctga ttacttcaga ggagaagaaa gcaatgcttc cgccaataag    480

tgtcttctta aagtggctca atatgcagcc caacttgaaa actatgaaaa agcagtggga    540

atttatcaag aagtggctta tgcagctctg gaaagctctc ttttaaaata cagtgcaaag    600

gaatacttat tcagagctgc cctttgtcac ctttgtgttg atgtactcaa tgcacaacat    660

gctatagaaa gctatatttc aaggtatccc gcatttcaag attcccgtga atacaaactt    720

ttgaaaaccc tcatagaaaa catcgaagag caaaacgtag atggatatac agaagccgtc    780

aaagattacg attcaatttc tcgtcttgat cagtggtata ctacaattct tttacgtatt    840

aagaaacaag taagcgaaag ccctgactta cgttaa                              876
```

<210> SEQ ID NO 111
<211> LENGTH: 609
<212> TYPE: DNA
<213> ORGANISM: Diabrotica virgifera

<400> SEQUENCE: 111

```
atgaatcccg agtatgatta tttattcaaa cttctgctga ttggagattc aggagtagga     60

aaatcttgtc ttctactgag atttgcagat gatacctaca cagaaagcta tattagtacc    120

attggcgtag attttaaaat caggacaatc gatttagatg gaaagacaat taaattgcaa    180

atttgggata cagcaggtca ggaaaggttt agaacgatta catcaagtta ttaccgagga    240

gcacatggta ttattgtagt gtacgattgc acagaccaag attcattcaa taacgttaaa    300

cagtggctcg aagaaatcga ccgttatgcg tgtgacaatg taaacaaatt actggtaggg    360

aataaaagcg atttgacaac taagaaagtt gtcgacttca ctacagccaa ggagtatgcc    420

gaccaattgg gtataccatt tttggaaacc tcagctaaga atgcaaccaa tgtagaacag    480
```

```
gcctttatga ctatggccgc tgaaataaaa aatagagtag gacctccatc ttctgcggta    540

gaccaaggaa ataaggttag gttcgatcaa agtcgcccag tcgaaacaac caaatccggt    600

tgctgctga                                                            609
```

<210> SEQ ID NO 112
<211> LENGTH: 789
<212> TYPE: DNA
<213> ORGANISM: Diabrotica virgifera

<400> SEQUENCE: 112

```
atggcagacg ctgatgatct attagattat gaagatgagg aacagacaga acaaaccgca     60

actgaaacgg caactacaga ggtacagaaa aagggtgtca agggcacata tgtatcaata    120

cacagttctg ggtttagaga ttttctgtta aaaccagcaa ttctcagagc tatagtggac    180

tgcgggttcg aacatccttc agaagttcaa catgaatgta ttcctcaagc tgtcattggc    240

atggatattc tgtgccaagc taaatccggt atgggaaaaa cggctgtttt tgtattagct    300

acactccaag taatagatcc tacagaaaat gttgtatatg ttctcgtcat gtgccatacc    360

agagagttag ccttccagat aagcaaagag tacgaacgtt tcagtaaata tatgcccaat    420

attaaagtag ggtcttcttt tggtggcttg cctatccaga aagatgagga aacgttaaaa    480

aataattgcc cgcatatcgt tgtgggtact ccaggaagaa ttttagcatt ggtcagatcg    540

aaaaaactta atctcaaaca tctaaagcat tttattttgg atgaatgtga taaaatgttg    600

gagttattag acatgagacg tgatgttcaa gaaatatatc gtaacactcc ccacgaaaaa    660

caagtcatga tgttcagtgc caccttaagt aaagaaatta gaccagtttg caagaaattt    720

atgcaagatg taattcaaaa ttcttataat acacaatttt gtaatgacgc acccactcgc    780

aatgtttga                                                            789
```

<210> SEQ ID NO 113
<211> LENGTH: 738
<212> TYPE: DNA
<213> ORGANISM: Diabrotica virgifera

<400> SEQUENCE: 113

```
atgccggtca ttgatggtta taaagtactt tacattttat tacacagttt atatacaatt     60

tttgaaaata tttggaggac tcttttattt atttatcaaa attgtataag ggttataaac    120

cctgaatcta cattcgatga tgctgaccag ttaaagaaaa gactgtctag actaacaaaa    180

aagcctcaac atttaactat cattattggt gtggaagaat attcattggt agatttggct    240

aacctcgtat attggtgttt aggtcttaat attccgtacg ttagtttcta tgattataaa    300

ggtaatttaa aaaagcatga agagaagttg caacaaattg tagaatccag aaaatcagag    360

aatatcaaca taatttggca cacccatgca gaacaaaggc ataaaaatgg atttttgggt    420

ccaaaaatcc acgtaaaagt gttaacacac gcggacggaa agcaaagtat agtaaatgtt    480

actaaaaaat tagctctaaa taaagaaaaa gacattagta aagaaaaaat tagtgaatta    540

ctattaaggc agtatgaatt tccagatcca gaaatggcta ttatttgtgg aaagaaactg    600

aacatttata attatcctcc ttggcagtta agactcacag aattctttaa agtcaacaaa    660

gtcaacaaca tcacattccc agtgtttgtg gaaaaattgg aaaagtacag caaatgtgaa    720

cagagggtgg gaaaataa                                                  738
```

<210> SEQ ID NO 114
<211> LENGTH: 480

<212> TYPE: DNA
<213> ORGANISM: Diabrotica virgifera

<400> SEQUENCE: 114
atgaccaact ctaaaggtta ccgccgagga accagggatc tatttgcccg caagtttaaa 60
aaacgtggtg taattccact ttccacatat ttgagagtct acaaagttgg agatattgta 120
gatatcaagg gtaatggtgc agttcaaaag ggtatgcccc acaaagtgta ccatggtaag 180
acaggacgtg ttttcaatgt tactgcacat gcattaggtg taattgtaaa caaaagggtt 240
cgaggaagaa tcatccccaa aagaatcaat ctccgtattg aacatgtaaa ccactccaag 300
tgtcgtcaag acttcttgca aagagtaaaa tccaacgaaa agctacgtaa agaagctaaa 360
gaaaagaaca ttaaagtaga acttaggaga caacctgccc aacctaggcc agcacatatt 420
gttagcggaa aggttccagc acaggtgctt gctcctatcc catatgaatt cattgcttag 480

<210> SEQ ID NO 115
<211> LENGTH: 537
<212> TYPE: DNA
<213> ORGANISM: Diabrotica virgifera

<400> SEQUENCE: 115
atggaaggaa tactactgga accaacattg tataccataa aaggtattgc tatattggac 60
tatgatggta atagagtgct ggctaaatac tacgataaag atatatttcc tacagcaaaa 120
gagcagaaag cttttgagaa aaatttgttc aataaaactc atagggcaga cgcagaaatt 180
atcatgttgg atggtttaac ttgtgtgtat agaagtaatg tagatttatt cttttatgtt 240
atgggcagtt cacatgaaaa tgagctaatt ttaatgagtg ttttaaattg cttgtatgac 300
tcagtaagtc aaatattgaa gaaaaatatg caaaaacgag ctgtcttgga atcactagat 360
attgttatgc tggctatgga tgaaattgtt gatggaggaa taattataga ttctgattca 420
agttcagtag tatctagaat agcattaagg actgatgata ttccattagg agaacaaact 480
gtagctcagg tattccaaac ggccaaagaa cagctgaaat ggtcattgct gaaataa 537

<210> SEQ ID NO 116
<211> LENGTH: 450
<212> TYPE: DNA
<213> ORGANISM: Diabrotica virgifera

<400> SEQUENCE: 116
atggctgacc aactcaccga agaacaaatt gctgaattca aagaagcttt ctcactattc 60
gataaagatg gtgatggtac aattacgact aaagaattag gaacagtaat gagatctcta 120
ggacaaaatc caacagaggc tgaattacag gatatgatca atgaagtaga tgccgatggt 180
aacggcacga tcgatttccc agaattttta acgatgatgg cacgtaaaat gaaagatacc 240
gatagtgagg aagaaattcg tgaagcattc cgagtgttcg acaaagacgg caatggtttc 300
atctcagcag cagaattgcg ccacgtcatg accaacttgg gtgaaaaatt gacagacgaa 360
gaagtcgatg aaatgattcg ggaggccgat atcgatggtg atggtcaagt caattacgaa 420
gagttcgtca ccatgatgac ttcaaagtga 450

<210> SEQ ID NO 117
<211> LENGTH: 2013
<212> TYPE: DNA
<213> ORGANISM: Diabrotica virgifera

<400> SEQUENCE: 117

-continued

```
atgatgcaag caaacaatcg agtcccacct ataaagttgg aaaacgatat agatctttac     60

gccgatgata tcgaggattt cgcacaagat gactttggtg gtgaaaatgt tgatctatat    120

gacgatgtaa tatccgctcc tcctggaaat aatgacaacc caggtgattc aaatcatcat    180

gctcctcctg gtgctggtga agatggtgga ggtaattttg ttgggtcagg aggagcaccc    240

aataatataa attcttctgg aagaagacat cagctgtatg ttggaaatct gacttggtgg    300

acaactgatc aagatataga aaatgcagtg catgatatag ggtaaccga cttccatgaa     360

gttaagtttt ttgaacacag agcaaatggt caatccaagg gattctgtgt catatctttg    420

ggatctgagg gaagcatgag actctgcctg gaactcctat ctaaaaaaga gatcaatggc    480

caaaatcccc ttgttaccct tcccacaaaa caagctctta gtaactttga aagtcagtct    540

aaaacacgcc cttctcctac taataattct aactcacgtc ctccccatcc taataataat    600

gttcattcag gtcctatgca gaattatgga ggtagaatgc ctatgaaccc ttccatgcgt    660

cccatgcccc caggtatgca aggtgctcca agaatgcagg gtccacctgg atttaatgga    720

ccaccaaaca tgaatcagca accccccagg ttccaaggta atccacaatg gaatggacct    780

agacctaatg gtcctgggcc caatatggga atgagaccca tggggccacc tcatggacaa    840

caagggcccc caagaccacc aatgcaggga ccaccgcagc aaggtcctcc aagaggaatg    900

ccgccacaag gtccaccgca gatgcgtcca gaatggaatc gaccaccaat gcaacaaggg    960

taccctcaag gcccgccgca tatgcaagga cctaacatgg gtccaagagg tccaccccaa   1020

atgggaccac ccggggcgcc tcaacagcaa ggaccagctc cgcacgtaaa tccagcattc   1080

tttcaacaag gaggaggacc accgccccca atgcaacaca tgcctggacc agggcccgtc   1140

atgcctcctc aaggaccccc gcaaggtcca ccacacggac ccgttggacc tccacacggc   1200

ccaccattgg gtccagcgaa tgttccgcct catggaccac ctcacggata tggtccacct   1260

gcagcgatgc cacagccgcc atacggtggc ccacctccag accaccgcgc tgagattcct   1320

cagttaacag agcaagagtt tgaggatata atgtcccgga atagaacagt ttccagttcg   1380

gcgattgggc gggccgtatc cgacgccgca gctggagaat ttgcaagcgc cattgagact   1440

ttggttactg ctatttcact catcaaacaa tccaaagtgg ctaacgacga tcgttgcaag   1500

atccttataa gttcgctgca agatactttg cgtggtgtcg aagacaaaag ctacagctcc   1560

agccgcagag accggtcaag atccagggac agatcacata gaagaactag aagagaacga   1620

tcctcgtcac ggtacagaga cagaagcaga gagagggagc gtgaacgcga tagagatcgt   1680

gatcgtgaac gtgacagata ttatgataga tacagcgaaa gagaaagaga ccgagatcgt   1740

tcaagaagca gagaaagaac agaaagggat agagaacgag attatagaga ccgggaaccc   1800

gaagagacag ataaagaaaa atctaaagta tccagagtct caagatcaag aaacaaatct   1860

ccggaacctg tcgaacctag cagcgaggta ccgaaatcat cccgctatta tgaggatagg   1920

tatcgggaac gagagagaga aggtcgacga gagagcgatc gcgaaagaga aagagataga   1980

agaggggaag acagccatag gtctcgacac tag                                2013
```

<210> SEQ ID NO 118
<211> LENGTH: 765
<212> TYPE: DNA
<213> ORGANISM: Diabrotica virgifera

<400> SEQUENCE: 118

```
atgagttcta ttggaactgg gtacgattta tcagcttccc aattctctcc tgatggaaga     60

gtatttcaag ttgaatatgc aatgaaagca gttgaaaata gtggcaccgt aataggcctc    120
```

```
cgaggtacag atggcattgt attggctgct gaaaagctca ttatgtcaaa attgcatgaa    180

ccaagtacaa ataaacgaat tttcaacatt gataaacaca taggaatggc attttcaggc    240

ttaatagctg atgcaaggca aatcgttgag attgctagaa aagaagcatc aaattataga    300

catcaatatg gttcaaatat tcctcttaaa tacctaaatg atagagtaag catgtacatg    360

catgcataca ctttatacag tgctgttaga ccatttggtt gcagtgtcat cttggccagt    420

tatgaagata gtgacccatc tatgtatctg attgatccat ctggagttag ctatggatac    480

tttggatgtg ctacaggtaa agcaaaacag tctgcaaaga ctgaaataga aaaattgaag    540

atggggaatc taacatgcaa agaacttgtt aaagaagcag ccaaaatcat ttatttggtc    600

catgatgagc tgaaggataa gaattttgaa ctggaacttt catgggtatg caaagatacg    660

aatggtttac ataccaaagt gcctgaatca gtgtttgctg atgcagaaaa agctgccaaa    720

caagcaatgg aagcagattc agaatcagat acagaagata tgtaa                    765
```

<210> SEQ ID NO 119
<211> LENGTH: 744
<212> TYPE: DNA
<213> ORGANISM: Diabrotica virgifera

<400> SEQUENCE: 119

```
atggcttcaa aagacagatt gatgattttt ccatctagag gagcccaaat gatgatgaaa     60

tccaggctaa agggagccca aaagggacat agtttattaa agaagaaagc tgatgcttta    120

caaatgagat ttagaatgat tttgaacaaa attattgaga ccaaaactct catgggtgaa    180

gtaatgaaag aagctgcctt ttctttagct gaagcaaagt ttgcaactgg tgacttcaat    240

caagttgttc ttcaaaatgt caccaaggct caaataaaaa taagaactaa gaaagacaac    300

gttgctggtg ttactttacc agtgtttgaa tgctaccaag atggtacaga tacatatgag    360

ttggctggtt tggctagggg aggtcaacaa ttgacaaaac tcaagaagaa ttatcaaagt    420

gctgttaaac tgttggttga attagcctct ttgcaaactt cttttgtaac tcttgatgat    480

gtaatcaaaa taacaaacag aagagtcaat gccattgaac atgttatcat tccaagaata    540

gagcgtactt tggcttacat catatccgaa ctggacgagt tagaaagaga ggagttctat    600

agattaaaga agatccagga caaaaagaag atcagcagag caaaggccga gaaacaaaaa    660

caagctcttc tccaagctgg gctacttaaa gagtcccagg caaacatgct tttggatgag    720

ggcgatgaag atctactttt ctag                                           744
```

<210> SEQ ID NO 120
<211> LENGTH: 4818
<212> TYPE: DNA
<213> ORGANISM: Diabrotica virgifera

<400> SEQUENCE: 120

```
atggaggcgg ctcccaagtt accgatgctc tcgttcgagt taaatacttg tacagagaac     60

gtccactttg gcccccagtt aaaacagtat attgctgctt tttatggtga agatccagaa    120

tcctacatta cagaaatcag caatcttgaa tccttaagat cagctgcagt tcgaccatca    180

acggatgtaa atggtgtaca actgttgaaa aagtatttct gtcagcttcg ttttctcaaa    240

tctaggtttc ccatggaaga gaatcaagat gctgcagttc tattttcatg gaaaaataat    300

gaattagaca taacttcaac atccagtgat atcagatatg aattaatggt aataatgtat    360

aacattggag ccttacacac ttttcttgga gccaacgact caagaaacaa tccggatggt    420
```

-continued

```
atgaaaatgg catgtactca ttttcaatgt gctgcatggg cttttcaaaa cgtaaaagaa    480
aagtaccacc aattcatatc aaacatctca ttggtagaac tggttcattt ttttcaacaa    540
gtctgtttag ctcaggctca ggagtgtata ttagagaaga gcatgtttga caataggaaa    600
cctaccatca ttgcaaaagt tgctatccaa gtctacagtt attacagaca gtctttacgt    660
gtcttggaat cagtaaatga agcctacttt agggataaaa cctacaagga gtggatgaaa    720
tatcttcaat tcaagctgac ctactacaaa tgcatctcgt tcctattcca agggcaacaa    780
gctgaggaac aacagaaaat gggagaaagg gttgcattct atcaagctgc atgtgaacag    840
ctggacgagg caaagaaaat tgctgctaca ttaaaaaacc aacaccacca gcaagaaata    900
aatgagggac tagcattcac tactgatgtg gttgaaggta aaagaaaagc agctaaaaat    960
gaaaatgagt tcatctacca tgaatcagtg cctgataaag accaattgcc agaggttaag   1020
ggtgcttcat tagtcaaagg aataccattc agtataaatg atatagaagt ttcaggacca   1080
gatattttct cccgattggt cccaatggag gcacacgaag cagcttcctt gtacagcgag   1140
aagaaagctc agagattaag acagatcggg gaacttattg aaaataaaga tcaaacattg   1200
gctgaattta tgtcgtcaat gcagctagat ctattgacca agatgcacca ggctactgga   1260
ataccgcagg agttgattga tagagcagcg gctctatctg ctaaacctaa cgccattcaa   1320
gatcttataa gtgctatggg aaagctatct aatatatacc aagacgttga agcaagtttg   1380
aatgagattg attctttatt aaaggccgaa gaacaaagtg aacaaaagta ccaagaaacg   1440
attggtaaaa gaccaccgag cattttagct acagatttaa ctagggaagc ggcaaaatac   1500
agggaggctc atactaaagc gaacgactca aaccaaactt tacacagggc gatgatggct   1560
cacgtggcta atctgaaaat actccaacaa ccgctaaagc agctgcaaca tcagctgccc   1620
tttgtcgagt ttccaaatcc aaatatcgac gaaaaatctt tgaaagatct ggaagcgcta   1680
gttgcaaaag tagacgaaat gagaacccaa agagccatgc tatgggctca acttcgagaa   1740
tctattcacc aagacgatat tacaagttcc cttgtaacga aacaaccaaa tcagtcgctg   1800
gaacagctgt tccagcaaga acttcaaaag catcaaaatc tgatttcgtt gattgaacaa   1860
aacacctcgg cacaagaaaa cattaagagc gccttagtcg attcttacgc ttacgctgta   1920
aattcaagaa aatacatcca agatatactc caaaagagaa ccacaaccat aacgtcactg   1980
atagcatcgt tcgactctta cgaagactta ttggcaaaag ctaacaaagg gatagagttt   2040
tactcaaaac ttgaaacgaa cgtatccaag ttactgcaaa gaataaggag tacctgcaaa   2100
gttcaacaag aagagcgaga tcagatgatg tcgactgcgc aagtgcctca atgggagagt   2160
catacgtcac ttgccgctcc taaactgaaa gattacttgg actccaggaa gaagagtgct   2220
gcgtattcgg agccgagtgt tcaaccacaa cagccaactt taagttactc agctgctatg   2280
gatctgcctc ctggtattag gccgactcca gttggatcag aaataacgga tgtaccgaaa   2340
aatattcaag gtgaaccaca aggttatatt ccatataatt accaacaacc ttctgttcct   2400
gcctcacaga atattgatga agagactatt aaaaaaatga acgcattgat gccaggtgct   2460
aagacgtcag tgcctagtca gtacggatac agcaactaca ttccaccaac ataccctcaa   2520
agtgcgtacc aaccaggtaa tcagtcttac ggaaaagaaa ctccagatat taactcaccg   2580
tacgacccta ccaaggcgtt cacggctact actaacgctt atcgttcggt gcagagctcc   2640
tcaactcaag gatacgtacc gtacgcagaa tctaacgttt cgaatgttga cagagttgga   2700
tatcctagca ggtatcagta ccaacaagta cctgagatag ctactactcc agctgatccc   2760
aatattaatg cgtactaccc acatgggtac tcaccgagcc agaatttacc gaatgctaat   2820
```

-continued

```
actcaacata ttaccggcca actgaagtac cattcggtgg agtacgcttc ttctgtgccg   2880
aacaacatca attataacag ctctacctac tcgtcgccgc tttctaatat gtctagtacc   2940
aattcctcaa atcctagtaa cttgaataat tcttacgagt actactatga cccgaatacc   3000
agtagtggtg cagtaccgaa tgcttcaaag cctcaacagt cgagcgccag ctctgcaaac   3060
ccgagtaccg ctatgaacaa ctacaattat tactacaata caagtaccag cggtagtgta   3120
gcagcggata cttcaaaaat acaacaacaa caacagtacc caggtactca gatgagtcaa   3180
gcgcagtact atcccgccaa tgccagttat tactcaacca gtacttacaa taccaacgtc   3240
caaggtggta ccaatccctc gtacgcaact ggacaaacat ataatcaagt gacaccagtg   3300
acctctcaaa atgtttctca aaattacaac tttaaccaag ttggttctgg agcaggacac   3360
cagcatcagt actactcgtc cgctaacgcc gcagtaccat cccaacaagc tgtaaataac   3420
agttcattac caaactacgg atacgatcag tattacggca acaactataa ttccagtcaa   3480
ccgagtacct acagcgcaaa ccaagcacct cctgcagcac aagctgctcc aagtaatatt   3540
cctgctgcca ccaaatcctc ctctaatgtg gatctgctca gtggcttgga cttcagcata   3600
agccaagctc ctctagtgcc tcaacaaaac attacgataa aaccccaaga aaaggaaaca   3660
aaaccaccgg ctgtttcttc tgaaaccaaa aaccaagatc caacaccagt aaccacgccc   3720
aaacaaccca ctggaccaga agtaaagcgc ttgtacgtca aaatcctgcc gagcaaaccc   3780
ttaaacaacg atgatgtgaa gaaattgttc ggccaagagc tggacaggta tgagaagttc   3840
gtggagacct tgacccacaa aactttgagc ggtccgacca ctctggatat taaatggaag   3900
gagatccaag accagcagga ttgcgagccg cagaagaaga tcatttccgt cgctagatgt   3960
tatcctatga agaataggtt cccggatatc ttgccttacg acttttccag ggtggagttg   4020
tgcgatagta aagatgatta tatcaacgct tcatacatta aggatatctc gccatatgct   4080
ccgtcattta ttgttacaca agtgccgttg tcttcaactg ttggtgatat gtggacgatg   4140
attagagaac aacaggtcga actgatcctc tgtttggtaa acgacaatga gatcggtgaa   4200
gatatttact ggcccaaaga aaaaggcagt agtcttaaca tacttaacat ggtcataacg   4260
ttgcaaaacg ttatagttaa gtctcattgg actgaaagac tgatagcgat aaacttacct   4320
gaaaaacggg agtcccgtgt gataatgcat ctacaattta catcgtggcc tggcagcttg   4380
tttccaacaa atcctgaacc gttcgtcagc tacaccttgg aatccatcaa cctataccaa   4440
caacagaaga ccaacaccca tccggtggtg gtccattgtt catctggcat aggaagaagc   4500
ggcctgctct gtttactgac agctgctatg ttcgatgctg ccaacaatgc taactcgata   4560
ccagatctta cagctttgag tatcaagttg tccaattgca ggaagaatat tctcagagat   4620
cgagagcatt tgaagtttgg ttacgaaagt tttttggcgt atattaggca tatagtttgt   4680
gaagataaag ccagaaagaa actgaacgag atccagccca aggttaagga ggaaccactg   4740
gaaccacctg tcatagttcc agaaccaaat atagatcctt taagtacttt agacccattt   4800
tgggctagta aaagataa                                                 4818
```

```
<210> SEQ ID NO 121
<211> LENGTH: 478
<212> TYPE: RNA
<213> ORGANISM: Diabrotica virgifera

<400> SEQUENCE: 121

gguuucauga ccccugagag aaagaagaaa cuuagguuac uguugagaaa gaaagccgcc     60
```

-continued

```
gaagaauuaa agaaagaaca agaacgcaaa gcagccgaaa ggaggcguau cauugaagaa    120
aggugcggua aacccaaacu ugucgaugac gcaaaugaag gcccauuaaa acaaguaugu    180
gagggauauc acagacguau uguagaccua gaaaauaaga aauuugaccu cgaaaaagaa    240
guggaauuca gagauuuuca gaucuccgaa uugaacagcc aaguaaacga ccuuagaggc    300
aaauucguca aaccaaccuu gaagaaggua uccaaauacg aaaacaaauu cgccaaacuu    360
caaaagaagg cagcugaauu uaacuucccgu aaccaacuca aaguugucaa gaagaaagaa    420
uucaccuuag aagaagaaga caaagaaaag aaaccagacu ggucaaagaa gggagacg      478
```

<210> SEQ ID NO 122
<211> LENGTH: 529
<212> TYPE: RNA
<213> ORGANISM: Diabrotica virgifera

<400> SEQUENCE: 122

```
agaaguugcc gcuuuagucg uagacaaugg auccgguaug ugcaaagcug guuuugcugg     60
ggaugaugca ccucgugcug uauucccuuc aauuguugga cgcccaagac aucagggugu    120
gaugguagga augggacaaa aagauuccua uguaggugau gaagcucaaa guaaaagagg    180
uauccuuacc uuaaaauacc ccaucgagca cggaauaguc acaaacuggg augauaugga    240
gaaaauuugg caucauacau ucuacaauga acucagagua gccccagaag aacacccugu    300
ucuguugaca gaagcuccuc ucaaccccaa ggccaacagg gaaaagauga cacaaauaau    360
guuugaaacu uucaacaccc cagccaugua uguugccauc caggcuguac ucuccuugua    420
ugcaucuggu cguacaacug guauuguguu ggauucuggu gaugguguau cccacacugu    480
cccaaucuau gaagguuaug cucuuccuca ugcaauccuu cguuuggac                529
```

<210> SEQ ID NO 123
<211> LENGTH: 592
<212> TYPE: RNA
<213> ORGANISM: Diabrotica virgifera

<400> SEQUENCE: 123

```
accggccuuu guaugucuug ggauaugugc cuaaagacga uagauuauac cucguagaua     60
aagaguugcg cguaguaagc uaccaauuac uucuuucugu ucuugaauau caaacugccg    120
ucaugagaag agacuuucca acagcagaca gaguacuucc guccauuccu aaggagcaca    180
gaacgagagu ggcacauuuc uuagaaaagc aaggcuucaa acagcaagcu uuggccguaa    240
guacagaucc agagcacaga uucgagcugg caguagcauu agaggaucuu aauauagcca    300
aaacucuagc ucaagaagcg aacaguccgc aaaaguggaa ucaacuagca gaauuggcag    360
cugcuacuaa uaauguaagc guagccaagg aauguaugca aaaagcgcaa gauuauggag    420
gcuuguugcu ucuugcuacg agcuccggug augaaaauuu aguccguacu cuaggagaaa    480
cgacacaagc ugaaagcaaa cauaacuuag cauuuuuguc acacuuguua guaggugauu    540
uaaacaaaug ucuagacauu cuuauuaaua ccgguagauu gccagaagcu gc            592
```

<210> SEQ ID NO 124
<211> LENGTH: 594
<212> TYPE: RNA
<213> ORGANISM: Diabrotica virgifera

<400> SEQUENCE: 124

```
gaaagcaguu ggaagauggc cguacucucu cagacuacaa cauucaaaaa gagucuaccc     60
uccauuuggu acuucgucuu agaggaggua ugcagauuuu uguuaaaacu uuaacuggaa    120
```

agaccaucac ccuugaagua gaaccuucug auaccaucga aaaugucaaa gccaaaauuc 180
aagacaaaga agguauucca ccagaucaac aaagauuaau cuuugccgga aagcaauugg 240
aagauggucg uacacucuca gacuacaaca uucaaaagga aucuacccuc cauuugguac 300
uucgucuuag aggagguaug caaaucuuug uaaaaacacu cacugguaag accaucaccc 360
ucgagguuga accaucagau accaucgaga augucaaagc uaaaauucaa gacaaagaag 420
guauuccacc agaucaacag agauuaaucu ucgcuggaaa gcaguuggaa gauggccgua 480
cucucucaga cuacaauauu cagaaagagu cuacccucca uuugguacuu cgucuuagag 540
gagguaugca aaucuuugua aaaacucuca cugguaagac caucacccuc gagg 594

<210> SEQ ID NO 125
<211> LENGTH: 547
<212> TYPE: RNA
<213> ORGANISM: Diabrotica virgifera

<400> SEQUENCE: 125
uaccccauug aacacggaau uaucacuaac ugggacgaua uggaaaagau cuggcaucac 60
accuucuaca augaacuuag aguagccccc gaagaacauc ccauucuuuu gacugaagcu 120
ccacuuaacc caaaagccaa cagagaaaag augacucaaa ucauguuuga aacuuucaau 180
accccugcca uguauguugc cauucaagcu guauugucuc uguacgcuuc cggucguacc 240
acugguauug uacuugauuc uggagauggu guaucccaca caguacccau cuaugaaggu 300
uacgcucucc cacacgccau cuugcguuug gacuuggccg guagagacuu gacugacuac 360
cuuaugaaga ucuuaaccga aagagguuac ucuuucacca ccacagcuga aagagaaaua 420
guucgugaca ucaaggaaaa auugugcuau guagcuuugg acuucgaaca ggaaauggcc 480
acagcagcca gcuccaccuc cuuagaaaag aguuaugaac uuccugacgg ucaagucauc 540
accauug 547

<210> SEQ ID NO 126
<211> LENGTH: 592
<212> TYPE: RNA
<213> ORGANISM: Diabrotica virgifera

<400> SEQUENCE: 126
aggaaaggaa ggacccaaga ccaaacaacc aucgagauac auccguuuua ucuacaaucg 60
cgucauauug gaauguccuu cuguaagagc ugcugcaguc uccgccaugg cacaauucgg 120
agccucuugu cccgauuugu uagaaaauau ccaaauauua cuuucgaggu gucagaugga 180
uucagacgau gaaguuaggg acagagcuac auauuauagu aauauacuua acaaaaauga 240
uaaaaguuua uacaacaauu acauuuugga uucuuugcag guuucaauuc cuucacuaga 300
aagaucgcuu agagaauaca uucaaaaucc aacugacgaa ccauuugaca uuaaguccgu 360
accuguagca gcagugccaa cagcagaaga acgagaaguu aaaaacaaau cugaaggacu 420
gcuagucucu caagguccag uccgaccucc uccggugucu agagaagaaa acuucgccga 480
aaaacuuagu aacguuccgg guauacaaca guuaggaccu uuguucaaaa cuuccgacgu 540
cguugaacuc acugaaucug aaacagagua uuuuguccgc uguaucaagc ac 592

<210> SEQ ID NO 127
<211> LENGTH: 500
<212> TYPE: RNA
<213> ORGANISM: Diabrotica virgifera -continued

<400> SEQUENCE: 127
uacuaggcga aagugccguc gguaagucga guuugguacu gagguucguc aaaggacagu 60
uccacgaaua ccaggagagu accauaggag cagcuuuccu uacacaaacc auaugccucg 120
acgauacaac uguuaaauuu gaaauuuggg acacagcggg ucaagaaagg uaccacaguu 180
uagcuccuau guacuauagg ggcgcacagg cagcuauagu cgucuacgac auaaccaauc 240
aagacacauu cggcagggcg aaaacguggg ugaaggaacu ucaaaggcag gccaguccga 300
cgaucgugau agcuuuggcc ggcaacaagc aagauuuggc caacaaacgu augguagaau 360
acgaagaggc gcagacguau gcugacgaaa acggcuuacu uuuuauggaa acuuccgcaa 420
agacggcaau gaacgucaac gauauauuuu uagcaauagc uaagaaacug cccaagaaug 480
aacaaaccac aggucaaggc 500

<210> SEQ ID NO 128
<211> LENGTH: 189
<212> TYPE: RNA
<213> ORGANISM: Diabrotica virgifera

<400> SEQUENCE: 128
cgaugagguu gaaggaagga gaaaaauuuu gauggggcga aaaagcauua ccaggacaua 60
ucuucgugga aaugcuguuc cugcguaugu gauaauaauc cuuguaggaa uuggucaaau 120
cauccuggga gggauauugu acguugcauu gaggaagaag aucauugcug caccuguaac 180
ggcaucaua 189

<210> SEQ ID NO 129
<211> LENGTH: 393
<212> TYPE: RNA
<213> ORGANISM: Diabrotica virgifera

<400> SEQUENCE: 129
ugaggucgag cccucagaua cuaucgaaaa ugugaaagcu aaaauccagg auaaagaagg 60 aauucccccca gaccagcaac gucucaucuu cgcuggaaaa caacucgaag auggucguac 120
cuugucugac uauaauauuc aaaaagaauc aacccuucac uuggugguuga gauugagagg 180 aggugcuaag aaacguaaga agaagaauua cuccaccccc aagaaaauca agcacaagaa 240
gaagaagguu aaguuagcug uauugaaauu uuauaagguu gacgaaaaug guaaaaucca 300
ccgauugaga cgugaaugcc ccgcugaaca auguggagcu ggugucuuca uggcagccau 360
ggaagacagg cauuacugug gcaagugcgg uua 393

<210> SEQ ID NO 130
<211> LENGTH: 524
<212> TYPE: RNA
<213> ORGANISM: Diabrotica virgifera

<400> SEQUENCE: 130
ucuuugccuu uggcuacgau ucgaggaggg cauucaagaa uggcuccaga aauuggauuc 60
agaacaauuu uacaucggag uauauguacu uauagucgcu ucacugaucg ucaugauugu 120
guccuuuaua ggauguauua gugcccugca ggagaguacc auggcccuuu uaguguacau 180
cggcacccaa gugcucaguu uuauauucgg uuuauccggu ucggcgguuc uucuggauaa 240
cagcgccaga gauucccacu uccaaccgag gauccgagag aguaugcgac gucuuaucau 300
gaaugcucau cacgaccaau ccagacaaac acuagccaug auucaggaaa auguugguug 360
cugcggagcu gauggcgcaa cagacuaccu cucucuucag cagccccuuc caagucagug 420

```
cagagacacc guuacuggaa acccauucuu ccacggaugu guagaugaac ucaccugguu    480

cuucgaagaa aaaugugguu ggauagcagg uuuagcuaug gcga                     524


<210> SEQ ID NO 131
<211> LENGTH: 267
<212> TYPE: RNA
<213> ORGANISM: Diabrotica virgifera

<400> SEQUENCE: 131

ucgugcuggu uuacaauuuc cuguaggucg uauucaucgu uuauugagaa aaggaaauua     60

ugccgaaaga guuggugcug gagcuccugu auacuuggca gcuguuaugg aauauuuagc    120

ugcugaaguu uuggaauugg caggaaaugc agcuagagau aacaaaaaga cccguauaau    180

uccuagacau uuacaauugg ccauaagaaa ugacgaggaa uugaacaaau uacugucagg    240

aguuaccauc gcccaaggug gaguauu                                        267


<210> SEQ ID NO 132
<211> LENGTH: 558
<212> TYPE: RNA
<213> ORGANISM: Diabrotica virgifera

<400> SEQUENCE: 132

gugcaugaag uuggauggug uagaucugcc cccaccaauu agcuucgaca uugcggaaga     60

gcaaccguua ccaccuugcc aacagacguu cuuauguaau ggugauggag gauccauagu    120

gcgacaguuu cucgagcugu auuucguaau auaugauuca gauaauaggc agucccuucu    180

ucaggcauau cacgaaaaag ccacauuuuc aaugacaaug gccuacccgu acggcuauuc    240

caaagacagu aaaggaguau cgugguugaa uugguaugcc accgauaaua gaaauuuauu    300

acgaguucaa gauccagaca gaagaaacaa guuguuaaga cagggacaag uugcuguagu    360

uucguucuug caagauaugc cgcacacgaa gcacgauauu cacaguuuua caguagauuu    420

gacaguuuuu acaccccaga uguuauguuu gacaguggcu gguauguuua aagaauugaa    480

aaguggccac aaaguaccuc cuuuaagaua uuucuucaga acccuuguaa uuguaccugc    540

uggaucaggu uuuugcau                                                  558


<210> SEQ ID NO 133
<211> LENGTH: 582
<212> TYPE: RNA
<213> ORGANISM: Diabrotica virgifera

<400> SEQUENCE: 133

gauucggagc ccuacaauga aaugcaacua aaaauggauu uagaaaaggg ugagguuaaa     60

guaaaaauaa gagcauuaga aaaaauaauu cacaugauuc uggcaggaga aagguugccg    120

aauggauuuc uaaugaccau cauaagaaac guuuuaccuu uacaagauca uuuggcaaaa    180

aaacuauuau ugauuuucug ggaaauaguu ccaaaaacaa auccagaagg uaaacuacua    240

caagagauga uuuugguaug ugaugccuau agaaaagauc ugcaacaccc aaaugaauuu    300

uugagagguu cuacacuucg cuucuugugc aaacugaagg aaccagaauu guuggaacca    360

uuaaugccca guauuagagc uuguuuggau cauaggcaca gcuaugugag gaggaaugcu    420

guacuggcaa uuuuuaccau uuacaaaaau uuugaagccc ucauuccaga ugcuccugaa    480

cugaucucca auuauuugga uggugagcaa gacaugucuu guaaaagaaa ugcguuuuua    540

augcuucuuc augcugacca agaaagggcg uugucguauu ug                       582
```

<210> SEQ ID NO 134
<211> LENGTH: 458
<212> TYPE: RNA
<213> ORGANISM: Diabrotica virgifera

<400> SEQUENCE: 134
uuggcaaaaa ggaaaugagg auauugaugg uaggacucga ugcagcuggu aaaaccacaa 60
uuuuauauaa acuuaaauua ggagaaauug uaacaacuau uccaacaauu ggauuuaaug 120
uggagacugu agaauauaag aacauuaguu uuacaguaug ggauguaggu ggucaagaua 180
aaauuaggcc auuguggaga cacuauuucc aaaacacaca aggccuaauu uucguaguag 240
acaguaacga cagggaacgu aucacugagg cuaaagauga auuaaugcgu auguuggccg 300
aagaugaacu uagagaugcc guacuucuca uuuucgccaa caaacaagau uugcccaaug 360
caaugaacgc ugcagaaauc accgacaaac ucggucucca uucacuacgc aaccgcaacu 420
gguacauuca agcuaccugu gcaacuagcg gagauggu 458

<210> SEQ ID NO 135
<211> LENGTH: 592
<212> TYPE: RNA
<213> ORGANISM: Diabrotica virgifera

<400> SEQUENCE: 135
ggucgcgaaa gaacagaaag auuuuuugac cguaucugcc gauggaugcg uacaaguaac 60
aaaaccucuc gaccgagauc cgccuuucgg uagcccaaca cgacaagucu ucaucuaugc 120
ucgugauaau gauggaggca caaauucauu guuggccacu gcagaaauug aaauuauuuu 180
aauagauaua aacgauaaug cucccuuuuu aaauguuaca gaaauuguuu auuaugaaaa 240
ccaggaucca gguuuuauag guaaccuaag ugccgaugau uacgaugguc cugauaaugg 300
accuccguuu gcuuuucgau uaucagacac ugcuucagau aguauuagau cgaaauuuuc 360
cauuaucgga aaccagcuuu ucgcuuuaga aauguuugau agagaagagc aaaaauauua 420
ugacauugcc auugacauua cagauagugg aguaccucca cuaacaggaa cuaguauucu 480
uagaguuaua aucggagaug uaaaugauaa uccagcuaca gacggaaaca gcacgaucuu 540
uguguauaag uacgucaaug ggccagaaaa uuucauggaa aucggacgug ua 592

<210> SEQ ID NO 136
<211> LENGTH: 214
<212> TYPE: RNA
<213> ORGANISM: Diabrotica virgifera

<400> SEQUENCE: 136
gcauggggua ucauccaguu ggguuucaug gguguauucu auuacauugg ggcuguggcu 60
uuagcagaag auauuccaga gguugaguuu aagggcgauu uagacaaauu uuauagcgac 120
gucaacacgg guuucacaca gaaugcuuac aacugcugga uugcugcucu ccuauaccug 180
auaacauuag caguaucagc ucaccaauuc uggg 214

<210> SEQ ID NO 137
<211> LENGTH: 459
<212> TYPE: RNA
<213> ORGANISM: Diabrotica virgifera

<400> SEQUENCE: 137
uagaugccgc agguaaaacc acaaucuuau acaaauugaa gcuuggugaa aucguaacua 60
caauaccaac caucggcuuc aauguagaaa ccguugagua caagaauaua ucuuucacgg 120
uaugggaugu agguggccag acgagaauca gaaaacucug gagacacuau uucgccaaca 180
cugauggacu cauuuuugug guugauucca acgaccgaga ccguaucgcg gaagccgaag 240
aagaauugca caauauguua ggagaggacg auuuaagaga cugcauuuug uuaauauucg 300
ccaacaaaca agauuuaccg aacucgaugu ccacugcuga auugaccgau aagcuuaagu 360
ugcacacuuu gaagaauagg aggugguaca uacaagccac augugcuacu caagggaaug 420
guuuguacga aggacuagau ugguugucga augaauugg 459

<210> SEQ ID NO 138
<211> LENGTH: 536
<212> TYPE: RNA
<213> ORGANISM: Diabrotica virgifera

<400> SEQUENCE: 138
gcuacccuag cguccacugu aacacugauu uuugcccucu acuacugccu cacgggaaaa 60
ggagagcaag uuaguuuagc augguuauug uugaaugugu cuccccacau gugggcaggu 120
cuaggaauug gccuugcugu aucauuauca guuguaggag cugcugcagg aauucacacu 180
acaggaguca guaucguagg agcugguguu aaagccccca gaaucaaaac caaaaauuua 240
auuucuauua uuuucuguga agcuguggcu aucuaugggu uaauuauggc uauaguacuc 300
uguggaaguu ggaagaauuu cgauguagac cuauucaacc ucaaaacuca uaacuuugcu 360
caaaaccauu auggaucaca uguuauuuuu ggauccgguu uaacuguugg auuuguaaau 420
cuauuaugug gauuuugugu uggaguaguu gguucuggug cagccauuuc ugaugcagcc 480
aauucaucau uauucgucaa aauuuugauu auugagauuu uuggaagugc cauugg 536

<210> SEQ ID NO 139
<211> LENGTH: 547
<212> TYPE: RNA
<213> ORGANISM: Diabrotica virgifera

<400> SEQUENCE: 139
accuuauggg aaagcgugug gacuuuucug cacguacugu caucacacca gaucccaauu 60
uacguaucga ccaaguagga gugccuagaa guauugcuca aaacaugacg uuuccagaaa 120
ucgucacacc uuucaauuuu gacaaaaugu uggaauuggu acagagaggu aauucucagu 180
auccaggagc uaaguauauc aucagagaca auggagagag gauugauuua cguuuccacc 240
caaaaccguc agauuuacau uugcagugug guuauaaggu agaaagacac aucagagacg 300
gcgaucuagu aaucuucaac cgucaaccaa cccuccacaa gaugaguaug augggccaca 360
gagucaaagu cuuacccugg ucgacguucc guaugaaucu cucgugcacc ucucccuaca 420
acgccgauuu ugacggcgac gaaaugaacc uccaugugcc ccaaaguaug gaaacucgag 480
cugaagucga aaaccuccac aucacuccca ggcaaaucau uacuccgcaa gcuaaccaac 540
ccgucau 547

<210> SEQ ID NO 140
<211> LENGTH: 564
<212> TYPE: RNA
<213> ORGANISM: Diabrotica virgifera

<400> SEQUENCE: 140
cggaucucua uuuggggau caagucguau ugaagaugca guggaauguu acacaagagc 60
ugcaaaccuu uuuaaaaugg ccaagagcug ggaugcugcc gguaaagccu uuugugaggc 120

```
ugcuaauuug cauuccagaa cugguggcucg ucaugacgcu gccacuaauu auauagaugc    180

ugcaaauugu uacaaaaaag ccgauguauu ugaggcugua aacugcuuua uaaaagcuau    240

agacauuuau accgaaaugg gucgcuuuac aauggcugca aaacaccauc agacuauugc    300

agaaauguau gagacugaug cuguggacau cgaaagggcu guucaacacu augaacaggc    360

ggcugauuac uucagaggag aagaaagcaa ugcuuccgcc aauaaguguc uucuuaaagu    420

ggcucaauau gcagcccaac uugaaaacua ugaaaaagca gugggaauuu aucaagaagu    480

ggcuuaugca gcucuggaaa gcucucuuuu aaaauacagu gcaaaggaau acuuauucag    540

agcugcccuu ugucaccuuu gugu                                            564
```

<210> SEQ ID NO 141
<211> LENGTH: 564
<212> TYPE: RNA
<213> ORGANISM: Diabrotica virgifera

<400> SEQUENCE: 141

```
ugcugauugg agauucagga guaggaaaau cuugucuucu acugagauuu gcagaugaua     60

ccuacacaga aagcuauauu aguaccauug gcguagauuu uaaaaucagg acaaucgauu    120

uagauggaaa gacaauuaaa uugcaaauuu gggauacagc aggucaggaa agguuuagaa    180

cgauuacauc aaguuauuac cgaggagcac augguauuau uguaguguac gauugcacag    240

accaagauuc auucaauaac guuaaacagu ggcucgaaga aaucgaccgu uaugcgugug    300

acaauguaaa caaauuacug guagggaaua aaagcgauuu gacaacuaag aaaguugucg    360

acuucacuac agccaaggag uaugccgacc aauuggguau accauuuuug gaaaccucag    420

cuaagaaugc aaccaaugua gaacaggccu uuaugacuau ggccgcugaa auaaaaaaua    480

gaguaggacc uccaucuucu gcgguagacc aaggaaauaa gguuagguuc gaucaaaguc    540

gcccagucga aacaaccaaa uccg                                            564
```

<210> SEQ ID NO 142
<211> LENGTH: 502
<212> TYPE: RNA
<213> ORGANISM: Diabrotica virgifera

<400> SEQUENCE: 142

```
gagcuauagu ggacugcggg uucgaacauc cuucagaagu ucaacaugaa uguauuccuc     60

aagcugucau uggcauggau auucugugcc aagcuaaauc cgguauggga aaaacggcug    120

uuuuuguauu agcuacacuc caaguaauag auccuacaga aaauguugua uauguucucg    180

ucaugugcca uaccagagag uuagccuucc agauaagcaa agaguacgaa cguuucagua    240

aauauaugcc caauauuaaa guaggggucu ucuuuggugg cuugccuauc cagaaagaug    300

aggaaacguu aaaaaauaau ugcccgcaua ucguuguggg uacuccagga agaauuuuag    360

cauuggucag aucgaaaaaa cuuaaucuca aacaucuaaa gcauuuuauu uuggaugaau    420

gugauaaaau guuggaguua uuagacauga gacgugaugu ucaagaaaua uaucguaaca    480

cuccccacga aaaacaaguc au                                              502
```

<210> SEQ ID NO 143
<211> LENGTH: 505
<212> TYPE: RNA
<213> ORGANISM: Diabrotica virgifera

<400> SEQUENCE: 143

```
ugguagauuu ggcuaaccuc guauauuggu guuuaggucu uaauauuccg uacguuaguu     60
```

ucuaugauua uaaagguaau uuaaaaaagc augaagagaa guugcaacaa auuguagaau 120
ccagaaaauc agagaauauc aacauaauuu ggcacaccca ugcagaacaa aggcauaaaa 180
auggauuuuu ggguccaaaa auccacguaa aaguguuaac acacgcggac ggaaagcaaa 240
guauaguaaa uguuacuaaa aaauuagcuc uaaauaaaga aaaagacauu aguaaagaaa 300
aaauuaguga auuacuauua aggcaguaug aauuuccaga uccagaaaug gcuauuauuu 360
guggaaagaa acugaacauu uauaauuauc cuccuuggca guuaagacuc acagaauucu 420
uuaaagucaa caaagucaac aacaucacau ucccaguguu uguggaaaaa uuggaaaagu 480
acagcaaaug ugaacagagg guggg 505

<210> SEQ ID NO 144
<211> LENGTH: 410
<212> TYPE: RNA
<213> ORGANISM: Diabrotica virgifera

<400> SEQUENCE: 144
aaccagggau cuauuugccc gcaaguuuaa aaaacguggu guaauuccac uuuccacaua 60
uuugagaguc uacaaaguug gagauauugu agauaucaag gguaauggug caguucaaaa 120
ggguaugccc cacaaagugu accaugguaa gacaggacgu guuuucaaug uuacugcaca 180
ugcauuaggu guaauuguaa acaaaagggu ucgaggaaga aucaucccca aaagaaucaa 240
ucuccguauu gaacauguaa accacuccaa gugucgucaa gacuucuugc aaagaguaaa 300
auccaacgaa aagcuacgua aagaagcuaa agaaaagaac auuaaaguag aacuuaggag 360
acaaccugcc caaccuaggc cagcacauau uguuagcgga aagguuccag 410

<210> SEQ ID NO 145
<211> LENGTH: 467
<212> TYPE: RNA
<213> ORGANISM: Diabrotica virgifera

<400> SEQUENCE: 145
ugaugguaau agagugcugg cuaaauacua cgauaaagau auauuuccua cagcaaaaga 60
gcagaaagcu uuugagaaaa auuuguucaa uaaaacucau agggcagacg cagaaauuau 120
cauguuggau gguuuaacuu guguguauag aaguaaugua gauuuauucu uuuauguuau 180
gggcaguuca caugaaaaug agcuaauuuu aaugaguguu uuaaauugcu uguaugacuc 240
aguaagucaa auauugaaga aaaauaugca aaaacgagcu gucuuggaau cacuagauau 300
uguuaugcug gcuauggaug aaauuguuga uggaggaaua auuauagauu cugauucaag 360
uucaguagua ucuagaauag cauuaaggac ugaugauauu ccauuaggag aacaaacugu 420
agcucaggua uuccaaacgg ccaaagaaca gcugaaaugg ucauugc 467

<210> SEQ ID NO 146
<211> LENGTH: 368
<212> TYPE: RNA
<213> ORGANISM: Diabrotica virgifera

<400> SEQUENCE: 146
caccgaagaa caaauugcug aauucaaaga agcuuucuca cuauucgaua aagaugguga 60
ugguacaauu acgacuaaag aauuaggaac aguaaugaga ucucuaggac aaaauccaac 120
agaggcugaa uuacaggaua ugaucaauga aguagaugcc gaugguaacg gcacgaucga 180
uuucccagaa uuuuuaacga ugauggcacg uaaaaugaaa gauaccgaua gugaggaaga 240
aauucgugaa gcauuccgag uguucgacaa agacggcaau gguuucaucu cagcagcaga 300
auugcgccac gucaugacca acuuggguga aaaauugaca gacgaagaag ucgaugaaau 360
gauucggg 368

<210> SEQ ID NO 147
<211> LENGTH: 430
<212> TYPE: RNA
<213> ORGANISM: Diabrotica virgifera

<400> SEQUENCE: 147
uucgcacaag augacuuugg uggugaaaau guugaucuau augacgaugu aauauccgcu 60
ccuccuggaa auaaugacaa cccaggugau ucaaaucauc augcuccucc uggugcuggu 120
gaagauggug gagguaauuu uguuggguca ggaggagcac ccaauaauau aaauucuucu 180
ggaagaagac aucagcugua uguuggaaau cugacuuggu ggacaacuga ucaagauaua 240
gaaaaugcag ugcaugauau aggguaacc gacuuccaug aaguuaaguu uuuugaacac 300
agagcaaaug gucaauccaa gggauucugu gucauaucuu ugggaucuga gggaagcaug 360
agacucugcc uggaacuccu aucuaaaaaa gagaucaaug gccaaaaucc ccuuguuacc 420
cuucccacaa 430

<210> SEQ ID NO 148
<211> LENGTH: 505
<212> TYPE: RNA
<213> ORGANISM: Diabrotica virgifera

<400> SEQUENCE: 148
uaggaauggc auuuucaggc uuaauagcug augcaaggca aaucguugag auugcuagaa 60
aagaagcauc aaauuauaga caucaauaug guucaaauau uccucuuaaa uaccuaaaug 120
auagaguaag cauguacaug caugcauaca cuuuauacag ugcuguuaga ccauuugguu 180
gcagugucau cuuggccagu uaugaagaua gugacccauc uauguaucug auugauccau 240
cuggaguuag cuauggauac uuuggaugug cuacagguaa agcaaaacag ucugcaaaga 300
cugaaauaga aaaauugaag auggggaauc uaacaugcaa agaacuuguu aaagaagcag 360
ccaaaaucau uuauuugguc caugaugagc ugaaggauaa gaauuuugaa cuggaacuuu 420 caugguaug caaagauacg aaugguuuac auaccaaagu gccugaauca guguuugcug 480
augcagaaaa agcugccaaa caagc 505

<210> SEQ ID NO 149
<211> LENGTH: 548
<212> TYPE: RNA
<213> ORGANISM: Diabrotica virgifera

<400> SEQUENCE: 149
uccaucuaga ggagcccaaa ugaugaugaa auccaggcua aagggagccc aaaagggaca 60
uaguuuauua aagaagaaag cugaugcuuu acaaaugaga uuuagaauga uuuugaacaa 120
aauuauugag accaaaacuc ucaugggguga aguaaugaaa gaagcugccu uuucuuuagc 180
ugaagcaaag uuugcaacug gugacuucaa ucaaguuguu cuucaaaaug ucaccaaggc 240
ucaaauaaaa auaagaacua agaaagacaa cguugcuggu guuacuuuac caguguuuga 300
augcuaccaa gaugguacag auacauauga guuggcuggu uuggcuaggg gaggucaaca 360
auugacaaaa cucaagaaga auuaucaaag ugcuguuaaa cuguugguug aauuagccuc 420
uuugcaaacu ucuuuuguaa cucuugauga uguaaucaaa auaacaaaca gaagagucaa 480
ugccauugaa cauguuauca uuccaagaau agagcguacu uuggcuuaca ucauauccga 540
acuggacg 548

<210> SEQ ID NO 150
<211> LENGTH: 521
<212> TYPE: RNA
<213> ORGANISM: Diabrotica virgifera

<400> SEQUENCE: 150
gaucuggaag cgcuaguugc aaaaguagac gaaaugagaa cccaaagagc caugcuaugg 60
gcucaacuuc gagaaucuau ucaccaagac gauauuacaa guucccuugu aacgaaacaa 120
ccaaaucagu cgcuggaaca gcuguuccag caagaacuuc aaaagcauca aaaucugauu 180
ucguugauug aacaaaacac cucggcacaa gaaaacauua agagcgccuu agucgauucu 240
uacgcuuacg cuguaaauuc aagaaaauac auccaagaua uacuccaaaa gagaaccaca 300
accauaacgu cacugauagc aucguucgac ucuuacgaag acuuauuggc aaaagcuaac 360
aaagggauag aguuuuacuc aaaacuugaa acgaacguau ccaaguuacu gcaaagaaua 420
aggaguaccu gcaaaguuca acaagaagag cgagaucaga ugaugucgac ugcgcaagug 480
ccucaauggg agagucauac gucacuugcc gcuccuaaac u 521

<210> SEQ ID NO 151
<211> LENGTH: 633
<212> TYPE: RNA
<213> ORGANISM: Diabrotica virgifera

<400> SEQUENCE: 151
auggcggacg augagagaaa gaaacuggag gaggaaaaga agaggaaaca ggccgaaauu 60
gaacgcaaaa gggccgaggu cagggcucgu auggaagagg ccucaaaagc caagaaggcc 120
aagaaagguu ucaugacccc ugagagaaag aagaaacuua gguuacuguu gagaaagaaa 180
gccgccgaag aauuaaagaa agaacaagaa cgcaaagcag ccgaaaggag gcguaucauu 240
gaagaaaggu gcgguaaacc caaacuuguc gaugacgcaa augaaggccc auuaaaacaa 300
guaugugagg gauaucacag acguauugua gaccuagaaa auaagaaauu ugaccucgaa 360
aaagaagugg aauucagaga uuuucagauc uccgaauuga acagccaagu aaacgaccuu 420
agaggcaaau ucgucaaacc aaccuugaag aagguaucca aauacgaaaa caaauucgcc 480
aaacuucaaa agaaggcagc ugaauuuaac uuccguaacc aacucaaagu ugucaagaag 540
aaagaauuca ccuuagaaga agaagacaaa gaaaagaaac cagacugguc aaagaaggga 600
gacgaaaaga agguacaaga ggcugaagca uga 633

<210> SEQ ID NO 152
<211> LENGTH: 603
<212> TYPE: RNA
<213> ORGANISM: Diabrotica virgifera

<400> SEQUENCE: 152
augugugaag aagaaguugc cgcuuuaguc guagacaaug gauccgguau gugcaaagcu 60
gguuuugcug gggaugaugc accucgugcu guauucccuu caauuguugg acgcccaaga 120
caucagggug ugaugguagg aaugggacaa aaagauuccu auguagguga ugaagcucaa 180
aguaaaagag guauccuuac cuuaaaauac cccaucgagc acggaauagu cacaaacugg 240
gaugauaugg agaaaauuug gcaucauaca uucuacaaug aacucagagu agccccagaa 300
gaacacccug uucuguugac agaagcuccu cucaacccca aggccaacag ggaaaagaug 360
acacaaauaa uguuugaaac uuucaacacc ccagccaugu auguugccau ccaggcugua 420
cucuccuugu augcaucugg ucguacaacu gguauugugu uggauucugg ugauggugua 480
ucccacacug ucccaaucua ugaagguuau gcucuuccuc augcaauccu ucguuuggac 540
uuagcuggua gagacuugac ugauuaccuc augaaaauuu ugacugaacg uggcuacucu 600
uuc 603

<210> SEQ ID NO 153
<211> LENGTH: 2742
<212> TYPE: RNA
<213> ORGANISM: Diabrotica virgifera

<400> SEQUENCE: 153
augccacuuc gauuagauau aaaaagaaag cuaacagcuc gcucagaccg gguaaaaugu 60
guggaucuuc acccuacaga accuuggaug cuguguucuc uuuacagcgg aaauauaaac 120
guuuggaaca ccgaaaauca gcaacugguu aagacuuuug aaguauguga uguaccuguu 180
cggacagcua aguuuuugcc caggaagaac uggauaguca gugggucuga ugauaugcag 240
auucgaguuu ucaauuacaa uaccuuagau cggguacauu cuuuugaggc ucauucggau 300
uaugugagau guauugucgu acacccuaca caaccuuaua uauuaacaag uagugaugau 360
augcuuauca agcuuuggaa uugggaaaaa gcaugggcuu gucagcaagu uuucgaagga 420
cacacucauu auauuaugca aaucgccaua aauccaaaag acaacaacac auuugccagu 480
gcaucccuag auagaacauu gaaaguaugg caauugggag cguccacagc gaauuucaca 540
cuagaagguc augagaaagg cguuaacugu guggacuauu aucacggugg agauaaaccu 600
uauuuaaucu caggcgcuga ugauagauua guaaaaaucu gggauuauca aaacaaaacu 660
uguguucaaa cuuuggaagg acaugcucaa aauguaaccg cugcauguuu ccauccagaa 720
cuuccuguag cucuuacugg aagugaagau gguacuguca gaguguggca ugccaacacc 780
cauagguuag aaaguagcuu aaauuauggc uuugaaagag uauggacuau uuucugccua 840
aagggaucca auaacguggc auuggguuau gaugaaggua gcauuuuggu uaaaguuggu 900
agagaagaac cagcuguuag uauggaugcc aguggaggca aaauuauuug ggccagacac 960
ucugaacuuc aacaggcaaa ucucaaggcg uuagcugaag gugcggaaau aagagaugga 1020
gaacgccuuc caguuucugu aaaagauaug ggugcuugcg agauauaccc ucagacaauu 1080
caacacaauc ccaauggccg uuuuguuguu gucugugggg auggagaaua cauaaucuac 1140
acagcaaugg cuuuaagaaa caaagcguuu gguagcgcac aagaauuugu gugggcucaa 1200
gauuccagcg aauaugccau cagagaaucc ggaucuacua ucagaauuuu uaagaauuuc 1260
aaagagaaga agaauuuuaa guccgauuuu ggagcugaag guauauacgg uggauaccuu 1320
uugggaguca aaucgguuuc ugguuugacu uucuaugauu gggaaacucu cgauuuaguc 1380
agaagaaucg agauacaacc aaaagcaguu uacuggucag auaguggaa auuaguaugu 1440 uuggccacag aagauagcua cuuuauucuu ucuuaugauu cugaugaagu ucaaaaagcc 1500
agagauaaca aucagguugc ggaugaugga guagaaucgg cuuucaaucu ucuaggugaa 1560
auaaacgaau cagugcgaac uggucucugg guaggcgacu guuuuaucua cacgaauucu 1620
guuaaucgua ucaacuacuu cguuggaggu gaacugguua caauugcuca uuuggaccgg 1680
ccuuuguaug ucuugggaua ugugccuaaa gacgauagau uauaccucgu agauaaagag 1740
uugcgcguag uaagcuacca auuacuucuu ucuguucuug aauaucaaac ugccgucaug 1800
agaagagacu uuccaacagc agacagagua cuuccgucca uuccuaagga gcacagaacg 1860
agaguggcac auuucuuaga aaagcaaggc uucaaacagc aagcuuuggc cguaaguaca 1920
gauccagagc acagauucga gcuggcagua gcauuagagg aucuuaauau agccaaaacu 1980
cuagcucaag aagcgaacag uccgcaaaag uggaaucaac uagcagaauu ggcagcugcu 2040
acuaauaaug uaagcguagc caaggaaugu augcaaaaag cgcaagauua uggaggcuug 2100
uugcuucuug cuacgagcuc cggugaugaa aauuuagucc guacucuagg agaaacgaca 2160
caagcugaaa gcaaacauaa cuuagcauuu uugucacacu uguuaguagg ugauuuaaac 2220
aaaugucuag acauucuuau uaauaccggu agauugccag aagcugcauu uuucgccaga 2280
ucuuaccuuc cugauaagau uacagaaguc guggaacugu ggaagacuca guuaucuuca 2340
gucaaucaaa aagcuggaca gagccuugcc gauccuaaaa acuacgaaaa ucuguucccu 2400
gguuuacaag aggcgguggu agcucagaaa uuuuuggaac agcagaauaa agguuuagcg 2460
cccgcaagag uugccaccac cauuccuccu aaucacgaca ggaauguugu agccgaaguu 2520
caagcacaau cgaaacacga uguaccauca uuuaguucuu cguuuauuuc aucagaaaua 2580
gaagcacaaa caaggaguuc ugcuaaaccu gaagaaucuu caaacauuau acagcuggac 2640
caagaugacg acgauaucga uuuagauuug gacgguguaa auaucgauga gaacauugac 2700
acgacggaua ucaacaucga ugaugauuug cugagugauu ga 2742

<210> SEQ ID NO 154
<211> LENGTH: 1146
<212> TYPE: RNA
<213> ORGANISM: Diabrotica virgifera

<400> SEQUENCE: 154
augcagaucu uuguaaaaac acucacuggu aaaaccauca cccucgaggu ugaaccauca 60
gauaccaucg agaaugucaa agcuaaaauu caagacaaag aagguauucc accagaucaa 120
cagagauuaa ucuuugcugg aaagcaguua gaagauggcc guacucucuc agacuacaac 180
auucagaaag aaucuacacu acacuuagug cuucgucuua gaggagguau gcacaucuuu 240
guaaaaacuc ucacugguaa gaccaucacc cuugagguug aaccaucaga uaccaucgag 300
aaugucaaag cuaaaauuca agacaaagaa gguauuccac cagaucaaca gagauuaauc 360
uuugcuggaa agcaguugga agauggccgu acucucucag acuacaacau ucaaaaagag 420
ucuacccucc auuugguacu ucgucuuaga ggagguaugc agauuuuugu uaaaacuuua 480
acuggaaaga ccaucacccu ugaaguagaa ccuucugaua ccaucgaaaa ugucaaagcc 540
aaaauucaag acaaagaagg uauuccacca gaucaacaaa gauuaaucuu ugccggaaag 600
caauuggaag auggucguac acucucagac uacaacauuc aaaaggaauc uacccuccau 660
uugguacuuc gucuuagagg agguaugcaa aucuuuguaa aaacacucac ugguaagacc 720
aucacccucg agguugaacc aucagauacc aucgagaaug ucaaagcuaa aauucaagac 780
aaagaaggua uuccaccaga ucaacagaga uuaaucuucg cuggaaagca guuggaagau 840
ggccguacuc ucucagacua caauauucag aaagagucua cccuccauuu gguacuucgu 900
cuuagaggag guaugcaaau cuuuguaaaa acucucacug guaagaccau cacccucgag 960
guugaaccau cagauaccau cgagaauguc aaagcuaaaa uucaagacaa agaagguauu 1020
ccaccagauc aacaaagauu aaucuuugcc ggaaagcagu uggaagaugg ccguacucuc 1080
ucagacuaca acauucaaaa agagucuacc cuucacuugg uacuucguuu aagaggagga 1140
aauuaa 1146

<210> SEQ ID NO 155
<211> LENGTH: 1131
<212> TYPE: RNA
<213> ORGANISM: Diabrotica virgifera

<400> SEQUENCE: 155
augugugacg acgauguagc ggcucuuguc gucgacaaug gcuccggaau gugcaaagcc 60
gguuucgccg gugaugacgc cccucgugcu gucuuuccau ccaucguagg ucgucccaga 120
caccaaggug ucaugguggg uaugggucaa aaagacuccu acguaggaga cgaagcccaa 180
agcaaaagag guauccucac cuuaaaauac cccauugaac acggaauuau cacuaacugg 240
gacgauaugg aaaagaucug gcaucacacc uucuacaaug aacuuagagu agcccccgaa 300
gaacauccca uucuuuugac ugaagcucca cuuaacccaa aagccaacag agaaaagaug 360
acucaaauca uguuugaaac uuucaauacc ccugccaugu auguugccau ucaagcugua 420
uugucucugu acgcuuccgg ucguaccacu gguauuguac uugauucugg agauggugua 480
ucccacacag uacccaucua ugaagguuac gcucucccac acgccaucuu gcguuuggac 540
uuggccggua gagacuugac ugacuaccuu augaagaucu uaaccgaaag agguuacucu 600
uucaccacca cagcugaaag agaaauaguu cgugacauca aggaaaaauu gugcuaugua 660
gcuuuggacu ucgaacagga aauggccaca gcagccagcu ccaccuccuu agaaaagagu 720
uaugaacuuc cugacgguca agucaucacc auugguaaug aaagguuccg uugcccugaa 780
gcucucuucc aaccuuccuu cuuggguaug gaaucuugcg guauccacga aacugucuac 840
aacuccauca ugaagugcga ugucgacauc cguaaagacu uguacgccaa cacuguccuu 900
ucuggaggua ccacaaugua cccugguauu gccgaucgua ugcaaaagga aaucacugcc 960
uuggcuccau caaccaucaa aaucaagauc aucgcucccc cagaaagaaa guacuccguu 1020
uggaucggug gcuccaucuu ggccucccuc uccaccuucc aacagaugug gaucuccaaa 1080
caagaauacg acgaauccgg cccuggaauu guucaccgca aaugcuucua a 1131

<210> SEQ ID NO 156
<211> LENGTH: 2640
<212> TYPE: RNA
<213> ORGANISM: Diabrotica virgifera

<400> SEQUENCE: 156
auggguacuu uuaaaagaga uacucaugau gaggacgggg gaucaagugc uuuucaaaau 60
cuggagaaaa cuacuguuuu gcaggaagcu agaguuuuua augaaacuag uguaaaucca 120
agaaaaugua caccgauacu aacaaaacug uuguacuuau ugaaccaggg ugaaacuuua 180
agugccaaag aggccacaga uguuuucuuu gccaugacca aacuguucca aucaaaagau 240 guaaauauuga gaaggauggu uuauuuggga auuaaagaac ucaguucugu ugcugaugau 300
gucauuauug uaacauccag ucuuacaaaa gauaugacug guaaagaaga cauguacaga 360
gcagcugcua uaagagcauu augcaguauu acugaugcua cuaugcuuca agcuauagaa 420
cguuauauga agcaagcuau uguagauaga aacgcagcug ucaguucagc agcacuaauu 480
aguucauuac auaugagcaa auuagcucca gauguaguaa aaagaugggu aaaugaagcu 540
caggaagcag uaaauaguga uaaugcaaug guacaguauc acgcauuagg ucuucuauac 600
cauauuagga agacugauaa gcuagcagug acaaaauuga uuuccaagcu gaauucaaug 660
gguuuaaaga gcccuuaugc uuuguguaug uugauaagaa ucacugcaaa acuuuuagaa 720
gaagaggacc aagagucacu ccucaacucc ccauauacaa uaauauuuac aaugggcuua 780
aggaacaaau cugaaauggu gguguaugaa gcugcacaug ccaugguuaa ccugaaguuc 840
acgaguagua augugcuagc acccgcuaua aguguucuac aacuauuuug uggaucuccu 900
aaagccacac ucagauuugc ugcuguuaga acuuuaaauc aaguggccac cacccacccu 960
gcgucaguga cagcuuguaa uuuggaucua gaaaauuuga uuacugaucc uaauagguca 1020
auugcuacac uggccauuac uacucuuuug aaaacaggug ccgaaucuuc uguugacaga 1080
cuaaugaaac aaaucgcuac uuuuguaucu gaaaucagug augaauuuaa agugguuguc 1140
auucaggcaa uuaagguauu agcuuugaaa uuuccaagga aacauagcac gcuuaugaau 1200
uuccuauccg ccauguuaag agaugaggga gguuuagaau auaaagcauc cauagcagau 1260
accauuauaa cccuaaucga agauaauccc gaagcuaaag aaucugguuu ggcgcaucuu 1320
ugcgaguuca uugaagacug ugaacauguu ucuuuggcug ugagaaucuu gcauuuguua 1380
ggaaaggaag gacccaagac caaacaacca ucgagauaca uccguuuuau cuacaaucgc 1440
gucauauugg aauguccuuc uguaagagcu gcugcagucu ccgccauggc acaauucgga 1500
gccucuuguc ccgauuuguu agaaaauauc caaauauuac uuucgaggug ucagauggau 1560
ucagacgaug aaguuaggga cagagcuaca uauuauagua auauacuuaa caaaaaugau 1620
aaaaguuuau acaacaauua cauuuuggau ucuuugcagg uuucaauucc uucacuagaa 1680
agaucgcuua gagaauacau ucaaaaucca acugacgaac cauuugacau uaaguccgua 1740
ccuguagcag cagugccaac agcagaagaa cgagaaguua aaaacaaauc ugaaggacug 1800
cuagucucuc aagguccagu ccgaccuccu ccggugucua gagaagaaaa cuucgccgaa 1860
aaacuuagua acguuccggg uauacaacag uuaggaccuu uguucaaaac uuccgacguc 1920
guugaacuca cugaaucuga aacagaguau uuuguccgcu guaucaagca cuguuucaaa 1980
caucacaucg uccuccaauu cgauugucug aauaccuugc cagaccagcu uuuagaaaac 2040
guuagagugg agauagacgc cggugaaacc uucgaaauuu uggcagaaau accuugugaa 2100
aaguugcacu auaacgaaac cgguaccaca uauguaguag uuaaguugcc ugaugaugau 2160
cuccccaacu cuguugguac guguggagcc guguugaagu ucuuagugaa agauugugau 2220
ccaucaacgg gaauaccaga uucugaugag gguuacgaug augaauauac acuggaagac 2280
aucgaaauaa cauuagggga ccaaauucaa aaaguaagca aaguaaauug ggcugcagcc 2340
ugggaagaag cugcagcuac uuauguagaa aaagaggaua cauacuccuu gaccaucaau 2400
acgcuaagug gcgcuguuaa gaauauuauu caguucuugg gauuacagcc ugcggaaagg 2460
acugacagag uaccggaggg uaaaucuacg cacacauuac uucuugcugg uguauucagg 2520
ggagguauug acauacuagu aagagcgaaa cuagcuuugg gcgaaugugu uacgaugcaa 2580
cuaacaguca ggucgccaga uccugacguu gcugagcuua uaacuucaac uguagguuaa 2640

<210> SEQ ID NO 157
<211> LENGTH: 651
<212> TYPE: RNA
<213> ORGANISM: Diabrotica virgifera

<400> SEQUENCE: 157
auggcggcaa acagaacugg accugcucag agaccaaaug gcgcuaccca aggaaagaua 60
ugucaguuca aacugguccu acuaggcgaa agugccgucg guaagucgag uuugguacug 120
agguucguca aaggacaguu ccacgaauac caggagagua ccauaggagc agcuuuccuu 180

-continued

```
acacaaacca uaugccucga cgauacaacu guuaaaauug aaauuuggga cacagcgggu    240

caagaaaggu accacaguuu agcuccuaug uacuauaggg gcgcacaggc agcuauaguc    300

gucuacgaca uaaccaauca agacacauuc ggcagggcga aaacgugggu gaaggaacuu    360

caaaggcagg ccaguccgac gaucgugaua gcuuuggccg gcaacaagca agauuuggcc    420

aacaaacgua ugguagaaua cgaagaggcg cagacguaug cugacgaaaa cggcuuacuu    480

uuuauggaaa cuuccgcaaa gacggcaaug aacgucaacg auauauuuuu agcaauagcu    540

aagaaacugc ccaagaauga acaaaccaca ggucaaggcg gcagugccca aggcaggcgg    600

cuagcggagg gcgauucggg cgccaaggca cccggaaauu guugcaagug a             651
```

<210> SEQ ID NO 158
<211> LENGTH: 279
<212> TYPE: RNA
<213> ORGANISM: Diabrotica virgifera

<400> SEQUENCE: 158

```
augaaguuuu uaagaucgac agugugcuac auugccaucu uggcaauucu cuuuacccuc     60

ugugccgaug agguugaagg aaggagaaaa auuuugaugg ggcgaaaaag cauuaccagg    120

acauaucuuc guggaaaugc uguuccugcg uaugugauaa uaauccuugu aggaauuggu    180

caaaucaucc ugggagggau auuguacguu gcauugagga agaagaucau ugcugcaccu    240

guaacggcau cauaugcagu ggcuagacaa gaaccauaa                           279
```

<210> SEQ ID NO 159
<211> LENGTH: 474
<212> TYPE: RNA
<213> ORGANISM: Diabrotica virgifera

<400> SEQUENCE: 159

```
augcagaucu ucguuaaaac cuuaacgggu aagaccauca cucuugaggu cgagcccuca     60

gauacuaucg aaaaugugaa agcuaaaauc caggauaaag aaggaauucc cccagaccag    120

caacgucuca ucuucgcugg aaaacaacuc gaagaugguc guaccuuguc ugacuauaau    180

auucaaaaag aaucaacccu ucacuuggug uugagauuga gaggaggugc uaagaaacgu    240

aagaagaaga auuacuccac ccccaagaaa aucaagcaca agaagaagaa gguuaaguua    300

gcuguauuga aauuuuauaa gguugacgaa aaugguaaaa uccaccgauu gagacgugaa    360

ugccccgcug aacaaugugg agcuggugu c uucauggcag ccauggaaga caggcauuac    420

uguggcaagu gcgguuacac ucuugucuuc uccaaaccag gagaugagaa auag          474
```

<210> SEQ ID NO 160
<211> LENGTH: 747
<212> TYPE: RNA
<213> ORGANISM: Diabrotica virgifera

<400> SEQUENCE: 160

```
augaugucca aagcagacac acaggaagau gccuccuucg ccaaauugga aaaucagauu     60

gcuaucauca aauacguaau acucuuuacc aacguuuugc aaugggcucu cggugcagca    120

aucuucgcuc uuugccuuug gcuacgauuc gaggagggca uucaagaaug gcuccagaaa    180

uuggauucag aacaauuuua caucggagua uauguacuua uagucgcuuc acugaucguc    240

augauugugu ccuuuauagg auguauuagu gcccugcagg agaguaccau ggcccuuuua    300

guguacaucg gcacccaagu gcucaguuuu auauucgguu uauccgguuc ggcgguucuu    360

cuggauaaca gcgccagaga uucccacuuc caaccgagga uccgagagag uaugcgacgu    420
```

cuuaucauga augcucauca cgaccaaucc agacaaacac uagccaugau ucaggaaaau 480
guugguugcu gcggagcuga uggcgcaaca gacuaccucu cucuucagca gccccuucca 540
agucagugca gagacaccgu uacuggaaac ccauucuucc acggaugugu agaugaacuc 600
accugguucu ucgaagaaaa augugguugg auagcagguu uagcuauggc gauaugcaug 660
auuaacgucc uuaguauugu uuuaucuacg guacucaucc aggcauugaa aaaagaagaa 720
gaagcauccg auucauacag gagauag 747

<210> SEQ ID NO 161
<211> LENGTH: 375
<212> TYPE: RNA
<213> ORGANISM: Diabrotica virgifera

<400> SEQUENCE: 161
augucuggac guggcaaggg aggcaaagua aagggaaaag caaagucccg aucaaaucgu 60
gcugguuuac aauuuccugu aggucguauu caucguuuau ugagaaaagg aaauuaugcc 120
gaaagaguug gugcuggagc uccuguauac uuggcagcug uuauggaaua uuuagcugcu 180
gaaguuuugg aauuggcagg aaaugcagcu agagauaaca aaaagacccg uauaauuccu 240
agacauuuac aauuggccau aagaaaugac gaggaauuga acaaauuacu gucaggaguu 300
accaucgccc aagguggagu auugccuaau auacaagcag uacuguuacc uaaaaaaacu 360
gaaaagaaag cuuaa 375

<210> SEQ ID NO 162
<211> LENGTH: 864
<212> TYPE: RNA
<213> ORGANISM: Diabrotica virgifera

<400> SEQUENCE: 162
augaaguugg augguguaga ucugccccca ccaauuagcu ucgacauugc ggaagagcaa 60
ccguuaccac cuugccaaca gacguucuua uguaauggug auggaggauc cauagugcga 120
caguuucucg agcuguauuu cguaauauau gauucagaua auaggcaguc ccuucuucag 180
gcauaucacg aaaaagccac auuuucaaug acaauggccu acccguacgg cuauuccaaa 240
gacaguaaag gaguaucgug guugaauugg uaugccaccg auaauagaaa uuuauuacga 300
guucaagauc cagacagaag aaacaaguug uuaagacagg gacaaguugc uguaguuucg 360
uucuugcaag auaugccgca cacgaagcac gauauucaca guuuuacagu agauuugaca 420
guuuuuacac cccagauguu auguuugaca guggcuggua uguuuaaaga auugaaaagu 480
ggccacaaag uaccuccuuu aagauauuuc uucagaaccc uuguaauugu accugcugga 540
ucagguuuuu gcauagcaaa ugaagaacuu cacauaucca augcaacucc ggaccaagca 600
aaagaugcuu ucaagaccac cguuaaugua gcuccggcac cagccccugu gauuaccucu 660
ccuggaccca guauaccaca acccgcugug ccagaugaug cuacaaaaca agaaauggua 720
aaacagaugu ccgcaguauc cggaaugaau cucgaguggu cgcuacagug ucucgaagaa 780
acacaauggg acuaccagaa agccauaaug guauuccaaa auuuaaacgc acaagguguu 840
guaccacaag cagcauuuau uaaa 864

<210> SEQ ID NO 163
<211> LENGTH: 2868
<212> TYPE: RNA
<213> ORGANISM: Diabrotica virgifera

<400> SEQUENCE: 163
augacugcgg uagaacaacc uuguuacaca cuaauaaacu ugccaacaga uucggagccc 60
uacaaugaaa ugcaacuaaa aauggauuua gaaaagggug agguuaaagu aaaaauaaga 120
gcauuagaaa aaauaauuca caugauucug gcaggagaaa gguugccgaa uggauuucua 180
augaccauca uaagaaacgu uuuaccuuua caagaucauu uggcaaaaaa acuauuauug 240
auuuucuggg aaauaguucc aaaaacaaau ccagaaggua aacuacuaca agagaugauu 300
uugguaugug augccuauag aaaagaucug caacacccaa augaauuuuu gagagguucu 360
acacuucgcu ucuugugcaa acugaaggaa ccagaauugu uggaaccauu aaugcccagu 420
auuagagcuu guuuggauca uaggcacagc uaugugagga ggaaugcugu acuggcaauu 480
uuuaccauuu acaaaaauuu ugaagcccuc auuccagaug cuccugaacu gaucuccaau 540
uauuuggaug gugagcaaga caugucuugu aaaagaaaug cguuuuuaau gcuucuucau 600
gcugaccaag aaagggcguu gucguauuug gcaucauguu uagaucaagu aaauucauuu 660
ggagauauuc uacaacuggu caucguugag uugauauaua agguguguca uuccaauccu 720
gcggaaagau cuagauuuau uagauguaua uauaacuugu ugaacucaag caguccugcu 780
gucagguacg aagcugcagg aacuuuaguc acccucucca gugccccgac ugccguuaaa 840
gcugcugcua gcuguuacau ugaguuaauu aucaaagaaa gugacaacaa uguaaaacuc 900
aucguuuugg acaggcugau agcacuuaag gagcuuccua aucacgaaag aauucugcag 960
gauuuaguua uggacauacu gagaguacuc ucugcuccug acuuagaagu ccgcaagaag 1020
acuuuaaguc uagcccuuga auuagucucu ucacggaaca uagaagaaau gguauuagua 1080
uuaacaaagg aagugaguaa aacgguagac agugaacaug aggauacagg aaaguacagg 1140
caauuguuag uaaggacucu acauucgugu uccauuaagu ucccagauau cgcacguagu 1200
guuauaccag ucuugauuga auuuuuaucc gauaauaaug aacuggcugc cacagaugua 1260
uugcuguucu uaagggaagc cauacagaag uuuaaagaau ugcaaccguu aauuauugag 1320
aaacucaucg aaacuuucaa agacauuaaa uuggucaaag uccauagagc agcaauuugg 1380
auuuugggag aauacgcgag uacugcuucc gauauagaag uuaucguugg agaaauuaac 1440
agauuguugg gugaaggauc ccucguugaa gcugagcaga aguuaauagc aggagauacg 1500
gaagagaaug cuccugcacc ugcugcaggc gccaccacuu uaguuacuuc cgauggaaca 1560
uaugcuaccc aaucagcuuu caacacuguc agccaaacca cuaaagaagc acgaccuccu 1620
cuaagacaau accucaugga uggugauuuu uucaucggag ccucuuuggc aucuacauua 1680
accaaacugu cuuugcggua ugaggaccuc accucuccug cugcuagcaa uggauucaau 1740
gccaaaauua ugcuuauuau ggcuggaauu cuucacuugg gaaaaucagg acuucccaca 1800
aaaucaauaa ccaacgacga uaaagaccac auucuguucu guuuacgagu ccuaucugau 1860
cguucuccaa ucauuguuga aauuuucaaa aaauugugcc gcucggcacu aaaugagaug 1920
cuucuagcua aggaaucggu agaagcgauc ucgcaaaaga gcaaagaaaa aaacaagcgu 1980
acgauucaaa cugacgacgc uauaagcuuc cugcaauuag agacagauaa aaguggagag 2040
cuaggagaaa acguauucga gaugucgcug ucacaagcuu uaguaggagg ucgaacggga 2100
gguggcgaau caguauuaag uuccaauaaa uuagauaaaa ucacacaacu gacugguuuu 2160
uccgauccag uuuauuccga agcauacguu cacgugaauc aguacgauau cgugcuugau 2220
gucuuaaucg uaaaccaaac uaacgauacu uuacaaaacu gcacgcuaga gcuggcuacu 2280
uuaggcgauu ugaaguuggu agagaagcca caaccugucg uauuggcgcc caaagacuuu 2340

```
ugcaacauua aagcuaacgu gaaaguggcc ucaacugaaa acggaauuau auuuggcaac   2400

auuguguaug augucauagg agcgggguca gauaggaaug uuguaguuuu gaaugauaua   2460

cacauagaua uaauggacua uauagugccu gcuaguugua cagauagcga guuuaugaga   2520

augugggcgg aauuugaaug ggaaaauaag guaaccguua acacaccccu cacggaacuu   2580

ucagaauacc ucgaacaucu acucaaaagc acaaauuuga aauguuuaac aucagaaaaa   2640

gcucugagcg ggcagugugg uuuuauggca gccaauuuau augcaaaauc cauuuuugga   2700

gaagacgcuu uggccaacuu aaguauagag aaaccuuuua auaaacccga ugcgccagua   2760

agcggucaua uuagaauaag ggccaaaagu cagggcaugg ccuuaaguuu aggagacaaa   2820

gucaauauga cacagaagag cacacaacau aaaguaguag cugcauaa               2868
```

<210> SEQ ID NO 164
<211> LENGTH: 549
<212> TYPE: RNA
<213> ORGANISM: Diabrotica virgifera

<400> SEQUENCE: 164

```
auggguaaug uguuugcaaa uuuauucaaa ggccucuuug gcaaaaagga aaugaggaua     60

uugaugguag gacucgaugc agcugguaaa accacaauuu uauauaaacu uaaauuagga    120

gaaauuguaa caacuauucc aacaauugga uuuaaugugg agacuguaga auauaagaac    180

auuaguuuua caguauggga uguaggugguu caagauaaaa uuaggccauu guggagacac    240

uauuuccaaa acacacaagg ccuaauuuuc guaguagaca guaacgacag ggaacguauc    300

acugaggcua aagaugaauu aaugcguaug uuggccgaag augaacuuag agaugccgua    360

cuucucauuu ucgccaacaa acaagauuug cccaaugcaa ugaacgcugc agaaaucacc    420

gacaaacucg gucuccauuc acuacgcaac cgcaacuggu acauucaagc uaccugugca    480

acuagcggag auggucucua ugaaggucug gacugguugu ccaaucaauu aaagaacgcc    540

aaucgcuag                                                          549
```

<210> SEQ ID NO 165
<211> LENGTH: 4425
<212> TYPE: RNA
<213> ORGANISM: Diabrotica virgifera

<400> SEQUENCE: 165

```
augggacggu ugcacuguuu auuuuguauu uuccuauguu uuaccgucau caacacgcag     60

acaacgaaua uacauggauu cucggaaaau uccguggaua cauuucuauc accucauggg    120

aaaagugcaa aauucgugca ccaaaaucac aaacccaaaa uugaaaauug ucagaacuac    180

aaacccucgg ugaaagaaga acagccaggc ggaacguacg uaacaacggu uaccgcuauc    240

gaugacgauc cuagggaggg aggaggaaca auuaguuaca aacuaauuca uagagaagga    300

gaacauguuu uauuugacau agacaacguu acuggugguuu ugacaacuau ccagccauuu    360

gaucgggaug aaccaguaag gcagaaggaa cuuuauguaa ccguacaagc uucagacaac    420

ggcaggccac cauuagcaga ugucuguaca uuuacaguua ccauuaccga cauuaaugau    480

aaugcgccac agcuugauaa acugaaauac gaugcacaag uuucugaaga uuuaaaagua    540

ggaagugaag ugaugagagu uuuugcuuac gacauugaug augggggaaaa uucaagauua    600

ucguauaacu uuucaaacga aaaugcucaa uucacccagu auuucaggau agaucgagau    660

acuggcguug uguauuuaaa ggaagcuuua acagacaaaa agaauacuag auuuaacagu    720
```

-continued

```
gcuguuuaug uagccgauaa uggcguuaac gaucaagaag gccaaaaaga uucaaccgcu    780
aagauaucua uaacaguagu agggucugau aaacagccuc ccagauuuac ucaaaaaaug    840
ccugauggaa ucuuggagau ccccgaagau uuuaaagacu uuucuaaaca uauugucaca    900
gucgaagcaa cguccaacau ugcggaucca caacuugcuu uugaauuggu gaagggaaag    960
acauaucaaa ccaauaaaga ccaaacguuu cuuuuggagg cagaaggaaa uaaagcgcac   1020
auaaagcuag ugcguccacu ggauuaugaa acaguaacgg aauauacucu aacuauucga   1080
guaaaaaaca aagauuuaau ggauucuucc auaaauauac caauuaaagu auuagauguu   1140
aaugaugaaa uuccuaauuu ccuugaauuu cuuaaaggua gugucgugga aaaugacaag   1200
ccaggugcac aagcgauuca aguaagagca aucgauaaag acggaacugc ugcuaacaac   1260
auugugagcu augaacucgu ugacaauaca gauuuguuug caauaaaccg aucuacggga   1320
guaauuacgu cgagagugga guuugaucgu gaaacuguac cucuauauca cguaaacguu   1380
aaagcuuaug auaacucucc gucugcuuug uauaacacga cauugccuaa cauuguaauu   1440
cagacauucc aaaucaguau agaagaucaa aaugacaaca aaccuguauu uacucaucca   1500
auuuaucagu ucaguaauau uacugagcuu gcugauaaau cgaguauugu uggugaaguc   1560
aaagcuuuag auaaugacac ggcuucaguu auaaguuaua guauuacaaa uggaaauauu   1620
gacgaugcgu uuaugauuga aaauucuacc ggcagaauaa gaguuaaugg aaaacuggau   1680
uacgagaaaa ucgaacaaua caacuuaacc guucgcgcau uugaugggc auuugaagau    1740
uuugcaauug uuuuaauuuc cauacuuaau gaaaaugacg aaccuccagu uuuugacgac   1800
uauaucagag aaauucaaau uaaagaggaa gaaccuauga uauccggaug cguuguuaga   1860
gugacugcuc augauccaga uauuaaagac aggcaugcug aucaacacau aguauaugag   1920
gucgcgaaag aacagaaaga uuuuuugacc guaucugccg auggaugcgu acaaguaaca   1980
aaaccucucg accgagaucc gccuuucggu agcccaacac gacaagucuu caucuaugcu   2040
cgugauaaug auggaggcac aaauucauug uuggccacug cagaaauuga aauuauuuua   2100
auagauauaa acgauaaugc ucccuuuuua aauguuacag aaauuguuua uuaugaaaac   2160
caggauccag guuuuauagg uaaccuaagu gccgaugauu acgauggucc ugauaaugga   2220
ccuccguuug cuuuucgauu aucagacacu gcuucagaua guauuagauc gaaauuuucc   2280
auuaucggaa accagcuuuu cgcuuuagaa auguuugaua gagaagagca aaaauauuau   2340
gacauugcca uugacauuac agauagugga guaccuccac uaacaggaac uaguauucuu   2400
agaguuauaa ucggagaugu aaaugauaau ccagcuacag acggaaacag cacgaucuuu   2460
guguauaagu acgucaaugg gccagaaaau uucauggaaa ucggacgugu auauguuaca   2520
gaccuagacg auugggauuu aaaugacaaa gucuuuguuc aagaagauaa cuuugaugaa   2580
uuuguguuaa accagcauaa caacgguaug auucugauga aaccaacaac ggcugaggga   2640
acuuaugagg uucauuacag ggucacugaa acccaugaac ccacaauaca cgaacauaca   2700
guuaaugcaa uagucacgau uacaguuaaa guacuuccag aggaagcggu uguaaaauca   2760
ggaucaauuc gauugagagg aacaacuaag gaagaauuca uagaaaauuc auugaaugga   2820
aagagcaaaa gagacauauu acaccaagaa cucuccaaaa uauuaaauac aucuuuagcg   2880
aauguugaug uauuuacugu uuuaaauuca ccccaccaga auaguucguu uguggauguu   2940
cgauuuucug cucauggauc uccauauuau gcuccagaga aacucgaaaa caaaguuaca   3000
gaucaucaaa uggagcuuga acaaaaauua gauguggaau ucuacaugau caacguaaac   3060
gagugccuua acgaaacaac guguggagcu gaaaacucau guacgaacaa auuaaacaua   3120
```

acacgagaac cagcuguagu guuuacuaac agaacauccu uugucggugu aaaugcauuu 3180
auugauccug ugugugccgc uuuaccaaga gauguuaugg aauguuucaa cggaggcguc 3240
cuuaucgaaa acacagcgug uaauuguccu gcaggauuug aaggaccaca uugugaaauc 3300
cuagcuauag gauuuacagg aacugguugg gcuauguauc cauccuuuga cgcuacaaac 3360
aggacugaga uuauacugca uauuuuauca caaacugaua augguuugau auuuuacaau 3420
ggaccuuuaa auauaagaca aacuucuuug ucuaaagauu auauaucauu agaacuuaaa 3480
gacggauauc cauuacuuca aauuugcacc ggcucaagca cucaagaaau uuaucugaaa 3540
gagcgcauuc acaaauugag cgauggaucg uuacacaaaa uaaaaauagg aucuggauuu 3600
gacgauauau cccuggaagu agacgacugu ggaacaacgu guucaauuug gacuaauaaa 3660
cuacauaaag guguuauccg agcaaauggc ccccuucaac ugggagguau gaaaaacaga 3720
uucaccgauc aagaauucaa acgaauuugg gaccauuugc caccgacugc cacccguuuc 3780
ucugguugua uuagaaauuu gacguauaau gaauuuuacu acaaccucgg ugcaccuucu 3840
gaugcauucc aagcguaucc cgacuguaac uaugcaguga ugcaagcugu gacuuucggu 3900
aucgacucca auuucuuggu ugcuauucug guuuguguag caauuuugau aauucuucuu 3960
cuggcaguag uuguacauag acguaaacac gacaacuuua acgaaaaaga aaucgaugau 4020
acucgcgaaa acauuaucaa cuacgaagau gaagguggcg gcgaauguga caccaacuac 4080
gaccugucug uuuuccauca gaacaacauu guggacgaaa aaccauugau gagagacaac 4140
cccgauguac cugcagauau aaguggcuuu uuagauaaca agaaagacaa cugugauaaa 4200
gaccccgaua auuugccuua ugacgacguu cgccauuaug ccuacgaggg agacggaaau 4260
agcaccggau ccuuaucuuc ucucgcuuca uguacggacg aaggagauuu aaaguucaac 4320
uacuuaucaa guuuuggacc cagauucaga aaguuagccg acauguaugg agaagaucca 4380
agcgaugaag acucacacga uggaaacgaa gaauccuggu gcuag 4425

<210> SEQ ID NO 166
<211> LENGTH: 291
<212> TYPE: RNA
<213> ORGANISM: Diabrotica virgifera

<400> SEQUENCE: 166
augccuuucu guggucccaa auugucccuc ugcggccuga uuaucagugc augggguauc 60
auccaguugg guuucauggg uguauucuau uacauugggg cuguggcuuu agcagaagau 120
auuccagagg uugaguuuaa gggcgauuua gacaaauuuu auagcgacgu caacacgggu 180
uucacacaga augcuuacaa cugcuggauu gcugcucucc uauaccugau aacauuagca 240
guaucagcuc accaauucug ggccaacaac agaucaucau ugaacgucua a 291

<210> SEQ ID NO 167
<211> LENGTH: 540
<212> TYPE: RNA
<213> ORGANISM: Diabrotica virgifera

<400> SEQUENCE: 167
augggucuua ccauaucagc aguguuuaau agguuguuua guaaaaagcc uaugagaauu 60
uuaaugguag gauuagaugc cgcagguaaa accacaaucu uauacaaauu gaagcuuggu 120
gaaaucguaa cuacaauacc aaccaucggc uucaauguag aaaccguuga guacaagaau 180
auaucuuuca cgguauggga uguaggugc cagacgagaa ucagaaaacu cuggagacac 240

-continued uauuucgcca acacugaugg acucauuuuu gugguugauu ccaacgaccg agaccguauc 300
gcggaagccg aagaagaauu gcacaauaug uuaggagagg acgauuuaag agacugcauu 360
uuguuaauau ucgccaacaa acaagauuua ccgaacucga uguccacugc ugaauugacc 420
gauaagcuua aguugcacac uuugaagaau aggagguggu acauacaagc cacaugugcu 480
acucaaggga augguuugua cgaaggacua gauugguugu cgaaugaauu ggccaaguga 540

<210> SEQ ID NO 168
<211> LENGTH: 618
<212> TYPE: RNA
<213> ORGANISM: Diabrotica virgifera
<400> SEQUENCE: 168
augcgguaca cuuugaguua caucggugcu acccuagcgu ccacuguaac acugauuuuu 60
gcccucuacu acugccucac gggaaaagga gagcaaguua guuuagcaug guuauuguug 120
aaugugucuc cccacaugug ggcaggucua ggaauuggcc uugcuguauc auuaucaguu 180
guaggagcug cugcaggaau ucacacuaca ggagucagua ucguaggagc ugguguuaaa 240
gcccccagaa ucaaaaccaa aaauuuaauu ucuauuauuu ucugugaagc uguggcuauc 300 uaugggguuaa uuauggcuau aguacucugu ggaaguugga agaauuucga uguagaccua 360
uucaaccuca aaacucauaa cuuugcucaa aaccauuaug gaucacaugu uauuuuugga 420
uccgguuuaa cuguuggauu uguaaaucua uuauguggau uuuguguugg aguaguuggu 480
ucuggugcag ccauuucuga ugcagccaau ucaucauuau ucgucaaaau uuugauuauu 540
gagauuuuug gaagugccau uggucucuuc ggucugauug uuggaguaua cuugacguca 600
agaggcucua ugguuuaa 618

<210> SEQ ID NO 169
<211> LENGTH: 5694
<212> TYPE: RNA
<213> ORGANISM: Diabrotica virgifera
<400> SEQUENCE: 169
auggcuacca acgauaguaa agcuccguug aggacaguua aaagagugca auuuggaaua 60
cuuaguccag augaaauuag acgaauguca gucacagaag ggggcauccg cuucccagaa 120
accauggaag caggccgccc caaacuaugc ggucuuaugg accccagaca aggugucaua 180
gacagaagcu caagaugcca gacaugugcc ggaaauauga cagaaugucc uggacauuuc 240
ggacauaucg agcuggcaaa accaguuuuc cacguaggau ucguaacaaa aacaauaaag 300
aucuugagau gcguuugcuu cuuuugcagu aaauuauuag ucaguccaaa uaauccgaaa 360
auuaaagaag uuguaaugaa aucaaaggga cagccacgua aaagauuagc uuucguuuau 420
gaucugugua aagguaaaaa uauuugugaa gguggagaug aaauggaugu ggguaaagaa 480
agcgaagauc ccaauaaaaa agcaggccau ggugguugug gucgauauca accaaauauc 540
agacgugccg guuuagauuu aacagcagaa uggaaacacg ucaaugaaga cacacaagaa 600
aagaaaaucg cacuaucugc cgaacguguc ugggaaaucc uaaaacauau cacagaugaa 660
gaauguuuca uucuugguau ggaucccaaa uuugcuagac cagauuggau gauaguaacg 720
guacuuccug uuccucccccu agcaguacga ccugcuguag uuaugcacgg aucugcaagg 780
aaucaggaug auaucacuca caaauuggcc gacauuauca aggcgaauaa cgaauuacag 840
aagaacgagu cugcaggugc agccgcucau auaaucacag aaaauauuaa gauguugcaa 900
uuucacgucg ccacuuuagu ugacaacgau augccgggaa ugccgagagc aaugcaaaaa 960

```
ucuggaaaac cccuaaaagc uaucaaagcu cggcugaaag guaaagaagg aaggauucga   1020
gguaaccuua ugggaaagcg uguggacuuu ucugcacgua cugucaucac accagauccc   1080
aauuuacgua ucgaccaagu aggagugccu agaaguauug cucaaaacau gacguuucca   1140
gaaaucguca caccuuucaa uuuugacaaa auguuggaau ugguacagag agguaauucu   1200
caguauccag gagcuaagua uaucaucaga gacaauggag agaggauuga uuuacguuuc   1260
cacccaaaac cgucagauuu acauuugcag ugugguuaua agguagaaag acacaucaga   1320
gacggcgauc uaguaaucuu caaccgucaa ccaacccucc acaagaugag uaugaugggc   1380
cacagaguca aagucuuacc cuggucgacg uuccguauga aucucucgug caccucuccc   1440
uacaacgccg auuuugacgg cgacgaaaug aaccuccaug ugccccaaag uauggaaacu   1500
cgagcugaag ucgaaaaccu ccacaucacu cccaggcaaa ucauuacucc gcaagcuaac   1560
caacccguca uggguauugu acaagauacg uugacagcug uuaggaagau gacaaaaagg   1620
gauguauuca ucgagaagga acaaaugaug aauauauuga uguucuugcc aauuugggau   1680
gguaaaaugc cccguccagc cauccucaaa cccaaaccgu uguggacagg aaaacagaua   1740
uuuucccuga ucauuccugg caauguaaau augauacgua cccauucuac gcauccagac   1800
gacgaggacg acggucccua uaaauggaua ucgccaggag auacgaaagu uaugguagaa   1860
cauggagaau uggucauggg uauauugugu aagaaaaguc uuggaacauc agcagguucc   1920
cugcugcaua uuuguauguu ggaauuagga cacgaagugu gugguagauu uuaugguaac   1980
auucaaacug uaaucaacaa cugguuguug uuagaagguc acagcaucgg uauuggagac   2040
accauugccg auccucagac uuacacagaa auucagagag ccaucaggaa agccaaagaa   2100
gauguaauag aagucaucca gaaagcucac aacauggaac uggaaccgac ucccgguaau   2160
acguugcguc agacuuucga aaaucaagua aacagaauuc uaaacgacgc ucgugacaaa   2220
acugguguuu ccgcuaagaa aucuuugacu gaauacaaua accuaaaggc uauggucgua   2280
ucgggaucca agggauccaa cauuaauauu ucccagguua uugcuugcgu gggucaacag   2340
aacguagaag guaaacguau uccauuuggc uucagaaaac gcacguugcc gcacuucauc   2400
aaggacgauu acgguccuga auccagaggu uucguagaaa auucguaucu ugccggucuc   2460
acuccuucgg aguucuauuu ccacgcuaug ggaggucgug aaggucuuau cgauacugcu   2520
guaaaaacug ccgaaacugg uuacauccag cgucgucuga ucaaggcuau ggagagugua   2580
augguacacu acgacgguac cguaagaaau ucuguaggac aacuuaucca guugagauac   2640
ggugaggacg gacucugugg agagauggua gaguuucaau auuuagcaac ggucaaauua   2700
aguaacaagg cguuugagag aaaauucaga uuugauccga guaaugaaag guauuugaga   2760
agaguuuuca augaagaagu uaucaagcaa cugaugggau caggggaagu cauuuccgaa   2820
cuugagagag aaugggaaca acuccagaaa gacagagaag ccuuaagaca aaucuucccu   2880
agcggagaau ccaaaguagu acuccccugu aauuuacaac guaugaucug gaauguacaa   2940
aaaauuuucc acauaaacaa acgagccccg acagaccugu ccccguuaag aguuauccaa   3000
ggcguucgag aauuacucag gaaaugcguc aucguagcug gcgaggaucg ucuguccaaa   3060
caagccaacg aaaacgcaac guuacucuuc cagugucuag ucagaucgac ccucugcacc   3120
aaaugcguuu cugaagaauu caggcucagc accgaagccu ucgagugguu gauaggagaa   3180
aucgagacga gguuccaaca agcccaagcc aauccuggag aaaugguggg cgcucuggcc   3240
gcgcagucac ugggagaacc cgcuacucag augacacuga acacuuucca uuuugcuggu   3300
```

-continued

```
guauccucca agaacguaac ccugggugua ccuagauuaa aggaaauuau uaauauuucc   3360
aagaaaccca aggcuccauc ucuaaccgug uuuuuaacug gugcggcugc uagagaugcg   3420
gaaaaagcga agaauguguu augcagacuu gaacacacca cucuucguaa aguaaccgcc   3480
aacaccgcca ucuauuacga uccugaccca caaaauaccg ucauuccuga ggaucaggag   3540
uucguuaacg ucuacuauga aaugcccgau uucgauccua cccguauauc gccgugguug   3600
cuucguaucg aacuggacag aaagagaaug acagauaaga aacuaacuau ggaacaaauu   3660
gcugaaaaga ucaacgcugg guucggggac gauuugaauu guauuuucaa cgacgacaau   3720
gcugaaaagu uggugcugcg uaucagaauc augaacagcg acgauggaaa auucggagaa   3780
ggugcugaug aggacguaga caaaauggau gacgacaugu uuugagaug caucgaagcg    3840
aacaugcuga gcgauaugac cuugcaaggu auagaagcga uuuccaaggu auacaugcac   3900
uugccacaga cugacucgaa aaaaaggauc gucaucacug aaacaggcga auuuaaggcc   3960
aucgcagaau ggcuauugga aacugacggu accagcauga ugaaaguacu gucagaaaga   4020
gacgucgauc cggucaggac guuuucuaac gacauuugug aaauauuuuc gguacuuggu   4080
aucgaggcug ugcguaaguc uguagagaag gaaaugaacg cuguccuuuc guucuacggu   4140
cuguauguaa acuaucgcca ucuugccuug cuuugugacg uaaugacagc caaaggucac   4200
uuaauggcca ucacccguca cgguaucaac agacaagaca cuggagcucu gaugaggugu   4260
uccuucgagg aaacuguaga uguauugaug gacgcugcca gucaugcgga ggucgaccca   4320
augagaggag uaucugaaaa cauuauccuc ggucaacuac caagaauggg cacaggcugc   4380
uucgaucuuu ugcuggacgc cgaaaaaugu aaaaugggaa uugccauacc ucaagcgcac   4440
agcagcgauc uaauggcuuc aggaauguuc uuuggauuag ccgcuacacc cagcaguaug   4500
aguccaggug gugcuaugac cccauggaau caagcagcua caccauacgu uggcaguauc   4560
uggucuccac agaauuuaau gggcagugga augacaccag gugguguccgc uuucuccccca 4620
ucagcugcgu cagaugcauc aggaauguca ccagcuuaug gcgguugguc accaacacca   4680
caaucuccug caaugucgcc auauauggcu ucuccacaug gacaaucgcc uuccuacagu   4740
ccaucaaguc cagcguucca accuacuuca ccauccauga cgccgaccuc uccuggauau   4800
ucucccaguu cuccugguua uucaccuacc agucucaauu acaguccaac gagucccagu   4860
uauucaccca cuucucagag uuacucccca accucaccua guuacucacc gacuucucca   4920
aauuauucac cuacuucccc aagcuacagu ccaacauccc cuaacuauuc accaacaucu   4980
cccaacuauu cacccacuuc accuaguuau ccuucaacuu cgccagguua cagccccacu   5040
ucacgcagcu acucacccac aucuccuagu uacucaggaa cuucgcccuc uuauucacca   5100
acuucgccaa guuacucccc uacuucuccu aguuauucgc cgucgucucc uaauuacucu   5160
cccacuucuc caaauuacag ucccacuucu ccuaauuacu caccguccuc uccuagguac   5220
acgcccgguu cuccuaguuu uuccccaagu ucgaacaguu acucucccac aucuccucaa   5280
uauucuccaa caucuccaag uuauucgccu ucuucgccca aauauucacc aacuuccccc   5340
aauuauucgc caacaucucc aucauuuucu ggaggaaguc cacaauauuc acccacauca   5400
ccgaaauacu cuccaaccuc gcccaauuac acucugucga guccgcagca cacuccaaca   5460
gguagcaguc gauauucacc gucaacuucg aguuauucuc cuaauucgcc caauuauuca   5520
ccgacgucuc cacaauacuc cauccacagu acaaaauauu ccccugcaag uccuacauuc   5580
acacccacca guccuaguuu cucucccgcu ucacccgcau auucgccuca accuauguau   5640
ucaccuucuu cuccuaauua uucucccacu agucccaguc aagacacuga cuaa         5694
```

<210> SEQ ID NO 170
<211> LENGTH: 876
<212> TYPE: RNA
<213> ORGANISM: Diabrotica virgifera

<400> SEQUENCE: 170
augucgucaa auauucaaaa ggcccagcag uugauggcgg augcagaaaa gaaaguaaca 60
ucucgagguu ucuucggauc ucuauuuggg ggaucaaguc guauugaaga ugcaguggaa 120
uguuacacaa gagcugcaaa ccuuuuuaaa auggccaaga gcugggaugc ugccgguaaa 180
gccuuuugug aggcugcuaa uuugcauucc agaacuggug cucgucauga cgcugccacu 240
aauuauauag augcugcaaa uuguuacaaa aaagccgaug uauuugaggc uguaaacugc 300
uuuauaaaag cuauagacau uuauaccgaa augggucgcu uuacaauggc ugcaaaacac 360
caucagacua uugcagaaau guaugagacu gaugcugugg acaucgaaag ggcuguucaa 420
cacuaugaac aggcggcuga uuacuucaga ggagaagaaa gcaaugcuuc cgccaauaag 480
ugucuucuua aaguggcuca auaugcagcc caacuugaaa acuaugaaaa agcaguggga 540
auuuaucaag aaguggcuua ugcagcucug gaaagcucuc uuuuaaaaua cagugcaaag 600
gaauacuuau ucagagcugc ccuuugucac cuuuguguug auguacucaa ugcacaacau 660
gcuauagaaa gcuauauuuc aagguauccc gcauuucaag auucccguga auacaaacuu 720
uugaaaaccc ucauagaaaa caucgaagag caaaacguag auggauauac agaagccguc 780
aaagauuacg auucaauuuc ucgucuugau cagugguaua cuacaauucu uuuacguauu 840
aagaaacaag uaagcgaaag cccugacuua cguuaa 876

<210> SEQ ID NO 171
<211> LENGTH: 609
<212> TYPE: RNA
<213> ORGANISM: Diabrotica virgifera

<400> SEQUENCE: 171
augaaucccg aguaugauua uuuauucaaa cuucugcuga uuggagauuc aggaguagga 60
aaaucuuguc uucuacugag auuugcagau gauaccuaca cagaaagcua uauuaguacc 120
auuggcguag auuuuaaaau caggacaauc gauuuagaug gaaagacaau uaaauugcaa 180
auuugggaua cagcagguca ggaaagguuu agaacgauua caucaaguua uuaccgagga 240
gcacauggua uuauuguagu guacgauugc acagaccaag auucauucaa uaacguuaaa 300
caguggcucg aagaaaucga ccguuaugcg ugugacaaug uaaacaaauu acugguaggg 360
aauaaaagcg auuugacaac uaagaaaguu gucgacuuca cuacagccaa ggaguaugcc 420
gaccaauugg guauaccauu uuuggaaacc ucagcuaaga augcaaccaa uguagaacag 480
gccuuuauga cuauggccgc ugaaauaaaa aauagaguag gaccuccauc uucugcggua 540
gaccaaggaa auaagguuag guucgaucaa agucgcccag ucgaaacaac caaauccggu 600
ugcugcuga 609

<210> SEQ ID NO 172
<211> LENGTH: 789
<212> TYPE: RNA
<213> ORGANISM: Diabrotica virgifera

<400> SEQUENCE: 172
auggcagacg cugaugaucu auuagauuau gaagaugagg aacagacaga acaaaccgca 60

```
acugaaacgg caacuacaga gguacagaaa aagggguguca agggcacaua uguaucaaua    120

cacaguucug gguuuagaga uuuucuguua aaaccagcaa uucucagagc uauaguggac    180

ugcggguucg aacauccuuc agaaguucaa caugaaugua uuccucaagc ugucauuggc    240

auggauauuc ugugccaagc uaaauccggu augggaaaaa cggcuguuuu uguauuagcu    300

acacuccaag uaauagaucc uacagaaaau guuguauaug uucucgucau gugccauacc    360

agagaguuag ccuuccagau aagcaaagag uacgaacguu ucaguaaaua uaugcccaau    420

auuaaaguag gggucuucuu ugguggcuug ccuauccaga aagaugagga aacguuaaaa    480

aauaauugcc cgcauaucgu ugugggguacu ccaggaagaa uuuuagcauu ggucagaucg    540

aaaaaacuua aucucaaaca ucuaaagcau uuuauuuugg augaauguga uaaaaauguug    600

gaguuauuag acaugagacg ugauguucaa gaaauauauc guaacacucc ccacgaaaaa    660

caagucauga uguucagugc caccuuaagu aaagaaauua gaccaguuug caagaaauuu    720

augcaagaug uaauucaaaa uucuuauaau acacaauuuu guaaugacgc acccacucgc    780

aauguuuga                                                          789
```

```
<210> SEQ ID NO 173
<211> LENGTH: 738
<212> TYPE: RNA
<213> ORGANISM: Diabrotica virgifera

<400> SEQUENCE: 173

augccgguca uugaugguua uaaaguacuu uacauuuuau uacacaguuu auauacaauu     60

uuugaaaaua uuuggaggac ucuuuuauuu auuuaucaaa auuguauaag gguuauaaac    120

ccugaaucua cauucgauga ugcugaccag uuaaagaaaa gacugucuag acuaacaaaa    180

aagccucaac auuuaacuau cauuauuggu guggaagaau auucauuggu agauuuggcu    240

aaccucguau auuggguguuu aggucuuaau auuccguacg uuaguuucua ugauuauaaa    300

gguaauuuaa aaaagcauga agagaaguug caacaaauug uagaauccag aaaaucagag    360

aauaucaaca uaauuuggca cacccaugca gaacaaaggc auaaaaaugg auuuuugggu    420

ccaaaaaucc acguaaaagu guuaacacac gcggacggaa agcaaaguau aguaaauguu    480

acuaaaaaau uagcucuaaa uaaagaaaaa gacauuagua aagaaaaaau uagugaauua    540

cuauuaaggc aguaugaauu uccagaucca gaaauggcua uuauuugugg aaagaaacug    600

aacauuuaua auuauccucc uuggcaguua agacucacag aauucuuuaa agucaacaaa    660

gucaacaaca ucacauuccc aguguuugug gaaaaauugg aaaaguacag caaaugugaa    720

cagaggggugg gaaaauaa                                                738
```

```
<210> SEQ ID NO 174
<211> LENGTH: 480
<212> TYPE: RNA
<213> ORGANISM: Diabrotica virgifera

<400> SEQUENCE: 174

augaccaacu cuaaagguua ccgccgagga accagggauc uauuugcccg caaguuuaaa     60

aaacguggug uaauuccacu uuccacauau uugagagucu acaaaguugg agauauugua    120

gauaucaagg guaauggugc aguucaaaag gguaugcccc acaaagugua ccaugguaag    180

acaggacgug uuuucaaugu uacugcacau gcauuaggug uaauuguaaa caaaaggguu    240

cgaggaagaa ucaucccccaa aagaaucaau cuccguauug aacauguaaa ccacuccaag    300

ugucgucaag acuucuugca aagaguaaaa uccaacgaaa agcuacguaa agaagcuaaa    360
```

gaaaagaaca uuaaaguaga acuuaggaga caaccugccc aaccuaggcc agcacauauu 420
guuagcggaa agguuccagc acaggugcuu gcuccuaucc cauaugaauu cauugcuuag 480

<210> SEQ ID NO 175
<211> LENGTH: 537
<212> TYPE: RNA
<213> ORGANISM: Diabrotica virgifera

<400> SEQUENCE: 175
auggaaggaa uacuacugga accaacauug uauaccauaa aagguauugc uauauuggac 60
uaugauggua auagagugcu ggcuaaauac uacgauaaag auauauuucc uacagcaaaa 120
gagcagaaag cuuuugagaa aaauuuguuc aauaaaacuc auagggcaga cgcagaaauu 180
aucauguugg augguuuaac uuguguguau agaaguaaug uagauuuauu cuuuuauguu 240
augggcaguu cacaugaaaa ugagcuaauu uuaaugagug uuuuaaauug cuuguaugac 300
ucaguaaguc aaauauugaa gaaaaauaug caaaaacgag cugucuugga aucacuagau 360
auuguuaugc uggcuaugga ugaaauuguu gauggaggaa uaauuauaga uucugauuca 420
aguucaguag uaucuagaau agcauuaagg acugaugaua uuccauuagg agaacaaacu 480
guagcucagg uauuccaaac ggccaaagaa cagcugaaau ggucauugcu gaaauaa 537

<210> SEQ ID NO 176
<211> LENGTH: 450
<212> TYPE: RNA
<213> ORGANISM: Diabrotica virgifera

<400> SEQUENCE: 176
auggcugacc aacucaccga agaacaaauu gcugaauuca aagaagcuuu cucacuauuc 60
gauaaagaug gugaugguac aauuacgacu aaagaauuag gaacaguaau gagaucucua 120
ggacaaaauc caacagaggc ugaauuacag gauaugauca augaaguaga ugccgauggu 180
aacggcacga ucgauuuccc agaauuuuua acgaugaugg cacguaaaau gaaagauacc 240
gauagugagg aagaaauucg ugaagcauuc cgagaguucg acaaagacgg caaugguuuc 300
aucucagcag cagaauugcg ccacgucaug accaacuugg gugaaaaauu gacagacgaa 360
gaagucgaug aaaugauucg ggaggccgau aucgauggug auggucaagu caauuacgaa 420
gaguucguca ccaugaugac uucaaaguga 450

<210> SEQ ID NO 177
<211> LENGTH: 2013
<212> TYPE: RNA
<213> ORGANISM: Diabrotica virgifera

<400> SEQUENCE: 177
augaugcaag caaacaaucg agucccaccu auaaaguugg aaaacgauau agaucuuuac 60
gccgaugaua ucgaggauuu cgcacaagau gacuuuggug gugaaaaugu ugaucuauau 120
gacgauguaa uauccgcucc uccuggaaau aaugacaacc caggugauuc aaaucaucau 180
gcuccuccug gugcugguga agauggugga gguaauuuug uugggucagg aggagcaccc 240
aauaauauaa auucuucugg aagaagacau cagcuguaug uuggaaaucu gacuuggugg 300
acaacugauc aagauauaga aaaugcagug caugauauag ggguaaccga cuuccaugaa 360
guuaaguuuu uugaacacag agcaaauggu caauccaagg gauucugugu cauaucuuug 420
ggaucugagg gaagcaugag acucugccug gaacuccuau cuaaaaaaga gaucaauggc 480
caaaaucccc uuguuacccu ucccacaaaa caagcucuua guaacuuuga aagucagucu 540
aaaacacgcc cuucuccuac uaauaauucu aacucacguc cuccccaucc uaauaauaau 600
guucauucag guccuaugca gaauuaugga gguagaaugc cuaugaaccc uuccaugcgu 660
cccaugcccc cagguaugca aggugcucca agaaugcagg guccaccugg auuuaaugga 720
ccaccaaaca ugaaucagca accccccagg uuccaaggua auccacaaug gaauggaccu 780
agaccuaaug guccugggcc caauauggga augagaccca uggggccacc ucauggacaa 840
caagggcccc caagaccacc aaugcaggga ccaccgcagc aagguccucc aagaggaaug 900
ccgccacaag guccaccgca gaugcgucca gaauggaauc gaccaccaau gcaacaaggg 960
uacccucaag gcccgccgca uaugcaagga ccuaacaugg guccaagagg uccaccccaa 1020
augggaccac ccggggcgcc ucaacagcaa ggaccagcuc cgcacguaaa uccagcauuc 1080
uuucaacaag gaggaggacc accgccccca augcaacaca ugccuggacc agggcccguc 1140
augccuccuc aaggaccccc gcaaggucca ccacacggac ccguuggacc uccacacggc 1200
ccaccauugg guccagcgaa uguuccgccu cauggaccac cucacggaua ugguccaccu 1260
gcagcgaugc cacagccgcc auacggugge ccaccuccag accaccgcgc ugagauuccu 1320
caguuaacag agcaagaguu ugaggauaua auguccegga auagaacagu uuccaguucg 1380
gcgauugggc gggccguauc cgacgccgca gcuggagaau uugcaagcgc cauugagacu 1440
uugguuacug cuauuucacu caucaaacaa uccaaagugg cuaacgacga ucguugcaag 1500
auccuuauaa guucgcugca agauacuuug cguggugucg aagacaaaag cuacagcucc 1560
agccgcagag accggucaag auccagggac agaucacaua gaagaacuag aagagaacga 1620
uccucgucac gguacagaga cagaagcaga gagagggagc gugaacgcga uagagaucgu 1680
gaucgugaac gugacagaua uuaugauaga uacagcgaaa gagaaagaga ccgagaucgu 1740
ucaagaagca gagaaagaac agaaagggau agagaacgag auuauagaga ccgggaaccc 1800
gaagagacag auaaagaaaa aucuaaagua uccagagucu caagaucaag aaacaaaucu 1860
ccggaaccug ucgaaccuag cagcgaggua ccgaaaucau cccgcuauua ugaggauagg 1920
uaucgggaac gagagagaga aggucgacga gagagcgauc gcgaaagaga aagagauaga 1980
agaggggaag acagccauag gucucgacac uag 2013

<210> SEQ ID NO 178
<211> LENGTH: 765
<212> TYPE: RNA
<213> ORGANISM: Diabrotica virgifera

<400> SEQUENCE: 178
augaguucua uuggaacugg guacgauuua ucagcuuccc aauucucucc ugauggaaga 60
guauuucaag uugaauaugc aaugaaagca guugaaaaua guggcaccgu aauaggccuc 120
cgagguacag auggcauugu auuggcugcu gaaaagcuca uuaugucaaa auugcaugaa 180
ccaaguacaa auaaacgaau uuucaacauu gauaaacaca uaggaauggc auuuucaggc 240
uuaauagcug augcaaggca aaucguugag auugcuagaa aagaagcauc aaauuauaga 300
caucaauaug guucaaauau uccucuuaaa uaccuaaaug auagaguaag cauguacaug 360
caugcauaca cuuuauacag ugcuguuaga ccauuugguu gcagugucau cuuggccagu 420
uaugaagaua gugacccauc uauguaucug auugauccau cuggaguuag cuauggauac 480
uuuggaugug cuacagguaa agcaaaacag ucugcaaaga cugaaauaga aaaauugaag 540 augggggaauc uaacaugcaa agaacuuguu aaagaagcag ccaaaaucau uuauuugguc 600
caugaugagc ugaaggauaa gaauuuugaa cuggaacuuu caugggguaug caaagauacg 660 aaugguuuac auaccaaagu gccugaauca guguuugcug augcagaaaa agcugccaaa 720
caagcaaugg aagcagauuc agaaucagau acagaagaua uguaa 765

<210> SEQ ID NO 179
<211> LENGTH: 744
<212> TYPE: RNA
<213> ORGANISM: Diabrotica virgifera

<400> SEQUENCE: 179
auggcuucaa aagacagauu gaugauuuuu ccaucuagag gagcccaaau gaugaugaaa 60
uccaggcuaa agggagccca aaagggacau aguuuauuaa agaagaaagc ugaugcuuua 120
caaaugagau uuagaaugau uuugaacaaa auuauugaga ccaaaacucu caugggugaa 180
guaaugaaag aagcugccuu uucuuuagcu gaagcaaagu uugcaacugg ugacuucaau 240
caaguuguuc uucaaaaugu caccaaggcu caaauaaaaa uaagaacuaa gaaagacaac 300
guugcuggug uuacuuuacc aguguuugaa ugcuaccaag augguacaga uacauaugag 360
uuggcugguu uggcuagggg aggucaacaa uugacaaaac ucaagaagaa uuaucaaagu 420
gcuguuaaac uguugguuga auuagccucu uugcaaacuu cuuuuguaac ucuugaugau 480
guaaucaaaa uaacaaacag aagagucaau gccauugaac auguuaucau uccaagaaua 540
gagcguacuu uggcuuacau cauauccgaa cuggacgagu uagaaagaga ggaguucuau 600
agauuaaaga agauccagga caaaaagaag aucagcagag caaaggccga gaaacaaaaa 660
caagcucuuc uccaagcugg gcuacuuaaa gagucccagg caaacaugcu uuuggaugag 720
ggcgaugaag aucuacuuuu cuag 744

<210> SEQ ID NO 180
<211> LENGTH: 4818
<212> TYPE: RNA
<213> ORGANISM: Diabrotica virgifera

<400> SEQUENCE: 180
auggaggcgg cucccaaguu accgaugcuc ucguucgagu uaaauacuug uacagagaac 60
guccacuuug gcccccaguu aaaacaguau auugcugcuu uuuaugguga agauccagaa 120
uccuacauua cagaaaucag caaucuugaa uccuuaagau cagcugcagu ucgaccauca 180
acggauguaa augguguaca acuguugaaa aaguauuucu gucagcuucg uuuucucaaa 240
ucuagguuuc ccauggaaga gaaucaagau gcugcaguuc uauuuucaug gaaaaauaau 300
gaauuagaca uaacuucaac auccagugau aucagauaug aauuaauggu aauaauguau 360
aacauuggag ccuuacacac uuuucuugga gccaacgacu caagaaacaa uccggauggu 420
augaaaaugg cauguacuca uuuucaaugu gcugcauggg cuuuucaaaa cguaaaagaa 480
aaguaccacc aauucauauc aaacaucuca uugguagaac ugguucauuu uuuucaacaa 540
gucuguuuag cucaggcuca ggaguguaua uuagagaaga gcauguuuga caauaggaaa 600
ccuaccauca uugcaaaagu ugcuauccaa gucuacaguu auuacagaca gucuuuacgu 660
gucuuggaau caguaaauga agccuacuuu agggauaaaa ccuacaagga guggaugaaa 720
uaucuucaau ucaagcugac cuacuacaaa ugcaucucgu uccuauucca agggcaacaa 780
gcugaggaac aacagaaaau gggagaaagg guugcauucu aucaagcugc augugaacag 840
cuggacgagg caaagaaaau ugcugcuaca uuaaaaaacc aacaccacca gcaagaaaua 900

-continued

```
aaugagggac uagcauucac uacugaugug guugaaggua aaagaaaagc agcuaaaaau    960
gaaaaugagu ucaucuacca ugaaucagug ccugauaaag accaauugcc agagguuaag   1020
ggugcuucau uagucaaagg aauaccauuc aguauaaaug auauagaagu uucaggacca   1080
gauauuuucu cccgauuggu cccaauggag gcacacgaag cagcuuccuu guacagcgag   1140
aagaaagcuc agagauuaag acagaucggg gaacuuauug aaaauaaaga ucaaacauug   1200
gcugaauuua ugucgucaau gcagcuagau cuauugacca agaugcacca ggcuacugga   1260
auaccgcagg aguugauuga uagagcagcg gcucuaucug cuaaaccuaa cgccauucaa   1320
gaucuuauaa gugcuauggg aaagcuaucu aauauauacc aagacguuga agcaaguuug   1380
aaugagauug auucuuuauu aaaggccgaa gaacaaagug aacaaaagua ccaagaaacg   1440
auugguaaaa gaccaccgag cauuuuagcu acagauuuaa cuagggaagc ggcaaaauac   1500
agggaggcuc auacuaaagc gaacgacuca aaccaaacuu uacacagggc gaugauggcu   1560
cacguggcua aucugaaaau acuccaacaa ccgcuaaagc agcugcaaca ucagcugccc   1620
uuugucgagu uuccaaaucc aaauaucgac gaaaaaucuu ugaaagaucu ggaagcgcua   1680
guugcaaaag uagacgaaau gagaacccaa agagccaugc uaugggcuca acuucgagaa   1740
ucuauucacc aagacgauau uacaaguucc cuuguaacga aacaaccaaa ucagucgcug   1800
gaacagcugu uccagcaaga acuucaaaag caucaaaauc ugauuucguu gauugaacaa   1860
aacaccucgg cacaagaaaa cauuaagagc gccuuagucg auucuuacgc uuacgcugua   1920
aauucaagaa aauacaucca agauauacuc caaaagagaa ccacaaccau aacgucacug   1980
auagcaucgu ucgacucuua cgaagacuua uuggcaaaag cuaacaaagg gauagaguuu   2040
uacucaaaac uugaaacgaa cguauccaag uuacugcaaa gaauaaggag uaccugcaaa   2100
guucaacaag aagagcgaga ucagaugaug ucgacugcgc aagugccuca augggagagu   2160
cauacgucac uugccgcucc uaaacugaaa gauuacuugg acuccaggaa gaagagugcu   2220
gcguauucgg agccgagugu ucaaccacaa cagccaacuu uaaguuacuc agcugcuaug   2280
gaucugccuc cugguauuag gccgacucca guuggaucag aaauaacgga uguaccgaaa   2340
aauauucaag gugaaccaca agguuauauu ccauauaauu accaacaacc uucuguuccu   2400
gccucacaga auauugauga agagacuauu aaaaaaauga acgcauugau gccaggugcu   2460
aagacgucag ugccuaguca guacggauac agcaacuaca uuccaccaac auacccucaa   2520
agugcguacc aaccagguaa ucagucuuac ggaaaagaaa cuccagauau uaacucaccg   2580
uacgacccua ccaaggcguu cacggcuacu acuaacgcuu aucguucggu gcagagcucc   2640
ucaacucaag gauacguacc guacgcagaa ucuaacguuu cgaauguuga cagaguugga   2700
uauccuagca gguaucagua ccaacaagua ccugagauag cuacuacucc agcugauccc   2760
aauauuaaug cguacuaccc acaugggguac ucaccgagcc agaauuuacc gaaugcuaau   2820
acucaacaua uuaccggcca acugaaguac cauucggugg aguacgcuuc uucugugccg   2880
aacaacauca auuauaacag cucuaccuac ucgucgccgc uuucuaauau gucuaguacc   2940
aauuccucaa auccuaguaa cuugaauaau ucuuacgagu acuacuauga cccgaauacc   3000
aguaguggug caguaccgaa ugcuucaaag ccucaacagu cgagcgccag cucugcaaac   3060
ccgaguaccg cuaugaacaa cuacaauuau uacuacaaua caaguaccag cgguagugua   3120
gcagcggaua cuucaaaaau acaacaacaa caacaguacc cagguacuca gaugagucaa   3180
gcgcaguacu aucccgccaa ugccaguuau uacucaacca guacuuacaa uaccaacguc   3240
caagguggua ccaaucccuc guacgcaacu ggacaaacau auaaucaagu gacaccagug   3300
```

accucucaaa auguuucuca aaauuacaac uuuaaccaag uugguucugg agcaggacac 3360
cagcaucagu acuacucguc cgcuaacgcc gcaguaccau cccaacaagc uguaaauaac 3420
aguucauuac caaacuacgg auacgaucag uauuacggca acaacuauaa uuccagucaa 3480
ccgaguaccu acagcgcaaa ccaagcaccu ccugcagcac aagcugcucc aaguaauauu 3540
ccugcugcca ccaaauccuc cucuaaugug gaucugcuca guggcuugga cuucagcaua 3600
agccaagcuc cucuagugcc ucaacaaaac auuacgauaa aaccccaaga aaaggaaaca 3660
aaaccaccgg cuguuucuuc ugaaaccaaa aaccaagauc caacaccagu aaccacgccc 3720
aaacaaccca cuggaccaga aguaaagcgc uuguacguca aaauccugcc gagcaaaccc 3780
uuaaacaacg augaugugaa gaaauuguuc ggccaagagc uggacaggua ugagaaguuc 3840
guggagaccu ugacccacaa aacuuugagc gguccgacca cucuggauau uaaauggaag 3900
gagauccaag accagcagga uugcgagccg cagaagaaga ucauuuccgu cgcuagaugu 3960
uauccuauga agaauagguu cccggauauc uugccuuacg acuuuuccag gguggaguug 4020
ugcgauagua aagaugauua uaucaacgcu ucauacauua aggauaucuc gccauaugcu 4080
ccgucauuua uuguuacaca agugccguug ucuucaacug uuggugauau guggacgaug 4140
auuagagaac aacaggucga acugauccuc uguuugguaa acgacaauga gaucggugaa 4200
gauauuuacu ggcccaaaga aaaaggcagu agucuuaaca uacuuaacau ggucauaacg 4260
uugcaaaacg uuauaguuaa gucucauugg acugaaagac ugauagcgau aaacuuaccu 4320
gaaaaacggg agucccgugu gauaaaugcau cuacaauuua caucguggcc uggcagcuug 4380
uuuccaacaa auccugaacc guucgucagc uacaccuugg aauccaucaa ccuauaccaa 4440
caacagaaga ccaacaccca uccggguggug guccauuguu caucuggcau aggaagaagc 4500
ggccugcucu guuuacugac agcugcuaug uucgaugcug ccaacaaugc uaacucgaua 4560
ccagaucuua cagcuuugag uaucaaguug uccaauugca ggaagaauau ucucagagau 4620
cgagagcauu ugaaguuugg uuacgaaagu uuuuuggcgu auauuaggca uauaguuugu 4680
gaagauaaag ccagaaagaa acugaacgag auccagccca agguuaagga ggaaccacug 4740
gaaccaccug ucauaguucc agaaccaaau auagauccuu uaaguacuuu agacccauuu 4800
ugggcuagua aaagauaa 4818

<210> SEQ ID NO 181
<211> LENGTH: 888
<212> TYPE: RNA
<213> ORGANISM: Diabrotica virgifera

<400> SEQUENCE: 181
auggcggacg augagagaaa gaaacuggag gaggaaaaga agaggaaaca ggccgaaauu 60
gaacgcaaaa gggccgaggu cagggcucgu auggaagagg ccucaaaagc caagaaggcc 120 aagaaaggguu ucaugacccc ugagagaaag aagaaacuua gguuacuguu gagaaagaaa 180
gccgccgaag aauuaaagaa agaacaagaa cgcaaagcag ccgaaaggag gcguaucauu 240
gaagaaaggu gcgguaaacc caaacuuguc gaugacgcaa augaaggccc auuaaaacaa 300
guaugugagg gauaucacag acguauugua gaccuagaaa auaagaaauu ugaccucgaa 360
aaagaagugg aauucagaga uuuucagauc uccgaauuga acagccaagu aaacgaccuu 420
agaggcaaau ucgucaaacc aaccuugaag aagguaucca aauacgaaaa caaauucgcc 480
aaacuucaaa agaaggcagc ugaauuuaac uuccguaacc aacucaaagu ugucaagaag 540
aaagaauuca ccuuagaaga agaagacaaa gaaaagaaac cagacugguc aaagaaggga 600
gacgaaaaga agguacaaga ggcugaagca ugauuuuucu ccuuuguuaa agcccuuuug 660
ucaacaucaa gggauauguc guuauuucga ugaucccauc gugauuucga uaucuuaaau 720
auauuuauuu uauucauuac uuuccagacu aaaagagugu cuguccgcau guauauuauu 780
uguuuaugua uaacuuauua aaaaauguga aguauuguaa aaaaaaaaaa aaaaaaaaaa 840
aaaaaaaaaa aaaaaaaaaa aaaaaaaaga aaaaaaaaaa aaaaaaaa 888

<210> SEQ ID NO 182
<211> LENGTH: 791
<212> TYPE: RNA
<213> ORGANISM: Diabrotica virgifera

<400> SEQUENCE: 182
ccgugaucuc gagcgguuuu uaacagagag ggaaaaugua aucauauaua ugguugaauu 60
cuugaagguu agacuucauu ccagucuugu gauauuuagu gcuuacuugg uacagcaguu 120
ucagugcugu gcuuuagaau aauuuauuuu uuaacauuua uauagaaauc aaauacuaac 180
caaucaacau gugugaagaa gaaguugccg cuuuagucgu agacaaugga uccgguaugu 240
gcaaagcugg uuuugcuggg gaugaugcac cucgugcugu auucccuuca auuguuggac 300
gcccaagaca ucagggugug augguaggaa ugggacaaaa agauuccuau guaggugaug 360
aagcucaaag uaaaagaggu auccuuaccu uaaaauaccc caucgagcac ggaauaguca 420
caaacuggga ugauauggag aaaauuuggc aucauacauu cuacaaugaa cucagaguag 480
ccccagaaga acacccuguu cuguugacag aagcuccucu caaccccaag gccaacaggg 540
aaaagaugac acaaauaaug uuugaaacuu ucaacacccc agccauguau guugccaucc 600
aggcuguacu cuccuuguau gcaucugguc guacaacugg uauuguguug gauucuggug 660
augguguauc ccacacuguc ccaaucuaug aagguuaugc ucuuccucau gcaauccuuc 720
guuuggacuu agcugguaga gacuugacug auuaccucau gaaaauuuug acugaacgug 780
gcuacucuuu c 791

<210> SEQ ID NO 183
<211> LENGTH: 2927
<212> TYPE: RNA
<213> ORGANISM: Diabrotica virgifera

<400> SEQUENCE: 183
uaauuuuuga caguucgaaa auggugaugu guuuauaauu cgugucaauu uagugaaaua 60
gcauucaauu uuuuguauaa gaucucuuca aaaugccacu ucgauuagau auaaaaagaa 120
agcuaacagc ucgcucagac cggguaaaau guguggaucu ucacccuaca gaaccuugga 180
ugcuguguuc ucuuuacagc ggaaauauaa acguuuggaa caccgaaaau cagcaacugg 240
uuaagacuuu ugaaguaugu gauguaccug uucggacagc uaaguuuuug cccaggaaga 300
acuggauagu caguggggucu gaugauaugc agauucgagu uuucaauuac aauaccuuag 360
aucggguaca uucuuuugag gcucauucgg auuaugugag auguauuguc guacacccua 420
cacaaccuua uauauuaaca aguagugaug auaugcuuau caagcuuugg aauugggaaa 480
aagcaugggc uugucagcaa guuuucgaag gacacacuca uuauauuaug caaaucgcca 540
uaaauccaaa agacaacaac acauuugcca gugcaucccu agauagaaca uugaaaguau 600
ggcaauuggg agcguccaca gcgaauuuca cacuagaagg ucaugagaaa ggcguuaacu 660
guguggacua uuaucacggu ggagauaaac cuuauuuaau cucaggcgcu gaugauagau 720
uaguaaaaau cugggauuau caaaacaaaa cuuguguuca aacuuuggaa ggacaugcuc 780
aaaauguaac cgcugcaugu uuccauccag aacuuccugu agcucuuacu ggaagugaag 840
augguacugu cagagugugg caugccaaca cccauagguu agaaaguagc uuaaauuaug 900
gcuuugaaag aguauggacu auuuucugcc uaaagggauc caauaacgug gcauuggguu 960
augaugaagg uagcauuuug guuaaaguug guagagaaga accagcuguu aguauggaug 1020
ccaguggagg caaaauuauu ugggccagac acucugaacu ucaacaggca aaucucaagg 1080
cguuagcuga aggugcggaa auaagagaug gagaacgccu uccaguuucu guaaaagaua 1140
ugggugcuug cgagauauac ccucagacaa uucaacacaa ucccaauggc cguuuuguug 1200
uugucugugg ggauggagaa uacauaaucu acacagcaau ggcuuuaaga aacaaagcgu 1260
uugguagcgc acaagaauuu gugugggcuc aagauuccag cgaauaugcc aucagagaau 1320
ccggaucuac uaucagaauu uuuaagaauu ucaaagagaa gaagaauuuu aaguccgauu 1380
uuggagcuga agguauauac gguggauacc uuuugggagu caaaucgguu ucugguuuga 1440
cuuucuauga uugggaaacu cucgauuuag ucagaagaau cgagauacaa ccaaaagcag 1500
uuuacugguc agauaguggu aaauuaguau guuuggccac agaagauagc uacuuuauuc 1560
uuucuuauga uucugaugaa guucaaaaag ccagagauaa caaucagguu gcggaugaug 1620
gaguagaauc ggcuuucaau cuucuaggug aaauaaacga aucagugcga acuggucucu 1680
ggguaggcga cuguuuuauc uacacgaauu cuguuaaucg uaucaacuac uucguuggag 1740
gugaacuggu uacaauugcu cauuuggacc ggccuuugua ugucuuggga uaugugccua 1800
aagacgauag auuauaccuc guagauaaag aguugcgcgu aguaagcuac caauuacuuc 1860
uuucuguucu ugaauaucaa acugccguca ugagaagaga cuuuccaaca gcagacagag 1920
uacuuccguc cauuccuaag gagcacagaa cgagaguggc acauuucuua gaaaagcaag 1980
gcuucaaaca gcaagcuuug gccguaagua cagauccaga gcacagauuc gagcuggcag 2040
uagcauuaga ggaucuuaau auagccaaaa cucuagcuca agaagcgaac aguccgcaaa 2100
aguggaauca acuagcagaa uuggcagcug cuacuaauaa uguaagcgua gccaaggaau 2160
guaugcaaaa agcgcaagau uauggaggcu uguugcuucu ugcuacgagc uccggugaug 2220
aaaauuuagu ccguacucua ggagaaacga cacaagcuga aagcaaacau aacuuagcau 2280
uuuugucaca cuuguuagua ggugauuuaa acaaaugucu agacauucuu auuaauaccg 2340
guagauugcc agaagcugca uuuuucgcca gaucuuaccu uccugauaag auuacagaag 2400
ucguggaacu guggaagacu caguuaucuu cagucaauca aaaagcugga cagagccuug 2460
ccgauccuaa aaacuacgaa aaucuguucc cugguuuaca agaggcggug guagcucaga 2520
aauuuuugga acagcagaau aaagguuuag cgcccgcaag aguugccacc accauuccuc 2580
cuaaucacga caggaauguu guagccgaag uucaagcaca aucgaaacac gauguaccau 2640
cauuuaguuc uucguuuauu ucaucagaaa uagaagcaca aacaaggagu ucugcuaaac 2700
cugaagaauc uucaaacauu auacagcugg accaagauga cgacgauauc gauuuagauu 2760
uggacggugu aaauaucgau gagaacauug acacgacgga uaucaacauc gaugaugauu 2820
ugcugaguga uugaaaauaa cuuuuuuacu uuaguauuaa aucuguauau ucauuccuau 2880
ucuuaagaaa aucuauauga auuuuaaugu uuuaauaguu aagaaau 2927

<210> SEQ ID NO 184
<211> LENGTH: 1620
<212> TYPE: RNA

<213> ORGANISM: Diabrotica virgifera

<400> SEQUENCE: 184
uucauuucgc cauuuugauu auuucaauuu uagaaaacgu ucaauaagca gggugcaggg 60
ucaagaagua aaguguucua gaaauacaga uuaaauuguu uccuuugugu uauugaaagg 120
caaaaauaaa auaaugcaga ucuuuguaaa aacacucacu gguaaaacca ucacccucga 180
gguugaacca ucagauacca ucgagaaugu caaagcuaaa auucaagaca aagaagguau 240
uccaccagau caacagagau uaaucuuuag aaagcguucg aguucgauaa gcaagcaggu 300
caagaaguaa aguguucuag aaauacagau uaaauuguuu ccuuuguguu auugaaaggc 360
aaaaaucaaa uaaugcagau cuuuguaaaa acacucacug guaaaaccau cacccucgag 420
guugaaccau cagauaccau cgagaauguc aaagcuaaaa uucaagacaa agaagguauu 480
ccaccagauc aacagagauu aaucuuugcu ggaaagcagu uagaagaugg ccguacucuc 540
ucagacuaca acauucagaa agaaucuaca cuacacuuag ugcuucgucu uagaggaggu 600
augcacaucu uuguaaaaac ucucacuggu aagaccauca cccuugaggu ugaaccauca 660
gauaccaucg agaaugucaa agcuaaaauu caagacaaag aagguauucc accagaucaa 720
cagagauuaa ucuuugcugg aaagcaguug gaagauggcc guacucucuc agacuacaac 780
auucaaaaag agucuacccu ccauuuggua cuucgucuua gaggagguau gcagauuuuu 840
guuaaaacuu uaacuggaaa gaccaucacc cuugaaguag aaccuucuga uaccaucgaa 900
aaugucaaag ccaaaauuca agacaaagaa gguauuccac cagaucaaca aagauuaauc 960
uuugccggaa agcaauugga agauggucgu acacucucag acuacaacau ucaaaaggaa 1020
ucuacccucc auuugguacu ucgucuuaga ggagguaugc aaaucuuugu aaaaacacuc 1080
acugguaaga ccaucacccu cgagguugaa ccaucagaua ccaucgagaa ugucaaagcu 1140
aaaauucaag acaaagaagg uauuccacca gaucaacaga gauuaaucuu cgcuggaaag 1200
caguuggaag auggccguac ucucucagac uacaauauuc agaaagaguc uacccuccau 1260
uugguacuuc gucuuagagg agguaugcaa aucuuuguaa aaacucucac ugguaagacc 1320
aucacccucg agguugaacc aucagauacc aucgagaaug ucaaagcuaa aauucaagac 1380
aaagaaggua uuccaccaga ucaacaaaga uuaaucuuug ccggaaagca guuggaagau 1440
ggccguacuc ucucagacua caacauucaa aaagagucua cccuucacuu gguacuucgu 1500
uuaagaggag gaaauuaaua ugguugaaau uaagcacauu uuuauauuuu caauaaauaa 1560
auuauaaauu auuaaaaaaa aaaaaaaaaa aaaaaaaaaa aaaaaaaaaa aaaaaaaaaa 1620

<210> SEQ ID NO 185
<211> LENGTH: 2430
<212> TYPE: RNA
<213> ORGANISM: Diabrotica virgifera

<400> SEQUENCE: 185
cucgaaacaa augacuguga augaaaagcc cuauagcaac agcaacaaca aauauuugaa 60
uuuucgguaa auaacguuua ugaaaaauaa uaauaauuuu aauuguuaca uaagacacau 120
aagaguacau aagauuguau uauggaagaa cgagauuuag uuucuaauag acgcagauca 180
uugcauaacu auggcgaaga gaaaccuguu ugucgaaaau uuccggauaa ugaugaacaa 240
aauuuccaau auccuccaga uuauauccac aaaguaaaua cagaaacgga aaaauggaau 300
gcucaccuca guaacaucuu agucgaccaa cagagguaca aagaaaaaau acgugaacuu 360
aaaacuguag uguacaauga aaacguuuug ucacaugauc agcaggaauu uuuaaaaucu 420
auagacuuua auacauacuu gagacaaacu gaaauauuuu guaaaaaggu gcauuuagcc 480
gcagaacuau acaguuucaa uaaaagugaa aaauaucaag aguuacagaa aaccauugaa 540
cauguucaag aaaucauuga uaguaaacug aagacauuua aaggucgcug uaccaccaaa 600
ccaaaaaacc auaaaucaug ugugacgacg auguagcggc ucuugucguc gacaauggcu 660
ccggaaugug caaagccggu uucgccggug augacgcccc ucgugcuguc uuuccaucca 720
ucguaggucg ucccagacac caagguguca uggugggauau gggucaaaaa gacuccuacg 780
uaggagacga agcccaaagc aaaagaggua uccucaccuu aaaauacccc auugaacacg 840
gaauuaucac uaacugggac gauauggaaa agaucuggca ucacaccuuc uacaaugaac 900
uuagaguagc ccccgaagaa caucccauuc uuuugacuga agcuccacuu aacccaaaag 960
ccaacagaga aaagaugacu caaaucaugu uugaaacuuu caauaccccu gccauguaug 1020
uugccauuca agcuguauug ucucuguacg cuuccggucg uaccacuggu auuguacuug 1080
auucuggaga ugguguaucc cacacaguac ccaucuauga agguuacgcu cucccacacg 1140
ccaucuugcg uuuggacuug gccgguagag acuugacuga cuaccuuaug aagaucuuaa 1200
ccgaaagagg uuacucuuuc accaccacag cugaaagaga aauaguucgu gacaucaagg 1260
aaaaauugug cuauguagcu uuggacuucg aacaggaaau ggccacagca gccagcucca 1320
ccuccuuaga aaagaguuau gaacuuccug acggucaagu caucaccauu gguaaugaaa 1380
gguuccguug cccugaagcu cucuuccaac cuuccuucuu ggguauggaa ucuugcggua 1440
uccacgaaac ugucuacaac uccaucauga agugcgaugu cgacauccgu aaagacuugu 1500
acgccaacac uguccuuucu ggagguacca caauguaccc ugguauugcc gaucguaugc 1560
aaaaggaaau cacugccuug gcuccaucaa ccaucaaaau caagaucauc gcucccccag 1620
aaagaaagua cuccguuugg aucgguggcu ccaucuuggc cucccucucc accuuccaac 1680
agauguggau cuccaaacaa gaauacgacg aauccggccc uggaauuguu caccgcaaau 1740
gcuucuaaac uacuuuauau auuuaucgua uacauauuaa guacaauacu gagaguugga 1800
gcaugaaugu auguuuuuau uuaugguuau auauaugaug acuuguugau auuguaacaa 1860
uaaaauucauu uuguauuacu cugguaauau uuuauuuaug agaacaacca gauugaaguc 1920
guaaagagcc aauaacaacc ugaagauauc aauugucaau ugcuacugag uaauaguuug 1980
agguacuuag cuccagcucc uuuucacacg aaaguaagaa guaucugagc gagaauacau 2040
ucuguauugu acuuuuuaaa uaugcgacuu uuguaacauc aauuucauug uaaaauauca 2100
ucaucauugu uuuuauggac cuacgugaca guaggagaca ccugacaaga cuucuuuucc 2160
ugcuguguau acgcaccuuu acaaacaucc ugcuggccua auuguagucc uguaagggac 2220
auccuuuguu gggcauggag uuuguuugug ggaauuguau ugacuacuau uauauaccua 2280
cuuuuauuau uaaggcauuu gaaaucguaa acuaaaauug guuguuuaua uuuuauauga 2340
guauuuuuag uaguagauaa gauuucaauu gcaaaacuac cuauguaugu auucauuaga 2400
aauaaaauucu uauuccaaaa uaaaguuuug 2430

<210> SEQ ID NO 186
<211> LENGTH: 2822
<212> TYPE: RNA
<213> ORGANISM: Diabrotica virgifera

<400> SEQUENCE: 186
guuuauuuug gucgucggcu gaugugacgu guaaagaaau uaaaucaaau uauuuuaaag 60

-continued

```
uuuuuaaauu aaaaugggua cuuuuaaaag agauacucau gaugaggacg ggggaucaag    120
ugcuuuucaa aaucuggaga aaacuacugu uuugcaggaa gcuagaguuu uuaaugaaac    180
uaguguaaau ccaagaaaau guacaccgau acuaacaaaa cuguuguacu uauugaacca    240
gggugaaacu uuaagugcca aagaggccac agauguuuuc uuugccauga ccaaacuguu    300
ccaaucaaaa gauguaauau ugagaaggau gguuuauuug ggaauuaaag aacucaguuc    360
uguugcugau gaugucauua uuguaacauc cagucuuaca aaagauauga cugguaaaga    420
agacauguac agagcagcug cuauaagagc auuaugcagu auuacugaug cuacuaugcu    480
ucaagcuaua gaacguuaua ugaagcaagc uauuguagau agaaacgcag cugucaguuc    540
agcagcacua auuaguucau uacauaugag caaauuagcu ccagauguag uaaaaagaug    600
gguaaaugaa gcucaggaag caguaaauag ugauaaugca augguacagu aucacgcauu    660
aggucuucua uaccauauua ggaagacuga uaagcuagca gugacaaaau ugauuuccaa    720
gcugaauuca augggguuaa agagcccuua ugcuuugugu auguugauaa gaaucacugc    780
aaaacuuuua gaagaagagg accaagaguc acuccucaac uccccauaua caauaauauu    840
uacaaugggc uuaaggaaca aaucugaaau gguggguaau gaagcugcac augccauggu    900
uaaccugaag uucacgagua guaaugugcu agcacccgcu auaaguguuc uacaacuauu    960
uuguggaucu ccuaaagcca cacucagauu ugcugcuguu agaacuuuaa aucaaguggc   1020
caccacccac ccugcgucag ugacagcuug uaauuuggau cuagaaaauu ugauuacuga   1080
uccuaauagg ucaauugcua cacuggccau uacuacucuu uugaaaacag gugccgaauc   1140
uucuguugac agacuaauga aacaaaucgc uacuuuugua ucugaaauca gugaugaauu   1200
uaaaguggcu gucauucagg caauuaaggu auuagcuuug aaauuuccaa ggaaacauag   1260
cacgcuuaug aauuuccuau ccgccauguu aagagaugag ggagguuuag aauauaaagc   1320
auccauagca gauaccauua uaacccuaau cgaagauaau cccgaagcua aagaaucugg   1380
uuuggcgcau cuuugcgagu ucauugaaga cugugaacau guuucuuugg cugugagaau   1440
cuugcauuug uuaggaaagg aaggacccaa gaccaaacaa ccaucgagau acauccguuu   1500
uaucuacaau cgcgucauau uggaaugucc uucuguaaga gcugcugcag ucuccgccau   1560
ggcacaauuc ggagccucuu gucccgauuu guuagaaaau auccaaauau uacuuucgag   1620
gugucagaug gauucagacg augaaguuag ggacagagcu acauauuaua guaauauacu   1680
uaacaaaaau gauaaaaguu uauacaacaa uuacauuuug gauucuuugc agguuucaau   1740
uccuucacua gaaagaucgc uuagagaaua cauucaaaau ccaacugacg aaccauuuga   1800
cauuaagucc guaccuguag cagcagugcc aacagcagaa gaacgagaag uuaaaaaacaa   1860
aucugaagga cugcuagucu cucaaggucc aguccgaccu ccuccggugu cuagagaaga   1920
aaacuucgcc gaaaaacuua guaacguucc ggguauacaa caguuaggac cuuuguucaa   1980
aacuuccgac gucguugaac ucacugaauc ugaaacagag uauuuugucc gcuguaucaa   2040
gcacuguuuc aaacaucaca ucguccucca auucgauugu cugaauaccu ugccagacca   2100
gcuuuuagaa aacguuagag uggagauaga cgccggugaa accuucgaaa uuuuggcaga   2160
aauaccuugu gaaaaguugc acuauaacga aaccgguacc acauauguag uaguuaaguu   2220
gccugaugau gaucucccca acucuguugg uacgugugga gccguguuga aguucuuagu   2280
gaaagauugu gauccaucaa cgggaauacc agauucugau gaggguuacg augaugaaua   2340
uacacuggaa gacaucgaaa uaacauuagg ggaccaaauu caaaaaguaa gcaaaguaaa   2400
uugggcugca gccugggaag aagcugcagc uacuuaugua gaaaaagagg auacauacuc   2460
```

cuugaccauc aauacgcuaa guggcgcugu uaagaauauu auucaguucu ugggauuaca 2520
gccugcggaa aggacugaca gaguaccgga ggguaaaucu acgcacacau uacuucuugc 2580 uggugauuc aggggaggua uugacauacu aguaagagcg aaacuagcuu ugggcgaaug 2640
uguuacgaug caacuaacag ucaggucgcc agauccugac guugcugagc uuauaacuuc 2700
aacuguaggu uaaguuuaaa ggcuacguua augauuauau uguauuacaa uuuuuccaua 2760
uguauaaaua uuuugauuua uuuaaauuuu auuagaaauu aaacaauuuu aaguaaaaaa 2820
aa 2822

<210> SEQ ID NO 187
<211> LENGTH: 3701
<212> TYPE: RNA
<213> ORGANISM: Diabrotica virgifera

<400> SEQUENCE: 187
gucguuuagu agaaguguca uuuuugucug cucucguuuu caucuuuugu guauaaaauu 60
ggugcuaagg uagauaaacu auauucgaau aggcguuuuu augucgcaag aaaguguuuu 120
guauauuugu gauacgugau cucguagagg gaguccagaa auucauaauu uauaguuaag 180
uaaaaaaugg cggcaaacag aacuggaccu gcucagagac caaauggcgc uacccaagga 240
aagauauguc aguucaaacu gguccuacua ggcgaaagug ccgucgguaa gucgaguuug 300
guacugaggu ucgucaaagg acaguuccac gaauaccagg agaguaccau aggagcagcu 360
uuccuuacac aaaccauaug ccucgacgau acaacuguua aauuugaaau uugggacaca 420
gcgggucaag aaagguacca caguuuagcu ccuauguacu auaggggcgc acaggcagcu 480
auagucgucu acgacauaac caaucaagac acauucggca gggcgaaaac gugggugaag 540
gaacuucaaa ggcaggccag uccgacgauc gugauagcuu uggccggcaa caagcaagau 600
uuggccaaca aacguauggu agaauacgaa gaggcgcaga cguaugcuga cgaaaacggc 660
uuacuuuuua uggaaacuuc cgcaaagacg gcaaugaacg ucaacgauau auuuuuagca 720
auagcuaaga aacugcccaa gaaugaacaa accacagguc aaggcggcag ugcccaaggc 780
aggcggcuag cggagggcga uucgggcgcc aaggcacccg gaaauuguug caagugaugg 840
uauacgccug caggucgagu guuguuauua aaccgucacg agaaaggacu ggcaagugca 900
gcggcacucu agugauaucu auguguaaua aagguccuuc uauuaacaaa aaaaaauuaa 960
uaaaaaaaua uauuaaacuu cauauacacu gucacauauu ccauuuagau gaugaaaaac 1020
aaaagagcag aagcauuuug gucucuaacg gucauguuga guuggaaugu cucguggggc 1080
auuuaaauuu gugauaauug uaccuauauu uuguuuuuuu uauauauaua auuaauauau 1140
cugacagugu aaguuaagcg uaaacuguuu auaucgaucg uauuagcagc accaauuaaa 1200
aaaauaaaua aaauugaaga ucuuuuuuau uguuuuugua auuuuaacuc uuuggggaag 1260
guuacaaaag aauugauaac guuguguuga aaacauugca uuauaauaaa guaauuccac 1320
ccacuuacga auuauuuuga aaggagaauc aaaaaugugu caauugucac cugucaucuu 1380
augaugacac ucuaugagag ugggggcaau ugcagcgcgc gcauacuauu cagucuagcu 1440
ucauuauguc aauuaaaugu cgauguuuaa aauuucaucg auuaguuuga caguucccaa 1500
augaaaaaac aguuacuucc gcauaaaaau guauugcuuc aaaacuuacu uucaguggca 1560
uuucaguggg uuuuagccau cuuauggaga guggucuaac acacuuucua gguacagcug 1620
ugguuuuuaa aaggaaauau aaugaaucgc uuuuguuuuc gaaauuuaca uugggaaucc 1680
cuuagugucc uuauauuugc ccuacagagu uucauuuaaa cugaaauugg guaauuuaca 1740
uagaccuaaa gcuuucacgu cuauauagcc uaauuagacc acaaaauuga cuugcuuuac 1800
gugaaaugua ugaaccauuc aaacauauuu auaugacaac aauauaaauau aauacaauau 1860 aauauaaaua acugacaaca uuuaaaauua gaauuuuuac ccacaauuuu ucucugccau 1920
gugucaucua guacaagaag uauggcaauu uagcccuacu ccucuuauug uacauuucuu 1980
guaauuccuc auuuucuuuu ucaauuacuu cgaucuuuua aacuuaauuc accaaguuua 2040
uuugcaauau uguucuugaa gucuauaguu ugaauuccuu caauauauuu guaauguuuu 2100
ucuucagugu caauccuugc auuccaugaa agaacacgaa aaagaugcag cacuuuauuu 2160
guccauauuc cugcuacaua guuauuuuuc gauuaacaca uucacugcca gcguauagua 2220
aacuggcacu uuacuauacg cuaaacaaaa auuuggccuu gcagauuuuc cuaaaacacg 2280
uagcagcuac gccacugaau ggacuuagga cccccuaucg uuucgcuggu ugcaauaguc 2340
cgguaacuag agaagcaauu auuauauaaa aguaaauuua aauaaauugua uuuugcuugc 2400 aguacugcau uuuaauaauu aguuuucuuu acuacauaca auuguuaccu uuuaauaaca 2460
uaaucuaaau cuuacuuuuu uuuuuuuauu uuuuugggcu auggccuuga caauuaucca 2520
guaaccagga cuaauauaau uggccaauau aauuaaaagu gcgaauaaua guacagagcg 2580
uagaaauagg ggucgcuuug ccgaacuugc acggucccaa uaguaaacug gcacuuuacu 2640
auacgcuaaa caaaaauuug gccuugcaua uuuuccuaaa acacguagca gcuacgccac 2700
ugaauggacu uaggaccccc uaucguuucg cugguugcaa uaguccggua acuagagaca 2760 aaagugggguc auuuugcaca cuucauauaa uucucguuuu cuguacuuca cgaguauuuu 2820
uuuugucgga uauguauuga auaguaucgg ugacaacaca cugcccugcg ugacaccccu 2880
uucaaaaccu augugggaac aauauguauc uuuagagaac uuuuuguacc cuuccccuaa 2940
aaacuaaaua uuuuuucacu uagugcaauu uuaauauuag ucucaccuua uuucuagaau 3000
acggucgguc uaaauguaua aucucaacuu ucagcuuaua cuucgaaaac cgagaaguau 3060
aaacuguaag aauauuuaac guuauaugua uuuuauuagg auaaugauug uugaaaguau 3120
guuucccaac acguguaagu uacauuucgu acucuuucca uuuuuauuac aaaaaaaaau 3180
guuuauuuag auaaacuguu gcggaacaua cuuucucgau gcaugacuga aaagaacguu 3240
aacauuuaua cguauuuguu uuuauuuugu gucugaugug acaacccaga ucuuagcgaa 3300
agcguagagg acaaaagaug aguuuuuaag uuucccauug aacuuuuucc guccuuaaau 3360
caaauacaac aacuauucac uuaaguuuuc uaaacauuuu ugcuaauaug ggccccugca 3420
ccauucccga cuuaacaguc uucauuuguu uuuauuaggu uuguucguag uacgauccaa 3480
acgaucggca accguugcca accauuagac gcaugcgcag uuaacaguga gugaucguag 3540
acuacgaaca cgcaugcguc ugaugguugg caacgguugc ugaucguucu acgaacaaac 3600
cuauuauaaa ccgccucuuu uguagguaaa guaaaccuua uaaucauuuu ccgagucuac 3660
aauuucugua ggacaucaag cauuguaaag uuuaaugaaa u 3701

<210> SEQ ID NO 188
<211> LENGTH: 671
<212> TYPE: RNA
<213> ORGANISM: Diabrotica virgifera

<400> SEQUENCE: 188
cugcgauaua ggugguguauu ucagcuggaa uuuguaauga aaaaaacgua gaaauauaua 60
cuacaaugaa guuuuuaaga ucgacagugu gcuacauugc caucuuggca auucucuuua 120

```
cccucugugc cgaugagguu gaaggaagga gaaaaauuuu gauggggcga aaaagcauua    180

ccaggacaua ucuucgugga aaugcuguuc cugcguaugu gauaauaauc cuuguaggaa    240

uuggucaaau cauccuggga gggauauugu acguugcauu gaggaagaag aucauugcug    300

caccuguaac ggcaucauau gcaguggcua gacaagaacc auaaaauuua uuugucuaga    360

auauuauuuu cuaaauaugc aucuuuuuua aauuauuguc uacguaaaua auaagucuag    420

aaauauauaa aaauuguaua aaaucaugua ccuauauuuu ucaauuuuua uaaaaaacaa    480

cccgaaauuu aauauuuuac ugaauuaaca uuaucauuuc uaucuacacu caccggcaca    540

aaauuccguc acccaaaauu uuugauuaag cuugacaauu uauaacuaua uuauuugugc    600

uccgauuuuc aacuucaugu ugugcaucag uuuguaggua cauguauuga uauuguuugg    660

uauuauuccg g                                                         671
```

```
<210> SEQ ID NO 189
<211> LENGTH: 693
<212> TYPE: RNA
<213> ORGANISM: Diabrotica virgifera

<400> SEQUENCE: 189

guagucggua uguauuugaa uuuaucuuaa uuuguuuaau auuaguaguu aaauauuaaa     60

cuauaguuag aaguuguuau auaguggacc aguaguugac uccccaaaau gcagaucuuc    120

guuaaaaccu uaacggguaa gaccaucacu cuugaggucg agcccucaga uacuaucgaa    180

aaugugaaag cuaaaaucca ggauaaagaa ggaauucccc cagaccagca acgucucauc    240

uucgcuggaa aacaacucga agauggucgu accuugucug acuauaauau ucaaaaagaa    300

ucaacccuuc acuuggugu u gagauugaga ggaggugcua agaaacguaa gaagaagaau    360

uacuccaccc ccaagaaaau caagcacaag aagaagaagg uuaaguuagc uguauugaaa    420

uuuuauaagg uugacgaaaa ugguaaaauc caccgauuga gacgugaaug ccccgcugaa    480

caauguggag cuggugucuu cauggcagcc auggaagaca ggcauuacug uggcaagugc    540

gguuacacuc uugucuucuc caaaccagga gaugagaaau agauauaugu ccuuguauau    600

uguuuaagaa aaaaauagaa aaaccuuugu uuauuugaau aaaauauucg aggaagaaaa    660

aaaaaaaaaa aaaaaaaaaa aaaaaaaaaa aaa                                 693
```

```
<210> SEQ ID NO 190
<211> LENGTH: 2684
<212> TYPE: RNA
<213> ORGANISM: Diabrotica virgifera

<400> SEQUENCE: 190

gaauuuaauu ucaaagauuu auguucagua agcuuuguuu caaagugcgg uacuaucggu     60

uucauuuuau aucucuuuau aacggugucg cgaguuuucu ugugaaaaau gauguccaaa    120

gcagacacac aggaagaugc cuccuucgcc aaauuggaaa aucagauugc uaucaucaaa    180

uacguaaauac ucuuuaccaa cguuuugcaa ugggcucucg gugcagcaau cuucgcucuu    240

ugccuuuggc uacgauucga ggagggcauu caagaauggc uccagaaauu ggauucagaa    300

caauuuuaca ucggaguaua uguacuuaua gucgcuucac ugaucgucau gauugugucc    360

uuuauaggau guauuagugc ccugcaggag aguaccaugg cccuuuuagu guacaucggc    420

acccaagugc ucaguuuuau auucgguuua uccgguucgg cgguucuucu ggauaacagc    480

gccagagauu cccacuucca accgaggauc cgagagagua ugcgacgucu uaucaugaau    540
```

-continued gcucaucacg accaauccag acaaacacua gccaugauuc aggaaaaugu ugguugcugc 600
ggagcugaug gcgcaacaga cuaccucucu cuucagcagc cccuuccaag ucagugcaga 660
gacaccguua cuggaaaccc auucuuccac ggauguguag augaacucac cugguucuuc 720
gaagaaaaau gugguuggau agcagguuua gcuauggcga uaugcaugau uaacguccuu 780
aguauuguuu uaucuacggu acucauccag gcauugaaaa aagaagaaga agcauccgau 840
ucauacagga gauagauuua gugagauaga gauauaaugu aguaauuaga auuuaaugua 900
ucuucaacua aauuacuuuu ucuuuagaga uauaccugaa auuguaaaga acaggaaaau 960
uaaauaagaa ccaaaaacua aagugaacca acaauaauug aacauuccaa aauacacuuu 1020
uuuuguuaag uuaacuaaac gacauaaauu uuucauuuuu uaaguuuuuu auuguuuuuu 1080
uuaguauuau aauuuggaua agguguuuuu auauuaagug uguaauuaua aaguuuuuuu 1140
auaggacgga accuaaauua uauagaauca uacaauaaac uauugucugc uuauugaauu 1200
uggaaaauaa acauuuggua uauauuaaaa auaauaauau augucuuaau gaggaacuaa 1260
ugaaaacguc uauacauuuu ugaauuuaau accaacagau auuguaauua uuaauuuuaa 1320
uuaaucaacu ccaagucaac aucuggaaag caauagaaau uaaaguaauu aacuaacuag 1380
uaacauucua gcaaccugua cauguggiug uauuacucug uuuugacauu gacaaaacua 1440
gcuuugugau caguuaucuc uagcaguaau aaacucuagc uguauuuugu uuuauauauu 1500
uguccaaaga auugguuuau uuuaaagcaa auauaauggu uuaacccagg ggugggcaaa 1560
cuuuuuuugg uaagggccau aaaauauuuu ugaucuauua ccgagagccg caauauuugu 1620
uaccuuaaca uauucgaauu uuuaacuuuu uacuaauuuu guuuacgugu guuggggggg 1680
ggggaugguu aaauuaaaua aacacaaaua aacauauuca guacgauuca aagauuauuc 1740
aaaaaaauuu aaaaccaaau auugaaaaau aagccaacgg uggcaaauuu uuacaggcag 1800
cucuaagaaa aaauggauuu ugcaguagau caaugcauau gaaacaaaaa auucaaaaau 1860
auguuauuag cuuaugaguu ucucgaggua acgcuguuga guuuuuuagu uuuaacgauu 1920
uuugaguuuu ugauaucacu caaaauacca gucaaaauaa ggaaauuuuu guaaaaagug 1980
ugaaaaucaa cauauuuauu auuguuaacc aaaacauauc ucgauagagu uacuucacga 2040
agugaccaaa gaaaaucuau gaaaaauuuu agguggagcu gucaaguagg uaguuuuuga 2100
guuacaaugu ccaccgccuu ugaaaaaagc aguuuugaga aaaacgcauu ugguuugaca 2160
acuuuuauuu cccuuuguuu uuugucuguc aaaucguaaa gugauguacg ccggaauaug 2220
uuuuugaauc guagaguaau uuauaaaaga gacgagaaca gcuguuguac guuucucccu 2280
acgcucaggc uacugcaaag cgagucgaag guagggauau uaaacaugcu uuacuuccgg 2340
uaauuuuacu ccagucaagc ugaaaauuuu agagaguagu cuugaaguuu auuuauuuau 2400
uuauuuaugu acuuucauuu aaaauauaaa aaaaaaucaa acauuuaaaa caaaaaaaau 2460
uuucaaaccg uaacccuccc cucuaaacag cauucgcauu uaauuaagca ugguauuucc 2520
cucaaauaua uguguaucua uauauuuauu uauuuuuauu uuaucucuga accuauuucu 2580
uuuuccuuaa uauuguucug aagcuauuug cuuguaacau cuuaugcaau uuacuguuuu 2640
guuugagaau gggccacagu uugaguuuga aauuaaauuu auuu 2684

<210> SEQ ID NO 191
<211> LENGTH: 458
<212> TYPE: RNA
<213> ORGANISM: Diabrotica virgifera

<400> SEQUENCE: 191

```
gcuugaucuu caagguagaa caacgcaagu agaaaucuaa aacaugucug gacguggcaa     60

gggaggcaaa guaaagggaa aagcaaaguc ccgaucaaau cgugcugguu uacaauuucc    120

uguaggucgu auucaucguu uauugagaaa aggaaauuau gccgaaagag uuggugcugg    180

agcuccugua uacuuggcag cuguuaugga auauuuagcu gcugaaguuu uggaauuggc    240

aggaaaugca gcuagagaua acaaaaagac ccguauaauu ccuagacauu uacaauuggc    300

cauaagaaau gacgaggaau ugaacaaauu acugucagga guuaccaucg cccaaggugg    360

aguauugccu aauauacaag caguacuguu accuaaaaaa acugaaaaga aagcuuaaga    420

guuaguauuc cuuuuuaucc aacccggccc uuuucagg                            458
```

```
<210> SEQ ID NO 192
<211> LENGTH: 2478
<212> TYPE: RNA
<213> ORGANISM: Diabrotica virgifera

<400> SEQUENCE: 192

acuagguaaa uauaccuugu auauuugucu auuaacggua uuauuuauau uauuuuaaag     60

ugcgcaugcg uguugugaca guuuauccaa uuuucuuaca auuucaggua cccucgaacg    120

caacuaaugu ucuuuuagau uguuagccag auuucacaca auacgugguc acgucaggcc    180

gccguauuca guuuuugauu ucaaacaaac ugacugcugu cugcauaaaa auccaaaaaa    240

ucuuuugcca auauuguugu gacauuuuau uacguauacu cguaaaggcg uaauaaucaa    300

cuugaaauug caauaaaacu aaaagcuaaa uaacgauuuu ucuaguaaua ucugucauac    360

gaauuugaau acuggaaaua gaugaaauua guaucguauu uuuucuuaaa uuuugucacc    420

caugaauuaa aagcuucaga gucaaauuag auacauuaau uuguaaugca gaaauuuaac    480

uguaacuucc ugucauggaa cuugauuuug auauuugaug guacuuucuu ucuauuguua    540

cugauaaaag auuaccaauu aaaaaauaua auguucauug uauucacaug auguauuaca    600

uuuguuggua cucuuuugcg acaauuucga ccaauguaca uuuagauuuu gagcuuuaca    660

gcaauggaac ugaaauuaac guucaagaua ucaauacaaa uaaaaagcuc aaaaucucug    720

gacgauaaga acacuuucau cacaugccaa ugcuugcuua acuuuuuuaa auuaaauuuu    780

uuuguuaaaa ucaaugcagu aaaaguuuuu uauguaagau aucucucccu aguguggaga    840

uaaacuaagg cauauagaau augacaguag uuauauucua uacaaaaaaa auuaaguauc    900

cauguggugg ggguaaaugu augaggguca acaggaucga uacugucugu guauuaaaua    960

aucuaugcuc uuagcgaaug uucccagguu aguguuaugu aaucgugggc cucaucggcc   1020

ucaacacuuu uuuuugucua cagugaagua agaaagcggu uuccaaagug caugaaguug   1080

gaugguguag aucugccccc accaauuagc uucgacauug cggaagagca accguuacca   1140

ccuugccaac agacguucuu auguaauggu gauggaggau ccauagugcg acaguuucuc   1200

gagcuguauu ucguaauaua ugauucagau aauaggcagu cccuucuuca ggcauaucac   1260

gaaaaagcca cauuuucaau gacaauggcc uacccguacg gcuauuccaa agacaguaaa   1320

ggaguaucgu gguugaauug guaugccacc gauaauagaa auuuauuacg aguucaagau   1380

ccagacagaa gaaacaaguu guuaagacag ggacaaguug cuguaguuuc guucuugcaa   1440

gauaugccgc acacgaagca cgauauucac aguuuuacag uagauuugac aguuuuuaca   1500

ccccagaugu uauguuugac aguggcuggu auguuuaaag aauugaaaag uggccacaaa   1560

guaccuccuu uaagauauuu cuucagaacc cuuguaauug uaccugcugg aucagguuuu   1620
```

-continued ugcauagcaa augaagaacu ucacauaucc aaugcaacuc cggaccaagc aaaagaugcu 1680
uucaagacca ccguuaaugu agcuccggca ccagccccug ugauuaccuc uccuggaccc 1740
aguauaccac aacccgcugu gccagaugau gcuacaaaac aagaaauggu aaaacagaug 1800
uccgcaguau ccggaaugaa ucucgagugg ucgcuacagu gucucgaaga aacacaaugg 1860
gacuaccaga aagccauaau gguauuccaa aauuuaaacg cacaaggugu uguaccacaa 1920
gcagcauuua uuaaaugaua cgaagauuau guuaacuuug guuaauuaau ugacaguuag 1980
uuauaucuug gcaaauguaa auaguaucuu aaauuauagc uaauuuuuag uuuuauuauu 2040
guuuaaggua auguuaguuu aagaugucga auuuuaaguu uguuacauac gaaaaucaaa 2100
ucgaaaaaau guuaauaguc ccuuagaaau accgguagcc cuuaucuuag aagaaaggug 2160
guagauuuua aauaaaaacu ggguuacuuc acaaaaaaau gucuauuuua auuaguugau 2220
cucgauaacu uaauaugauu auauaaauac uggccuaacc uaacaaaucg gacugaaacu 2280
uuuaauauua ccuaaacaag caagauccau uuagacuaaa guuugaaguu uuggaauugu 2340
auugaaauuu gaacauuaca uaaacgguua auuuuauaug agaacuucuu agacaauaau 2400
acuaauuaac uauuuucaau gggaaauaag ccacaauuuu accaaaaaaa ugauuuuauu 2460
aacguuucga cgcccaag 2478

<210> SEQ ID NO 193
<211> LENGTH: 3274
<212> TYPE: RNA
<213> ORGANISM: Diabrotica virgifera

<400> SEQUENCE: 193
caaaacguca acaaucugac acgucuguaa uguuuagccu gacuuuugag uaaaauuacc 60
gaaaaacaua auuaaaauug auuuauuaag aguacauaau aacguacgaa aaugacugcg 120
guagaacaac cuuguuacac acuaauaaac uugccaacag auucggagcc cuacaaugaa 180
augcaacuaa aaauggauuu agaaaagggu gagguuaaag uaaaaauaag agcauuagaa 240
aaaauaauuc acaugauucu ggcaggagaa agguugccga auggauuucu aaugaccauc 300
auaagaaacg uuuuaccuuu acaagaucau uuggcaaaaa aacuauuauu gauuuucugg 360
gaaauaguuc caaaaacaaa uccagaaggu aaacuacuac aagagaugau uuugguaugu 420
gaugccuaua gaaaagaucu gcaacaccca aaugaauuuu ugagagguuc uacacuucgc 480
uucuugugca aacugaagga accagaauug uuggaaccau uaaugcccag uauuagagcu 540
uguuuggauc auaggcacag cuaugugagg aggaaugcug uacuggcaau uuuuaccauu 600
uacaaaaauu uugaagcccu cauuccagau gcuccugaac ugaucuccaa uuauuuggau 660
ggugagcaag acaugucuug uaaaagaaau gcguuuuuaa ugcuucuuca ugcugaccaa 720
gaaagggcgu ugucguauuu ggcaucaugu uuagaucaag uaaauucauu uggagauauu 780
cuacaacugg ucaucguuga guugauauau aaggugugc auuccaaucc ugcggaaaga 840
ucuagauuua uuagauguau auauaacuug uugaacucaa gcaguccugc ugucagguac 900
gaagcugcag gaacuuuagu cacccucucc agugccccga cugccguuaa agcugcugcu 960
agcuguuaca uugaguuaau uaucaaagaa agugacaaca auguaaaacu caucguuuug 1020
gacaggcuga uagcacuuaa ggagcuuccu aaucacgaaa gaauucugca ggauuuaguu 1080
auggacauac ugagaguacu cucugcuccu gacuuagaag uccgcaagaa gacuuuaagu 1140
cuagcccuug aauuagucuc uucacggaac auagaagaaa ugguauuagu auuaacaaag 1200
gaagugagua aaacgguaga cagugaacau gaggauacag gaaaguacag gcaauuguua 1260

```
guaaggacuc uacauucgug uuccauuaag uucccagaua ucgcacguag uguuauacca   1320
gucuugauug aauuuuuauc cgauaaauau gaacuggcug ccacagaugu auugcuguuc   1380
uuaagggaag ccauacagaa guuuaaagaa uugcaaccgu uaauuauuga gaaacucauc   1440
gaaacuuuca aagacauuaa auuggucaaa guccauagag cagcaauuug gauuuuggga   1500
gaauacgcga guacugcuuc cgauauagaa guuaucguug gagaaauuaa cagauuguug   1560
ggugaaggau cccucguuga agcugagcag aaguuaauag caggagauac ggaagagaau   1620
gcuccugcac cugcugcagg cgccaccacu uuaguuacuu ccgauggaac auaugcuacc   1680
caaucagcuu ucaacacugu cagccaaacc acuaaagaag cacgaccucc ucuaagacaa   1740
uaccucaugg augguuauuu uuucaucgga gccucuuugg caucuacauu aaccaaacug   1800
ucuuugcggu augaggaccu caccucuccu gcugcuagca auggauucaa ugccaaaauu   1860
augcuuauua uggcuggaau ucuucacuug ggaaaaucag gacuucccac aaaaucaaua   1920
accaacgacg auaaagacca cauucuguuc uguuuacgag uccuaucuga ucguucucca   1980
aucauuguug aaauuuucaa aaaauugugc cgcucggcac uaaaugagau gcuucuagcu   2040
aaggaaucgg uagaagcgau cucgcaaaag agcaaagaaa aaaacaagcg uacgauucaa   2100
acugacgacg cuauaagcuu ccugcaauua gagacagaua aaaguggaga gcuaggagaa   2160
aacguauucg agaugucgcu gucacaagcu uuaguaggag gucgaacggg agguggcgaa   2220
ucaguauuaa guuccaauaa auuagauaaa aucacacaac ugacugguuu uuccgaucca   2280
guuuauuccg aagcauacgu ucacgugaau caguacgaua ucgugcuuga ugucuuaaauc   2340
guaaaccaaa cuaacgauac uuuacaaaac ugcacgcuag agcuggcuac uuuaggcgau   2400
uugaaguugg uagagaagcc acaaccuguc guauuggcgc ccaaagacuu uugcaacauu   2460
aaagcuaacg ugaaagugc cucaacugaa aacggaauua uauuuggcaa cauuguguau   2520
gaugucauag gagcggggguc agauaggaau guuguaguuu ugaaugauau acacauagau   2580
auaaauggacu auauagugcc ugcuaguugu acagauagcg aguuuaugag aaugugggcg   2640
gaauuugaau gggaaaauaa gguaaccguu aacacacccc ucacggaacu uucagaauac   2700
cucgaacauc uacucaaaag cacaaauuug aaauguuuaa caucagaaaa agcucugagc   2760
gggcagugug guuuuauggc agccaauuua uaugcaaaau ccauuuuugg agaagacgcu   2820
uuggccaacu uaaguauaga gaaaccuuuu aauaaacccg augcgccagu aagcggucau   2880
auuagaauaa gggccaaaag ucagggcaug gccuuaaguu uaggagacaa agucaauaug   2940
acacagaaga gcacacaaca uaaaguagua gcugcauaaa uaaaaacguu uuuuucuguu   3000
ucaacccuuu ucuucauuuu aaaucauauu cuguaauuua auuaauuuaa uaucauauua   3060
cugguuacac auuguuagau uauaaauauc uuuuaaagaa uaaaauuuau uuagcuuuua   3120
caaagagcgg aaagcaaucu uuaucuucuu cuaauaagau caacaucaag uuuucuggaa   3180
aauauaauau auaaauuaaa gauguuuagc auuuauuagu gaaauacaug gcuuacuauu   3240
uugaugacaa agucagugua auauagaaaa gcag                               3274
```

<210> SEQ ID NO 194
<211> LENGTH: 3652
<212> TYPE: RNA
<213> ORGANISM: Diabrotica virgifera

<400> SEQUENCE: 194

```
gguagaugau gaugacccua auaaugaaaa caacucaagu cuucuuuuua aaaacugcaa     60
```

-continued

```
aaaagaaccc uacggagucc accucugaau uagguccaaa ucuuugaaca aaacuccuug    120
cuucgucuga aagagaaguu ccgagccauc cagguucucc uaaaguuaaa ucugguugga    180
cuaauuccaa gaaauuaaaa cuuuuuaaag cccaagcuac aaugccucg uucucagaua    240
ggguuauagu acauguacug uagaccauga uuccaccugg cuucaauaau uuugcugcau    300
uuucaaacag uuuucuuugu aauggaacga augacuugau cucguuuucu gacgaccuau    360
uggccaguug uggucuuuuc ccaagaacac uacacggugc aucuaaaagu auuuugucga    420
acgauugggg ugcgaauggu ggaccgucua uaacauuuuu ggaacuuaaa guaucugaaa    480
uuauugcagu agaaucagcu ugaaaacuau acacuuuggc gccgaaaucc ucacagcguu    540
uuugaaguug ggcaaccuuc uuuggaguuu ugucuauggc uauuaauauu cccuuauucu    600
gcauuagcuc ugcuauauga guaguuuuau ucccaggaga agcacacaua ucaaguacua    660
caucaccagg uuugggauua agauuaugaa cacauacaau agaugguaua uuuuguagua    720
aaauaucucc gacugguaau aaacuuucgc uuaucgguac acauccugaa auuguuucug    780
uuacuucuac agcaauacca cugggcgcaa uauuaucagu ugcaaacaac uggugccucu    840
gcaucuuaac uaucccauuu ccaaugaaua uuuugaaguc gucuucauau auuuucugaa    900
gucccuuuuu acacuuuuuu gcaacaucgg cguaaauacu aacguuuucg uuuaucugac    960
aaccugaaac cauuccuaau acuccugggg caaauauaug agcaccccga agaauugcug   1020
cagcacaauc agugucuacu auaauuucuu uaucaaacuu uuuaaagccu gcuggacaau   1080
uuaaacuguc aauuauuauc acauugguaa aagagggaug uauguaaaca uuugguguau   1140
cauuacaauu uucugcaaaa uagguuuuua auaccuuuaa aacuuuggca guauuuguuu   1200
uuauuguauu uacucuuauc gaaguuauuu uuggugcaga acauaaccau ugcuguauuu   1260
uuaauaauuc uucauuugaa accgauguuu uuguuuuggu gacacuaucg ucaagaaaua   1320
aauucguuau uaauuuauug uugaacguug ucuuaaacgg ggaauuaggg uaaaccaucu   1380
uaaccuuuaa gauaauuuaa aaucaacgua aaauaauucu guaaacaaaa uuaaagucac   1440
aaaacgugca uacuugauag guuagaaguu gaugacuaaa aacuaaaagg ucacguguca   1500
ugcgccaacc aaugcgacac gcugguuccc aagacguggc augagcuacg auucucuuuc   1560
aaguccgcca uauugacauu cgacaacuuu uuugggagga caggugaaug uuauagcguu   1620
uuucaaagug uaagguguuu auuuucaaaa aguuuauaaa auaagcaauc acuaugggua   1680
auguguuugc aaauuuauuc aaaggccucu uuggcaaaaa ggaaaugagg auauugaugg   1740
uaggacucga ugcagcuggu aaaaccacaa uuuuauauaa acuuaaauua ggagaaauug   1800
uaacaacuau uccaacaauu ggauuuaaug uggagacugu agaauauaag aacauuaguu   1860
uuacaguaug ggauguaggu ggucaagaua aaauuaggcc auuguggaga cacuauuucc   1920
aaaacacaca aggccuaauu uucguaguag acaguaacga cagggaacgu aucacugagg   1980
cuaaagauga auuaaugcgu auguuggccg aagaugaacu uagagaugcc guacuucuca   2040
uuuucgccaa caaacaagau uugcccaaug caaugaacgc ugcagaaauc accgacaaac   2100
ucggucucca uucacuacgc aaccgcaacu gguacauuca agcuaccugu gcaacuagcg   2160
gagaugqucu cuaugaaggu cuggacuggu uguccaauca auuaaagaac gccaaucgcu   2220
agaacauagg aaaagagagg agugcgcaaa aaagugugcg agugcagaug guuuuuuucu   2280
uguacucuug ucgugucuac uaccucgcgc gcgcgcgaaa cguuucguau accauauguu   2340
gcaauuuuug uguccgaugg ggaaauucgu cauguuucac uuuggggguu auaaaauugg   2400
cuguuggcga caaguggugu augaggugaa uccgaaaaua guuuuaggca auauaucaua   2460
```

ugaaucucag cuuucuuuag guugagaguu guuuuuguag uaaaagaacc uuaaacaucc 2520
uucauuggcg auuuauuauu uuuuaacugc augaaaaucu uaguuuuaau guuuuuauau 2580
aacacuuuua gauuguacua acuuuuaaca uuccacaaau uucucauaaa auugugauau 2640
cuuuucuaau accucuuaua ucaaugaacu uauuuuugca ggccaaaaua uuuucuuaga 2700
aaguaauuuu guaucaucua uaaaaauuua auuuugggaa uucaauuaaa gacuuuaacu 2760
ggcaaauuuu aaaauguuac aagguucuag ucacguauuu agucuggacu ugcacuuuau 2820
agcacuuguc gcagaaagca ucuaaccccc aaacacguau ggugaugucc uauuugcaga 2880
aaaugcacua uaauauacga uaguaauuau uuauuguccu cuuucuggug aaaacaggcu 2940
uuuuguaaca uauauuuuuu auuguuugua auagguuaaa auguacagua gacacuuaua 3000
uuuaaaauaa auauuauuuu uuaucuauca auccuuuuug uaacauaugg uaaggcuguu 3060
cguauuuaaa aaauaaaaca agaacauguu uuugaaaagu uuugggcacg gcucaaguau 3120
uuuauuguuu aaauuuaaga ugaaguacga augggcgcgc ccgaauccga caagauauug 3180
uauagccccg uauucguugu caaaccaacg ggucuugcuc ugguaguuaa uuucggcguu 3240
agaguucaag aaggaaguag auuuuuuuau acuuauagua aauauauuau gggauauuua 3300
aagacuggcc gauuggcuua ccagacuuac gucccgcaga ucuuaaccgg cgaugaguau 3360
ucgagguuug uuucugguca gauucgggca cgucguacug uacauaaaau acuuuuguuu 3420
acuucucaaa uuuguaacuc aguuguggau acuuugaggc guaauuuuau uuugacaaac 3480
uguggauuua agguuacauu auaagugauu uauuuaaaga aauauguuuu ugauuuaucg 3540
uggacauucc cuguuuguca gcuguauuau caaauaaauu uauacuauua aaaaaaaaaa 3600
aaaaaaaaaa aaaaaaaaaa aaaaaaaaaa aaaaaaaaaa aaaaaaaaaa aa 3652

<210> SEQ ID NO 195
<211> LENGTH: 7631
<212> TYPE: RNA
<213> ORGANISM: Diabrotica virgifera

<400> SEQUENCE: 195
cuucacuuuu acggguaaac gugcggaagg uacguuccaa guucgaaccu agcgcuugau 60
guucugugua cacucuguac aauuaaaaug gcuuccaagu ucuuugugag uuaacuuugu 120
uaggugcauu uuaguaaauu ucugaauugg guuguuaaau uuagaguguu agugcauagu 180
aacuauuaaa uaguggccuu aaaaagugcu cuuaaugagg auuauaauaa gaaaaacgaa 240
cuuuuaacaa gaacaacgag uguccauucu aauguuauua caaguagcua cuaaaaauau 300
ugcaaaaaaa acuuucggua acuaaaaugg gacgguugca cuguuuauuu uguauuuucc 360
uauguuuuac cgucaucaac acgcagacaa cgaauauaca uggauucucg gaaaauuccg 420
uggauacauu ucuaucaccu caugggaaaa gugcaaaauu cgugcaccaa aaucacaaac 480
ccaaaauuga aaauugucag aacuacaaac ccucggugaa agaagaacag ccaggcggaa 540
cguacguaac aacgguuacc gcuaucgaug acgauccuag ggagggagga ggaacaauua 600
guuacaaacu aauucauaga gaaggagaac auguuuuauu ugacauagac aacguuacug 660
guguuuugac aacuauccag ccauuugauc gggaugaacc aguaaggcag aaggaacuuu 720
auguaaccgu acaagcuuca gacaacggca ggccaccauu agcagauguc uguacauuua 780
caguuaccau uaccgacauu aaugauaaug cgccacagcu ugauaaacug aaauacgaug 840
cacaaguuuc ugaagauuua aaaguaggaa gugaagugau gagaguuuuu gcuuacgaca 900

-continued

```
uugaugaugg ggaaaauuca agauuaucgu auaacuuuuc aaacgaaaau gcucaauuca    960
cccaguauuu caggauagau cgagauacug gcguugugua uuuaaaggaa gcuuuaacag   1020
acaaaaagaa uacuagauuu aacagugcug uuuauguagc cgauaauggc guuaacgauc   1080
aagaaggcca aaaagauuca accgcuaaga uaucuauaac aguaguaggg ucugauaaac   1140
agccucccag auuuacucaa aaaaugccug auggaaucuu ggagaucccc gaagauuuua   1200
aagacuuuuc uaaacauauu gucacagucg aagcaacguc caacauugcg gauccacaac   1260
uugcuuuuga auuggugaag ggaaagacau aucaaaccaa uaaagaccaa acguuucuuu   1320
uggaggcaga aggaaauaaa gcgcacauaa agcuagugcg uccacuggau uaugaaacag   1380
uaacggaaua uacucuaacu auucgaguaa aaaacaaaga uuuaauggau ucuuccauaa   1440
auauaccaau uaaaguauua gauguuaaug augaaauucc uaauuuccuu gaauuucuua   1500
aagguagugu cguggaaaau gacaagccag gugcacaagc gauucaagua agagcaaucg   1560
auaaagacgg aacugcugcu aacaacauug ugagcuauga acucguugac aauacagauu   1620
uguuugcaau aaaccgaucu acgggaguaa uuacgucgag aguggaguuu gaucgugaaa   1680
cuguaccucu auaucacgua aacguuaaag cuuaugauaa cucuccgucu gcuuuguaua   1740
acacgacauu gccuaacauu guaauucaga cauuccaaau caguauagaa gaucaaaaug   1800
acaacaaacc uguauuuacu cauccaauuu aucaguucag uaauauuacu gagcuugcug   1860
auaaaucgag uauuguuggu gaagucaaag cuuuagauaa ugacacggcu ucaguuauaa   1920
guuauaguau uacaaaugga aauauugacg augcguuuau gauugaaaau ucuaccggca   1980
gaauaagagu uaauggaaaa cuggauuacg agaaaaucga acaauacaac uuaaccguuc   2040
gcgcauuuga uggggcauuu gaagauuuug caauuguuuu aauuuccaua cuuaaugaaa   2100
augacgaacc uccaguuuuu gacgacuaua ucagagaaau ucaaauuaaa gaggaagaac   2160
cuaugauauc cggaugcguu guuagaguga cugcucauga uccagauauu aaagacaggc   2220
augcugauca acacauagua uaugaggucg cgaaagaaca gaaagauuuu uugaccguau   2280
cugccgaugg augcguacaa guaacaaaac cucucgaccg agauccgccu uucgguagcc   2340
caacacgaca agucuucauc uaugcucgug auaaugaugg aggcacaaau ucauuguugg   2400
ccacugcaga aauugaaauu auuuuaauag auauaaacga uaaugcuccc uuuuuaaaug   2460
uuacagaaau uguuuauuau gaaaaccagg auccagguuu uauagguaac cuaagugccg   2520
augauuacga ugguccugau aauggaccuc cguuugcuuu ucgauuauca gacacugcuu   2580
cagauaguau uagaucgaaa uuuuccauua ucggaaacca gcuuuucgcu uuagaaaugu   2640
uugauagaga agagcaaaaa uauuaugaca uugccauuga cauuacagau aguggaguac   2700
cuccacuaac aggaacuagu auucuuagag uuauaaucgg agauguaaau gauaauccag   2760
cuacagacgg aaacagcacg aucuuugugu auaaguacgu caaugggcca gaaaauuuca   2820
uggaaaucgg acguguauau guuacagacc uagacgauug ggauuuaaau gacaaagucu   2880
uuguucaaga agauaacuuu gaugaauuug uguuaaacca gcauaacaac gguaugauuc   2940
ugaugaaacc aacaacggcu gagggaacuu augagguuca uuacagggucacugaaaccc   3000
augaacccac aauacacgaa cauacaguua augcaauagu cacgauuaca guuaaaguac   3060
uuccagagga agcgguugua aaaucaggau caauucgauu gagaggaaca acuaaggaag   3120
aauucauaga aaauucauug aauggaaaga gcaaaagaga cauauuacac caagaacucu   3180
ccaaaauauu aaauacaucu uuagcgaaug uugauguauu uacuguuuua aauucacccc   3240
accagaauag uucguuugug gauguucgau uuucugcuca uggaucucca uauuaugcuc   3300
```

-continued

```
cagagaaacu cgaaaacaaa guuacagauc aucaaaugga gcuugaacaa aaauuagaug   3360
uggaauucua caugaucaac guaaacgagu gccuuaacga aacaacgugu ggagcugaaa   3420
acucauguac gaacaaauua aacauaacac gagaaccagc uguaguguuu acuaacagaa   3480
cauccuuugu cgguguaaau gcauuuauug auccugugug ugccgcuuua ccaagagaug   3540
uuauggaaug uuucaacgga ggcguccuua ucgaaaacac agcguguaau uguccugcag   3600
gauuugaagg accacauugu gaaauccuag cuauaggauu uacaggaacu gguugggcua   3660
uguauccauc cuuugacgcu acaaacagga cugagauuau acugcauauu uuaucacaaa   3720
cugauaaugg uuugauauuu uacaauggac cuuuaaauau aagacaaacu ucuuugucua   3780
aagauuauau aucauuagaa cuuaaagacg gauauccauu acuucaaauu ugcaccggcu   3840
caagcacuca agaaauuuau cugaaagagc gcauucacaa auugagcgau ggaucguuac   3900
acaaaauaaa aauaggaucu ggauuugacg auauaucccu ggaaguagac gacuguggaa   3960
caacguguuc aauuuggacu aauaaacuac auaaaggugu uauccgagca aauggccccc   4020
uucaacuggg agguaugaaa aacagauuca ccgaucaaga auucaaacga auuugggacc   4080
auuugccacc gacugccacc cguuucucug guuguauuag aaauuugacg uauaaugaau   4140
uuuacuacaa ccucggugca ccuucugaug cauuccaagc guaucccgac uguaacuaug   4200
cagugaugca agcugugacu uucgguaucg acuccaauuu cuugguugcu auucugguuu   4260
guguagcaau uuugauaauu cuucuucugg caguaguugu acauagacgu aaacacgaca   4320
acuuuaacga aaaagaaauc gaugauacuc gcgaaaacau uaucaacuac gaagaugaag   4380
guggcggcga augugacacc aacuacgacc ugucuguuuu ccaucagaac aacauugugg   4440
acgaaaaacc auugaugaga gacaaccccg auguaccugc agauauaagu ggcuuuuuag   4500
auaacaagaa agacaacugu gauaaagacc ccgauaauuu gccuuaugac gacguucgcc   4560
auuaugccua cgagggagac ggaaauagca ccggauccuu aucuucucuc gcuucaugua   4620
cggacgaagg agauuuaaag uucaacuacu uaucaaguuu uggacccaga uucagaaagu   4680
uagccgacau guauggagaa gauccaagcg augaagacuc acacgaugga aacgaagaau   4740
ccuggugcua gacuaaauuc caugacuccu uagaaaguga cauuuuugua cuuaaauucu   4800
uuuauguuaa ccaaagauug cgaaauuuuu uggaauggaa cugaacaaac uuguacauau   4860
uuuugaaaaa ggauguuuca acuguuugca auacaagaau uguuacguau gcguuucaaa   4920
acauauauuu acauguaacc guucuuguau uguaaauauu uuuauacuau cuuuauacug   4980
acacuuagau aauguuaucu auuaaguggc aagcaguuug guuaagaaua acuuugaguc   5040
uucuauccca agguacugug auuugaacaa aguuagaaua agcaacuucc auaccaucaa   5100
uccacuucau uuuauucaac auacugguuu uccgaaacua aagaagcagc cuaauacaua   5160
gaguucaaua acuuuuauua aacaauccgu auuaggugca cauauucauc gcgcacaagu   5220
acauauugug gaacuguaca cugacgagga acaaauauuc aauaagaauc uuuaaagcga   5280
aaaauauuga aauacacgau cagauuuaac auauuauugu cuagcucaaa agaaaauaau   5340
uuuuaucuug acaauagaca uuuuucauau auaagcuagu agauuuauau caaaaucuau   5400
aaaaaaagug gcuuaaaagu uucuuugauu uuugcgauuc ucuugaauga cuucaguauu   5460
uuuuacaaaa uuauaagacu guuaaucguu uaagcuggca gcaugguaag auacguaugu   5520
gaaaacuugu auauuuuaca aaauaacuga aaauuaguau guugcgaaaa acaaauggaa   5580
acaaauauac agugaauguc gaauaguauu gucaaaauua aagucauaau uuuuaaagau   5640
```

```
uguccaaacu agguuguuga uguauguuaa ucucugaaug ccauccuuua gccaucauug   5700

uguauaucag cuguuuccuu uugcaguuug ugugguacuc cugaauguac ggaauaauca   5760

cauaguuuuc acgaucuuuu acuuuucuuu ucugcagcua auuacagggu gguuguuccc   5820

uuaucaauau ugaaauucuu auauaaucag uuuuuccaga cuuagaaaag uuaaaaaaac   5880

agcaucauau cccugcuaug uuuauucuuc guuguaagga cacucuaauu auuuccaauu   5940

agagaucuca agauguuaug uuuacuagca gguauugaac gaaaacaaua auaaaagcaa   6000

accgaguaau caacaauagu uacaauaccu acaauuuacu augccuucgu agcuuauauu   6060

ggagagauga guggaauuuc ucaauaggcg cauauacaca uaauaauaag acacauauuc   6120

aaauugguug gugguuaaau agcucaaaaa cgauacaaag gaaacauaua gguaacaaca   6180

aaauacaagg uaaaaauaga gguacuuaca aucaggacgc uccaacgaag ucacuauuuu   6240

acgucuuuac acucgaaucg ucugaaugca ucucuuuccu uauguccucg ggguagaauc   6300

uugcaccuca agugguugaa aguuccuuuc uucgucacau guggauuucg cuaauaugcg   6360

aacaaggaac aacacaggcg ucaaaaagga auaugauuuc gaacuauuua aaacaaucaa   6420

aucaauuuau cggaauucca acacaagauu uauaucagca uuucaguagu aaucucacca   6480

uauuccaaau uugucuuuuu guauccaucu uauuuuugucu uuaucuuacu uuauauuguu   6540

uuguuuauuu uuuauuuauc uguauccuua ucuuuuucuc uuugacuauc acagcaaauu   6600

uuuguaauuu ggauuuacaa uuaguuauga cuuuaaugaa aacaauacuu accaucucuu   6660

uccuuaaauc gugcgauaua auuuaucaac aauguaguau cauaccacaa caaugucuaa   6720

uaugaaacau acgagaggcc uuaugcauau gccuuaacac guuuaggcac aaauaccaau   6780

aaaaaccuua cacgguucgg caauaaaaug agagaaccgc uauuuuauau acacgcauuu   6840

uuucuauuuu uauuaggauu uuguuaguuu uguuauuacu uaguauaaau uuaggauagu   6900

uauuuuguau uuuuauucuc acguagggcu cagucgacgu agucguuuga auaacauuuu   6960

auuuaaaacu gcagguuuga gaauagccau ucauuggugc cguauuuaaa aaaagauuuu   7020

aaauguuucu uuacuggaua uaucgaaaua caguuuuuuc uuuacguaag gcaguuagau   7080

uauuaaaaua gucuugugaa agcguauagc ucagauguuu uuacaauaua guuucuaaau   7140

uagucuuaaa aggcaacuau ucuuauugca auauuuccca agcuaaauuc acucgagacu   7200

uuggacucau aaauauacaa ugacugaguu cuacuugauu uccguuucau ugacuauuua   7260

auauuuauuu uuacaagucu ugaugaaaau uuggaaauac augauaucaa agcaauuuau   7320

aaucguaauu aggcuaauag uauccuaagg ugauaguauu uccugauuuu caucaauuau   7380

auauauauau uaguaucaca aaauacaguc uguagagacc cgugucauag auaaccuaac   7440

cuuccauugu uacacaucuu guuaacaagu cgauuugaag uggugccggu ugugaagaug   7500

cguaucuuga uguuccacgg cuaaaaucgg uucguucaca aaagcuuuua uauauuuuuu   7560

auuuacuuuu cuucuuaaau guccggcuug aauuuucaag auccagugcu gguacacagg   7620

agggcgcgac g                                                       7631
```

<210> SEQ ID NO 196
<211> LENGTH: 1028
<212> TYPE: RNA
<213> ORGANISM: Diabrotica virgifera

<400> SEQUENCE: 196

```
gucagugcug ugugcuguca cugucacuac ucuaguguca cgauuuuuua gcccugaaau     60

ugucagauua ucacaugaca uuuugagaaa acuaaauuag uaagugaaca cgaauuuagu    120
```

ucaaaaugcc uuucugugguu cccaaauugu cccucugcgg ccugauuauc agugcauggg 180
guaucaucca guuggguuuc augggugauau ucuauuacau uggggcugug gcuuuagcag 240
aagauauucc agagguugag uuuaagggcg auuuagacaa auuuuauagc gacgucaaca 300
cggguuucac acagaaugcu uacaacugcu ggauugcugc ucuccuauac cugauaacau 360
uagcaguauc agcucaccaa uucugggcca acaacagauc aucauugaac gucuaagaau 420
cuuuuaauuu gcuuuuguau auauuuauuu acauuccuuc uccagcugua gauuuuaaau 480
guauagaccc ucaaauacuu cagaguacca auuuuucugu uaaacuuagc ggacucguac 540
accaaagcaa uauccaaacg caacaugaaa cacucaacau cccauaaaua ucagagguua 600
uguaucccuu gaacgcgcuu aaaacuaccu aggaguccuc gaacuuuguu caccgacgca 660
augcggauaa ggaucaucca ccgaaaacca gaugcgacac ucagugcaua uuaucuuucc 720
acaguguaug uuauaugcga uuucgauagg guauugcuuu ggguguacgag uccgcuuagg 780 ucagucaaug uagcauguug uuguuuuuaa aguuuucauu gguacuaaaa cuuuuguuca 840
ccaacguagu auuauaaaaa ucauaguaau auaaauaacg cugcaauguu augaaucuua 900
ccaaauuauu uuaugguucu guuguauuag ugauuugaau uuaaaaauug uacacauuua 960
cuaugaaaua aauugauuua uuguuaaaaa aaaaaaaaaa aaaaaaaaaa aaaaaaaaaa 1020
aaaaaaaa 1028

<210> SEQ ID NO 197
<211> LENGTH: 3012
<212> TYPE: RNA
<213> ORGANISM: Diabrotica virgifera

<400> SEQUENCE: 197
auuuauggua cacaucacua aaguauuaau caccacacuu uauaaauuca aauuuuuaga 60
guuggaaucu acaaaguuag ugauaauuag aaccauugug gcauucagaa acggucuaaa 120
cuuucaaugu uagcaaccuu uuguauauag cuacaauacc gauauaacag ugaacugaaa 180
aacucuagug uagugauaca aagcauuuac caugggucuu accauaucag caguguuuaa 240
uagguuguuu aguaaaaagc cuaugagaau uuuaauggua ggauuagaug ccgcagguaa 300
aaccacaauc uuauacaaau ugaagcuugg ugaaaucgua acuacaauac caaccaucgg 360
cuucaaugua gaaaccguug aguacaagaa uauaucuuuc acgguauggg auguaggugg 420
ccagacgaga aucagaaaac ucuggagaca cuauuucgcc aacacugaug gacucauuuu 480
ugugguugau uccaacgacc gagaccguau cgcggaagcc gaagaagaau ugcacaauau 540
guuaggagag gacgauuuaa gagacugcau uuuguuaaua uucgccaaca aacaagauuu 600
accgaacucg auguccacug cugaauugac cgauaagcuu aaguugcaca cuuugaagaa 660
uaggaggugg uacauacaag ccacaugugc uacucaaggg aaugguuugu acgaaggacu 720
agauugguug ucgaaugaau uggccaagug aauagguaga uguugugaag aguagcuuuu 780
auauuuuuua uugauaaugu aaaauccugu uuuauuugcc ucaguuuggu agaauucaua 840
caauauugcu ucuauguuga uaacuuuaua uguuucuauc auuaaaauau ggauaauuuu 900
auccaaaauc uagcuaaacc acuauauaac gcguuggcug uguuacgaga caaauagacc 960
ucguauuaua cuaacaguug gcucugucga cuauguugua auacacugug gcauuacugg 1020
acauauaugc cucguaaagc acucaaugcg ggcuuauaaa uaucucuaaa ugcagccaaa 1080
guauuaaucu uagcuuuaac ucuugauauu uuucaggauu uguguauaau uuauugaaag 1140

```
uuuaguuaaa uauuacauuu uucuucgauu uuguucauuu aggcaaucuc acauuauuua   1200

uauguaacau guuauugaau cauacccgcc auagccaauu auauacccgc cauagucuaa   1260

uuucagagau uauuuuuuug uuuuauugac gugaguacau uuuuuaagaa auucguuuca   1320

acauuuuugu cucuccucua uucauucauu cauuaaagcc ggauuuacau auacaaguac   1380

uuggauccga gauaucagua gaacugcgaa uuuuuacauu aaauaccagu gauucaaagg   1440

aaauauucau uauaucugca auagcuucau augcauuauu uauuuuguug auaucacaau   1500

auuccuugag uuuacauucc acaaacauuc aaaugaucag uaaaaacuaa uaaacugucc   1560

caucuguucu ccagacaauc uuaguuccac uuuuuuuuuu auuuguaaau uacaugugcu   1620

cuuguauugc uacuugguuu guguucaacu uccauccaug cucguaucca aguaacaaga   1680

ggcccugaga aggcguuuau acuucugaca ugcacucuga guagaguaac ucgaauucaa   1740

guacuuguaa gggcgacuuu agaguuacaa ucccuaggga uuauaucuaa ugccauggug   1800

uucaaaaucc uaugcuuagg ugagguggau uauuccuuug ugucauguau aguuuccugu   1860

augucuuugc ugcuguugug acucuuuuuc auuucuuccu guccuugcac cgaaauuucg   1920

agucuuguuu ugaauuuaau aguauuuugu auuuugacaa cgaaacccga uuugggcuuc   1980

gaaacguuaa uaaauucauu uuuuaguaaa auuguggcuu auuucccaua aaaaauacgu   2040

aauuguuuug aauuauuugc ucaaucuuau caauuguuac auuuacauau uuuuuauuug   2100

ggucgauuuu cuuuguuuau ucacaaaauu guuauaaccu gucugagaaa ucuuucaaau   2160

guuuuuuuac auuuccauua uucaauauua cacaauaucu cuauugggaa cgugcuuagu   2220

uuaucucuau uaggaagacu aguuuuaaaa acuaaaaaug uuuucuucga uaguaaaaua   2280

aacaaccagu guuuaacauc uuugccacau uuaaagauau uuauaacacu acguugggug   2340

cgucaugagg cauauauguc ccgaauaccc ccauuugcca cuguguuacg acacaguuga   2400

cguagccaag cguuagugua guacgaggug ucccguaaca cagccaagau guuaacaaua   2460

aacauaaaca aaauacaauu uugugcuacu aucuaaauaa gaugucaaug aguuauagaa   2520

caaagaauau uguaugaauc uauucgacca uaucauaaac ugacuuuuuc auguaguaaa   2580

caacguuucu gcaacuccuu cuucugugaa uucacuuuuu guucuaccua gauuuaaaua   2640

uuuauauaaa uaaguuuccu auuauauacu acaguggaac cucgauaacu cggauuaauc   2700

gggaccgcgg ccgauccggg uuaucgaaaa uccggguuag ccggagaaua uaguaaaaau   2760

uaauaaauaa ccuccauuau aauuacaaaa acaugaaaca cauaugcaca guacacaucu   2820

aaauuacgua uaguuguaua gaguguagag uuuuguucau uucuugguaa aaaacucagu   2880

cauacuguag agauguaccg acaccauaau augguagguc uggauccugc guacaaaaaa   2940

aaauugauaa auagcaagcc gaaaauuugu uguuagcuug ggggugucua gucggacaga   3000

cauugauaua ug                                                       3012
```

<210> SEQ ID NO 198
<211> LENGTH: 1212
<212> TYPE: RNA
<213> ORGANISM: Diabrotica virgifera

<400> SEQUENCE: 198

```
caacacugcu aucugggcug uugcacuaau cauaugggu gguuguuagu ucacuuuuuu      60

cuacaguacc augugucacu agcauaauac ucaaaaaauu aauauuuaau uuugugaacu    120

uaguuaacau cauuuugaaa aaugcgguac acuuugaguu acaucggugc uacccuagcg    180

uccacuguaa cacugauuuu ugcccucuac uacugccuca cgggaaaagg agagcaaguu    240
```

aguuuagcau gguuauuguu gaaugugucu ccccacaugu gggcaggucu aggaauuggc 300
cuugcuguau cauuaucagu uguaggagcu gcugcaggaa uucacacuac aggagucagu 360
aucguaggag cugguguuaa agcccccaga aucaaaacca aaaauuuaau uucuauuauu 420
uucugugaag cuguggcuau cuaugguua auuauggcua uaguacucug uggaaguugg 480
aagaauuucg auguagaccu auucaaccuc aaaacucaua acuuugcuca aaaccauuau 540
ggaucacaug uuauuuuugg auccgguuua acuguuggau uuguaaaucu auuaugugga 600
uuuuguguug gaguaguugg uucuggugca gccauuucug augcagccaa uucaucauua 660
uucgucaaaa uuuugauuau ugagauuuuu ggaagugcca uuggucucuu cggucugauu 720
guuggaguau acuugacguc aagaggcucu augguuuaaa uguucaguaa augaacauga 780
aaaauaaaau gaauaauuug uuaaaagugu gugugaugaa gauacaacua uuuucacuag 840
uuuacgcccc aaaauauuuc auuguggguu uugaacaaua uuuaaaaucc auucuaaauu 900
aaaauucuuc aaauaauugu ugaaaacaga uucaagggc uuuaaucagu guauauaaua 960
guauuaaaua aauauuccac uaauuuuguu aaucauuguu aaacauugua uaguuacaaa 1020
agaaauuuuu aauuuagaau aauaugcuug uacagcaugu agucccacua guauuaguau 1080
uuaaaaacug uauuaaaaau ugucuuuucu augucuaaua aaauuacaga cgauuuuguu 1140
aaauuuuaau acagaucuaa aaaaaaaaaa aaaaaaaaaa aaaaaaaaaa aaaaaaaaaa 1200
aaaaaaaaaa aa 1212

<210> SEQ ID NO 199
<211> LENGTH: 7646
<212> TYPE: RNA
<213> ORGANISM: Diabrotica virgifera

<400> SEQUENCE: 199
cggauuucgg agaguucgau ucguugucga gccuucaaaa uggcuaccaa cgauaguaaa 60
gcuccguuga ggacaguuaa aagagugcaa uuuggaauac uuaguccaga ugaaauuaga 120
cgaaugucag ucacagaagg gggcauccgc uucccagaaa ccauggaagc aggccgcccc 180
aaacuaugcg gucuuaugga ccccagacaa ggugucauag acagaagcuc aagaugccag 240
acaugugccg gaaauaugac agaaugucu ggacauuucg gacauaucga gcuggcaaaa 300
ccaguuuucc acguaggauu cguaacaaaa acaauaaaga ucuugagaug cguuugcuuc 360
uuuugcagua aauuauuagu caguccaaau aauccgaaaa uuaaagaagu uguaaugaaa 420
ucaaagggac agccacguaa aagauuagcu uucguuuaug aucuguguaa agguaaaaau 480
auuugugaag guggagauga aauggaugug gguaaagaaa gcgaagaucc caauaaaaaa 540
gcaggccaug gugguugugg ucgauaucaa ccaaauauca gacgugccgg uuuagauuua 600
acagcagaau ggaaacacgu caaugaagac acacaagaaa agaaaaucgc acuaucugcc 660
gaacgugucu gggaaauccu aaaacauauc acagaugaag aauguuucau ucuugguaug 720
gaucccaaau uugcuagacc agauuggaug auaguaacgg uacuuccugu ucucucccua 780
gcaguacgac cugcuguagu uaugcacgga ucugcaagga aucaggauga uaucacucac 840
aaauuggccg acauuaucaa ggcgaauaac gaauuacaga agaacgaguc ugcaggugca 900
gccgcucaua uaaucacaga aaauauuaag auguugcaau uucacgucgc cacuuuaguu 960
gacaacgaua ugccgggaau gccgagagca augcaaaaau cuggaaaacc ccuaaaagcu 1020
aucaaagcuc ggcugaaagg uaaagaagga aggauucgag guaaccuuau gggaaagcgu 1080

-continued

```
guggacuuuu cugcacguac ugucaucaca ccagauccca auuuacguau cgaccaagua   1140
ggagugccua gaaguauugc ucaaaacaug acguuuccag aaaucgucac accuuucaau   1200
uuugacaaaa uguuggaauu gguacagaga gguaauucuc aguauccagg agcuaaguau   1260
aucaucagag acaauggaga gaggauugau uuacguuucc acccaaaacc gucagauuua   1320
cauuugcagu gugguuauaa gguagaaaga cacaucagag acggcgaucu aguaaucuuc   1380
aaccgucaac caacccucca caagaugagu augaugggcc acagagucaa agucuuaccc   1440
uggucgacgu uccguaugaa ucucucgugc accucucccu acaacgccga uuuugacggc   1500
gacgaaauga accuccaugu gccccaaagu auggaaacuc gagcugaagu cgaaaaccuc   1560
cacaucacuc ccaggcaaau cauuacuccg caagcuaacc aacccgucau ggguauugua   1620
caagauacgu ugacagcugu uaggaagaug acaaaaaggg auguauucau cgagaaggaa   1680
caaaugauga auauauugau guucuugcca auuugggaug guaaaaugcc ccguccagcc   1740
auccucaaac ccaaaccguu guggacagga aaacagauau uuucccugau cauuccuggc   1800
aauguaaaua ugauacguac ccauucuacg cauccagacg acgaggacga cggucccuau   1860
aaauggauau cgccaggaga uacgaaaguu augguagaac auggagaauu ggucaugggu   1920
auauugugua agaaaagucu uggaacauca gcagguuccc ugcugcauau uuguauguug   1980
gaauuaggac acgaagugug ugguagauuu uaugguaaca uucaaacugu aaucaacaac   2040
ugguuguugu uagaagguca cagcaucggu auuggagaca ccauugccga uccucagacu   2100
uacacagaaa uucagagagc caucaggaaa gccaaagaag auguaauaga agucauccag   2160
aaagcucaca acauggaacu ggaaccgacu cccgguaaua cguugcguca gacuuucgaa   2220
aaucaaguaa acagaauucu aaacgacgcu cgugacaaaa cugguggguuc cgcuaagaaa   2280
ucuuugacug aauacaauaa ccuaaaggcu auggucguau cgggauccaa gggauccaac   2340
auuaauauuu cccagguuau ugcuugcgug ggucaacaga acguagaagg uaaacguauu   2400
ccauuuggcu ucagaaaacg cacguugccg cacuucauca aggacgauua cgguccugaa   2460
uccagagguu ucguagaaaa uucguaucuu gccggucuca cuccuucgga guucuauuuc   2520
cacgcuaugg gaggucguga aggucuuauc gauacugcug uaaaaacugc cgaaacuggu   2580
uacauccagc gucgucugau caaggcuaug gagaguguaa ugguacacua cgacgguacc   2640
guaagaaauu cuguaggaca acuuauccag uugagauacg gugaggacgg acucugugga   2700
gagaugguag aguuucaaua uuuagcaacg gucaaauuaa guaacaaggc guuugagaga   2760
aaauucagau uugauccgag uaaugaaagg uauuugagaa gaguuuucaa ugaagaaguu   2820
aucaagcaac ugaugggguuc aggggaaguc auuuccgaac uugagagaga augggaacaa   2880
cuccagaaag acagagaagc cuuaagacaa aucuucccua gcggagaauc caaaguagua   2940
cuccccugua auuuacaacg uaugaucugg aauguacaaa aaauuuucca cauaaacaaa   3000
cgagccccga cagaccuguc cccguuaaga guuauccaag gcguucgaga auuacucagg   3060
aaaugcguca ucguagcugg cgaggaucgu cuguccaaac aagccaacga aaacgcaacg   3120
uuacucuucc agugucuagu cagaucgacc cucugcacca aaugcguuuc ugaagaauuc   3180
aggcucagca ccgaagccuu cgaguggguug auaggagaaa ucgagacgag guuccaacaa   3240
gcccaagcca auccuggaga aaauggugggc gcucuggccg cgcagucacu gggagaaccc   3300
gcuacucaga ugacacugaa cacuuuccau uuugcuggug uauccuccaa gaacguaacc   3360
cugggguguac cuagauuaaa ggaaauuauu aauauuucca agaaacccaa ggcuccaucu   3420
cuaaccgugu uuuuaacugg ugcggcugcu agagaugcgg aaaaagcgaa gaauguguua   3480
```

-continued ugcagacuug aacacaccac ucuucguaaa guaaccgcca acaccgccau cuauuacgau 3540
ccugacccac aaaauaccgu cauuccugag gaucaggagu ucguuaacgu cuacuaugaa 3600
augcccgauu ucgauccuac ccguauaucg ccgugguugc uucguaucga acuggacaga 3660
aagagaauga cagauaagaa acuaacuaug gaacaaauug cugaaaagau caacgcuggg 3720
uucggggacg auuugaauug uauuuucaac gacgacaaug cugaaaaguu ggugcugcgu 3780
aucagaauca ugaacagcga cgauggaaaa uucggagaag gugcugauga ggacguagac 3840
aaaauggaug acgacauguu uuugagaugc aucgaagcga acaugcugag cgauaugacc 3900
uugcaaggua uagaagcgau uuccaaggua uacaugcacu ugccacagac ugacucgaaa 3960
aaaaggaucg ucaucacuga aacaggcgaa uuuaaggcca ucgcagaaug gcuauuggaa 4020
acugacggua ccagcaugau gaaaguacug ucagaaagag acgucgaucc ggucaggacg 4080
uuuucuaacg acauuuguga aauauuuucg guacuuggua ucgaggcugu gcguaagucu 4140
guagagaagg aaaugaacgc uguccuuucg uucuacgguc uguauguaaa cuaucgccau 4200
cuugccuugc uuugugacgu aaugacagcc aaaggucacu uaauggccau cacccgucac 4260
gguaucaaca gacaagacac uggagcucug augaggugu ccuucgagga aacuguagau 4320
guauugaugg acgcugccag ucaugcggag gucgacccaa ugagaggagu aucugaaaac 4380
auuauccucg gucaacuacc aagaaugggc acaggcugcu ucgaucuuuu gcuggacgcc 4440
gaaaaaugua aaaugggaau ugccauaccu caagcgcaca gcagcgaucu aauggcuuca 4500
ggaauguucu uuggauuagc cgcuacaccc agcaguauga guccaggugg ugcuaugacc 4560
ccauggaauc aagcagcuac accauacguu ggcaguaucu ggucuccaca gaauuuaaug 4620
ggcaguggaa ugacaccagg uggugccgcu uucuccccau cagcugcguc agaugcauca 4680
ggaaugucac cagcuuaugg cgguugguca ccaacaccac aaucuccugc aaugucgcca 4740
uauauggcuu cuccacaugg acaaucgccu uccuacaguc caucaagucc agcguuccaa 4800
ccuacuucac cauccaugac gccgaccucu ccuggauauu cucccaguuc uccugguuau 4860
ucaccuacca gucucaauua caguccaacg agucccaguu auucacccac uucucagagu 4920
uacuccccaa ccucaccuag uuacucaccg acuucuccaa auuauucacc uacuucccca 4980
agcuacaguc caacaucccc uaacuauuca ccaacaucuc ccaacuauuc acccacuuca 5040
ccuaguuauc cuucaacuuc gccagguuac agccccacuu cacgcagcua cucacccaca 5100
ucuccuaguu acucaggaac uucgcccucu uauucaccaa cuucgccaag uuacuccccu 5160
acuucuccua guuauucgcc gucgucuccu aauuacucuc ccacuucucc aaauuacagu 5220
cccacuucuc cuaauuacuc accguccucu ccuagguaca cgcccgguuc uccuaguuuu 5280
uccccaaguu cgaacaguua cucucccaca ucuccucaau auucuccaac aucuccaagu 5340
uauucgccuu cuucgcccaa auauucacca acuuccccca auuauucgcc aacaucucca 5400
ucauuuucug gaggaagucc acaauauuca cccacaucac cgaaauacuc uccaaccucg 5460
cccaauuaca cucugucgag uccgcagcac acuccaacag guagcagucg auauucaccg 5520
ucaacuucga guuauucucc uaauucgccc aauuauucac cgacgucucc acaauacucc 5580
auccacagua caaaauauuc cccugcaagu ccuacauuca cacccaccag uccuaguuuc 5640 ucuccccgcuu cacccgcaua uucgccucaa ccuauguauu caccuucuuc uccuaauuau 5700
ucucccacua gucccaguca agacacugac uaaauauaau cauaagauug uagugguuag 5760
uuguauuuua uacauagauu uuaauucaga auuuaauauu auuuuuuacu auuuaccagg 5820
gacauuuuua aaguuguaaa aacacuuaca uuuguuccaa cggauuuuug cacaaacgua 5880
acgaaguuaa aucaaaacau uacaacugaa acauacgucg guauguacug ucaaugugau 5940
cauuaggaaa uggcuauuau cccggaggac guauuuuaua aaguuauuuu auugaagugu 6000
uugaucuuuu uucacuauug aggagauuua uggacucaac auuaaacagc uugaacauca 6060
uaccgacuac uacuaauaua aagauaaaua uagaacggua agaaauagau uaaaaaaaaa 6120
uacaauaagu uaaacaguaa ucuuaaaaau aaacaaauaa guuuccguuc cgacagaacu 6180
auagccagau ucuuguagua uaaugaaaau uuguagguua aaaauauuac uugucacauu 6240
agcuuaaaaa uaaauaauua ccggaaguaa ucaaauaaga gagcaacagu uagucguucu 6300
aacaauuagg uuugaaaaua aaaauuauaa ugaaauauac aaagacuaaa aguuuaaaua 6360
auaugaaaac cauuuuuaac ccuccguuag ucgcuaucgg ugucacacac cgacgacaga 6420
auuauucauu cgggauuuac aaaauaacug uuuuuuucua uaccacuuuc uguaccucuu 6480
ccuaucaacu aaccucgugu uaguauacau ucuuaccuac uuggguacag uugugcgagu 6540
uuuauagcua uuuucggugc aagacuccgu agcgacuaac ggugugguua uuacuuuauu 6600
ggcguaacuu gcaguucagg uaaagauuua gcaucuuauu auugcauuuu aucgguaagu 6660
uuuggucaaa uuuuauuuau agauguccuu ugaagccgaa cgaaaacguu uguuggaauu 6720
augggaaaug guuccuagcg aauauuuuua uauuacaaau aacaauaugu uuauuguuau 6780
acuaggguuu uucauuuuau aucugucguu uuucaaugaa gcauuuucaa aaauauuuuu 6840
uagucauucc uauacacaau auaaaauauu uguaugaauu uuauagcaau aacuuuuuuu 6900
uuuaaauugu cggucucuga caccguagcg acucuugaug cuccguuuau ccuagcgacu 6960 aacgggggguu aaugugaauu uaucacaagc acaaagcaca uagauaaaac caaaccuaua 7020
aguuacuucu aauacaaaau aauuaaaugg uuuugaaguc auaaucucgc caguuuugug 7080
aagaauuauu aaggaccaga caggucuuca agucgugccg uuuucugucu gcuugucucu 7140
gcaauaaauc uuaaacgaaa aguccuaaug auuuaaaacu uaauauuaug uauauuugua 7200
cauaggauau uuacgaucca aggaagaaca aaggaauuug gugucaaugg gucaaaguuu 7260
accaaaaaaa guuacugaua auuccgauua gaaaggacgu agagccuuuu accaucaguu 7320
agagguuaga gguucggcaa aggcuuuugu uacuuuacau aauucuguca gguccuuugg 7380
uacucauuau acaaaagcuu uuaauuuugc accuuucacu uccuuccacu aauucgguac 7440
cacggacuau cgaaggacca aauauaauuu uuuaacauac cuaaagcccu ugccgaaugu 7500
cuaaccgaag auucaauauu ucacauccca ucuggaguuc ucuguaacuu ugagaugauu 7560
uuuaaucuau ugacgcgaaa uucaauaguu uucuuggacc aaaaggacgc uguguaccaa 7620
guuucaugac uuuuccugaa agaguu 7646

<210> SEQ ID NO 200
<211> LENGTH: 2600
<212> TYPE: RNA
<213> ORGANISM: Diabrotica virgifera

<400> SEQUENCE: 200
guugacauug acagugggga caccuauucu ggcaauugga auuaauuugu caauaucauu 60
uuuugucgug aaauugugug uuguaggaga aaguaauauu auuaaaaaau gucgucaaau 120
auucaaaagg cccagcaguu gauggcggau gcagaaaaga aaguaacauc ucgagguuuc 180
uucggaucuc uauuuggggg aucaagucgu auugaagaug caguggaaug uuacacaaga 240
gcugcaaacc uuuuuaaaau ggccaagagc ugggaugcug ccgguaaagc cuuuugugag 300

-continued

```
gcugcuaauu ugcauuccag aacuggugcu cgucaugacg cugccacuaa uuauauagau    360
gcugcaaauu guuacaaaaa agccgaugua uuugaggcug uaaacugcuu uauaaaagcu    420
auagacauuu auaccgaaau gggucgcuuu acaauggcug caaaacacca ucagacuauu    480
gcagaaaugu augagacuga ugcuguggac aucgaaaggg cuguucaaca cuaugaacag    540
gcggcugauu acuucagagg agaagaaagc aaugcuuccg ccaauaagug ucuucuuaaa    600
guggcucaau augcagccca acuugaaaac uaugaaaaag cagugggaau uuaucaagaa    660
guggcuuaug cagcucugga aagcucucuu uuaaaauaca gugcaaagga auacuuauuc    720
agagcugccc uuugucaccu uuguguugau guacucaaug cacaacaugc uauagaaagc    780
uauauuucaa gguaucccgc auuucaagau ucccgugaau acaaacuuuu gaaaacccuc    840
auagaaaaca ucgaagagca aaacguagau ggauauacag aagccgucaa agauuacgau    900
ucaauuucuc gucuugauca gugguauacu acaauucuuu uacguauuaa gaaacaagua    960
agcgaaagcc cugacuuacg uuaagacgua uuuagaaauu ucuuauuaau auuucuuuaa   1020
guguuauuua agagacccau aguuuauuua uuguuggauu auuauuugag uaugucggua   1080
uacaugaagu gauuuaaccu ucauauagca uuuuuaaaua uggaagcgau acauuuaaca   1140
uucauuuuuu acaaaaaaaa uuaguauagc auuuugcaau uuaugguuuc uaaggauaaa   1200
guuaucaaau gagcaaauuc acuuaaguuc uaacauguuc gauaguauaa uaagauuaac   1260
gauacuuuua acgauauauc uguauaaaua uucaaugaaa auacguaagu auuaagcaau   1320
uaccaacuaa uauuauuauu ugcucauuua gguucucauu uuucaauuuu ugaaauuguu   1380
auucuugcua uuagaguaaa aagacuuaac aauaacaguu gguacuacaa uugcuuacua   1440
uauuagcagg caaaucuugg uuaucacaac accaucuuau aucagacuuu agaaacagcu   1500
uguaaaauua uauauaauga gcacuguuau auugauucuu uuaaauauuu ucucaucauc   1560
uaaaggugcg aacugacuug agcauuuuuc uccgaacgaa cugaaugagc agagcgugcu   1620
guagcaaauu gcucuagucu cuagucagua cguguucacg agcaaaauuc ugcugaacug   1680
aauuuucgga ggagugucgg uaaucguuga aagaucaaaa gcuaucauuu guucuuuugu   1740
gcucaauagc uacagacauu uaguguauuu ggugguguucc gauugauuua uaugagcccu   1800
uuucuguagu auguaaucca aucaucauaa ucauucaacu cggaucuauc cacugcugga   1860
uguaggucuc ccucagucug uuccauguau uucuguuuug ugcuguuugc auccaauuuu   1920
ugucgagccg uuuuauguca ucagaccauc uuguuggcgg augaccucua cuucgauauu   1980
cuuguuguca ugguauccag uguauuauuc gcugugucca uuuguuauuc gacauucuag   2040
cuaugugucc agcccaguuc cacuuuaggg ucauaaauau uucuauagca ucugucacuc   2100
cuguucuucg ucuuauuucc uuguuuguaa uucgaucccu acgagaaaug uguaauauug   2160
agcguuccau ggcucuuugg guaacacaaa uuuuauuucu uacuuuguug guuauuguua   2220
aaguuucugc accauaugua aguacuggca acacacacug aucaaagacu uuccuuuuga   2280
gacauacaua uguguaaucc aauacacggg caauauuauc auaaaauaua gaaaaugaug   2340
cauggauauu aauagcugaa guaggaugua ccuccaaaga agcaaagaaa aagucauauu   2400
uauaugaauc uccugucgcu auuaaccaca aaguaacagu uaagcgaucu cgaagagaua   2460
uauauuauac cuuuucgaaa uguuuugcaa uuguaggacc uacuauaguc cgucccaucu   2520
ugacuuuaca guaugggggag caggggcggu gcaguccuua ugagaguuuu uagcgcggug   2580
augccgauuu uaccaaaaac                                                  2600
```

<210> SEQ ID NO 201
<211> LENGTH: 4648
<212> TYPE: RNA
<213> ORGANISM: Diabrotica virgifera
<400> SEQUENCE: 201
uuggcaauac gucuaauacg ucagucaaau gaaucaaguu guugggauug ggauuuaaca 60
aauacgucgu ucuaaauuuc uaaaacugca uacaaaaaau ccuuaaaaaa cuagugaaga 120
uuacuaaagu gcaauagaua caaaaacaau auuuuuacgu auucaccaua auaauauaaa 180
cguagaaaau gaaucccgag uaugauuauu uauucaaacu ucugcugauu ggagauucag 240
gaguaggaaa aucuugucuu cuacugagau uugcagauga uaccuacaca gaaagcuaua 300
uuaguaccau uggcguagau uuuaaaauca ggacaaucga uuuagaugga aagacaauua 360
aauugcaaau uugggauaca gcaggucagg aaagguuuag aacgauuaca ucaaguuauu 420
accgaggagc acaugguauu auuguagugu acgauugcac agaccaagau ucauucaaua 480
acguuaaaca guggcucgaa gaaaucgacc guuaugcgug ugacaaugua aacaaauuac 540
ugguagggaa uaaaagcgau uugacaacua agaaaguugu cgacuucacu acagccaagg 600
aguaugccga ccaauugggu auaccauuuu uggaaaccuc agcuaagaau gcaaccaaug 660
uagaacaggc cuuuaugacu auggccgcug aaauaaaaaa uagaguagga ccuccaucuu 720
cugcgguaga ccaaggaaau aagguuaggu ucgaucaaag ucgcccaguc gaaacaacca 780
aauccgguug cugcugaaaa uauuuaguuc ucuuugguug aaggugguca cucaugucau 840
cucuuuugua cgguagcagc gcuacaguua cucuuauucu aguaaauauc gucuguaugu 900
auaguuauuu uaaaguuuuu gauuugauuu ucacuuuaga uuuuuuuuuc aaaaauauag 960
aaaacaccaa uaucucuuag ccuaaucuua acucccuuag auaaauaugu aauuaacaaa 1020
aauauuuaua aaaccauuuu uacuaaacua uuaguccaca guauaucguu ccuuuucaaa 1080
aaugauuaca aaagucuuaa aaaugguuuu aauuguuucg uuuaaacgag ucuaccacuu 1140
uaugaaaaau uucagaaaga uuauacguua aaauaaaaua aauuauuuuu gucggacaaa 1200
aaagaggggc aaacacccgc aagaugucac ucuagcgcgg uacaguuuug uuaauuuauu 1260
aguccacagu auaucguucc uuuucaaaaa ugauuacaaa agucuuaaaa augguuuuaa 1320
uuguuucguu uaaacgaguc uaccacuuua ugaaaaauuu cagaaagauu auacguugaa 1380
auaaaaugaa uuauuuuugu cggacaaaaa agaggggcaa acacccgcaa gaugucacuc 1440
uagcgcggua caguuuuguu aauuacaaaa cucauaauuu ucaauugaaa guauugauaa 1500
uuacuaaaua uuguggaucu cuuguccgac agauuugcag ccucguuucu uuagugggac 1560
agcggaaaua uguuaauuau gguagguuau gguuugcggu uacaaaaguc auaauuuuaa 1620
uuuuuuaacg uucaaacugu ucaaaaagua auuguccgac aaaaaaauug uucgacgcaa 1680
acuuauaaca aaaacaguga cagucuacuu guguuugucg guauaaucgc aaauuaccua 1740
ccucuaguau agaugcuuag ucuaguaauu agucuguucc gcucugcgga auugaguaaa 1800
uggaauuaau uaaaaauaag uguaaacuau gaacaauaau auauuuauuu gugucgauaa 1860
aaagacgugu uuugcucgaa agggugugu u guugacgcac cgcaucuauc ccgacgcccg 1920
cuggggugug acugccgacg ggagguugua aaucgacccg ugguuaugua ucgacugacg 1980
cuguggcuga aaaaaaccac aaacgcuaau auguuuguac uucuaacauc uggccagaaa 2040
agcgauaaau uacuacaucu guaguuuuaa gaaacgucuu cgaaugcauu uccaugcauu 2100
gacauggaau cugauaaggu aauuaauuca uggggaauuc aguuuguuaa acugaacaca 2160

-continued

```
ccaaaaauau gguuagggau acauuucguu ucguaaaacu ucuuagcauc ugguuuguau   2220
auuaaaugug aauuuauaug accguuuuga gaaaugauau uaaaaaauaa aauuagcaaa   2280
aauaguaauu aaagcguguc gccacaaguc uauguuuaca uucgguuucu auacauuuuc   2340
ugacguucua gacgucacua gacauaaaac uaaacagugc aacaaguaaa ggguccaggg   2400
cuauguuagc ucaauuuauc uaguacugug gcgguugcag uaaaaaaagu uuugaaauua   2460
auuugucgga cuggcuaucu gauacccaau uuuugucgga cauugcucua uuuggauaaa   2520
gaacccucca aucuaucacu uucguguucg aaauuuuaua aucgcaaucu gcauaauugu   2580
uaauuauuaa cauauuuacg uuguucgacu aaagagggga ggcugcgaau uugucugaca   2640
agagaucaac aaucuaguaa uuaauuauua auaaacuaaa agugggguagu ucccugggu   2700
ggcuguauac cauguaguua aaaaacucua aacauguagu aaaaccacuu cuauauaaaa   2760
gguauaugua cugaaauuuu aaaaaucccg auggauugaa uaaacuaggu ucauucagaa   2820
cguuuucgga ccugucaguc caucaucagu gaauucauau auacuugcgc uaacuagucc   2880
cagaaccaaa caaugguugu acuuauaaau caaucuacau uauaguguua uguauuugga   2940
aaggcuaagc gccgauguuc ugauggacug auagguccga aaacguucug aaugaaccua   3000
uuuuauuuaa uucauuggga uuuuuaaaau uguaguaaau auaccuuuua cacagaagug   3060
guuuuauuuc auguuuuuug uccgacgaaa auaauuuauu uuauucuaac gcguaauuuu   3120
uugauuaaaa uuaaaaauua uaguuuugca aucucaaaac aaccgcgcua gagcuacagg   3180
uuuaaaagga agucaucaaa accauuuuua agacuuuugu aaucauuuuu gaaaaacgac   3240
gauauacugu ggacuacaua uaugagauca uuagaacgag aaagauauac ucaucgacug   3300
uuaauuuugu auuguuuuua guauaccuuu cucuguuuua uaaauccaga ucaugauaga   3360
uugacguuag aaauuauugu ucgcuuuuca aacguguauu agcagaauuu uggcaaauua   3420
aauauaaaaa uucgagaucc uuuauaaaaa gguauauuua aaauucccua aguaaggguu   3480
auauuaagua acagaacguu uucggauuaa aaaauccacc aucaguguua caaaaaaaaa   3540
auagcaugcc ugaggcaccg aaauguuacg gguaaaaacc cuuuaaaugu ugacaguugu   3600
ugucuuauac uaugauguug cuaauauucc uggauauuac ccagggcaac acaggacucu   3660
ucccacgugg uugaaauuug agaauuucaa ucacgaauuu gacacuucca aaauacguaa   3720
aguuuccac aucuuuaauc ugcauguugu gaauaguaaa uagagugucg uuccuugcau   3780
ugguucucau ggacuugauu uuacuaauau uaauuuucaa aucuauuuua uuggcuucag   3840
uggaaaguga auuuugaaaa aaaaucugcu aaaaauaguu uaaaaaauau uuuuuuuuag   3900
uugugacacu auacagauaa aauaacgaaa aauuuacgaa auaauauuua ucaaaagugg   3960
cucuugcagu acagaauaua auaucauuau uauuaucuag uuaauagacu cguacuuuuu   4020
aacgauguaa cuuuaaaaac aauuaacaac guuaaaaaaa uacugcaaaa aggaagauaa   4080
auaagugaua aaugugucac uuuucuugag cacuacgcag auuguuugga auaaagcuau   4140
cacguauuau acuguguaaa cuccacaaac gacacuuuau acacaucuua gaugaacaaa   4200
ugccuggcac aagucgauau gugacacugu uuauguucgg ugcaccguca guuuugguua   4260
aucauuagug ucagcuaacg aaaauacuuu aacuauaaac uugacacuuu uugagauaag   4320
auuuuguagu uuuauuaaac uguuggugca auaaaaccgu uuuuaaaauu uuuugaguug   4380
ugacacuauu ugagcggagg ugcgacaugu ggaaaauauu uacaauuauu ucauauauca   4440
cuuguucuau acaauaaaaa aacgucauuu cuaacaugau uuuuagugau uucuguuggu   4500
```

ccaaaacaau uuauuauauu auccauauau acuuguuauu uuuuauguaa ugauuuuucu 4560
uauucgcuac acauuaacgu cauuuuuugu uuauaucaaa uaaaaaguaa uauuguaagu 4620
aauaugugau uguaaaucuu ggucaaua 4648

<210> SEQ ID NO 202
<211> LENGTH: 1577
<212> TYPE: RNA
<213> ORGANISM: Diabrotica virgifera

<400> SEQUENCE: 202
agaaaacaag cgguuuauuu gccgccauuu ugacaagcuu acguaccuac auuuuuaauu 60
cguuguuuua uuuuuaguuu ucaauaauac ucuaaaaaau ggcagacgcu gaugaucuau 120
uagauuauga agaugaggaa cagacagaac aaaccgcaac ugaaacggca acuacagagg 180
uacagaaaaa gggugucaag ggcacauaug uaucaauaca caguucuggg uuuagagauu 240
uucuguuaaa accagcaauu cucagagcua uaguggacug cggguucgaa cauccuucag 300
aaguucaaca ugaauguauu ccucaagcug ucauuggcau ggauauucug ugccaagcua 360
aauccgguau gggaaaaacg gcuguuuuug uauuagcuac acuccaagua auagauccua 420
cagaaaaugu uguauauguu cucgucaugu gccauaccag agaguuagcc uuccagauaa 480
gcaaagagua cgaacguuuc aguaaauaua ugcccaauau uaaaguaggg gucuucuuug 540
guggcuugcc uauccagaaa gaugaggaaa cguuaaaaaa uaauugcccg cauaucguug 600
uggguacucc aggaagaauu uuagcauugg ucagaucgaa aaaacuuaau cucaaacauc 660
uaaagcauuu uauuuuggau gaaugugaua aaauguugga guuauuagac augagacgug 720
auguucaaga aauauaucgu aacacucccc acgaaaaaca agucaugaug uucagugcca 780
ccuuaaguaa agaaauuaga ccaguuugca agaaauuuau gcaagaugua auucaaaauu 840
cuuauaauac acaauuuugu aaugacgcac ccacucgcaa uguuugaaaa guucuaauuc 900
aaaauacggg ccaaaguuuu auuaaaucga aucauuuaaa agaugagggu guuggguuua 960
aaucauuagc gcauuguagc ccaacgagua ggcaggggug ggccgggcca agaagaggac 1020
acuauacagg auuuucuaaa uuuccguaaa ggguuccgcg accacauuuu cggccgagcu 1080
acaauguaga aaaauuuaca cacccuccaa guccaauaga auuaaugggg uuaauguuug 1140
aaguaccgau ggaguucuuu guugauuuau uuagaagagu auuuuuggau aauuguucag 1200
agaucauuuc aauggugaug cagcgaugau gggaugcgag auaucaacug acuguaugua 1260
cgauggauuc agucaagacu ccugagccuc guaacugcag acuauuucau uauuuuauua 1320
acuaaaguaa uaauugaguu uuuuaucgcc ucaauuauua uuucaaauaa uuuauauaaa 1380
gauuuagaaa acuaugauuu uguugauggu uauauuuaac ugucggugag uauuuucauu 1440
cacaaaagug uguguguuau ugcguugccg cuccugaaau aucuagaggc caccuaucga 1500
uggaucaaga guaaacuacc uuuauaguuc auaacauuua aauuagaaug auauaauugc 1560
acauuaaaac auaauua 1577

<210> SEQ ID NO 203
<211> LENGTH: 1039
<212> TYPE: RNA
<213> ORGANISM: Diabrotica virgifera

<400> SEQUENCE: 203
gcaucugguc ugcccgcaua agcuuguugg aacugccagu gaguacacag ugauguucac 60
agggaagaca gugaacggug aggugug gag uaaugagaau caugaguuuc aucaggugcu 120
aaugcaacuu ccaacaaaaa cagauuuuuu ucguaaaaug ugaacguguu agucagucaa 180
aauagcauca aaaugccggu cauugauggu uauaaaguac uuuacauuuu auuacacagu 240
uuauauacaa uuuuugaaaa uauuuggagg acucuuuuau uuauuuauca aaauuguaua 300
aggguuauaa acccugaauc uacauucgau gaugcugacc aguuaaagaa aagacugucu 360
agacuaacaa aaaagccuca acauuuaacu aucauuauug guguggaaga auauucauug 420
guagauuugg cuaaccucgu auauuggugu uuaggucuua auauuccgua cguuaguuuc 480
uaugauuaua aagguaauuu aaaaaagcau gaagagaagu ugcaacaaau uguagaaucc 540
agaaaaucag agaauaucaa cauaauuugg cacacccaug cagaacaaag gcauaaaaau 600
ggauuuuugg guccaaaaau ccacguaaaa guguuaacac acgcggacgg aaagcaaagu 660
auaguaaaug uuacuaaaaa auuagcucua aauaaagaaa aagacauuag uaaagaaaaa 720
auuagugaau uacuauuaag gcaguaugaa uuuccagauc cagaaauggc uauuauuugu 780
ggaaagaaac ugaacauuua uaauuauccu ccuuggcagu uaagacucac agaauucuuu 840
aaagucaaca aagucaacaa caucacauuc ccaguguuug uggaaaaauu ggaaaaguac 900
agcaaaugug aacagagggu gggaaaauaa uuguuuuaua aaaaacuguu uuuguuuugg 960
uuaucuuuau uauuaagaaa aaaaaaaaaa aaaaaaaaaa aaaaaaaaaa aaaaaaaaaa 1020
aaaaagaaca gagggugggg 1039

<210> SEQ ID NO 204
<211> LENGTH: 697
<212> TYPE: RNA
<213> ORGANISM: Diabrotica virgifera

<400> SEQUENCE: 204
cucgaauaaa cgccacaucc aaacaagagu ugacguugac agcgacauuu ccuccgccau 60
uuccuuuuac uguguuucuu aggauuugga agguacaaaa ugaccaacuc uaaagguuac 120
cgccgaggaa ccagggaucu auuugcccgc aaguuuaaaa aacguggugu aauuccacuu 180
uccacauauu ugagagucua caaaguugga gauauuguag auaucaaggg uaauggugca 240
guucaaaagg guaugcccca caaaguguac caugguaaga caggacgugu uuucaauguu 300
acugcacaug cauuaggugu aauuguaaac aaaaggguuc gaggaagaau cauccccaaa 360
agaaucaauc uccguauuga acauguaaac cacuccaagu gucgucaaga cuucuugcaa 420
agaguaaaau ccaacgaaaa gcuacguaaa gaagcuaaag aaaagaacau uaaaguagaa 480
cuuaggagac aaccugccca accuaggcca gcacauauug uuagcggaaa gguuccagca 540
caggugcuug cuccuauccc auaugaauuc auugcuuagg uuuguuuauc uuaaaauaaa 600
auccuuuaua uaauaaaaaa aaaaaaaaaa aaaaaaaaaa aaaaaaaaaa aaaaaaaaaa 660
aaaaaaaaaa aaaaaaaaaa aaaaaaaaaa aaaaaaa 697

<210> SEQ ID NO 205
<211> LENGTH: 784
<212> TYPE: RNA
<213> ORGANISM: Diabrotica virgifera

<400> SEQUENCE: 205
cugacuucaa uuaaauggcc ucugucaaug ucagaguaaa ugucaaagug uaaaaaaauaa 60 aaaaaguaac aacacaacag auuuuauuaa guuguagacg uguaauuuuu guaaauuuau 120
ucuaagccau uauuaauuaa aguaauacua aaauggaagg aauacuacug gaaccaacau 180
uguauaccau aaaagguauu gcuauauugg acuaugaugg uaauagagug cuggcuaaau 240
acuacgauaa agauauauuu ccuacagcaa aagagcagaa agcuuuugag aaaaauuugu 300
ucaauaaaac ucauagggca gacgcagaaa uuaucauguu ggaugguuua acuugugugu 360
auagaaguaa uguagauuua uucuuuuaug uuaugggcag uucacaugaa aaugagcuaa 420
uuuuaaugag uguuuuaaau ugcuuguaug acucaguaag ucaaauauug aagaaaaaua 480
ugcaaaaacg agcugucuug gaaucacuag auauuguuau gcuggcuaug gaugaaauug 540
uugauggagg aauaauuaua gauucugauu caaguucagu aguaucuaga auagcauuaa 600
ggacugauga uauuccauua ggagaacaaa cuguagcuca gguauuccaa acggccaaag 660
aacagcugaa auggucauug cugaaauaaa gugcguauuu uaaaacaagg uaaucgguau 720
uuauuucaug uacaauuuaa uuauuaagug uaaauaaauu uuuucuguuu aaagaugaaa 780
aaaa 784

<210> SEQ ID NO 206
<211> LENGTH: 1850
<212> TYPE: RNA
<213> ORGANISM: Diabrotica virgifera

<400> SEQUENCE: 206
guuugacgca uugcagguac aagccuacca aucacaaaca cacauuguac gaguagacgu 60
uguaaacaag ccgcacccga uguucaaacu ugacauaaca uacgccacgu caacuagauc 120
gcccaacacu acacaauuuc ccucacgaaa aaccaccgca uccaacacag uuuaaaauug 180
uacagcgaaa auaccaucuu caauaguuug uaaagcuggg aaaacaaaua ggaaaauuua 240
aacguuucgu guguuggcgu aggaauauuu cuaccgguuu cugucauugc cgcacuauug 300
cgcuuuggug guuucgcagc agcaguuccc cccucucuuc ucuuacgucg auccuaaaca 360
aaacgagaaa agacaguugg cuggugcacu uugacgagag gcguuguuag uuacuucguu 420
gugucgacau uuuucuguuu aguguaccga uuaaucuuca aauauuacaa uggcugacca 480
acucaccgaa gaacaaauug cugaauucaa agaagcuuuc ucacuauucg auaaagaugg 540
ugaugguaca auuacgacua aagaauuagg aacaguaaug agaucucuag gacaaaaucc 600
aacagaggcu gaauuacagg auaugaucaa ugaaguagau gccgauggua acggcacgau 660
cgauuuccca gaauuuuuaa cgaugauggc acguaaaaug aaagauaccg auagugagga 720
agaaauucgu gaagcauucc gaguguucga caaagacggc aaugguuuca ucucagcagc 780
agaauugcgc cacgucauga ccaacuuggg ugaaaaauug acagacgaag aagucgauga 840
aaugauucgg gaggccgaua ucgaugguga uggucaaguc aauuacgaag aguucgucac 900
caugaugacu ucaaagugag gaaaccagag uugcauuuuc agcuuuccau uguuucaucc 960
cggcucauug ucuacauuuu ucaacaccuc gaacuuuuug cuuuguggcc ggguccacua 1020
aagugaauaa cuuaaccguu auuugauuua caagacaaau uuaauuaaua aauauauuua 1080
uaaauuaaua uaauugugua aauuuuugua auauauuugu uuuucuuucg caggagucgu 1140
uggcgagauc uagucgcugg cgauucuugu acuguaucaa auucugugcu acaugucuag 1200
uugaaguuua aaaagaguua caaagucaca aaguaugaaa acacguauau auaaugaaga 1260
uaaaaaaauc guucuauuug auguuaguuu aggggauaca gcauuagaca cuuucaauuu 1320
uuuucauacu uugugaugua aauuacaucu gaucugugca cuuacuauau aguauguauc 1380
cccuuuuuug acauguucau ucauuuuucc ccuuucuugu acuguagguu uuacauuuuu 1440
agucuaggau uugaauuugc uggaaaguaa gcacauuuuu auugucaucc ugugaugcgu 1500
auggaaaugu uaauauuuuu uggcucuuac uguaucacag gaaauggucu uuagaaauug 1560
aucgaaauuu uuuacaacaa aaauuuuauu cuaauuucuu aagaccacuc ccuuucuuau 1620
uguaagauuu cguuuuuauu caagccuguu aauuuuuuua uuuauucuua cuauuuaaga 1680
uccaguaacg cauccguuac aaugugaaau uauuagaugu uuaaauuuga aauaaaugug 1740
acuaaaauau uuuccuguga cuuacuggua cccaauauau uauuacuaua aaguuuuuau 1800
guuagaauuu uuuucuuuau uuaaaauaaa auauuugaau uaaaaaaaaa 1850

<210> SEQ ID NO 207
<211> LENGTH: 3245
<212> TYPE: RNA
<213> ORGANISM: Diabrotica virgifera

<400> SEQUENCE: 207
cagcgccauu uuaguauuua gcucugaaga uugaguuuuu acuuccguga aaaauuuuua 60
cgaguuuuua uugucaucgu uauaauauuu ucgacaacug caguucugua uauagucggu 120
uugaaaaucu uaaagaaaau aaugagggua ugaauuuaaa cgugcuccaa uauuagcgcu 180
uagcguguau uugccggugu auuguguuca acgucaccau caaccaugau gcaagcaaac 240
aaucgagucc caccuauaaa guuggaaaac gauauagauc uuuacgccga ugauaucgag 300
gauuucgcac aagaugacuu ugguggugaa aauguugauc uauaugacga uguaauaucc 360
gcuccuccug gaaauaauga caacccaggu gauucaaauc aucaugcucc uccuggugcu 420
ggugaagaug guggagguaa uuuuguuggg ucaggaggag cacccaauaa uauaaauucu 480
ucuggaagaa gacaucagcu guauguugga aaucugacuu gguggacaac ugaucaagau 540
auagaaaaug cagugcauga uauaggggua accgacuucc augaaguuaa guuuuuugaa 600
cacagagcaa auggucaauc caagggauuc ugugucauau cuuugggauc ugagggaagc 660
augagacucu gccuggaacu ccuaucuaaa aaagagauca auggccaaaa uccccuuguu 720
acccuuccca caaaacaagc ucuuaguaac uuugaaaguc agucuaaaac acgcccuucu 780
ccuacuaaua auucuaacuc acguccuccc cauccuaaua auaauguuca uucagguccu 840
augcagaauu auggagguag aaugccuaug aacccuucca ugcgucccau gcccccaggu 900
augcaaggug cuccaagaau gcagggucca ccuggauuua auggaccacc aaacaugaau 960
cagcaacccc ccagguucca agguaaucca caauggaaug gaccuagacc uaaugguccu 1020
gggcccaaua ugggaaugag acccaugggg ccaccucaug gacaacaagg gcccccaaga 1080
ccaccaaugc agggaccacc gcagcaaggu ccuccaagag gaaugccgcc acaaggucca 1140
ccgcagaugc guccagaaug gaaucgacca ccaaugcaac aaggguaccc ucaaggcccg 1200
ccgcauaugc aaggaccuaa caugggucca agagguccac cccaaauggg accacccggg 1260
gcgccucaac agcaaggacc agcuccgcac guaaauccag cauucuuuca acaaggagga 1320
ggaccaccgc ccccaaugca acacaugccu ggaccagggc ccgucaugcc uccucaagga 1380
cccccgcaag guccaccaca cggacccguu ggaccuccac acggcccacc auugggucca 1440
gcgaauguuc cgccucaugg accaccucac ggauaugguc caccugcagc gaugccacag 1500
ccgccauacg guggcccacc uccagaccac cgcgcugaga uuccucaguu aacagagcaa 1560
gaguuugagg auauaauguc ccggaauaga acaguuucca guucggcgau ugggcgggcc 1620
guauccgacg ccgcagcugg agaauuugca agcgccauug agacuuuggu uacugcuauu 1680
ucacucauca aacaauccaa aguggcuaac gacgaucguu gcaagauccu uauaaguucg 1740
cugcaagaua cuuugcgugg ugucgaagac aaaagcuaca gcuccagccg cagagaccgg 1800
ucaagaucca gggacagauc acauagaaga acuagaagag aacgauccuc gucacgguac 1860
agagacagaa gcagagagag ggagcgugaa cgcgauagag aucgugaucg ugaacgugac 1920
agauauuaug auagauacag cgaaagagaa agagaccgag aucguucaag aagcagagaa 1980
agaacagaaa gggauagaga acgagauuau agagaccggg aacccgaaga gacagauaaa 2040
gaaaaaucua aaguauccag agucucaaga ucaagaaaca aaucuccgga accugucgaa 2100
ccuagcagcg agguaccgaa aucaucccgc uauuaugagg auagguaucg ggaacgagag 2160
agagaagguc gacgagagag cgaucgcgaa agagaaagag auagaagagg ggaagacagc 2220
cauaggucuc gacacuagca uauaguuagc gguucacaga aacaacaaca aacaaguuau 2280
aguuggaguu caaacaaaga uuaucguguu uaauuuagag auagguuaua auaugugaug 2340
uuacuuuaca uaaauuuaaa cagguuccga auguguaagu uaaaagagca aaggaaacau 2400
ucacuaacuc auauuuugcu acuuguuuca uuuugcaaug gaacuucugg cuaucuuaaa 2460
uguauucaua aaaaggauaa aaaacauuua ccuguuuauu guuguauuaa guaaaucauu 2520
gacuauaaua uugcgauaaa uguuagauau uuuacuucau gggguuauac uuuugaugua 2580
aaaguuucac auauuuagcu uuaagcaaac gugacuuacu augaauauaa uaaauuaugu 2640
aagaacaaaa uuaaguaaug aauauaccac auaaauucuuc aacuaaugag uuacuaugua 2700
caguauauuc uucuuacuau uucuucaguu uucuccugga guagcaaaac uuguuuuugu 2760
aaaaugaauu uauuguuuag gcugugcuau auuaacacug ggucgucuau uaaucuguua 2820
aaaaacaguu uuugagagaa uucuguucuu uauaaaaaau uacaggaggg ugaugaaagg 2880
cuuuauuguu acgugcaugu ugguaaaucg ggaugcuucu aaaugauaaa uaacuuuagg 2940
caacuuguug uuucugugag cuguauuuuu ucacauuuuu auguaaucau acauaaguaa 3000
aucauguaac guauaguuga uaaguacaau auagauggaa aucaaguuuu guuuuugugu 3060
guaguauaug gauuuaaaac auguaucuuu uaauaagaug auguuucaac auacaaugaa 3120
uaauuugugu aauaaauuga auacuauuca acaugaauug ucaaauucuu acaaaaaauc 3180
augauaauuu gaaggcaauu gaccaugaac uacucacaau gcaucuaaau gugaguguau 3240
ccucc 3245

<210> SEQ ID NO 208
<211> LENGTH: 1023
<212> TYPE: RNA
<213> ORGANISM: Diabrotica virgifera

<400> SEQUENCE: 208
gucgucaguc gucaacauca auuucaaguu ucaagaaaaa gcaaaucacu acgacuugcc 60
ggauuuugua guaguguuaa uuuuguauua aaaaaucaaa augaguucua uuggaacugg 120
guacgauuua ucagcuuccc aauucucucc ugauggaaga guauuucaag uugaauaugc 180
aaugaaagca guugaaaaua guggcaccgu aauaggccuc cgagguacag auggcauugu 240
auuggcugcu gaaaagcuca uuaugucaaa auugcaugaa ccaaguacaa auaaacgaau 300
uuucaacauu gauaaacaca uaggaauggc auuuucaggc uuaauagcug augcaaggca 360
aaucguugag auugcuagaa aagaagcauc aaauuauaga caucaauaug guucaaauau 420
uccucuuaaa uaccuaaaug auagaguaag cauguacaug caugcauaca cuuuauacag 480
ugcuguuaga ccauuugguu gcagugucau cuuggccagu uaugaagaua gugacccauc 540
uauguaucug auugauccau cuggaguuag cuauggauac uuuggaugug cuacagguaa 600

```
agcaaaacag ucugcaaaga cugaaauaga aaaauugaag auggggaauc uaacaugcaa    660

agaacuuguu aaagaagcag ccaaaaucau uuauuugguc caugaugagc ugaaggauaa    720

gaauuuugaa cuggaacuuu caugguauug caaagauacg aaugguuuac auaccaaagu    780

gccugaauca guguuugcug augcagaaaa agcugccaaa caagcaaugg aagcagauuc    840

agaaucagau acagaagaua uguaauaacu acauuuaguu uuuaauauuu cgcugauggu    900

ggcuguucuu acaauauuuc guguguuaug uucauauauu auguaauacu gugagaauuu    960

ccauuucaag gauagguuua uaacuuuuuu uucuaauaaa uacauaacuu uaaaaaaaaa   1020

aaa                                                                 1023
```

<210> SEQ ID NO 209
<211> LENGTH: 1439
<212> TYPE: RNA
<213> ORGANISM: Diabrotica virgifera

<400> SEQUENCE: 209

```
aaagugucag gugcuguugg ugucagcuga cuuuuuacuu uuuguuccag uccuauauuc     60

aacacacuuu ggauauuaaa uauuuuauuc uaaaucucaa gaauggcuuc aaaagacaga    120

uugaugauuu uuccaucuag aggagcccaa augaugauga aauccaggcu aaagggagcc    180

caaaagggac auaguuuauu aaagaagaaa gcugaugcuu uacaaaugag auuuagaaug    240

auuuugaaca aaauuauuga gaccaaaacu cucaugggug aaguaaugaa agaagcugcc    300

uuuucuuuag cugaagcaaa guuugcaacu ggugacuuca aucaaguugu ucuucaaaau    360

gucaccaagg cucaaauaaa aauaagaacu aagaaagaca acguugcugg uguuacuuua    420

ccaguguuug aaugcuacca agaugguaca gauacauaug aguuggcugg uuuggcuagg    480

ggaggucaac aauugacaaa acucaagaag aauuaucaaa gugcuguuaa acuguugguu    540

gaauuagccu cuuugcaaac uucuuuugua acucuugaug auguaaucaa aauaacaaac    600

agaagaguca augccauuga acauguuauc auuccaagaa uagagcguac uuuggcuuac    660

aucauauccg aacuggacga guuagaaaga gaggaguucu auagauuaaa gaagauccag    720

gacaaaaaga agaucagcag agcaaaggcc gagaaacaaa aacaagcucu ucuccaagcu    780

gggcuacuua aagaguccca ggcaaacaug cuuuuggaug agggcgauga agaucuacuu    840

uucuagaaca ucaaacagcc ugaagugugg uucuguacau augaauaaau auauaacgcu    900

aacuuguuuu uagacgguaa cuguuuauuu uucgcauuaa uuaauacauu uuuaagauau    960

aucuuuauuu uuaacugguu uuuauucuua ugccuugcaa uaguaaaaga uauacgaacc   1020

cggauauuuc cuauauaaau aacuuccuac uuuuuauuaa cuccaguuuu uaggauuuua   1080

auacaauauu caacacaucg ugcaauagaa uuugaaguga auauuacuug cgaaaauuaa   1140

aaagguacca aauauuuuuc uuaauauuga acguauauuc cagaauagua uuauaaaagu   1200

uuugauugaa auucuuguac gugacacuau gaacuuguag auuuuagaga aagcagcuuu   1260

ucaauggaaa augcuuuauu gauauggaca cuagauaaug uaaauacuug uuaauauacu   1320

uugaacagau aaaauaguuu auucguuuua aauucuuuaa aacucuaaau uguuuuucau   1380

caaauguaua cauggccugu aaauuguugg uuagaaauaa aacucuguuc aaaaaaaaa    1439
```

<210> SEQ ID NO 210
<211> LENGTH: 5226
<212> TYPE: RNA
<213> ORGANISM: Diabrotica virgifera

<400> SEQUENCE: 210
gcgauugcgu cugcugaaug cacccauagu auugugguga cugugacagg ugacagucgg 60
agucgacagu gaaguacaaa ucaaaaucau ucccuauuug ucaaacaaaa augaaauuac 120
guguauuauu auuuacccaa guaacuuuuu aauaauuuaa gccgauuauu gcacuguuag 180
uacguaugua caccacaaau aaccaauaua uucuuuguuu cccaugauaa cacaguucua 240
auuucacugu uagaugcaug uuacauguuu uuaguggaau cauuacugga uaaaguccuc 300
ucccauaauu aaauaaauac uuaaaaaaug gaggcggcuc ccaaguuacc gaugcucucg 360
uucgaguuaa auacuuguac agagaacguc cacuuuggcc cccaguuaaa acaguauauu 420
gcugcuuuuu auggugaaga uccagaaucc uacauuacag aaaucagcaa ucuugaaucc 480
uuaagaucag cugcaguucg accaucaacg gauguaaaug guguacaacu guugaaaaag 540
uauuucuguc agcuucguuu ucucaaaucu agguuuccca uggaagagaa ucaagaugcu 600
gcaguucuau uuucauggaa aaauaaugaa uuagacauaa cuucaacauc cagugauauc 660
agauaugaau uaaugguaau aauguauaac auuggagccu uacacacuuu ucuuggagcc 720
aacgacucaa gaaacaaucc ggaugguaug aaaauggcau guacucauuu ucaaugugcu 780
gcaugggcuu uucaaaacgu aaaagaaaag uaccaccaau ucauaucaaa caucucauug 840
guagaacugg uucauuuuuu ucaacaaguc uguuuagcuc aggcucagga guguauauua 900
gagaagagca uguuugacaa uaggaaaccu accaucauug caaaaguugc uauccaaguc 960
uacaguuauu acagacaguc uuuacguguc uuggaaucag uaaaugaagc cuacuuuagg 1020
gauaaaaccu acaaggagug gaugaaauau cuucaauuca agcugaccua cuacaaaugc 1080
aucucguucc uauuccaagg gcaacaagcu gaggaacaac agaaaauggg agaaaggguu 1140
gcauucuauc aagcugcaug ugaacagcug gacgaggcaa agaaaauugc ugcuacauua 1200
aaaaaccaac accaccagca agaaauaaau gagggacuag cauucacuac ugaugugguu 1260
gaagguaaaa gaaaagcagc uaaaaaugaa aaugaguuca ucuaccauga aucagugccu 1320
gauaaagacc aauugccaga gguuaagggu gcuucauuag ucaaaggaau accauucagu 1380
auaaaaugaua uagaaguuuc aggaccagau auuuucuccc gauugguccc aauggaggca 1440
cacgaagcag cuuccuugua cagcgagaag aaagcucaga gauuaagaca gaucggggaa 1500
cuuauugaaa auaaagauca aacauuggcu gaauuuaugu cgucaaugca gcuagaucua 1560
uugaccaaga ugcaccaggc uacuggaaua ccgcaggagu ugauugauag agcagcggcu 1620
cuaucugcua aaccuaacgc cauucaagau cuuauaagug cuaugggaaa gcuaucuaau 1680
auauaccaag acguugaagc aaguuugaau gagauugauu cuuuauuaaa ggccgaagaa 1740
caaagugaac aaaaguacca agaaacgauu gguaaaagac caccgagcau uuuagcuaca 1800
gauuuaacua gggaagcggc aaaauacagg gaggcucaua cuaaagcgaa cgacucaaac 1860
caaacuuuac acagggcgau gauggcucac guggcuaauc ugaaaauacu ccaacaaccg 1920
cuaaagcagc ugcaacauca gcugcccuuu gucgaguuuc caaauccaaa uaucgacgaa 1980
aaaucuuuga aagaucugga agcgcuaguu gcaaaaguag acgaaaugag aacccaaaga 2040
gccaugcuau gggcucaacu ucgagaaucu auucaccaag acgauauuac aaguucccuu 2100
guaacgaaac aaccaaauca gucgcuggaa cagcuguucc agcaagaacu ucaaaagcau 2160
caaaaucuga uuucguugau ugaacaaaac accucggcac aagaaaacau uaagagcgcc 2220
uuagucgauu cuuacgcuua cgcuguaaau ucaagaaaau acauccaaga uauacuccaa 2280
aagagaacca caaccauaac gucacugaua gcaucguucg acucuuacga agacuuauug 2340
gcaaaagcua acaaagggau agaguuuuac ucaaaacuug aaacgaacgu auccaaguua 2400
cugcaaagaa uaaggaguac cugcaaaguu caacaagaag agcgagauca gaugaugucg 2460
acugcgcaag ugccucaaug ggagagucau acgucacuug ccgcuccuaa acugaaagau 2520
uacuuggacu ccaggaagaa gagugcugcg uauucggagc cgaguguuca accacaacag 2580
ccaacuuuaa guuacucagc ugcuauggau cugccuccug guauuaggcc gacuccaguu 2640
ggaucagaaa uaacggaugu accgaaaaau auucaaggug aaccacaagg uuauauucca 2700
uauaauuacc aacaaccuuc uguuccugcc ucacagaaua uugaugaaga gacuauuaaa 2760
aaaaugaacg cauugaugcc aggugcuaag acgucagugc cuagucagua cggauacagc 2820
aacuacauuc caccaacaua cccucaaagu gcguaccaac cagguaauca gucuuacgga 2880
aaagaaacuc cagauauuaa cucaccguac gacccuacca aggcguucac ggcuacuacu 2940
aacgcuuauc guucggugca gagcuccuca acucaaggau acguaccgua cgcagaaucu 3000
aacguuucga auguugacag aguuggauau ccuagcaggu aucaguacca acaaguaccu 3060
gagauagcua cuacuccagc ugaucccaau auuaaugcgu acuacccaca uggguacuca 3120
ccgagccaga auuuaccgaa ugcuaauacu caacauauua ccggccaacu gaaguaccau 3180
ucgguggagu acgcuucuuc ugugccgaac aacaucaauu auaacagcuc uaccuacucg 3240
ucgccgcuuu cuaauauguc uaguaccaau uccucaaauc cuaguaacuu gaauaauucu 3300
uacgaguacu acuaugaccc gaauaccagu aguggugcag uaccgaaugc uucaaagccu 3360
caacagucga gcgccagcuc ugcaaacccg aguaccgcua ugaacaacua caauuauuac 3420
uacaauacaa guaccagcgg uaguguagca gcggauacuu caaaaauaca acaacaacaa 3480
caguacccag guacucagau gagucaagcg caguacuauc ccgccaaugc caguuauuac 3540
ucaaccagua cuuacaauac caacguccaa ggugguacca aucccucgua cgcaacugga 3600
caaacauaua aucaagugac accagugacc ucucaaaaug uuucucaaaa uuacaacuuu 3660
aaccaaguug guucuggagc aggacaccag caucaguacu acucguccgc uaacgccgca 3720
guaccauccc aacaagcugu aaauaacagu ucauuaccaa acuacggaua cgaucaguau 3780
uacggcaaca acuauaauuc cagucaaccg aguaccuaca gcgcaaacca agcaccuccu 3840
gcagcacaag cugcuccaag uaauauuccu gcugccacca aauccuccuc uaauguggau 3900
cugcucagug gcuuggacuu cagcauaagc caagcuccuc uagugccuca acaaaacauu 3960
acgauaaaac cccaagaaaa ggaaacaaaa ccaccggcug uuucuucuga aaccaaaaac 4020
caagauccaa caccaguaac cacgcccaaa caacccacug gaccagaagu aaagcgcuug 4080
uacgucaaaa uccugccgag caaacccuua aacaacgaug augugaagaa auuguucggc 4140
caagagcugg acagguauga gaaguucgug gagaccuuga cccacaaaac uuugagcggu 4200
ccgaccacuc uggauauuaa auggaaggag auccaagacc agcaggauug cgagccgcag 4260
aagaagauca uuuccgucgc uagauguuau ccuaugaaga auagguuccc ggauaucuug 4320
ccuuacgacu uuuccagggu ggaguugugc gauaguaaag augauuauau caacgcuuca 4380
uacauuaagg auaucucgcc auaugcuccg ucauuuauug uuacacaagu gccguugucu 4440
ucaacuguug gugauaugug gacgaugauu agagaacaac aggucgaacu gauccucugu 4500
uugguaaacg acaaugagau cggugaagau auuuacuggc ccaaagaaaa aggcaguagu 4560
cuuaacauac uuaacauggu cauaacguug caaaacguua uaguuaaguc ucauuggacu 4620
gaaagacuga uagcgauaaa cuuaccugaa aaacgggagu cccgugugau aaugcaucua 4680

-continued caauuuacau cguggccugg cagcuuguuu ccaacaaauc cugaaccguu cgucagcuac 4740
accuuggaau ccaucaaccu auaccaacaa cagaagacca acacccaucc gguggugguc 4800
cauuguucau cuggcauagg aagaagcggc cugcucuguu uacugacagc ugcuauguuc 4860
gaugcugcca acaaugcuaa cucgauacca gaucuuacag cuuugaguau caaguugucc 4920
aauugcagga agaauauucu cagagaucga gagcauuuga aguuugguua cgaaaguuuu 4980
uuggcguaua uuaggcauau aguuugugaa gauaaagcca gaaagaaacu gaacgagauc 5040
cagcccaagg uuaaggagga accacuggaa ccaccuguca uaguuccaga accaaauaua 5100
gauccuuuaa guacuuuaga cccauuuugg gcuaguaaaa gauaagcuuu acauaguaaa 5160
uauuuauaca augauguauu auuauuuuga auguuaucua caccuucauu aauauuaaau 5220
ucccug 5226

<210> SEQ ID NO 211
<211> LENGTH: 633
<212> TYPE: RNA
<213> ORGANISM: Diabrotica virgifera

<400> SEQUENCE: 211
uaccgccugc uacucucuuu cuuugaccuc cuccuuuucu ucuccuuugu ccggcuuuaa 60
cuugcguuuu cccggcucca gucccgagca uaccuucucc ggaguuucg guucuuccgg 120 uucuuuccaa aguacugggg acucucuuuc uucuuugaau ccaaugacaa cucuuucuuu 180
cggcggcuuc uuaauuucuu ucuuguucuu gcguuucguc ggcuuuccuc cgcauaguaa 240
cuucuuucca cgccauuugg guuugaacag cuacugcguu uacuuccggg uaauuuuguu 300
cauacacucc cuauaguguc ugcauaacau cuggaucuuu uauucuuuaa acuggagcuu 360
uuucuucacc uuaagucucu aaaagucuag aggcuuaacu ugucgguuca uuugcuggaa 420
ucuccguuua agcaguuugg uuggaacuuc uuccauaggu uuaugcuuuu guuuaagcgg 480
uuugaaguuu ucuuccgucg acuuaaauug aaggcauugg uugaguuuca acaguucuuc 540
uuucuuaagu ggaaucuucu ucuucuguuu cuuuucuuug gucugaccag uuucuucccu 600
cugcuuuucu uccauguucu ccgacuucgu acu 633

<210> SEQ ID NO 212
<211> LENGTH: 603
<212> TYPE: RNA
<213> ORGANISM: Diabrotica virgifera

<400> SEQUENCE: 212
uacacacuuc uucuucaacg gcgaaaucag caucuguuac cuaggccaua cacguuucga 60
ccaaaacgac cccuacuacg uggagcacga cauaagggaa guuaacaacc ugcggguucu 120
guagucccac acuaccaucc uuacccuguu uuucuaagga uacauccacu acuucgaguu 180
ucauuuucuc cauaggaaug gaauuuuaug ggguagcucg ugccuuauca guguuugacc 240
cuacuauacc ucuuuuaaac cguaguaugu aagauguuac uugagucuca ucggggucuu 300
cuugugggac aagacaacug ucuucgagga gaguuggggu uccgguuguc ccuuuucuac 360
uguguuuauu acaaacuuug aaaguugugg ggucgguaca uacaacggua gguccgacau 420
gagaggaaca uacguagacc agcauguuga ccauaacaca accuaagacc acuaccacau 480
agggugugac aggguuagau acuuccaaua cgagaaggag uacguuagga agcaaaccug 540
aaucgaccau cucugaacug acuaauggag uacuuuuaaa acugacuugc accgaugaga 600
aag 603

<210> SEQ ID NO 213
<211> LENGTH: 2742
<212> TYPE: RNA
<213> ORGANISM: Diabrotica virgifera

<400> SEQUENCE: 213
uacggugaag cuaaucuaua uuuuucuuuc gauugucgag cgagucuggc ccauuuuaca 60
caccuagaag ugggaugucu uggaaccuac gacacaagag aaaugucgcc uuuauauuug 120
caaaccuugu ggcuuuuagu cguugaccaa uucugaaaac uucauacacu acauggacaa 180
gccugucgau ucaaaaacgg guccuucuug accuaucagu cacccagacu acuauacguc 240
uaagcucaaa aguuaauguu auggaaucua gcccauguaa gaaaacuccg aguaagccua 300
auacacucua cauaacagca ugugggaugu guuggaauau auaauuguuc aucacuacua 360
uacgaauagu ucgaaaccuu aacccuuuuu cguacccgaa cagucguuca aaagcuuccu 420
gugugaguaa uauaauacgu uuagcgguau uuagguuuuc uguuguugug uaaacgguca 480
cguagggauc uaucuuguaa cuuucauacc guuaacccuc gcaggugucg cuuaaagugu 540
gaucuuccag uacucuuucc gcaauugaca caccugauaa uagugccacc ucuauuugga 600
auaaauuaga guccgcgacu acuaucuaau cauuuuuaga cccuaauagu uuuguuuuga 660
acacaaguuu gaaaccuucc uguacgaguu uuacauuggc gacguacaaa gguaggucuu 720
gaaggacauc gagaaugacc uucacuucua ccaugacagu cucacaccgu acgguugugg 780
guauccaauc uuucaucgaa uuuaauaccg aaacuuucuc auaccugaua aaagacggau 840
uucccuaggu uauugcaccg uaacccaaua cuacuuccau cguaaaacca auuucaacca 900
ucucuucuug gucgacaauc auaccuacgg ucaccuccgu uuuaauaaac ccggucugug 960
agacuugaag uuguccguuu agaguuccgc aaucgacuuc cacgccuuua uucucuaccu 1020
cuugcggaag gucaaagaca uuuucuauac ccacgaacgc ucuauauggg agucuguuaa 1080
guuguguuag gguuaccggc aaaacaacaa cagacacccc uaccucuuau guauuagaug 1140
ugucguuacc gaaauucuuu guuucgcaaa ccaucgcgug uucuuaaaca cacccgaguu 1200
cuaaggucgc uuauacggua gucucuuagg ccuagaugau agucuuaaaa auucuuaaag 1260
uuucucuucu ucuuaaaauu caggcuaaaa ccucgacuuc cauauaugcc accuauggaa 1320
aacccucagu uuagccaaag accaaacuga aagauacuaa cccuuugaga gcuaaaucag 1380
ucuucuuagc ucuauguugg uuuucgucaa augaccaguc uaucaccauu uaaucauaca 1440
aaccggugug uucuaucgau gaaauaagaa agaauacuaa gacuacuuca aguuuuucgg 1500
ucucuauugu uaguccaacg ccuacuaccu caucuuagcc gaaaguuaga agauccacuu 1560
uauuugcuua gucacgcuug accagagacc cauccgcuga caaaauagau gugcuuaaga 1620
caauuagcau aguugaugaa gcaaccucca cuugaccaau guuaacgagu aaaccuggcc 1680
ggaaacauac agaacccuau acacggauuu cugcuaucua auauggagca ucuauuucuc 1740
aacgcgcauc auucgauggu uaaugaagaa agacaagaac uuauaguuug acggcaguac 1800
ucuucucuga aagguugucg ucugucucau gaaggcaggu aaggauuccu cgugucuugc 1860
ucucaccgug uaaagaaucu uuucguuccg aaguuugucg uucgaaaccg gcauucaugu 1920
cuaggucucg ugucuaagcu cgaccgucau cguaaucucc uagaauuaua ucgguuuuga 1980
gaucgaguuc uucgcuuguc aggcguuuuc accuuaguug aucgucuuaa ccgucgacga 2040
ugauuauuac auucgcaucg guuccuuaca uacguuuuuc gcguucuaau accuccgaac 2100

```
aacgaagaac gaugcucgag gccacuacuu uuaaaaucagg caugagaucc ucuuugcugu   2160

guucgacuuu cguuuguauu gaaucguaaa aacagugugga acaaucaucc acuaaauuug   2220

uuuacagauc uguaagaaua auuauggcca ucuaacgguc uucgacguaa aaagcggucu   2280

agaauggaag gacuauucua augucuucag caccuugaca ccuucugagu caauagaagu   2340

caguuaguuu uucgaccugu cucggaacgg cuaggauuuu ugaugcuuuu agacaaggga   2400

ccaaauguuc uccgccacca ucgagucuuu aaaaaccuug ucgucuuauu uccaaaucgc   2460

gggcguucuc aacggugggug guaaggagga uuagugcugu ccuuacaaca ucggcuucaa   2520

guucguguua gcuuugugcu acaugguagu aaaucaagaa gcaaauaaag uagucuuuau   2580

cuucguguuu guuccucaag acgauuugga cuucuuagaa guuuguaaua ugucgaccug   2640

guucuacugc ugcuauagcu aaaucuaaac cugccacauu uauagcuacu cuuguaacug   2700

ugcugccuau aguuguagcu acuacuaaac gacucacuaa cu                       2742
```

<210> SEQ ID NO 214
<211> LENGTH: 1173
<212> TYPE: RNA
<213> ORGANISM: Diabrotica virgifera

<400> SEQUENCE: 214

```
cacaauaacu uuccguuuuu aguuuauuac gucuagaaac auuuuuguga gugaccauuu     60

ugguaguggg agcuccaacu ugguagucua ugguagcucu uacaguuucg auuuuaaguu    120

cuguuucuuc cauaaggugg ucuaguuguc ucuaauuaga aacgaccuuu cgucaaucuu    180

cuaccggcau gagagagucu gauguuguaa gucuuucuua gaugugaugu gaaucacgaa    240

gcagaaucuc cuccauacgu guagaaacau uuuugagagu gaccauucug guagugggaa    300

cuccaacuug guagucuaug guagcucuua caguuucgau uuuaaguucu guuucuucca    360

uaaggugguc uaguugucuc uaauuagaaa cgaccuuucg ucaaccuucu accggcauga    420

gagagucuga uguuguaagu uuuucucaga ugggagguaa accaugaagc agaaucuccu    480

ccauacgucu aaaaacaauu uugaaauuga ccuuucuggu agugggaacu ucaucuugga    540

agacuauggu agcuuuuaca guuucgguuu uaaguucugu uucuuccaua agguggucua    600

guuguuucua auuagaaacg gccuuucguu aaccuucuac cagcauguga gagucugaug    660

uuguaaguuu uccuuagaug ggagguaaac caugaagcag aaucuccucc auacguuuag    720

aaacauuuuu gugagugacc auucugguag ugggagcucc aacuugguag ucuaugguag    780

cucuuacagu uucgauuuua aguucuguuu cuuccauaag gugguucuagu ugucucuaau    840

uagaagcgac cuuucgucaa ccuucuaccg gcaugagaga gucugauguu auaagucuuu    900

cucagauggg agguaaacca ugaagcagaa ucuccuccau acguuuagaa acauuuuuga    960

gagugaccau ucugguagug ggagcuccaa cuugguaguc uaugguagcu cuuacaguuu   1020

cgauuuuaag uucuguuucu uccauaaggu ggucuaguug uuucuaauua gaaacggccu   1080

uucgucaacc uucuaccggc augagagagu cugauguugu aaguuuuucu cagaugggaa   1140

gugaaccaug aagcaaauuc uccuccuuua auu                                1173
```

<210> SEQ ID NO 215
<211> LENGTH: 1131
<212> TYPE: RNA
<213> ORGANISM: Diabrotica virgifera

<400> SEQUENCE: 215

```
uacacacugc ugcuacaucg ccgagaacag cagcuguuac cgaggccuua cacguuucgg     60
```

ccaaagcggc cacuacugcg gggagcacga cagaaaggua gguagcaucc agcagggucu 120
gugguuccac aguaccaccc auacccaguu uuucugagga ugcauccucu gcuucggguu 180
ucguuuucuc cauaggagug gaauuuuaug ggguaacuug ugccuuaaua gugauugacc 240
cugcuauacc uuuucuagac cguaguguggg aagauguuac uugaaucuca ucgggggcuu 300
cuuguagggu aagaaaacug acuucgaggu gaauugggguu uucgguuguc ucuuuucuac 360
ugaguuuagu acaaacuuug aaaguuaugg ggacgguaca uacaacggua aguucgacau 420
aacagagaca ugcgaaggcc agcauggguga ccauaaacaug aacuaagacc ucuaccacau 480 agggugugucc augggguagau acuuccaaug cgagagggug ugcgguagaa cgcaaaccug 540
aaccggccau cucugaacug acugauggaa uacuucuaga auuggcuuuc uccaaugaga 600
aagugguggu gucgacuuuc ucuuuaucaa gcacuguagu uccuuuuuaa cacgauacau 660
cgaaaccuga agcuuguccu uuaccggugu cgucggucga gguggaggaa ucuuuucuca 720
auacuugaag gacugccagu ucaguagugg uaaccauuac uuuccaaggc aacgggacuu 780
cgagagaagg uuggaaggaa gaacccauac cuuagaacgc cauaggugcu uugacagaug 840
uugagguagu acuucacgcu acagcuguag gcauuucuga acaugcgguu gugacaggaa 900
agaccuccau gguguuacau gggaccauaa cggcuagcau acguuuuccu uuagugacgg 960
aaccgaggua guugguaguu uuaguucuag uagcgagggg gucuuucuuu caugaggcaa 1020
accuagccac cgagguagaa ccggagggag agguggaagg uugucuacac cuagagguuu 1080
guucuuaugc ugcuuaggcc gggaccuuaa caaguggcgu uuacgaagau u 1131

<210> SEQ ID NO 216
<211> LENGTH: 2640
<212> TYPE: RNA
<213> ORGANISM: Diabrotica virgifera

<400> SEQUENCE: 216
uacccaugaa aauuuucucu augaguacua cuccugcccc cuaguucacg aaaaguuuua 60
gaccucuuuu gaugacaaaa cguccuucga ucucaaaaau uacuuugauc acauuuaggu 120
ucuuuuacau guggcuauga uuguuuugac aacaugaaua acuuggucccc acuuugaaau 180 ucacgguuuc uccggugucu acaaaagaaa cgguacuggu uugacaaggu uaguuuucua 240
cauuauaacu cuuccuacca aauaaacccu uaauuucuug agucaagaca acgacuacua 300
caguaauaac auuguagguc agaauguuuu cuauacugac cauuucuucu guacaugucu 360
cgucgacgau auucucguaa uacgucauaa ugacuacgau gauacgaagu ucgauaucuu 420
gcaauauacu ucguucgaua acaucuaucu uugcgucgac agucaagucg ucgugauuaa 480
ucaaguaaug uauacucguu uaaucgaggu cuacaucauu uuucuaccca uuuacuucga 540
guccuucguc auuuaucacu auuacguuac caugucauag ugcguaaucc agaagauaug 600
guauaauccu ucugacuauu cgaucgucac uguuuuaacu aaagguucga cuuaaguuac 660
ccaaauuucu cgggaauacg aaacacauac aacuauucuu agugacguuu ugaaaaucuu 720
cuucuccugg uucucaguga ggaguugagg gguauauguu auuauaaaug uuacccgaau 780
uccuuguuua gacuuuacca ccacauacuu cgacguguac gguaccaauu ggacuucaag 840
ugcucaucau uacacgaucg ugggcgauau ucacaagaug uugauaaaac accuagagga 900
uuucggugug agucuaaacg acgacaaucu ugaaauuuag uucaccggug gugggguggga 960 cgcagucacu gucgaacauu aaaccuagau cuuuuaaacu aaugacuagg auuauccagu 1020
uaacgaugug accgguaaug augagaaaac uuuuguccac ggcuuagaag acaacugucu 1080
gauuacuuug uuuagcgaug aaaacauaga cuuuagucac uacuuaaauu ucaccaacag 1140
uaaguccguu aauuccauaa ucgaaacuuu aaagguuccu uuguaucgug cgaauacuua 1200
aaggauaggc gguacaauuc ucuacucccu ccaaaucuua uauuucguag guaucgucua 1260
ugguaauauu gggauuagcu ucuauuaggg cuucgauuuc uuagaccaaa ccgcguagaa 1320
acgcucaagu aacuucugac acuuguacaa agaaaccgac acucuuagaa cguaaacaau 1380
ccuuuccuuc cuggguucug guuuguuggu agcucuaugu aggcaaaaua gauguuagcg 1440
caguauaacc uuacaggaag acauucucga cgacgucaga ggcgguaccg uguuaagccu 1500
cggagaacag ggcuaaacaa ucuuuuauag guuuauaaug aaagcuccac agucuaccua 1560
agucugcuac uucaaucccu gucucgaugu auaauaucau uauaugaauu guuuuuacua 1620
uuuucaaaua uguuguuaau guaaaaccua agaaacgucc aaaguuaagg aagugaucuu 1680
ucuagcgaau cucuuaugua aguuuuaggu ugacugcuug guaaacugua auucaggcau 1740
ggacaucguc gucacgguug ucgucuucuu gcucuucaau uuuuguuuag acuuccugac 1800
gaucagagag uuccagguca ggcuggagga ggccacagau cucuucuuuu gaagcggcuu 1860
uuugaaucau ugcaaggccc auauguuguc aauccuggaa acaaguuuug aaggcugcag 1920
caacuugagu gacuuagacu uugucucaua aaacaggcga cauaguucgu gacaaaguuu 1980
guaguguagc aggagguuaa gcuaacagac uuauggaacg gucuggucga aaaucuuuug 2040
caaucucacc ucuaucugcg gccacuuugg aagcuuuaaa accgucuuua uggaacacuu 2100
uucaacguga uauugcuuug gccauggugu auacaucauc aauucaacgg acuacuacua 2160 gaggggguuga gacaaccaug cacaccucgg cacaacuuca agaaucacuu ucuaacacua 2220
gguaguugcc cuuauggucu aagacuacuc ccaaugcuac uacuuauaug ugaccuucug 2280
uagcuuuauu guaaucccu gguuuaaguu uuucauucgu uucauuuaac ccgacgucgg 2340
acccuucuuc gacgucgaug aauacaucuu uuucuccuau guaugaggaa cugguaguua 2400
ugcgauucac cgcgacaauu cuuauaauaa gucaagaacc cuaaugucgg acgccuuucc 2460
ugacugucuc auggccuccc auuuagaugc guguguaaug aagaacgacc acauaagucc 2520
ccuccauaac uguaugauca uucucgcuuu gaucgaaacc cgcuuacaca augcuacguu 2580
gauugucagu ccagcggucu aggacugcaa cgacucgaau auugaaguug acauccaauu 2640

<210> SEQ ID NO 217
<211> LENGTH: 651
<212> TYPE: RNA
<213> ORGANISM: Diabrotica virgifera

<400> SEQUENCE: 217
uaccgccguu ugucuugacc uggacgaguc ucugguuuac cgcgaugggu uccuuucuau 60
acagucaagu uugaccagga ugauccgcuu ucacggcagc cauucagcuc aaaccaugac 120
uccaagcagu uuccugucaa ggugcuuaug guccucucau gguauccucg ucgaaaggaa 180
uguguuuggu auacggagcu gcuauguuga caauuuaaac uuuaaacccu gugucgccca 240
guucuuucca uggugucaaa ucgaggauac augauauccc cgcguguccg ucgauaucag 300
cagaugcugu auugguuagu ucuguguaag ccgucccgcu uuugcaccca cuuccuugaa 360
guuuccgucc ggucaggcug cuagcacuau cgaaaccggc cguuguucgu ucuaaaccgg 420
uuguuugcau accaucuuau gcuucuccgc gucugcauac gacugcuuuu gccgaaugaa 480
aaauaccuuu gaaggcguuu cugccguuac uugcaguugc uauauaaaaa ucguuaucga 540
uucuuugacg gguucuuacu uguuuggugu ccaguuccgc cgucacgggu uccguccgcc 600
gaucgccucc cgcuaagccc gcgguuccgu gggccuuuaa caacguucac u 651

<210> SEQ ID NO 218
<211> LENGTH: 279
<212> TYPE: RNA
<213> ORGANISM: Diabrotica virgifera

<400> SEQUENCE: 218
uacuucaaaa auucuagcug ucacacgaug uaacgguaga accguuaaga gaaaugggag 60
acacggcuac uccaacuucc uuccucuuuu uaaaacuacc ccgcuuuuuc guaaaggucc 120
uguauagaag caccuuuacg acaaggacgc auacacuauu auuaggaaca uccuuaacca 180
guuuaguagg acccucccua uaacaugcaa cguaacuccu ucuucuagua acgacgugga 240
cauugccgua guauacguca ccgaucuguu cuugguauu 279

<210> SEQ ID NO 219
<211> LENGTH: 474
<212> TYPE: RNA
<213> ORGANISM: Diabrotica virgifera

<400> SEQUENCE: 219
uacgucuaga agcaauuuug gaauugccca uucugguagu gagaacucca gcucgggagu 60
cuaugauagc uuuuacacuu ucgauuuuag guccuauuuc uuccuuaagg gggucugguc 120
guugcagagu agaagcgacc uuuuguugag cuucuaccag cauggaacag acugauauua 180
uaaguuuuuc uuaguuggga agugaaccac aacucuaacu cuccuccacg auucuuugca 240
uucuucuucu uaaugaggug ggggucuuu uaguucgugu ucuucuucuu ccaauucaau 300
cgacauaacu uuaaaaauau ccaacugcuu uuaccauuuu agguggcuaa cucugcacuu 360
acggggcgac uuguuacacc ucgaccacag aaguaccguc gguaccuucu guccguaaug 420
acaccguuca cgccaaugug agaacagaag agguuugguc cucuacucuu uauc 474

<210> SEQ ID NO 220
<211> LENGTH: 747
<212> TYPE: RNA
<213> ORGANISM: Diabrotica virgifera

<400> SEQUENCE: 220
uacuacaggu uucgucugug uguccuucua cggaggaagc gguuuaaccu uuuagucuaa 60
cgauaguagu uuaugcauua ugagaaaugg uugcaaaacg uuacccgaga gccacgucgu 120
uagaagcgag aaacggaaac cgaugcuaag cuccucccgu aaguucuuac cgaggucuuu 180
aaccuaaguc uuguuaaaau guagccucau auacaugaau aucagcgaag ugacuagcag 240
uacuaacaca ggaaauaucc uacauaauca cgggacgucc ucucauggua ccgggaaaau 300
cacauguagc cgugggguuca cgagucaaaa uauaagccaa auaggccaag ccgccaagaa 360
gaccuauugu cgcggucucu aagggugaag guuggcuccu aggcucucuc auacgcugca 420
gaauaguacu uacgaguagu gcugguuagg ucuguuugug aucgguacua aguccuuuua 480
caaccaacga cgccucgacu accgcguugu cugauggaga gagaagucgu cggggaaggu 540
ucagucacgu cucuguggca augaccuuug gguaagaagg ugccuacaca ucuacuugag 600
uggaccaaga agcuucuuuu uacaccaacc uaucguccaa aucgauaccg cuauacguac 660
uaauugcagg aaucauaaca aaauagaugc caugaguagg uccguaacuu uuuucuucuu 720

-continued

```
cuucguaggc uaaguauguc cucuauc                                       747


<210> SEQ ID NO 221
<211> LENGTH: 375
<212> TYPE: RNA
<213> ORGANISM: Diabrotica virgifera

<400> SEQUENCE: 221

uacagaccug caccguuccc uccguuucau uucccuuuuc guuucagggc uaguuuagca     60

cgaccaaaug uuaaaggaca uccagcauaa guagcaaaua acucuuuucc uuuaauacgg    120

cuuucucaac cacgaccucg aggacauaug aaccgucgac aauaccuuau aaaucgacga    180

cuucaaaacc uuaaccgucc uuuacgucga ucucuauugu uuuucugggc auauuaagga    240

ucuguaaaug uuaaccggua uucuuuacug cuccuuaacu uguuuaauga caguccucaa    300

ugguagcggg uuccaccuca uaacggauua uauguucguc augacaaugg auuuuuuuga    360

cuuuucuuuc gaauu                                                    375


<210> SEQ ID NO 222
<211> LENGTH: 864
<212> TYPE: RNA
<213> ORGANISM: Diabrotica virgifera

<400> SEQUENCE: 222

uacuucaacc uaccacaucu agacgggggu gguuaaucga agcuguaacg ccuucucguu     60

ggcaauggug gaacgguugu cugcaagaau acauuaccac uaccuccuag guaucacgcu    120

gucaaagagc ucgacauaaa gcauuauaua cuaagucuau uauccgucag ggaagaaguc    180

cguauagugc uuuuucggug uaaaaguuac uguuaccgga ugggcaugcc gauaagguuu    240

cugucauuuc cucauagcac caacuuaacc auacgguggc uauuaucuuu aaauaaugcu    300

caaguucuag gucugucuuc uuuguucaac aauucugucc cuguucaacg acaucaaagc    360

aagaacguuc uauacggcgu gugcuucgug cuauaagugu caaaauguca ucuaaacugu    420

caaaaaugug ggucuacaa uacaaacugu caccgaccau acaaauuucu uaacuuuuca    480

ccggguguuc auggaggaaa uucuauaaag aagucuuggg aacauuaaca uggacgaccu    540

aguccaaaaa cguaucguuu acuucuugaa guguauaggu uacguugagg ccugguucgu    600

uuucuacgaa aguucuggug gcaauuacau cgaggccgug gucggggaca cuaauggaga    660

ggaccugggu cauauggugu ugggcgacac ggucuacuac gauguuuugu ucuuuaccau    720

uuugucuaca ggcgucauag gccuuacuua gagcucacca gcgaugucac agagcuucuu    780

uguguuaccc ugauggucuu ucgguauuac cauaagguuu uaaauuugcg uguuccacaa    840

caugguguuc gucguaaaua auuu                                          864


<210> SEQ ID NO 223
<211> LENGTH: 2868
<212> TYPE: RNA
<213> ORGANISM: Diabrotica virgifera

<400> SEQUENCE: 223

uacugacgcc aucuuguugg aacaaugugu gauuauuuga acgguugucu aagccucggg     60

auguuacuuu acguugauuu uuaccuaaau cuuuucccac uccaauuuca uuuuuauucu    120

cguaaucuuu uuuauuaagu guacuaagac cguccucuuu ccaacggcuu accuaaagau    180

uacugguagu auucuuugca aaauggaaau guucuaguaa accguuuuuu ugauaauaac    240

uaaaagaccc uuuaucaagg uuuuuguuua ggucuuccau uugaugaugu ucucuacuaa    300
```

-continued

```
aaccauacac uacggauauc uuuucuagac guuguggguu uacuuaaaaa cucuccaaga    360
ugugaagcga agaacacguu ugacuuccuu ggucuuaaca accuugguaa uuacggguca    420
uaaucucgaa caaaccuagu auccgugucg auacacuccu ccuuacgaca ugaccguuaa    480
aaaugguaaa uguuuuuaaa acuucgggag uaaggucuac gaggacuuga cuagagguua    540
auaaaccuac cacucguucu guacagaaca uuuucuuuac gcaaaaauua cgaagaagua    600
cgacugguuc uuucccgcaa cagcauaaac cguaguacaa aucuaguuca uuuaaguaaa    660
ccucuauaag auguugacca guagcaacuc aacuauauau uccacacagu aagguuagga    720
cgccuuucua gaucuaaaua aucuacauau auauugaaca acuugaguuc gucaggacga    780
caguccaugc uucgacgucc uugaaaucag ugggagaggu cacggggcug acggcaauuu    840
cgacgacgau cgacaaugua acucaauuaa uaguuucuuu cacuguuguu acauuuugag    900
uagcaaaacc uguccgacua ucgugaauuc cucgaaggau uagugcuuuc uuaagacguc    960
cuaaaucaau accuguauga cucucaugag agacgaggac ugaaucuuca ggcguucuuc   1020
ugaaauucag aucgggaacu uaaucagaga agugccuugu aucuucuuua ccauaaucau   1080
aauuguuucc uucacucauu uugccaucug ucacuuguac uccuaugucc uuucaugucc   1140
guuaacaauc auuccugaga uguaagcaca agguaauuca agggucuaua gcgugcauca   1200
caauaugguc agaacuaacu uaaaaauagg cuauuauuac uugaccgacg gugucuacau   1260
aacgacaaga auucccuucg guaugucuuc aaauuucuua acguuggcaa uuaauaacuc   1320
uuugaguagc uuugaaaguu ucuguaauuu aaccaguuuc agguaucucg ucguuaaacc   1380
uaaaacccuc uuaugcgcuc augacgaagg cuauaucuuc aauagcaacc ucuuuaauug   1440
ucuaacaacc cacuuccuag ggagcaacuu cgacucgucu ucaauuaucg uccucuaugc   1500
cuucucuuac gaggacgugg acgacguccg cgguggugaa aucaaugaag gcuaccuugu   1560
auacgauggg uuagucgaaa guugugacag ucgguuuggu gauuucuucg ugcuggagga   1620
gauucuguua uggaguaccu accacuaaaa aaguagccuc ggagaaaccg uagauguaau   1680
ugguuugaca gaaacgccau acuccuggag uggagaggac gacgaucguu accuaaguua   1740
cgguuuuaau acgaauaaua ccgaccuuaa gaagugaacc cuuuuagucc ugaagggugu   1800
uuuaguuauu gguugcugcu auuucuggug uaagacaaga caaaugcuca ggauagacua   1860
gcaagagguu aguaacaacu uuaaaaguuu uuuaacacgg cgagccguga uuuacucuac   1920
gaagaucgau uccuuagcca ucuucgcuag agcguuuucu cguuucuuuu uuuguucgca   1980
ugcuaaguuu gacugcugcg auauucgaag gacguuaauc ucugucuauu uucaccucuc   2040
gauccucuuu ugcauaagcu cuacagcgac aguguucgaa aucauccucc agcuugcccu   2100
ccaccgcuua gucauaauuc aagguuauuu aaucuauuuu aguguguuga cugaccaaaa   2160
aggcuagguc aaauaaggcu ucguaugcaa gugcacuuag ucaugcuaua gcacgaacua   2220
cagaauuagc auuugguuug auugcuauga aauguuuuga cgugcgaucu cgaccgauga   2280
aauccgcuaa acuucaacca ucucuucggu guuggacagc auaaccgcgg guuucugaaa   2340
acguuguaau uucgauugca cuuucaccgg aguugacuuu ugccuuaaua uaaaccguug   2400
uaacacauac uacaguaucc ucgccccagu cuauccuuac aacaucaaaa cuuacuauau   2460
guguaucuau auuaccugau auaucacgga cgaucaacau gucuaucgcu caaauacucu   2520
uacacccgcc uuaaacuuac ccuuuuauuc cauuggcaau ugugugggga gugccuugaa   2580
agucuuaugg agcuuguaga ugaguuucg uguuuaaacu uuacaaauug uagucuuuuu   2640
```

cgagacucgc ccgucacacc aaaauaccgu cgguuaaaua uacguuuuag guaaaaaccu 2700
cuucugcgaa accgguugaa uucauaucuc uuuggaaaau uauuugggcu acgcggucau 2760
ucgccaguau aaucuuauuc ccgguuuuca gucccguacc ggaauucaaa uccucuguuu 2820
caguuauacu gugucuucuc guguguugua uuucaucauc gacguauu 2868

<210> SEQ ID NO 224
<211> LENGTH: 549
<212> TYPE: RNA
<213> ORGANISM: Diabrotica virgifera

<400> SEQUENCE: 224
uacccauuac acaaacguuu aaauaaguuu ccggagaaac cguuuuuccu uuacuccuau 60
aacuaccauc cugagcuacg ucgaccauuu ugguguuaaa auauauuuga auuuaauccu 120
cuuuaacauu guugauaagg uuguuaaccu aaauuacacc ucugacaucu uauauucuug 180
uaaucaaaau gucauacccu acauccacca guucuauuuu aauccgguaa caccucugug 240
auaaagguuu uguguguucc ggauuaaaag caucaucugu cauugcuguc ccuugcauag 300
ugacuccgau uucuacuuaa uuacgcauac aaccggcuuc uacuugaauc ucuacggcau 360
gaagaguaaa agcgguuguu uguucuaaac ggguuacguu acuugcgacg ucuuuagugg 420
cuguuugagc cagagguaag ugaugcguug gcguugacca uguaaguucg auggacacgu 480
ugaucgccuc uaccagagau acuuccagac cugaccaaca gguuaguuaa uuucuugcgg 540
uuagcgauc 549

<210> SEQ ID NO 225
<211> LENGTH: 4425
<212> TYPE: RNA
<213> ORGANISM: Diabrotica virgifera

<400> SEQUENCE: 225
uacccugcca acgugacaaa uaaaacauaa aaggauacaa aauggcagua guugugcguc 60
uguugcuuau auguaccuaa gagccuuuua aggcaccuau guaaagauag uggaguaccc 120
uuuucacguu uuaagcacgu gguuuuagug uuuggguuuu aacuuuuaac agucuugaug 180
uuugggagcc acuuucuucu ugucgguccg ccuugcaugc auuguugcca auggcgauag 240
cuacugcuag gaucccuccc uccuccuugu uaaucaaugu uugauuaagu aucucuuccu 300
cuuguacaaa auaaacugua ucuguugcaa ugaccacaaa acuguugaua ggucgguaaa 360
cuagcccuac uuggucauuc cgucuuccuu gaaauacauu ggcauguucg aagucuguug 420
ccguccggug guaaucgucu acagacaugu aaaugucaau gguaauggcu guaauuacua 480
uuacgcggug ucgaacuauu ugacuuuaug cuacguguuc aaagacuucu aaauuuucau 540
ccuucacuuc acuacucuca aaaacgaaug cuguaacuac uaccccuuuu aaguucuaau 600
agcauauuga aaaguuugcu uuuacgaguu aaguggguca uaaaguccua ucuagcucua 660
ugaccgcaac acauaaauuu ccuucgaaau ugucuguuuu ucuuaugauc uaaauuguca 720
cgacaaauac aucggcuauu accgcaauug cuaguucuuc cgguuuuucu aaguuggcga 780
uucuauagau auugucauca ucccagacua uuugucggag ggucuaaaug aguuuuuuac 840
ggacuaccuu agaaccucua ggggcuucua aaauuucuga aaagauuugu auaacagugu 900
cagcuucguu gcagguugua acgccuaggu guugaacgaa aacuuaacca cuucccuuuc 960
uguauaguuu gguuauuucu gguuugcaaa gaaaaccucc gucuuccuuu auuucgcgug 1020
uauuucgauc acgcagguga ccuaauacuu ugucauugcc uuauaugaga uugauaagcu 1080

```
cauuuuuugu uucuaaauua ccuaagaagg uauuuauaug guuaauuuca uaaucuacaa   1140
uuacuacuuu aaggauuaaa ggaacuuaaa gaauuuccau cacagcaccu uuuacuguuc   1200
gguccacgug uucgcuaagu ucauucucgu uagcuauuuc ugccuugacg acgauuguug   1260
uaacacucga uacuugagca acuguuaugu cuaaacaaac guuauuuggc uagaugcccu   1320
cauuaaugca gcucucaccu caaacuagca cuuugacaug gagauauagu gcauuugcaa   1380
uuucgaauac uauugagagg cagacgaaac auauugugcu guaacggauu guaacauuaa   1440
gucuguaagg uuuagucaua ucuucuaguu uuacuguugu uuggacauaa augaguaggu   1500
uaaauaguca agucauuaua augacucgaa cgacuauuua gcucauaaca accacuucag   1560
uuucgaaauc uauuacugug ccgaagucaa uauucaauau cauaauguuu accuuuauaa   1620
cugcuacgca aauacuaacu uuuaagaugg ccgucuuauu cucaauuacc uuuugaccua   1680
augcucuuuu agcuuguuau guugaauugg caagcgcgua aacuaccccg uaaacuucua   1740
aaacguuaac aaaauuaaag guaugaauua cuuuuacugc uuggagguca aaaacugcug   1800
auauagucuc uuuaaguuua auuucuccuu cuuggauacu auaggccuac gcaacaaucu   1860
cacugacgag uacuaggucu auaaauuucug uccguacgac uaguugugua ucauauacuc   1920
cagcgcuuuc uugucuuucu aaaaaacugg cauagacggc uaccuacgca uguucauugu   1980
uuuggagagc uggcucuagg cggaaagcca ucggguugug cuguucagaa guagauacga   2040
gcacuauuac uaccuccgug uuuaaguaac aaccggugac gucuuuaacu uuaauaaaau   2100
uaucuauauu ugcuauuacg agggaaaaau uuacaauguc uuuaacaaau aauacuuuug   2160
guccuagguc caaaauaucc auuggauuca cggcuacuaa ugcuaccagg acuauuaccu   2220
ggaggcaaac gaaaagcuaa uagucuguga cgaagucuau cauaaucuag cuuuaaaagg   2280
uaauagccuu uggucgaaaa gcgaaaucuu uacaaacuau cucuucucgu uuuuauaaua   2340
cuguaacggu aacuguaaug ucuaucaccu cauggaggug auuguccuug aucauaagaa   2400
ucucaauauu agccucuaca uuuacuauua ggucgauguc ugccuuuguc gugcuagaaa   2460
cacauauuca ugcaguuacc cggucuuuua aaguaccuuu agccugcaca uauacaaugu   2520
cuggaucugc uaacccuaaa uuuacuguuu cagaaacaag uucuucuauu gaaacuacuu   2580
aaacacaauu uggucguauu guugccauac uaagacuacu uugguuguug ccgacucccu   2640
ugaauacucc aaguaauguc ccagugacuu uggguacuug gguguuaugu gcuuguaugu   2700
caauuacguu aucagugcua augucaauuu caugaagguc uccuucgcca acauuuuagu   2760
ccuaguuaag cuaacucucc uuguugauuc cuucuuaagu aucuuuuaag uaacuuaccu   2820
uucucguuuu cucuguauaa ugugguucuu gagagguuuu auaauuuaug uagaaaucgc   2880
uuacaacuac auaaaugaca aaauuuaagu ggggugguucu uaucaagcaa acaccuacaa   2940
gcuaaaagac gaguaccuag agguauaaua cgaggucucu uugagcuuuu guuucaaugu   3000
cuaguaguuu accucgaacu uguuuuuaau cuacaccuua agauguacua guugcauuug   3060
cucacggaau ugcuuuguug cacaccucga cuuuugagua caugcuuguu uaauuuguau   3120
ugugcucuug gucgacauca caaaugauug ucuuguagga aacagccaca uuuacguaaa   3180
uaacuaggac acacacggcg aaauggguucu cuacaauacc uuacaaaguu gccuccgcag   3240
gaauagcuuu ugugucgcac auuaacagga cguccuaaac uuccuggugu aacacuuuag   3300
gaucgauauc cuaaaugucc uugaccaacc cgauacauag guaggaaacu gcgauguuug   3360
uccugacucu aauaugacgu auaaaauagu guuugacuau uaccaaacua uaaaauguua   3420
```

-continued

```
ccuggaaauu uauauucugu uugaagaaac agauuucuaa uauauaguaa ucuugaauuu   3480

cugccuauag guaaugaagu uuaaacgugg ccgaguucgu gaguucuuua aauagacuuu   3540

cucgcguaag uguuuaacuc gcuaccuagc aauguguuuu auuuuuaucc uagaccuaaa   3600

cugcuauaua gggaccuuca ucugcugaca ccuuguugca caaguuaaac cugauuauuu   3660

gauguauuuc cacaauaggc ucguuuaccg ggggaaguug acccuccaua cuuuuugucu   3720

aaguggcuag uucuuaaguu ugcuuaaacc cugguaaacg guggcugacg gugggcaaag   3780

agaccaacau aaucuuuaaa cugcauauua cuuaaaauga uguuggagcc acguggaaga   3840

cuacguaagg uucgcauagg gcugacauug auacgucacu acguucgaca cugaaagcca   3900

uagcugaggu uaaagaacca acgauaagac caaacacauc guuaaaacua uuaagaagaa   3960

gaccgucauc aacauguauc ugcauuugug cuguugaaau ugcuuuuucu uuagcuacua   4020

ugagcgcuuu uguaauaguu gaugcuucua cuuccaccgc cgcuuacacu gugguugaug   4080

cuggacagac aaaagguagu cuuguuguaa caccugcuuu uugguaacua cucucuguug   4140

gggcuacaug gacgucuaua uucaccgaaa aaucuauugu ucuuucuguu gacacuauuu   4200

cuggggcuau uaaacggaau acugcugcaa gcgguaauac ggaugcuccc ucugccuuua   4260

ucguggccua ggaauagaag agagcgaagu acaugccugc uuccucuaaa uuucaaguug   4320

augaauaguu caaaaccugg gucuaagucu uucaaucggc uguacauacc ucuucuaggu   4380

ucgcuacuuc ugagugugcu accuuugcuu cuuaggacca cgauc                   4425


<210> SEQ ID NO 226
<211> LENGTH: 291
<212> TYPE: RNA
<213> ORGANISM: Diabrotica virgifera

<400> SEQUENCE: 226

uacggaaaga caccaggguu uaacagggag acgccggacu aauagucacg uaccccauag     60

uaggucaacc caaaguaccc acauaagaua auguaacccc gacaccgaaa ucgucuucua    120

uaaggucucc aacucaaauu cccgcuaaau cuguuuaaaa uaucgcugca guugugccca    180

aagugugucu uacgaauguu gacgaccuaa cgacgagagg auauggacua uuguaaucgu    240

cauagucgag ugguuaagac ccgguuguug ucuaguagua acuugcagau u             291


<210> SEQ ID NO 227
<211> LENGTH: 540
<212> TYPE: RNA
<213> ORGANISM: Diabrotica virgifera

<400> SEQUENCE: 227

uacccagaau gguauagucg ucacaaauua uccaacaaau cauuuuucgg auacucuuaa     60

aauuaccauc cuaaucuacg gcguccauuu ugguguuaga auauguuuaa cuucgaacca    120

cuuuagcauu gauguuaugg uugguagccg aaguuacauc uuuggcaacu cauguucuua    180

uauagaaagu gccauacccu acauccaccg gucugcucuu agucuuuuga gaccucugug    240

auaaagcggu ugugacuacc ugaguaaaaa caccaacuaa gguugcuggc ucuggcauag    300

cgccuucggc uucuucuuaa cguguuauac aauccucucc ugcuaaauuc ucugacguaa    360

aacaauuaua agcgguuguu uguucuaaau ggcuugagcu acaggugacg acuuaacugg    420

cuauucgaau ucaacgugug aaacuucuua uccuccacca uguauguucg guguacacga    480

ugaguucccu uaccaaacau gcuuccugau cuaaccaaca gcuuacuuaa ccgguucacu    540
```

-continued

<210> SEQ ID NO 228
<211> LENGTH: 618
<212> TYPE: RNA
<213> ORGANISM: Diabrotica virgifera

<400> SEQUENCE: 228
uacgccaugu gaaacucaau guagccacga ugggaucgca ggugacauug ugacuaaaaa 60
cgggagauga ugacggagug cccuuuuccu cucguucaau caaaucguac caauaacaac 120
uuacacagag gggguguacac ccguccagau ccuuaaccgg aacgacauag uaauagucaa 180
cauccucgac gacguccuua agugugaugu ccucagucau agcauccucg accacaauuu 240
cgggggucuu aguuuugguu uuuaaauuaa agauaauaaa agacacuucg acaccgauag 300
auacccaauu aauaccgaua ucaugagaca ccuucaaccu ucuuaaagcu acaucuggau 360
aaguuggagu uuugaguauu gaaacgaguu uugguaauac cuaguguaca auaaaaaccu 420
aggccaaauu gacaaccuaa acauuuagau aauacaccua aaacacaacc ucaucaacca 480
agaccacguc gguaaagacu acgucgguua aguaguaaua agcaguuuua aaacuaauaa 540
cucuaaaaac cuucacggua accagagaag ccagacuaac aaccucauau gaacugcagu 600
ucuccgagau accaaauu 618

<210> SEQ ID NO 229
<211> LENGTH: 5694
<212> TYPE: RNA
<213> ORGANISM: Diabrotica virgifera

<400> SEQUENCE: 229
uaccgauggu ugcuaucauu ucgaggcaac uccugucaau uuucucacgu uaaaccuuau 60
gaaucagguc uacuuuaauc ugcuuacagu cagugucuuc ccccguaggc gaagggucuu 120
ugguaccuuc guccggcggg guuugauacg ccagaauacc uggggucugu uccacaguau 180
cugucuucga guucuacggu cuguacacgg ccuuuauacu gucuuacagg accuguaaag 240
ccuguauagc ucgaccguuu uggucaaaag gugcauccua agcauuguuu uuguuauuuc 300
uagaacucua cgcaaacgaa gaaaacguca uuuaauaauc agucagguuu auuaggcuuu 360
uaauuucuuc aacauuacuu uaguuucccu gucggugcau uuucuaaucg aaagcaaaua 420
cuagacacau uuccauuuuu auaaacacuu ccaccucuac uuuaccuaca cccauuucuu 480
ucgcuucuag gguuauuuuu ucguccggua ccaccaacac cagcuauagu ugguuuauag 540
ucugcacggc caaaucuaaa uugucgucuu accuuugugc aguuacuucu guguguucuu 600
uucuuuuagc gugauagacg gcuugcacag acccuuuagg auuuuguaua gugucuacuu 660
cuuacaaagu aagaaccaua ccuaggguuu aaacgaucug gucuaaccua cuaucauugc 720
caugaaggac aaggagggga ucgucaugcu ggacgacauc aauacgugcc uagacguucc 780
uuaguccuac uauagugagu guuuaaccgg cuguaauagu uccgcuuauu gcuuaauguc 840
uucuugcuca gacguccacg ucggcgagua uauuagugug uuuuauaauu cuacaacguu 900
aaagugcagc ggugaaauca acuguugcua uacggcccuu acggcucucg uuacguuuuu 960
agaccuuuug gggauuuucg auaguuucga gccgacuuuc cauuucuucc uuccuaagcu 1020
ccauuggaau acccuuucgc acaccugaaa agacgugcau gacaguagug uggucuaggg 1080
uuaaaugcau agcugguuca ucccucacgga ucuucauaac gaguuuugua cugcaaaggu 1140
cuuuagcagu guggaaaguu aaaacuguuu uacaaccuua accaugucuc uccauuaaga 1200
gucauagguc cucgauucau auaguagucu cuguuaccuc ucuccuaacu aaaugcaaag 1260
gugggguuug gcagucuaaa uguaaacguc acaccaauau uccaucuuuc uguguagucu 1320
cugccgcuag aucauuagaa guuggcaguu gguugggagg uguucuacuc auacuacccg 1380
gugucucagu uucagaaugg gaccagcugc aaggcauacu uagagagcac guggagaggg 1440
auguugcggc uaaaacugcc gcugcuuuac uuggagguac acgggguuuc auaccuuuga 1500
gcucgacuuc agcuuuugga gguguaguga ggguccguuu aguaaugagg cguucgauug 1560
guugggcagu acccauaaca uguucuaugc aacugucgac aauccuucua cuguuuuucc 1620
cuacauaagu agcucuuccu uguuuacuac uuauauaacu acaagaacgg uuaaacccua 1680
ccauuuuacg gggcaggucg guaggaguuu ggguuuggca acaccugucc uuuugucuau 1740
aaaagggacu aguaaggacc guuacauuua uacuaugcau ggguaagaug cguaggucug 1800
cugcuccugc ugccagggau auuuaccuau agcgguccuc uaugcuuuca auaccaucuu 1860
guaccucuua accaguaccc auauaacaca uucuuuucag aaccuuguag ucguccaagg 1920
gacgacguau aaacauacaa ccuuaauccu gugcuucaca caccaucuaa aauaccauug 1980
uaaguuugac auuaguuguu gaccaacaac aaucuuccag ugucguagcc auaaccucug 2040
ugguaacggc uaggagucug aaugugucuu uaagucucuc gguaguccuu ucgguuucuu 2100
cuacauuauc uucaguaggu cuuucgagug uuguaccuug accuuggcug agggccauua 2160
ugcaacgcag ucugaaagcu uuuaguucau uugucuuaag auuugcugcg agcacuguuu 2220
ugaccaccaa ggcgauucuu uagaaacuga cuuauguuau uggauuuccg auaccagcau 2280
agcccuaggu ucccuagguu guaauuauaa aggguccaau aacgaacgca cccaguuguc 2340
uugcaucuuc cauuugcaua agguaaaccg aagucuuuug cgugcaacgg cgugaaguag 2400
uuccugcuaa ugccaggacu uaggucucca aagcaucuuu uaagcauaga acggccagag 2460
ugaggaagcc ucaagauaaa ggugcgauac ccuccagcac uuccagaaua gcuaugacga 2520
cauuuuugac ggcuuugacc aauguagguc gcagcagacu aguuccgaua ccucucacau 2580
uaccauguga ugcugccaug gcauucuuua agacauccug uugaauaggu caacucuaug 2640
ccacuccugc cugagacacc ucucuaccau cucaaaguua uaaaucguug ccaguuuaau 2700
ucauuguucc gcaaacucuc uuuuaagucu aaacuaggcu cauuacuuuc cauaaacucu 2760
ucucaaaagu uacuucuuca auaguucguu gacuacccaa guccccuuca guaaaggcuu 2820
gaacucucuc uuacccuugu ugaggucuuu cugucucuuc ggaauucugu uuagaaggga 2880
ucgccucuua gguuucauca ugaggggaca uuaaaauguug cauacuagac cuuacauguu 2940
uuuuaaaagg uguauuuguu ugcucggggc ugucuggaca ggggcaauuc ucaauagguu 3000
ccgcaagcuc uuaaugaguc cuuuacgcag uagcaucgac cgcuccuagc agacagguuu 3060
guucgguugc uuuugcguug caaugagaag gucacagauc agucuagcug ggagacgugg 3120
uuuacgcaaa gacuucuuaa guccgagucg uggcuucgga agcucaccaa cuauccucuu 3180
uagcucugcu ccaagguugu ucggguucgg uuaggaccuc uuuaccaccc gcgagaccgg 3240
cgcgucagug acccucuugg gcgaugaguc uacugugacu ugugaaaggu aaaacgacca 3300
cauaggaggu ucuugcauug ggacccacau ggaucuaauu uccuuuaaua auuauaaagg 3360
uucuuugggu uccgagguag agauuggcac aaaaauugac cacgccgacg aucucuacgc 3420
cuuuuucgcu ucuuacacaa uacgucugaa cuuguguggu gagaagcauu ucauuggcgg 3480
uuguggcggu agauaaugcu aggacugggu guuuuauggc aguaaggacu ccuaguccuc 3540
aagcaauugc agaugauacu uuacgggcua aagcuaggau gggcauauag cggcaccaac 3600
gaagcauagc uugaccuguc uuucucuuac ugucuauucu uugauugaua ccuuguuuaa 3660

-continued

```
cgacuuuucu aguugcgacc caagccccug cuaaacuuaa cauaaaaguu gcugcuguua   3720
cgacuuuuca accacgacgc auagucuuag uacuugucgc ugcuaccuuu uaagccucuu   3780
ccacgacuac uccugcaucu guuuuaccua cugcuguaca aaaacucuac guagcuucgc   3840
uuguacgacu cgcuauacug gaacguucca uaucuucgcu aaagguucca uauguacgug   3900
aacggugucu gacugagcuu uuuuuccuag caguagugac uuuguccgcu uaaauuccgg   3960
uagcgucuua ccgauaaccu uugacugcca uggucguacu acuuucauga cagucuuucu   4020
cugcagcuag gccaguccug caaaagauug cuguaaacac uuuauaaaag ccaugaacca   4080
uagcuccgac acgcauucag acaucucuuc cuuuacuugc gacaggaaag caagaugcca   4140
gacauacauu ugauagcggu agaacggaac gaaacacugc auuacugucg guuuccagug   4200
aauuaccggu agugggcagu gccauaguug ucuguucugu gaccucgaga cuacuccaca   4260
aggaagcucc uuugacaucu acauaacuac cugcgacggu caguacgccu ccagcugggu   4320
uacucuccuc auagacuuuu guaauaggag ccaguugaug guucuuaccc guguccgacg   4380
aagcuagaaa acgaccugcg gcuuuuuaca uuuuacccuu aacgguaugg aguucgcgug   4440
ucgucgcuag auuaccgaag uccuuacaag aaaccuaauc ggcgaugugg gucgucauac   4500
ucagguccac cacgauacug ggguaccuua guucgucgau gugguaugca accgucauag   4560
accagaggug ucuuaaauua cccgucaccu uacugugguc caccacggcg aaagaggggu   4620
agucgacgca gucuacguag uccuuacagu ggucgaauac cgccaaccag ugguuguggu   4680
guuagaggac guuacagcgg uauauaccga agaggugaac cuguuagcgg aaggauguca   4740
gguaguucag gucgcaaggu uggaugaagu gguagguacu gcggcuggag aggaccuaua   4800
agagggucaa gaggaccaau aaguggaugg ucagaguuaa ugucagguug cucaggguca   4860
auaagugggu gaagagucuc aaugaggggu uggaguggau caaugagugg cugaagaggu   4920
uuaauaagug gaugaagggg uucgauguca gguuguaggg gauugauaag ugguuguaga   4980
ggguugauaa gugggugaag uggaucaaua ggaaguugaa gcgguccaau gucgggguga   5040
agugcgucga ugagugggug uagaggauca augaguccuu gaagcgggag aauaaguggu   5100
ugaagcgguu caaugagggg augaagagga ucaauaagcg gcagcagagg auuaaugaga   5160
gggugaagag guuuaauguc agggugaaga ggauuaauga guggcaggag aggauccaug   5220
ugcgggccaa gaggaucaaa aaggggguuca agcuugucaa ugagagggug uagaggaguu   5280
auaagagguu guagagguuc aauaagcgga agaagcgggu uuauaagugg uugaaggggg   5340
uuaauaagcg guuguagagg uaguaaaaga ccuccuucag guguuauaag ugggguguagu   5400 ggcuuuauga gagguuggag cggguuaaug ugagacagcu caggcgucgu gugagguugu   5460
ccaucgucag cuauaagugg caguugaagc ucaauaagag gauuaagcgg guuaauaagu   5520
ggcugcagag guguuaugag guagguguca uguuuuauaa ggggacguuc aggauguaag   5580 ugugggguggu caggaucaaa gagagggcga agugggcgua uaagcggagu uggauacaua   5640
aguggaagaa gaggauuaau aagaggguga ucagggucag uucugugacu gauu         5694
```

<210> SEQ ID NO 230
<211> LENGTH: 876
<212> TYPE: RNA
<213> ORGANISM: Diabrotica virgifera

<400> SEQUENCE: 230

```
uacagcaguu uauaaguuuu ccgggucguc aacuaccgcc uacgucuuuu cuuucauugu     60
```

agagcuccaa agaagccuag agauaaaccc ccuaguucag cauaacuucu acgucaccuu 120
acaauguguu cucgacguuu ggaaaaauuu uaccgguucu cgacccuacg acggccauuu 180
cggaaaacac uccgacgauu aaacguaagg ucuugaccac gagcaguacu gcgacgguga 240
uuaauauauc uacgacguuu aacaauguuu uuucggcuac auaaacuccg acauuugacg 300
aaauauuuuc gauaucugua aauauggcuu uacccagcga aauguuaccg acguuuugug 360
guagucugau aacgucuuua cauacucuga cuacgacacc uguagcuuuc ccgacaaguu 420
gugauacuug uccgccgacu aaugaagucu ccucuucuuu cguuacgaag gcgguuauuc 480
acagaagaau uucaccgagu uauacgucgg guugaacuuu ugauacuuuu ucgucacccu 540
uaaauaguuc uucaccgaau acgucgagac cuuucgagag aaaauuuuau gucacguuuc 600
cuuaugaaua agucucgacg ggaaacagug gaaacacaac uacaugaguu acguguugua 660
cgauaucuuu cgauauaaag uuccauaggg cguaaaguuc uaagggcacu uauguuugaa 720
aacuuuuggg aguaucuuuu guagcuucuc guuuugcauc uaccuauaug ucuucggcag 780
uuucuaaugc uaaguuaaag agcagaacua gucaccauau gauguuaaga aaaugcauaa 840
uucuuuguuc auucgcuuuc gggacugaau gcaauu 876

<210> SEQ ID NO 231
<211> LENGTH: 609
<212> TYPE: RNA
<213> ORGANISM: Diabrotica virgifera

<400> SEQUENCE: 231
uacuuagggc ucauacuaau aaauaaguuu gaagacgacu aaccucuaag uccucauccu 60
uuuagaacag aagaugacuc uaaacgucua cuauggaugu gucuuucgau auaaucaugg 120
uaaccgcauc uaaaauuuua guccuguuag cuaaaucuac cuuucuguua auuuaacguu 180
uaaacccuau gucguccagu ccuuuccaaa ucuugcuaau guaguucaau aauggcuccu 240
cguguaccau aauaacauca caugcuaacg ugucugguuc uaaguaaguu auugcaauuu 300
gucaccgagc uucuuuagcu ggcaauacgc acacuguuac auuuguuuaa ugaccauccc 360
uuauuuucgc uaaacuguug auucuuucaa cagcugaagu gaugucgguu ccucauacgg 420
cugguuaacc cauaugguaa aaaccuuugg agucgauucu uacguugguu acaucuuguc 480
cggaaauacu gauaccggcg acuuuauuuu uuaucucauc cuggagguag aagacgccau 540
cugguuccuu uauuccaauc caagcuaguu ucagcggguc agcuuuguug guuuaggcca 600
acgacgacu 609

<210> SEQ ID NO 232
<211> LENGTH: 789
<212> TYPE: RNA
<213> ORGANISM: Diabrotica virgifera

<400> SEQUENCE: 232
uaccgucugc gacuacuaga uaaucuaaua cuucuacucc uugucugucu uguuuggcgu 60
ugacuuugcc guugaugucu ccaugucuuu uucccacagu ucccguguau acauaguuau 120
gugucaagac ccaaaucucu aaaagacaau uuuggucguu aagagucucg auaucaccug 180
acgcccaagc uuguaggaag ucuucaaguu guacuuacau aaggaguucg acaguaaccg 240
uaccuauaag acacgguucg auuuaggcca uacccuuuuu gccgacaaaa acauaaucga 300
ugugagguuc auuaucuagg augucuuuua caacauauac aagagcagua cacgguaugg 360
ucucucaauc ggaaggucua uucguuucuc augcuugcaa agucauuuau auacggguua 420
uaauuucauc cccagaagaa accaccgaac ggauaggucu uucuacuccu uugcaauuuu 480
uuauuaacgg gcguauagca acacccauga gguccuucuu aaaaucguaa ccagucuagc 540
uuuuuugaau uagaguuugu agauuucgua aaauaaaacc uacuuacacu auuuuacaac 600
cucaauaauc uguacucugc acuacaaguu cuuuauauag cauugugagg ggugcuuuuu 660
guucaguacu acaagucacg guggaauuca uuucuuuaau cuggucaaac guucuuuaaa 720
uacguucuac auuaaguuuu aagaauauua uguguuaaaa cauuacugcg ugggugagcg 780
uuacaaacu 789

<210> SEQ ID NO 233
<211> LENGTH: 738
<212> TYPE: RNA
<213> ORGANISM: Diabrotica virgifera

<400> SEQUENCE: 233
uacggccagu aacuaccaau auuucaugaa auguaaaaua augugucaaa uauauguuaa 60
aaacuuuuau aaaccuccug agaaaauaaa uaaauaguuu uaacauauuc ccaauauuug 120
ggacuuagau guaagcuacu acgacugguc aauuucuuuu cugacagauc ugauuguuuu 180
uucggaguug uaaauugaua guaauaacca caccuucuua uaaguaacca ucuaaaccga 240
uuggagcaua uaaccacaaa uccagaauua uaaggcaugc aaucaaagau acuaauauuu 300
ccauuaaauu uuuucguacu ucucuucaac guuguuuaac aucuuagguc uuuuagucuc 360
uuauaguugu auuaaaccgu guggguacgu cuuguuuccg uauuuuuacc uaaaaaccca 420
gguuuuuagg ugcauuuuca caauugugug cgccugccuu ucguuucaua ucauuuacaa 480
ugauuuuuua aucgagauuu auuucuuuuu cuguaaucau uucuuuuuua aucacuuaau 540
gauaauuccg ucauacuuaa aggucuaggu cuuuaccgau aauaaacacc uuucuuugac 600
uuguaaauau uaauaggagg aaccgucaau ucugagugac uuaagaaauu ucaguuguuu 660
caguuguugu aguguaaggg ucacaaacac cuuuuuaacc uuuucauguc guuuacacuu 720
gucucccacc cuuuuauu 738

<210> SEQ ID NO 234
<211> LENGTH: 480
<212> TYPE: RNA
<213> ORGANISM: Diabrotica virgifera

<400> SEQUENCE: 234
uacugguuga gauuuccaau ggcggcuccu ugguccuag auaaacgggc guucaaauuu 60
uuugcaccac auuaagguga aaggugauaa aacucucaga uguuucaacc ucuauaacau 120
cuauaguucc cauuaccacg ucaaguuuuc ccauacgggg uguuucacau gguaccauuc 180
uguccugcac aaaaguuaca augacgugua cguaauccac auuaacauuu guuuucccaa 240
gcuccuucuu aguaggggguu uucuuaguua gaggcauaac uuguacauuu ggugagguuc 300
acagcaguuc ugaagaacgu uucucauuuu agguugcuuu ucgaugcauu ucuucgauuu 360
cuuuucuugu aauuucaucu ugaauccucu guuggacggg uuggauccgg ucguguauaa 420
caaucgccuu uccaaggucg uguccacgaa cgaggauagg guauacuuaa guaacgaauc 480

<210> SEQ ID NO 235
<211> LENGTH: 537
<212> TYPE: RNA
<213> ORGANISM: Diabrotica virgifera

<400> SEQUENCE: 235
uaccuuccuu augaugaccu ugguuguaac auaugguauu uuccauaacg auauaaccug 60
auacuaccau uaucucacga ccgauuuaug augcuauuuc uauauaaagg augucguuuu 120
cucgucuuuc gaaaacucuu uuuaaacaag uuauuuugag uaucccgucu gcgucuuuaa 180
uaguacaacc uaccaaauug aacacacaua ucuucauuac aucuaaauaa gaaaauacaa 240
uacccgucaa guguacuuuu acucgauuaa aauuacucac aaaauuuaac gaacauacug 300
agucauucag uuuauaacuu cuuuuuauac guuuuugcuc gacagaaccu uagugaucua 360
uaacaauacg accgauaccu acuuuaacaa cuaccuccuu auuaauaucu aagacuaagu 420
ucaagucauc auagaucuua ucguaauucc ugacuacuau aagguaaucc ucuuguuuga 480
caucgagucc auaagguuug ccgguuucuu gucgacuuua ccaguaacga cuuuauu 537

<210> SEQ ID NO 236
<211> LENGTH: 450
<212> TYPE: RNA
<213> ORGANISM: Diabrotica virgifera

<400> SEQUENCE: 236
uaccgacugg uugaguggcu ucuuguuuaa cgacuuaagu uucuucgaaa gagugauaag 60
cuauuucuac cacuaccaug uuaaugcuga uuucuuaauc cuugucauua cucuagagau 120
ccuguuuuag guugucuccg acuuaauguc cuauacuagu uacuucaucu acggcuacca 180
uugccgugcu agcuaaaggg ucuuaaaaau ugcuacuacc gugcauuuua cuucuaugg 240 cuaucacucc uucuuuaagc acuucguaag gcucacaagc uguuucugcc guuaccaaag 300
uagagucguc gucuuaacgc ggugcaguac ugguugaacc cacuuuuuaa cugucugcuu 360
cuucagcuac uuuacuaagc ccuccggcua uagcuaccac uaccaguuca guuaaugcuu 420
cucaagcagu gguacuacug aaguuucacu 450

<210> SEQ ID NO 237
<211> LENGTH: 2013
<212> TYPE: RNA
<213> ORGANISM: Diabrotica virgifera

<400> SEQUENCE: 237
uacuacguuc guuuguuagc ucagggugga uauuucaacc uuuugcuaua ucuagaaaug 60
cggcuacuau agcuccuaaa gcguguucua cugaaaccac cacuuuuaca acuagauaua 120
cugcuacauu auaggcgagg aggaccuuua uuacuguugg guccacuaag uuuaguagua 180
cgaggaggac cacgaccacu ucuaccaccu ccauuaaaac aacccagucc uccucguggg 240
uuauuauauu uaagaagacc uucuucugua gucgacauac aaccuuuaga cugaaccacc 300
uguugacuag uucuauaucu uuuacgucac guacuauauc cccauuggcu gaagguacuu 360
caauucaaaa aacuuguguc ucguuuacca guuagguucc cuaagacaca guauagaaac 420
ccuagacucc cuucguacuc ugagacggac cuugaggaua gauuuuuucu cuaguuaccg 480
guuuuagggg aacaauggga agggguuuuu guucgagaau cauugaaacu uucagucaga 540
uuuugugcgg gaagaggaug auuauuaaga uugagugcag gaggggguagg auuauuauua 600 caaguaaguc caggauacgu cuuaauaccu ccaucuuacg gauacuuggg aagguacgca 660
ggguacgggg guccauacgu uccacgaggu ucuuacgucc cagguggacc uaaauuaccu 720
ggugguuugu acuuagucgu ugggggguccc aagguuccau uagguguuac cuuaccugga 780
ucuggauuac caggacccgg guuauacccu uacucugggu accccggugg aguaccuguu 840
guucccgggg guucuggugg uuacgucccu gguggcgucg uuccaggagg uucuccuuac 900
ggcgguguuc cagguggcgu cuacgcaggu cuuaccuuag cuggugguua cguuguuccc 960
augggaguuc cgggcggcgu auacguuccu ggauuguacc cagguucucc agguggggguu 1020 uacccuggug ggccccgcgg aguugucguu ccuggucgag gcgugcauuu aggucguaag 1080
aaaguuguuc cuccuccugg uggcgggggu uacguugugu acggaccugg ucccgggcag 1140
uacggaggag uuccuggggg cguuccaggu ggugugccug ggcaaccugg aggugugccg 1200
ggugguaacc caggucgcuu acaaggcgga guaccuggug gagugccuau accaggugga 1260
cgucgcuacg gugucggcgg uaugccaccg gguggaggluc ugguggcgcg acucuaagga 1320
gucaauuguc ucguucucaa acuccuauau uacagggccu uaucuuguca aaggucaagc 1380
cgcuaacccg cccggcauag gcugcggcgu cgaccucuua aacguucgcg guaacucuga 1440
aaccaaugac gauaaaguga guaguuuguu agguuucacc gauugcugcu agcaacguuc 1500
uaggaauauu caagcgacgu ucuaugaaac gcaccacagc uucuguuuuc gaugucgagg 1560
ucggcgucuc uggccaguuc uagguccccug ucuaguguau cuucuugauc uucucuugcu 1620
aggagcagug ccaugucucu gucuucgucu cucucccucg cacuugcgcu aucucuagca 1680
cuagcacuug cacugucuau aauacuaucu augucgcuuu cucuuucucu ggcucuagca 1740
aguucuucgu cucuuucuug ucuuucccua ucucuugcuc uaauaucucu ggcccuuggg 1800
cuucucuguc uauuucuuuu uagauuucau aggucucaga guucuaguuc uuuguuuaga 1860
ggccuuggac agcuuggauc gucgcuccau ggcuuuagua gggcgauaau acuccuaucc 1920
auagcccuug cucucucucu uccagcugcu cucucgcuag cgcuuucucu uucucuaucu 1980
ucuccccuuc ugucgguauc cagagcugug auc 2013

<210> SEQ ID NO 238
<211> LENGTH: 765
<212> TYPE: RNA
<213> ORGANISM: Diabrotica virgifera

<400> SEQUENCE: 238
uacucaagau aaccuugacc caugcuaaau agucgaaggg uuaagagagg acuaccuucu 60
cauaaaguuc aacuuauacg uuacuuucgu caacuuuuau caccguggca uuauccggag 120
gcuccauguc uaccguaaca uaaccgacga cuuuucgagu aauacaguuu uaacguacuu 180
gguucauguu uauuugcuua aaaguuguaa cuauuugugu auccuuaccg uaaaaguccg 240
aauuaucgac uacguuccgu uuagcaacuc uaacgaucuu uucuucguag uuuaauaucu 300
guaguuauac caaguuuaua aggagaauuu auggauuuac uaucucauuc guacauguac 360
guacguaugu gaaauauguc acgacaaucu gguaaaccaa cgucacagua gaaccgguca 420
auacuucuau cacuggguag auacauagac uaacuaggua gaccucaauc gauaccuaug 480
aaaccuacac gauguccauu ucguuuuguc agacguuucu gacuuuaucu uuuuaacuuc 540
uaccccuuag auuguacguu ucuugaacaa uuucuucguc gguuuuagua aauaaaccag 600
guacuacucg acuuccuauu cuuaaaacuu gaccuugaaa guacccauac guuucuaugc 660
uuaccaaaug uaugguuuca cggacuuagu cacaaacgac uacgucuuuu ucgacgguuu 720
guucguuacc uucgucuaag ucuuagucua ugucuucuau acauu 765

<210> SEQ ID NO 239
<211> LENGTH: 744
<212> TYPE: RNA

<213> ORGANISM: Diabrotica virgifera

<400> SEQUENCE: 239
uaccgaaguu uucugucuaa cuacuaaaaa gguagaucuc cucggguuua cuacuacuuu 60
agguccgauu ucccucgggu uuucccugua ucaaauaauu ucuucuuucg acuacgaaau 120
guuuacucua aaucuuacua aaacuuguuu uaauaacucu gguuuugaga guacccacuu 180
cauuacuuuc uucgacggaa aagaaaucga cuucguuuca aacguugacc acugaaguua 240
guucaacaag aaguuuuaca gugguuccga guuuauuuuu auucuugauu cuuucuguug 300
caacgaccac aaugaaaugg ucacaaacuu acgaugguuc uaccaugucu auguauacuc 360
aaccgaccaa accgaucccc uccaguuguu aacuguuuug aguucuucuu aauaguuuca 420
cgacaauuug acaaccaacu uaaucggaga aacguuugaa gaaaacauug agaacuacua 480
cauuaguuuu auuguuuguc uucucaguua cgguaacuug uacaauagua agguucuuau 540
cucgcaugaa accgaaugua guauaggcuu gaccugcuca aucuuucucu ccucaagaua 600
ucuaauuucu ucuagguccu guuuuucuuc uagucgucuc guuuccggcu cuuuguuuuu 660
guucgagaag agguucgacc cgaugaauuu cucagggucc guuuguacga aaaccuacuc 720
ccgcuacuuc uagaugaaaa gauc 744

<210> SEQ ID NO 240
<211> LENGTH: 4818
<212> TYPE: RNA
<213> ORGANISM: Diabrotica virgifera

<400> SEQUENCE: 240
uaccuccgcc gaggguucaa uggcuacgag agcaagcuca auuuaugaac augucucuug 60
caggugaaac cgggggucaa uuuugucaua uaacgacgaa aaauaccacu ucuaggucuu 120
aggauguaau gucuuuaguc guuagaacuu aggaauucua gucgacguca agcugguagu 180
ugccuacauu uaccacaugu ugacaacuuu uucauaaaga cagucgaagc aaaagaguuu 240
agauccaaag gguaccuucu cuuaguucua cgacgucaag auaaaaguac cuuuuuauua 300
cuuaaucugu auugaaguug uaggucacua uagucuauac uuaauuacca uuauuacaua 360
uuguaaccuc ggaaugugug aaaagaaccu cgguugcuga guucuuuguu aggccuacca 420
uacuuuuacc guacaugagu aaaaguuaca cgacguaccc gaaaaguuuu gcauuuucuu 480
uucauggugg uuaaguauag uuuguagagu aaccaucuug accaaguaaa aaaaguuguu 540
cagacaaauc gaguccgagu ccucacauau aaucucuucu cguacaaacu guuauccuuu 600
ggaugguagu aacguuuuca acgauagguu cagaugucaa uaaugucugu cagaaaugca 660
cagaaccuua gucauuuacu ucggaugaaa ucccuauuuu ggauguuccu caccuacuuu 720
auagaaguua aguucgacug gaugauguuu acguagagca aggauaaggu ucccguuguu 780
cgacuccuug uugucuuuua cccucuuucc caacguaaga uaguucgacg uacacuuguc 840
gaccugcucc guuucuuuua acgacgaugu aauuuuuugg uuguggugu cguucuuuau 900 uuacucccug aucguaagug augacuacac caacuuccau uuucuuuucg ucgauuuuua 960
cuuuuacuca aguagauggu acuuagucac ggacuauuuc ugguuaacgg ucuccaauuc 1020
ccacgaagua aucaguuucc uuaugguaag ucauauuuac uauaucuuca aaguccuggu 1080
cuauaaaaga gggcuaacca ggguuaccuc cgugugcuuc gucgaaggaa caugucgcuc 1140
uucuuucgag ucucuaauuc ugucuagccc cuugaauaac uuuuauuucu aguuuguaac 1200
cgacuuaaau acagcaguua cgucgaucua gauaacuggu ucuacguggu ccgaugaccu 1260
uauggcgucc ucaacuaacu aucucgucgc cgagauagac gauuuggauu gcgguaaguu 1320
cuagaauauu cacgauaccc uuucgauaga uuauauaugg uucugcaacu ucguucaaac 1380
uuacucuaac uaagaaauaa uuuccggcuu cuuguuucac uuguuuucau gguucuuugc 1440
uaaccauuuu cugguggcuc guaaaaucga ugucuaaauu gaucccuucg ccguuuuaug 1500
ucccuccgag uaugauuucg cuugcugagu uugguuugaa augugucccg cuacuaccga 1560
gugcaccgau uagacuuuua ugagguuguu ggcgauuucg ucgacguugu agucgacggg 1620
aaacagcuca aagguuuagg uuuauagcug cuuuuuagaa acuuucuaga ccuucgcgau 1680
caacguuuuc aucugcuuua cucuugggu ucucgguacg auacccgagu ugaagcucuu 1740
agauaagugg uucugcuaua auguucaagg gaacauugcu uuguugguuu agucagcgac 1800
cuugucgaca aggucguucu ugaaguuuuc guaguuuuag acuaaagcaa cuaacuuguu 1860
uuguggagcc guguucuuuu guaauucucg cggaaucagc uaagaaugcg aaugcgacau 1920
uuaaguucuu uuauguaggu ucuauaugag guuuucucuu gguguuggua uugcagugac 1980
uaucguagca agcugagaau gcuucugaau aaccguuuuc gauuguuucc cuaucucaaa 2040
augaguuuug aacuuugcuu gcauagguuc aaugacguuu cuuauuccuc auggacguuu 2100
caaguuguuc uucucgcucu agucuacuac agcugacgcg uucacggagu uacccucuca 2160
guaugcagug aacggcgagg auuugacuuu cuaaugaacc ugagguccuu cuucucacga 2220
cgcauaagcc ucggcucaca aguuggugu gucgguugaa auucaaugag ucgacgauac 2280
cuagacggag gaccauaauc cggcugaggu caaccuaguc uuuauugccu acauggcuuu 2340
uuauaaguuc cacuuggugu uccaauauaa gguauauuaa ugguuguugg aagacaagga 2400
cggagugucu uauaacuacu ucucugauaa uuuuuuuacu ugcguaacua cgguccacga 2460
uucugcaguc acggaucagu caugccuaug ucguugaugu aaggugguug uaugggaguu 2520
ucacgcaugg uugguccauu agucagaaug ccuuuucuuu gaggucuaua auugaguggc 2580
augcugggau gguuccgcaa gugccgauga ugauugcgaa uagcaagcca cgucucgagg 2640
aguugaguuc cuaugcaugg caugcgucuu agauugcaaa gcuuacaacu gucucaaccu 2700
auaggaucgu ccauagucau gguuguucau ggacucuauc gaugaugagg ucgacuaggg 2760
uuauaauuac gcaugauggg uguacccaug aguggcucgg ucuuaaaugg cuuacgauua 2820
ugaguuguau aauggccggu ugacuucaug guaagccacc ucaugcgaag aagacacggc 2880
uuguuguagu uaauauuguc gagauggaug agcagcggcg aaagauuaua cagaucaugg 2940
uuaaggaguu uaggaucauu gaacuuauua agaaugcuca ugaugauacu gggcuuaugg 3000
ucaucaccac gucauggcuu acgaaguuuc ggaguuguca gcucgcgguc gagacguuug 3060
ggcucauggc gauacuuguu gauguuaaua augauguuau guucaugguc gccaucacau 3120
cgucgccuau gaaguuuuua uguuguuguu guugucaugg guccaugagu cuacucaguu 3180
cgcgucauga uagggcgguu acggucaaua augaguuggu caugaauguu augguugcag 3240
guuccaccau gguuagggag caugcguuga ccuguuugua uauuaguuca cuguggucac 3300
uggagaguuu uacaaagagu uuuaauguug aaauugguuc aaccaagacc ucguccugug 3360
gucguaguca ugaugagcag gcgauugcgg cgucauggua ggguuguucg acauuuauug 3420
ucaaguaaug guuugaugcc uaugcuaguc auaaugccgu uguugauauu aaggucaguu 3480
ggcucaugga ugucgcguuu gguucgugga ggacgucgug uucgacgagg uucauuauaa 3540
ggacgacggu gguuuaggag gagauuacac cuagacgagu caccgaaccu gaagucguau 3600
ucgguucgag gagaucacgg aguuguuuug uaaugcuauu uugggguucu uuuccuuugu 3660
uuugguggcc gacaaagaag acuuugguuu uugguucuag guugugguca uuggugcggg 3720
uuuguugggu gaccuggucu ucauuucgcg aacaugcagu uuuaggacgg cucguuuggg 3780
aauuuguugc uacuacacuu cuuuaacaag ccgguucucg accuguccau acucuucaag 3840
caccucugga acugggugu uugaaacucg ccaggcuggu gagaccuaua auuuaccuuc 3900
cucuagguuc uggucguccu aacgcucggc gucuucuucu aguaaaggca gcgaucuaca 3960
auaggauacu ucuuauccaa gggccuauag aacggaaugc ugaaaagguc ccaccucaac 4020
acgcuaucau uucuacuaau auaguugcga aguauguaau uccuauagag cgguauacga 4080
ggcaguaaau aacaaugugu ucacggcaac agaaguugac aaccacuaua caccugcuac 4140
uaaucucuug uuguccagcu ugacuaggag acaaaccauu ugcuguuacu cuagccacuu 4200
cuauaaauga ccggguuucu uuuuccguca ucagaauugu augaauugua ccaguauugc 4260
aacguuuugc aauaucaauu cagaguaacc ugacuuucug acuaucgcua uuugaaugga 4320
cuuuuugccc ucagggcaca cuauuacgua gauguuaaau guagcaccgg accgucgaac 4380
aaagguuguu uaggacuugg caagcagucg auguggaacc uuagguaguu ggauaugguu 4440
guugucuucu gguuguggu aggccaccac cagguaacaa guagaccgua uccuucuucg 4500
ccggacgaga caaaugacug ucgacgauac aagcuacgac gguuguuacg auugagcuau 4560
ggucuagaau gucgaaacuc auaguucaac agguuaacgu ccuucuuaua agagucucua 4620
gcucucguaa acuucaaacc aaugcuuuca aaaaaccgca uauaauccgu auaucaaaca 4680
cuucuauuuc ggucuuucuu ugacuugcuc uaggucgggu uccaauuccu ccuuggugac 4740
cuugguggac aguaucaagg ucuugguuua uaucuaggaa auucaugaaa ucugguaaa 4800 acccgaucau uuucuauu 4818

<210> SEQ ID NO 241
<211> LENGTH: 166
<212> TYPE: PRT
<213> ORGANISM: Diabrotica virgifera

<400> SEQUENCE: 241

Met Thr Pro Glu Arg Lys Lys Lys Leu Arg Leu Leu Leu Arg Lys Lys
1 5 10 15

Ala Ala Glu Glu Leu Lys Lys Glu Gln Glu Arg Lys Ala Ala Glu Arg
20 25 30

Arg Arg Ile Ile Glu Glu Arg Cys Gly Lys Pro Lys Leu Val Asp Asp
35 40 45

Ala Asn Glu Gly Pro Leu Lys Gln Val Cys Glu Gly Tyr His Arg Arg
50 55 60

Ile Val Asp Leu Glu Asn Lys Lys Phe Asp Leu Glu Lys Glu Val Glu
65 70 75 80

Phe Arg Asp Phe Gln Ile Ser Glu Leu Asn Ser Gln Val Asn Asp Leu
85 90 95

Arg Gly Lys Phe Val Lys Pro Thr Leu Lys Lys Val Ser Lys Tyr Glu
100 105 110

Asn Lys Phe Ala Lys Leu Gln Lys Lys Ala Ala Glu Phe Asn Phe Arg
115 120 125

Asn Gln Leu Lys Val Val Lys Lys Lys Glu Phe Thr Leu Glu Glu Glu
130 135 140

Asp Lys Glu Lys Lys Pro Asp Trp Ser Lys Lys Gly Asp Glu Lys Lys
145 150 155 160

Val Gln Glu Ala Glu Ala
165

<210> SEQ ID NO 242
<211> LENGTH: 201
<212> TYPE: PRT
<213> ORGANISM: Diabrotica virgifera

<400> SEQUENCE: 242

Met Cys Glu Glu Glu Val Ala Ala Leu Val Val Asp Asn Gly Ser Gly
1 5 10 15

Met Cys Lys Ala Gly Phe Ala Gly Asp Asp Ala Pro Arg Ala Val Phe
20 25 30

Pro Ser Ile Val Gly Arg Pro Arg His Gln Gly Val Met Val Gly Met
35 40 45

Gly Gln Lys Asp Ser Tyr Val Gly Asp Glu Ala Gln Ser Lys Arg Gly
50 55 60

Ile Leu Thr Leu Lys Tyr Pro Ile Glu His Gly Ile Val Thr Asn Trp
65 70 75 80

Asp Asp Met Glu Lys Ile Trp His His Thr Phe Tyr Asn Glu Leu Arg
85 90 95

Val Ala Pro Glu Glu His Pro Val Leu Leu Thr Glu Ala Pro Leu Asn
100 105 110

Pro Lys Ala Asn Arg Glu Lys Met Thr Gln Ile Met Phe Glu Thr Phe
115 120 125

Asn Thr Pro Ala Met Tyr Val Ala Ile Gln Ala Val Leu Ser Leu Tyr
130 135 140

Ala Ser Gly Arg Thr Thr Gly Ile Val Leu Asp Ser Gly Asp Gly Val
145 150 155 160

Ser His Thr Val Pro Ile Tyr Glu Gly Tyr Ala Leu Pro His Ala Ile
165 170 175

Leu Arg Leu Asp Leu Ala Gly Arg Asp Leu Thr Asp Tyr Leu Met Lys
180 185 190

Ile Leu Thr Glu Arg Gly Tyr Ser Phe
195 200

<210> SEQ ID NO 243
<211> LENGTH: 913
<212> TYPE: PRT
<213> ORGANISM: Diabrotica virgifera

<400> SEQUENCE: 243

Met Pro Leu Arg Leu Asp Ile Lys Arg Lys Leu Thr Ala Arg Ser Asp
1 5 10 15

Arg Val Lys Cys Val Asp Leu His Pro Thr Glu Pro Trp Met Leu Cys
20 25 30

Ser Leu Tyr Ser Gly Asn Ile Asn Val Trp Asn Thr Glu Asn Gln Gln
35 40 45

Leu Val Lys Thr Phe Glu Val Cys Asp Val Pro Val Arg Thr Ala Lys
50 55 60

Phe Leu Pro Arg Lys Asn Trp Ile Val Ser Gly Ser Asp Asp Met Gln
65 70 75 80

Ile Arg Val Phe Asn Tyr Asn Thr Leu Asp Arg Val His Ser Phe Glu
85 90 95

Ala His Ser Asp Tyr Val Arg Cys Ile Val Val His Pro Thr Gln Pro
100 105 110

-continued

```
Tyr Ile Leu Thr Ser Ser Asp Asp Met Leu Ile Lys Leu Trp Asn Trp
        115                 120                 125

Glu Lys Ala Trp Ala Cys Gln Gln Val Phe Glu Gly His Thr His Tyr
    130                 135                 140

Ile Met Gln Ile Ala Ile Asn Pro Lys Asp Asn Asn Thr Phe Ala Ser
145                 150                 155                 160

Ala Ser Leu Asp Arg Thr Leu Lys Val Trp Gln Leu Gly Ala Ser Thr
                165                 170                 175

Ala Asn Phe Thr Leu Glu Gly His Glu Lys Gly Val Asn Cys Val Asp
            180                 185                 190

Tyr Tyr His Gly Gly Asp Lys Pro Tyr Leu Ile Ser Gly Ala Asp Asp
        195                 200                 205

Arg Leu Val Lys Ile Trp Asp Tyr Gln Asn Lys Thr Cys Val Gln Thr
    210                 215                 220

Leu Glu Gly His Ala Gln Asn Val Thr Ala Ala Cys Phe His Pro Glu
225                 230                 235                 240

Leu Pro Val Ala Leu Thr Gly Ser Glu Asp Gly Thr Val Arg Val Trp
                245                 250                 255

His Ala Asn Thr His Arg Leu Glu Ser Ser Leu Asn Tyr Gly Phe Glu
            260                 265                 270

Arg Val Trp Thr Ile Phe Cys Leu Lys Gly Ser Asn Asn Val Ala Leu
        275                 280                 285

Gly Tyr Asp Glu Gly Ser Ile Leu Val Lys Val Gly Arg Glu Glu Pro
    290                 295                 300

Ala Val Ser Met Asp Ala Ser Gly Gly Lys Ile Ile Trp Ala Arg His
305                 310                 315                 320

Ser Glu Leu Gln Gln Ala Asn Leu Lys Ala Leu Ala Glu Gly Ala Glu
                325                 330                 335

Ile Arg Asp Gly Glu Arg Leu Pro Val Ser Val Lys Asp Met Gly Ala
            340                 345                 350

Cys Glu Ile Tyr Pro Gln Thr Ile Gln His Asn Pro Asn Gly Arg Phe
        355                 360                 365

Val Val Val Cys Gly Asp Gly Glu Tyr Ile Ile Tyr Thr Ala Met Ala
    370                 375                 380

Leu Arg Asn Lys Ala Phe Gly Ser Ala Gln Glu Phe Val Trp Ala Gln
385                 390                 395                 400

Asp Ser Ser Glu Tyr Ala Ile Arg Glu Ser Gly Ser Thr Ile Arg Ile
                405                 410                 415

Phe Lys Asn Phe Lys Glu Lys Lys Asn Phe Lys Ser Asp Phe Gly Ala
            420                 425                 430

Glu Gly Ile Tyr Gly Gly Tyr Leu Leu Gly Val Lys Ser Val Ser Gly
        435                 440                 445

Leu Thr Phe Tyr Asp Trp Glu Thr Leu Asp Leu Val Arg Arg Ile Glu
    450                 455                 460

Ile Gln Pro Lys Ala Val Tyr Trp Ser Asp Ser Gly Lys Leu Val Cys
465                 470                 475                 480

Leu Ala Thr Glu Asp Ser Tyr Phe Ile Leu Ser Tyr Asp Ser Asp Glu
                485                 490                 495

Val Gln Lys Ala Arg Asp Asn Asn Gln Val Ala Asp Asp Gly Val Glu
            500                 505                 510

Ser Ala Phe Asn Leu Leu Gly Glu Ile Asn Glu Ser Val Arg Thr Gly
        515                 520                 525
```

```
Leu Trp Val Gly Asp Cys Phe Ile Tyr Thr Asn Ser Val Asn Arg Ile
    530                 535                 540

Asn Tyr Phe Val Gly Gly Glu Leu Val Thr Ile Ala His Leu Asp Arg
545                 550                 555                 560

Pro Leu Tyr Val Leu Gly Tyr Val Pro Lys Asp Asp Arg Leu Tyr Leu
                565                 570                 575

Val Asp Lys Glu Leu Arg Val Val Ser Tyr Gln Leu Leu Leu Ser Val
            580                 585                 590

Leu Glu Tyr Gln Thr Ala Val Met Arg Arg Asp Phe Pro Thr Ala Asp
        595                 600                 605

Arg Val Leu Pro Ser Ile Pro Lys Glu His Arg Thr Arg Val Ala His
    610                 615                 620

Phe Leu Glu Lys Gln Gly Phe Lys Gln Gln Ala Leu Ala Val Ser Thr
625                 630                 635                 640

Asp Pro Glu His Arg Phe Glu Leu Ala Val Ala Leu Glu Asp Leu Asn
                645                 650                 655

Ile Ala Lys Thr Leu Ala Gln Glu Ala Asn Ser Pro Gln Lys Trp Asn
            660                 665                 670

Gln Leu Ala Glu Leu Ala Ala Ala Thr Asn Asn Val Ser Val Ala Lys
        675                 680                 685

Glu Cys Met Gln Lys Ala Gln Asp Tyr Gly Gly Leu Leu Leu Leu Ala
    690                 695                 700

Thr Ser Ser Gly Asp Glu Asn Leu Val Arg Thr Leu Gly Glu Thr Thr
705                 710                 715                 720

Gln Ala Glu Ser Lys His Asn Leu Ala Phe Leu Ser His Leu Leu Val
                725                 730                 735

Gly Asp Leu Asn Lys Cys Leu Asp Ile Leu Ile Asn Thr Gly Arg Leu
            740                 745                 750

Pro Glu Ala Ala Phe Phe Ala Arg Ser Tyr Leu Pro Asp Lys Ile Thr
        755                 760                 765

Glu Val Val Glu Leu Trp Lys Thr Gln Leu Ser Ser Val Asn Gln Lys
    770                 775                 780

Ala Gly Gln Ser Leu Ala Asp Pro Lys Asn Tyr Glu Asn Leu Phe Pro
785                 790                 795                 800

Gly Leu Gln Glu Ala Val Val Ala Gln Lys Phe Leu Glu Gln Gln Asn
                805                 810                 815

Lys Gly Leu Ala Pro Ala Arg Val Ala Thr Thr Ile Pro Pro Asn His
            820                 825                 830

Asp Arg Asn Val Val Ala Glu Val Gln Ala Gln Ser Lys His Asp Val
        835                 840                 845

Pro Ser Phe Ser Ser Ser Phe Ile Ser Ser Glu Ile Glu Ala Gln Thr
    850                 855                 860

Arg Ser Ser Ala Lys Pro Glu Glu Ser Ser Asn Ile Ile Gln Leu Asp
865                 870                 875                 880

Gln Asp Asp Asp Asp Ile Asp Leu Asp Leu Asp Gly Val Asn Ile Asp
                885                 890                 895

Glu Asn Ile Asp Thr Thr Asp Ile Asn Ile Asp Asp Asp Leu Leu Ser
            900                 905                 910

Asp
```

<210> SEQ ID NO 244
<211> LENGTH: 381
<212> TYPE: PRT
<213> ORGANISM: Diabrotica virgifera

<400> SEQUENCE: 244

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Met His Ile Phe
65                  70                  75                  80

Val Lys Thr Leu Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ser Asp Tyr Asn Ile Gln Lys Glu Ser Thr Leu His
    130                 135                 140

Leu Val Leu Arg Leu Arg Gly Gly Met Gln Ile Phe Val Lys Thr Leu
145                 150                 155                 160

Thr Gly Lys Thr Ile Thr Leu Glu Val Glu Pro Ser Asp Thr Ile Glu
                165                 170                 175

Asn Val Lys Ala Lys Ile Gln Asp Lys Glu Gly Ile Pro Pro Asp Gln
            180                 185                 190

Gln Arg Leu Ile Phe Ala Gly Lys Gln Leu Glu Asp Gly Arg Thr Leu
        195                 200                 205

Ser Asp Tyr Asn Ile Gln Lys Glu Ser Thr Leu His Leu Val Leu Arg
    210                 215                 220

Leu Arg Gly Gly Met Gln Ile Phe Val Lys Thr Leu Thr Gly Lys Thr
225                 230                 235                 240

Ile Thr Leu Glu Val Glu Pro Ser Asp Thr Ile Glu Asn Val Lys Ala
                245                 250                 255

Lys Ile Gln Asp Lys Glu Gly Ile Pro Pro Asp Gln Gln Arg Leu Ile
            260                 265                 270

Phe Ala Gly Lys Gln Leu Glu Asp Gly Arg Thr Leu Ser Asp Tyr Asn
        275                 280                 285

Ile Gln Lys Glu Ser Thr Leu His Leu Val Leu Arg Leu Arg Gly Gly
    290                 295                 300

Met Gln Ile Phe Val Lys Thr Leu Thr Gly Lys Thr Ile Thr Leu Glu
305                 310                 315                 320

Val Glu Pro Ser Asp Thr Ile Glu Asn Val Lys Ala Lys Ile Gln Asp
                325                 330                 335

Lys Glu Gly Ile Pro Pro Asp Gln Gln Arg Leu Ile Phe Ala Gly Lys
            340                 345                 350

Gln Leu Glu Asp Gly Arg Thr Leu Ser Asp Tyr Asn Ile Gln Lys Glu
        355                 360                 365

Ser Thr Leu His Leu Val Leu Arg Leu Arg Gly Gly Asn
    370                 375                 380

<210> SEQ ID NO 245
<211> LENGTH: 376
<212> TYPE: PRT

<213> ORGANISM: Diabrotica virgifera

<400> SEQUENCE: 245

Met Cys Asp Asp Asp Val Ala Ala Leu Val Val Asp Asn Gly Ser Gly
1 5 10 15

Met Cys Lys Ala Gly Phe Ala Gly Asp Asp Ala Pro Arg Ala Val Phe
20 25 30

Pro Ser Ile Val Gly Arg Pro Arg His Gln Gly Val Met Val Gly Met
35 40 45

Gly Gln Lys Asp Ser Tyr Val Gly Asp Glu Ala Gln Ser Lys Arg Gly
50 55 60

Ile Leu Thr Leu Lys Tyr Pro Ile Glu His Gly Ile Ile Thr Asn Trp
65 70 75 80

Asp Asp Met Glu Lys Ile Trp His His Thr Phe Tyr Asn Glu Leu Arg
85 90 95

Val Ala Pro Glu Glu His Pro Ile Leu Leu Thr Glu Ala Pro Leu Asn
100 105 110

Pro Lys Ala Asn Arg Glu Lys Met Thr Gln Ile Met Phe Glu Thr Phe
115 120 125

Asn Thr Pro Ala Met Tyr Val Ala Ile Gln Ala Val Leu Ser Leu Tyr
130 135 140

Ala Ser Gly Arg Thr Thr Gly Ile Val Leu Asp Ser Gly Asp Gly Val
145 150 155 160

Ser His Thr Val Pro Ile Tyr Glu Gly Tyr Ala Leu Pro His Ala Ile
165 170 175

Leu Arg Leu Asp Leu Ala Gly Arg Asp Leu Thr Asp Tyr Leu Met Lys
180 185 190

Ile Leu Thr Glu Arg Gly Tyr Ser Phe Thr Thr Thr Ala Glu Arg Glu
195 200 205

Ile Val Arg Asp Ile Lys Glu Lys Leu Cys Tyr Val Ala Leu Asp Phe
210 215 220

Glu Gln Glu Met Ala Thr Ala Ala Ser Ser Thr Ser Leu Glu Lys Ser
225 230 235 240

Tyr Glu Leu Pro Asp Gly Gln Val Ile Thr Ile Gly Asn Glu Arg Phe
245 250 255

Arg Cys Pro Glu Ala Leu Phe Gln Pro Ser Phe Leu Gly Met Glu Ser
260 265 270

Cys Gly Ile His Glu Thr Val Tyr Asn Ser Ile Met Lys Cys Asp Val
275 280 285

Asp Ile Arg Lys Asp Leu Tyr Ala Asn Thr Val Leu Ser Gly Gly Thr
290 295 300

Thr Met Tyr Pro Gly Ile Ala Asp Arg Met Gln Lys Glu Ile Thr Ala
305 310 315 320

Leu Ala Pro Ser Thr Ile Lys Ile Lys Ile Ile Ala Pro Pro Glu Arg
325 330 335

Lys Tyr Ser Val Trp Ile Gly Gly Ser Ile Leu Ala Ser Leu Ser Thr
340 345 350

Phe Gln Gln Met Trp Ile Ser Lys Gln Glu Tyr Asp Glu Ser Gly Pro
355 360 365

Gly Ile Val His Arg Lys Cys Phe
370 375

<210> SEQ ID NO 246
<211> LENGTH: 879

<212> TYPE: PRT
<213> ORGANISM: Diabrotica virgifera

<400> SEQUENCE: 246

```
Met Gly Thr Phe Lys Arg Asp Thr His Asp Glu Asp Gly Gly Ser Ser
1               5                   10                  15

Ala Phe Gln Asn Leu Glu Lys Thr Thr Val Leu Gln Glu Ala Arg Val
            20                  25                  30

Phe Asn Glu Thr Ser Val Asn Pro Arg Lys Cys Thr Pro Ile Leu Thr
        35                  40                  45

Lys Leu Leu Tyr Leu Leu Asn Gln Gly Glu Thr Leu Ser Ala Lys Glu
    50                  55                  60

Ala Thr Asp Val Phe Phe Ala Met Thr Lys Leu Phe Gln Ser Lys Asp
65                  70                  75                  80

Val Ile Leu Arg Arg Met Val Tyr Leu Gly Ile Lys Glu Leu Ser Ser
                85                  90                  95

Val Ala Asp Asp Val Ile Ile Val Thr Ser Ser Leu Thr Lys Asp Met
            100                 105                 110

Thr Gly Lys Glu Asp Met Tyr Arg Ala Ala Ala Ile Arg Ala Leu Cys
        115                 120                 125

Ser Ile Thr Asp Ala Thr Met Leu Gln Ala Ile Glu Arg Tyr Met Lys
    130                 135                 140

Gln Ala Ile Val Asp Arg Asn Ala Ala Val Ser Ser Ala Ala Leu Ile
145                 150                 155                 160

Ser Ser Leu His Met Ser Lys Leu Ala Pro Asp Val Val Lys Arg Trp
                165                 170                 175

Val Asn Glu Ala Gln Glu Ala Val Asn Ser Asp Asn Ala Met Val Gln
            180                 185                 190

Tyr His Ala Leu Gly Leu Leu Tyr His Ile Arg Lys Thr Asp Lys Leu
        195                 200                 205

Ala Val Thr Lys Leu Ile Ser Lys Leu Asn Ser Met Gly Leu Lys Ser
    210                 215                 220

Pro Tyr Ala Leu Cys Met Leu Ile Arg Ile Thr Ala Lys Leu Leu Glu
225                 230                 235                 240

Glu Glu Asp Gln Glu Ser Leu Leu Asn Ser Pro Tyr Thr Ile Ile Phe
                245                 250                 255

Thr Met Gly Leu Arg Asn Lys Ser Glu Met Val Val Tyr Glu Ala Ala
            260                 265                 270

His Ala Met Val Asn Leu Lys Phe Thr Ser Ser Asn Val Leu Ala Pro
        275                 280                 285

Ala Ile Ser Val Leu Gln Leu Phe Cys Gly Ser Pro Lys Ala Thr Leu
    290                 295                 300

Arg Phe Ala Ala Val Arg Thr Leu Asn Gln Val Ala Thr Thr His Pro
305                 310                 315                 320

Ala Ser Val Thr Ala Cys Asn Leu Asp Leu Glu Asn Leu Ile Thr Asp
                325                 330                 335

Pro Asn Arg Ser Ile Ala Thr Leu Ala Ile Thr Thr Leu Leu Lys Thr
            340                 345                 350

Gly Ala Glu Ser Ser Val Asp Arg Leu Met Lys Gln Ile Ala Thr Phe
        355                 360                 365

Val Ser Glu Ile Ser Asp Glu Phe Lys Val Val Val Ile Gln Ala Ile
    370                 375                 380

Lys Val Leu Ala Leu Lys Phe Pro Arg Lys His Ser Thr Leu Met Asn
385                 390                 395                 400
```

-continued

```
Phe Leu Ser Ala Met Leu Arg Asp Glu Gly Gly Leu Glu Tyr Lys Ala
                405                 410                 415

Ser Ile Ala Asp Thr Ile Ile Thr Leu Ile Glu Asp Asn Pro Glu Ala
            420                 425                 430

Lys Glu Ser Gly Leu Ala His Leu Cys Glu Phe Ile Glu Asp Cys Glu
        435                 440                 445

His Val Ser Leu Ala Val Arg Ile Leu His Leu Leu Gly Lys Glu Gly
    450                 455                 460

Pro Lys Thr Lys Gln Pro Ser Arg Tyr Ile Arg Phe Ile Tyr Asn Arg
465                 470                 475                 480

Val Ile Leu Glu Cys Pro Ser Val Arg Ala Ala Ala Val Ser Ala Met
                485                 490                 495

Ala Gln Phe Gly Ala Ser Cys Pro Asp Leu Leu Glu Asn Ile Gln Ile
            500                 505                 510

Leu Leu Ser Arg Cys Gln Met Asp Ser Asp Asp Glu Val Arg Asp Arg
        515                 520                 525

Ala Thr Tyr Tyr Ser Asn Ile Leu Asn Lys Asn Asp Lys Ser Leu Tyr
    530                 535                 540

Asn Asn Tyr Ile Leu Asp Ser Leu Gln Val Ser Ile Pro Ser Leu Glu
545                 550                 555                 560

Arg Ser Leu Arg Glu Tyr Ile Gln Asn Pro Thr Asp Glu Pro Phe Asp
                565                 570                 575

Ile Lys Ser Val Pro Val Ala Ala Val Pro Thr Ala Glu Glu Arg Glu
            580                 585                 590

Val Lys Asn Lys Ser Glu Gly Leu Leu Val Ser Gln Gly Pro Val Arg
        595                 600                 605

Pro Pro Pro Val Ser Arg Glu Glu Asn Phe Ala Glu Lys Leu Ser Asn
    610                 615                 620

Val Pro Gly Ile Gln Gln Leu Gly Pro Leu Phe Lys Thr Ser Asp Val
625                 630                 635                 640

Val Glu Leu Thr Glu Ser Glu Thr Glu Tyr Phe Val Arg Cys Ile Lys
                645                 650                 655

His Cys Phe Lys His His Ile Val Leu Gln Phe Asp Cys Leu Asn Thr
            660                 665                 670

Leu Pro Asp Gln Leu Leu Glu Asn Val Arg Val Glu Ile Asp Ala Gly
        675                 680                 685

Glu Thr Phe Glu Ile Leu Ala Glu Ile Pro Cys Glu Lys Leu His Tyr
    690                 695                 700

Asn Glu Thr Gly Thr Thr Tyr Val Val Val Lys Leu Pro Asp Asp Asp
705                 710                 715                 720

Leu Pro Asn Ser Val Gly Thr Cys Gly Ala Val Leu Lys Phe Leu Val
                725                 730                 735

Lys Asp Cys Asp Pro Ser Thr Gly Ile Pro Asp Ser Asp Glu Gly Tyr
            740                 745                 750

Asp Asp Glu Tyr Thr Leu Glu Asp Ile Glu Ile Thr Leu Gly Asp Gln
        755                 760                 765

Ile Gln Lys Val Ser Lys Val Asn Trp Ala Ala Ala Trp Glu Glu Ala
    770                 775                 780

Ala Ala Thr Tyr Val Glu Lys Glu Asp Thr Tyr Ser Leu Thr Ile Asn
785                 790                 795                 800

Thr Leu Ser Gly Ala Val Lys Asn Ile Ile Gln Phe Leu Gly Leu Gln
                805                 810                 815
```

Pro Ala Glu Arg Thr Asp Arg Val Pro Glu Gly Lys Ser Thr His Thr
820 825 830

Leu Leu Leu Ala Gly Val Phe Arg Gly Gly Ile Asp Ile Leu Val Arg
835 840 845

Ala Lys Leu Ala Leu Gly Glu Cys Val Thr Met Gln Leu Thr Val Arg
850 855 860

Ser Pro Asp Pro Asp Val Ala Glu Leu Ile Thr Ser Thr Val Gly
865 870 875

<210> SEQ ID NO 247
<211> LENGTH: 216
<212> TYPE: PRT
<213> ORGANISM: Diabrotica virgifera

<400> SEQUENCE: 247

Met Ala Ala Asn Arg Thr Gly Pro Ala Gln Arg Pro Asn Gly Ala Thr
1 5 10 15

Gln Gly Lys Ile Cys Gln Phe Lys Leu Val Leu Leu Gly Glu Ser Ala
20 25 30

Val Gly Lys Ser Ser Leu Val Leu Arg Phe Val Lys Gly Gln Phe His
35 40 45

Glu Tyr Gln Glu Ser Thr Ile Gly Ala Ala Phe Leu Thr Gln Thr Ile
50 55 60

Cys Leu Asp Asp Thr Thr Val Lys Phe Glu Ile Trp Asp Thr Ala Gly
65 70 75 80

Gln Glu Arg Tyr His Ser Leu Ala Pro Met Tyr Tyr Arg Gly Ala Gln
85 90 95

Ala Ala Ile Val Val Tyr Asp Ile Thr Asn Gln Asp Thr Phe Gly Arg
100 105 110

Ala Lys Thr Trp Val Lys Glu Leu Gln Arg Gln Ala Ser Pro Thr Ile
115 120 125

Val Ile Ala Leu Ala Gly Asn Lys Gln Asp Leu Ala Asn Lys Arg Met
130 135 140

Val Glu Tyr Glu Glu Ala Gln Thr Tyr Ala Asp Glu Asn Gly Leu Leu
145 150 155 160

Phe Met Glu Thr Ser Ala Lys Thr Ala Met Asn Val Asn Asp Ile Phe
165 170 175

Leu Ala Ile Ala Lys Lys Leu Pro Lys Asn Glu Gln Thr Thr Gly Gln
180 185 190

Gly Gly Ser Ala Gln Gly Arg Arg Leu Ala Glu Gly Asp Ser Gly Ala
195 200 205

Lys Ala Pro Gly Asn Cys Cys Lys
210 215

<210> SEQ ID NO 248
<211> LENGTH: 92
<212> TYPE: PRT
<213> ORGANISM: Diabrotica virgifera

<400> SEQUENCE: 248

Met Lys Phe Leu Arg Ser Thr Val Cys Tyr Ile Ala Ile Leu Ala Ile
1 5 10 15

Leu Phe Thr Leu Cys Ala Asp Glu Val Glu Gly Arg Arg Lys Ile Leu
20 25 30

Met Gly Arg Lys Ser Ile Thr Arg Thr Tyr Leu Arg Gly Asn Ala Val
35 40 45

-continued

```
Pro Ala Tyr Val Ile Ile Ile Leu Val Gly Ile Gly Gln Ile Ile Leu
    50                  55                  60

Gly Gly Ile Leu Tyr Val Ala Leu Arg Lys Lys Ile Ile Ala Ala Pro
65                  70                  75                  80

Val Thr Ala Ser Tyr Ala Val Ala Arg Gln Glu Pro
                85                  90


<210> SEQ ID NO 249
<211> LENGTH: 157
<212> TYPE: PRT
<213> ORGANISM: Diabrotica virgifera

<400> SEQUENCE: 249

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Ala Lys Lys Arg
65                  70                  75                  80

Lys Lys Lys Asn Tyr Ser Thr Pro Lys Lys Ile Lys His Lys Lys Lys
                85                  90                  95

Lys Val Lys Leu Ala Val Leu Lys Phe Tyr Lys Val Asp Glu Asn Gly
            100                 105                 110

Lys Ile His Arg Leu Arg Arg Glu Cys Pro Ala Glu Gln Cys Gly Ala
        115                 120                 125

Gly Val Phe Met Ala Ala Met Glu Asp Arg His Tyr Cys Gly Lys Cys
    130                 135                 140

Gly Tyr Thr Leu Val Phe Ser Lys Pro Gly Asp Glu Lys
145                 150                 155


<210> SEQ ID NO 250
<211> LENGTH: 248
<212> TYPE: PRT
<213> ORGANISM: Diabrotica virgifera

<400> SEQUENCE: 250

Met Met Ser Lys Ala Asp Thr Gln Glu Asp Ala Ser Phe Ala Lys Leu
1               5                   10                  15

Glu Asn Gln Ile Ala Ile Ile Lys Tyr Val Ile Leu Phe Thr Asn Val
            20                  25                  30

Leu Gln Trp Ala Leu Gly Ala Ala Ile Phe Ala Leu Cys Leu Trp Leu
        35                  40                  45

Arg Phe Glu Glu Gly Ile Gln Glu Trp Leu Gln Lys Leu Asp Ser Glu
    50                  55                  60

Gln Phe Tyr Ile Gly Val Tyr Val Leu Ile Val Ala Ser Leu Ile Val
65                  70                  75                  80

Met Ile Val Ser Phe Ile Gly Cys Ile Ser Ala Leu Gln Glu Ser Thr
                85                  90                  95

Met Ala Leu Leu Val Tyr Ile Gly Thr Gln Val Leu Ser Phe Ile Phe
            100                 105                 110

Gly Leu Ser Gly Ser Ala Val Leu Leu Asp Asn Ser Ala Arg Asp Ser
        115                 120                 125
```

```
His Phe Gln Pro Arg Ile Arg Glu Ser Met Arg Arg Leu Ile Met Asn
    130                 135                 140

Ala His His Asp Gln Ser Arg Gln Thr Leu Ala Met Ile Gln Glu Asn
145                 150                 155                 160

Val Gly Cys Cys Gly Ala Asp Gly Ala Thr Asp Tyr Leu Ser Leu Gln
                165                 170                 175

Gln Pro Leu Pro Ser Gln Cys Arg Asp Thr Val Thr Gly Asn Pro Phe
            180                 185                 190

Phe His Gly Cys Val Asp Glu Leu Thr Trp Phe Phe Glu Glu Lys Cys
        195                 200                 205

Gly Trp Ile Ala Gly Leu Ala Met Ala Ile Cys Met Ile Asn Val Leu
    210                 215                 220

Ser Ile Val Leu Ser Thr Val Leu Ile Gln Ala Leu Lys Lys Glu Glu
225                 230                 235                 240

Glu Ala Ser Asp Ser Tyr Arg Arg
                245


<210> SEQ ID NO 251
<211> LENGTH: 124
<212> TYPE: PRT
<213> ORGANISM: Diabrotica virgifera

<400> SEQUENCE: 251

Met Ser Gly Arg Gly Lys Gly Gly Lys Val Lys Gly Lys Ala Lys Ser
1               5                   10                  15

Arg Ser Asn Arg Ala Gly Leu Gln Phe Pro Val Gly Arg Ile His Arg
            20                  25                  30

Leu Leu Arg Lys Gly Asn Tyr Ala Glu Arg Val Gly Ala Gly Ala Pro
        35                  40                  45

Val Tyr Leu Ala Ala Val Met Glu Tyr Leu Ala Ala Glu Val Leu Glu
    50                  55                  60

Leu Ala Gly Asn Ala Ala Arg Asp Asn Lys Lys Thr Arg Ile Ile Pro
65                  70                  75                  80

Arg His Leu Gln Leu Ala Ile Arg Asn Asp Glu Glu Leu Asn Lys Leu
                85                  90                  95

Leu Ser Gly Val Thr Ile Ala Gln Gly Gly Val Leu Pro Asn Ile Gln
            100                 105                 110

Ala Val Leu Leu Pro Lys Lys Thr Glu Lys Lys Ala
        115                 120


<210> SEQ ID NO 252
<211> LENGTH: 288
<212> TYPE: PRT
<213> ORGANISM: Diabrotica virgifera

<400> SEQUENCE: 252

Met Lys Leu Asp Gly Val Asp Leu Pro Pro Pro Ile Ser Phe Asp Ile
1               5                   10                  15

Ala Glu Glu Gln Pro Leu Pro Pro Cys Gln Gln Thr Phe Leu Cys Asn
            20                  25                  30

Gly Asp Gly Gly Ser Ile Val Arg Gln Phe Leu Glu Leu Tyr Phe Val
        35                  40                  45

Ile Tyr Asp Ser Asp Asn Arg Gln Ser Leu Leu Gln Ala Tyr His Glu
    50                  55                  60

Lys Ala Thr Phe Ser Met Thr Met Ala Tyr Pro Tyr Gly Tyr Ser Lys
65                  70                  75                  80
```

-continued

Asp Ser Lys Gly Val Ser Trp Leu Asn Trp Tyr Ala Thr Asp Asn Arg
85 90 95

Asn Leu Leu Arg Val Gln Asp Pro Asp Arg Arg Asn Lys Leu Leu Arg
100 105 110

Gln Gly Gln Val Ala Val Val Ser Phe Leu Gln Asp Met Pro His Thr
115 120 125

Lys His Asp Ile His Ser Phe Thr Val Asp Leu Thr Val Phe Thr Pro
130 135 140

Gln Met Leu Cys Leu Thr Val Ala Gly Met Phe Lys Glu Leu Lys Ser
145 150 155 160

Gly His Lys Val Pro Pro Leu Arg Tyr Phe Phe Arg Thr Leu Val Ile
165 170 175

Val Pro Ala Gly Ser Gly Phe Cys Ile Ala Asn Glu Glu Leu His Ile
180 185 190

Ser Asn Ala Thr Pro Asp Gln Ala Lys Asp Ala Phe Lys Thr Thr Val
195 200 205

Asn Val Ala Pro Ala Pro Ala Pro Val Ile Thr Ser Pro Gly Pro Ser
210 215 220

Ile Pro Gln Pro Ala Val Pro Asp Asp Ala Thr Lys Gln Glu Met Val
225 230 235 240

Lys Gln Met Ser Ala Val Ser Gly Met Asn Leu Glu Trp Ser Leu Gln
245 250 255

Cys Leu Glu Glu Thr Gln Trp Asp Tyr Gln Lys Ala Ile Met Val Phe
260 265 270

Gln Asn Leu Asn Ala Gln Gly Val Val Pro Gln Ala Ala Phe Ile Lys
275 280 285

<210> SEQ ID NO 253
<211> LENGTH: 955
<212> TYPE: PRT
<213> ORGANISM: Diabrotica virgifera

<400> SEQUENCE: 253

Met Thr Ala Val Glu Gln Pro Cys Tyr Thr Leu Ile Asn Leu Pro Thr
1 5 10 15

Asp Ser Glu Pro Tyr Asn Glu Met Gln Leu Lys Met Asp Leu Glu Lys
20 25 30

Gly Glu Val Lys Val Lys Ile Arg Ala Leu Glu Lys Ile Ile His Met
35 40 45

Ile Leu Ala Gly Glu Arg Leu Pro Asn Gly Phe Leu Met Thr Ile Ile
50 55 60

Arg Asn Val Leu Pro Leu Gln Asp His Leu Ala Lys Lys Leu Leu Leu
65 70 75 80

Ile Phe Trp Glu Ile Val Pro Lys Thr Asn Pro Glu Gly Lys Leu Leu
85 90 95

Gln Glu Met Ile Leu Val Cys Asp Ala Tyr Arg Lys Asp Leu Gln His
100 105 110

Pro Asn Glu Phe Leu Arg Gly Ser Thr Leu Arg Phe Leu Cys Lys Leu
115 120 125

Lys Glu Pro Glu Leu Leu Glu Pro Leu Met Pro Ser Ile Arg Ala Cys
130 135 140

Leu Asp His Arg His Ser Tyr Val Arg Arg Asn Ala Val Leu Ala Ile
145 150 155 160

Phe Thr Ile Tyr Lys Asn Phe Glu Ala Leu Ile Pro Asp Ala Pro Glu
165 170 175

```
Leu Ile Ser Asn Tyr Leu Asp Gly Glu Gln Asp Met Ser Cys Lys Arg
            180                 185                 190

Asn Ala Phe Leu Met Leu Leu His Ala Asp Gln Glu Arg Ala Leu Ser
        195                 200                 205

Tyr Leu Ala Ser Cys Leu Asp Gln Val Asn Ser Phe Gly Asp Ile Leu
    210                 215                 220

Gln Leu Val Ile Val Glu Leu Ile Tyr Lys Val Cys His Ser Asn Pro
225                 230                 235                 240

Ala Glu Arg Ser Arg Phe Ile Arg Cys Ile Tyr Asn Leu Leu Asn Ser
                245                 250                 255

Ser Ser Pro Ala Val Arg Tyr Glu Ala Ala Gly Thr Leu Val Thr Leu
            260                 265                 270

Ser Ser Ala Pro Thr Ala Val Lys Ala Ala Ala Ser Cys Tyr Ile Glu
        275                 280                 285

Leu Ile Ile Lys Glu Ser Asp Asn Asn Val Lys Leu Ile Val Leu Asp
    290                 295                 300

Arg Leu Ile Ala Leu Lys Glu Leu Pro Asn His Glu Arg Ile Leu Gln
305                 310                 315                 320

Asp Leu Val Met Asp Ile Leu Arg Val Leu Ser Ala Pro Asp Leu Glu
                325                 330                 335

Val Arg Lys Lys Thr Leu Ser Leu Ala Leu Glu Leu Val Ser Ser Arg
            340                 345                 350

Asn Ile Glu Glu Met Val Leu Val Leu Thr Lys Glu Val Ser Lys Thr
        355                 360                 365

Val Asp Ser Glu His Glu Asp Thr Gly Lys Tyr Arg Gln Leu Leu Val
    370                 375                 380

Arg Thr Leu His Ser Cys Ser Ile Lys Phe Pro Asp Ile Ala Arg Ser
385                 390                 395                 400

Val Ile Pro Val Leu Ile Glu Phe Leu Ser Asp Asn Asn Glu Leu Ala
                405                 410                 415

Ala Thr Asp Val Leu Leu Phe Leu Arg Glu Ala Ile Gln Lys Phe Lys
            420                 425                 430

Glu Leu Gln Pro Leu Ile Ile Glu Lys Leu Ile Glu Thr Phe Lys Asp
        435                 440                 445

Ile Lys Leu Val Lys Val His Arg Ala Ala Ile Trp Ile Leu Gly Glu
    450                 455                 460

Tyr Ala Ser Thr Ala Ser Asp Ile Glu Val Ile Val Gly Glu Ile Asn
465                 470                 475                 480

Arg Leu Leu Gly Glu Gly Ser Leu Val Glu Ala Glu Gln Lys Leu Ile
                485                 490                 495

Ala Gly Asp Thr Glu Glu Asn Ala Pro Ala Pro Ala Ala Gly Ala Thr
            500                 505                 510

Thr Leu Val Thr Ser Asp Gly Thr Tyr Ala Thr Gln Ser Ala Phe Asn
        515                 520                 525

Thr Val Ser Gln Thr Thr Lys Glu Ala Arg Pro Pro Leu Arg Gln Tyr
    530                 535                 540

Leu Met Asp Gly Asp Phe Phe Ile Gly Ala Ser Leu Ala Ser Thr Leu
545                 550                 555                 560

Thr Lys Leu Ser Leu Arg Tyr Glu Asp Leu Thr Ser Pro Ala Ala Ser
                565                 570                 575

Asn Gly Phe Asn Ala Lys Ile Met Leu Ile Met Ala Gly Ile Leu His
            580                 585                 590
```

```
Leu Gly Lys Ser Gly Leu Pro Thr Lys Ser Ile Thr Asn Asp Asp Lys
        595                 600                 605

Asp His Ile Leu Phe Cys Leu Arg Val Leu Ser Asp Arg Ser Pro Ile
    610                 615                 620

Ile Val Glu Ile Phe Lys Lys Leu Cys Arg Ser Ala Leu Asn Glu Met
625                 630                 635                 640

Leu Leu Ala Lys Glu Ser Val Glu Ala Ile Ser Gln Lys Ser Lys Glu
                645                 650                 655

Lys Asn Lys Arg Thr Ile Gln Thr Asp Asp Ala Ile Ser Phe Leu Gln
            660                 665                 670

Leu Glu Thr Asp Lys Ser Gly Glu Leu Gly Glu Asn Val Phe Glu Met
        675                 680                 685

Ser Leu Ser Gln Ala Leu Val Gly Gly Arg Thr Gly Gly Gly Glu Ser
    690                 695                 700

Val Leu Ser Ser Asn Lys Leu Asp Lys Ile Thr Gln Leu Thr Gly Phe
705                 710                 715                 720

Ser Asp Pro Val Tyr Ser Glu Ala Tyr Val His Val Asn Gln Tyr Asp
                725                 730                 735

Ile Val Leu Asp Val Leu Ile Val Asn Gln Thr Asn Asp Thr Leu Gln
            740                 745                 750

Asn Cys Thr Leu Glu Leu Ala Thr Leu Gly Asp Leu Lys Leu Val Glu
        755                 760                 765

Lys Pro Gln Pro Val Val Leu Ala Pro Lys Asp Phe Cys Asn Ile Lys
    770                 775                 780

Ala Asn Val Lys Val Ala Ser Thr Glu Asn Gly Ile Ile Phe Gly Asn
785                 790                 795                 800

Ile Val Tyr Asp Val Ile Gly Ala Gly Ser Asp Arg Asn Val Val Val
                805                 810                 815

Leu Asn Asp Ile His Ile Asp Ile Met Asp Tyr Ile Val Pro Ala Ser
            820                 825                 830

Cys Thr Asp Ser Glu Phe Met Arg Met Trp Ala Glu Phe Glu Trp Glu
        835                 840                 845

Asn Lys Val Thr Val Asn Thr Pro Leu Thr Glu Leu Ser Glu Tyr Leu
    850                 855                 860

Glu His Leu Leu Lys Ser Thr Asn Leu Lys Cys Leu Thr Ser Glu Lys
865                 870                 875                 880

Ala Leu Ser Gly Gln Cys Gly Phe Met Ala Ala Asn Leu Tyr Ala Lys
                885                 890                 895

Ser Ile Phe Gly Glu Asp Ala Leu Ala Asn Leu Ser Ile Glu Lys Pro
            900                 905                 910

Phe Asn Lys Pro Asp Ala Pro Val Ser Gly His Ile Arg Ile Arg Ala
        915                 920                 925

Lys Ser Gln Gly Met Ala Leu Ser Leu Gly Asp Lys Val Asn Met Thr
    930                 935                 940

Gln Lys Ser Thr Gln His Lys Val Val Ala Ala
945                 950                 955


<210> SEQ ID NO 254
<211> LENGTH: 447
<212> TYPE: PRT
<213> ORGANISM: Diabrotica virgifera

<400> SEQUENCE: 254

Met Val Tyr Pro Asn Ser Pro Phe Lys Thr Thr Phe Asn Asn Lys Leu
1               5                   10                  15
```

-continued

```
Ile Thr Asn Leu Phe Leu Asp Asp Ser Val Thr Lys Thr Lys Thr Ser
            20                  25                  30

Val Ser Asn Glu Glu Leu Leu Lys Ile Gln Gln Trp Leu Cys Ser Ala
        35                  40                  45

Pro Lys Ile Thr Ser Ile Arg Val Asn Thr Ile Lys Thr Asn Thr Ala
    50                  55                  60

Lys Val Leu Lys Val Leu Lys Thr Tyr Phe Ala Glu Asn Cys Asn Asp
65                  70                  75                  80

Thr Pro Asn Val Tyr Ile His Pro Ser Phe Thr Asn Val Ile Ile Ile
                85                  90                  95

Asp Ser Leu Asn Cys Pro Ala Gly Phe Lys Lys Phe Asp Lys Glu Ile
            100                 105                 110

Ile Val Asp Thr Asp Cys Ala Ala Ala Ile Leu Arg Gly Ala His Ile
        115                 120                 125

Phe Ala Pro Gly Val Leu Gly Met Val Ser Gly Cys Gln Ile Asn Glu
    130                 135                 140

Asn Val Ser Ile Tyr Ala Asp Val Ala Lys Lys Cys Lys Lys Gly Leu
145                 150                 155                 160

Gln Lys Ile Tyr Glu Asp Asp Phe Lys Ile Phe Ile Gly Asn Gly Ile
                165                 170                 175

Val Lys Met Gln Arg His Gln Leu Phe Ala Thr Asp Asn Ile Ala Pro
            180                 185                 190

Ser Gly Ile Ala Val Glu Val Thr Glu Thr Ile Ser Gly Cys Val Pro
        195                 200                 205

Ile Ser Glu Ser Leu Leu Pro Val Gly Asp Ile Leu Leu Gln Asn Ile
    210                 215                 220

Pro Ser Ile Val Cys Val His Asn Leu Asn Pro Lys Pro Gly Asp Val
225                 230                 235                 240

Val Leu Asp Met Cys Ala Ser Pro Gly Asn Lys Thr Thr His Ile Ala
                245                 250                 255

Glu Leu Met Gln Asn Lys Gly Ile Leu Ile Ala Ile Asp Lys Thr Pro
            260                 265                 270

Lys Lys Val Ala Gln Leu Gln Lys Arg Cys Glu Asp Phe Gly Ala Lys
        275                 280                 285

Val Tyr Ser Phe Gln Ala Asp Ser Thr Ala Ile Ile Ser Asp Thr Leu
    290                 295                 300

Ser Ser Lys Asn Val Ile Asp Gly Pro Pro Phe Ala Pro Gln Ser Phe
305                 310                 315                 320

Asp Lys Ile Leu Leu Asp Ala Pro Cys Ser Val Leu Gly Lys Arg Pro
                325                 330                 335

Gln Leu Ala Asn Arg Ser Ser Glu Asn Glu Ile Lys Ser Phe Val Pro
            340                 345                 350

Leu Gln Arg Lys Leu Phe Glu Asn Ala Ala Lys Leu Leu Lys Pro Gly
        355                 360                 365

Gly Ile Met Val Tyr Ser Thr Cys Thr Ile Thr Leu Ser Glu Asn Glu
    370                 375                 380

Gly Ile Val Ala Trp Ala Leu Lys Ser Phe Asn Phe Leu Glu Leu Val
385                 390                 395                 400

Gln Pro Asp Leu Thr Leu Gly Glu Pro Gly Trp Leu Gly Thr Ser Leu
                405                 410                 415

Ser Asp Glu Ala Arg Ser Phe Val Gln Arg Phe Gly Pro Asn Ser Glu
            420                 425                 430
```

-continued

```
Val Asp Ser Val Gly Phe Phe Phe Ala Val Phe Lys Lys Lys Thr
        435                 440                 445


<210> SEQ ID NO 255
<211> LENGTH: 1474
<212> TYPE: PRT
<213> ORGANISM: Diabrotica virgifera

<400> SEQUENCE: 255

Met Gly Arg Leu His Cys Leu Phe Cys Ile Phe Leu Cys Phe Thr Val
1               5                   10                  15

Ile Asn Thr Gln Thr Thr Asn Ile His Gly Phe Ser Glu Asn Ser Val
            20                  25                  30

Asp Thr Phe Leu Ser Pro His Gly Lys Ser Ala Lys Phe Val His Gln
        35                  40                  45

Asn His Lys Pro Lys Ile Glu Asn Cys Gln Asn Tyr Lys Pro Ser Val
    50                  55                  60

Lys Glu Glu Gln Pro Gly Gly Thr Tyr Val Thr Thr Val Thr Ala Ile
65                  70                  75                  80

Asp Asp Asp Pro Arg Glu Gly Gly Gly Thr Ile Ser Tyr Lys Leu Ile
                85                  90                  95

His Arg Glu Gly Glu His Val Leu Phe Asp Ile Asp Asn Val Thr Gly
            100                 105                 110

Val Leu Thr Thr Ile Gln Pro Phe Asp Arg Asp Glu Pro Val Arg Gln
        115                 120                 125

Lys Glu Leu Tyr Val Thr Val Gln Ala Ser Asp Asn Gly Arg Pro Pro
    130                 135                 140

Leu Ala Asp Val Cys Thr Phe Thr Val Thr Ile Thr Asp Ile Asn Asp
145                 150                 155                 160

Asn Ala Pro Gln Leu Asp Lys Leu Lys Tyr Asp Ala Gln Val Ser Glu
                165                 170                 175

Asp Leu Lys Val Gly Ser Glu Val Met Arg Val Phe Ala Tyr Asp Ile
            180                 185                 190

Asp Asp Gly Glu Asn Ser Arg Leu Ser Tyr Asn Phe Ser Asn Glu Asn
        195                 200                 205

Ala Gln Phe Thr Gln Tyr Phe Arg Ile Asp Arg Asp Thr Gly Val Val
    210                 215                 220

Tyr Leu Lys Glu Ala Leu Thr Asp Lys Lys Asn Thr Arg Phe Asn Ser
225                 230                 235                 240

Ala Val Tyr Val Ala Asp Asn Gly Val Asn Asp Gln Glu Gly Gln Lys
                245                 250                 255

Asp Ser Thr Ala Lys Ile Ser Ile Thr Val Val Gly Ser Asp Lys Gln
            260                 265                 270

Pro Pro Arg Phe Thr Gln Lys Met Pro Asp Gly Ile Leu Glu Ile Pro
        275                 280                 285

Glu Asp Phe Lys Asp Phe Ser Lys His Ile Val Thr Val Glu Ala Thr
    290                 295                 300

Ser Asn Ile Ala Asp Pro Gln Leu Ala Phe Glu Leu Val Lys Gly Lys
305                 310                 315                 320

Thr Tyr Gln Thr Asn Lys Asp Gln Thr Phe Leu Leu Glu Ala Glu Gly
                325                 330                 335

Asn Lys Ala His Ile Lys Leu Val Arg Pro Leu Asp Tyr Glu Thr Val
            340                 345                 350

Thr Glu Tyr Thr Leu Thr Ile Arg Val Lys Asn Lys Asp Leu Met Asp
        355                 360                 365
```

```
Ser Ser Ile Asn Ile Pro Ile Lys Val Leu Asp Val Asn Asp Glu Ile
    370                 375                 380

Pro Asn Phe Leu Glu Phe Leu Lys Gly Ser Val Val Glu Asn Asp Lys
385                 390                 395                 400

Pro Gly Ala Gln Ala Ile Gln Val Arg Ala Ile Asp Lys Asp Gly Thr
                405                 410                 415

Ala Ala Asn Asn Ile Val Ser Tyr Glu Leu Val Asp Asn Thr Asp Leu
            420                 425                 430

Phe Ala Ile Asn Arg Ser Thr Gly Val Ile Thr Ser Arg Val Glu Phe
        435                 440                 445

Asp Arg Glu Thr Val Pro Leu Tyr His Val Asn Val Lys Ala Tyr Asp
    450                 455                 460

Asn Ser Pro Ser Ala Leu Tyr Asn Thr Thr Leu Pro Asn Ile Val Ile
465                 470                 475                 480

Gln Thr Phe Gln Ile Ser Ile Glu Asp Gln Asn Asp Asn Lys Pro Val
                485                 490                 495

Phe Thr His Pro Ile Tyr Gln Phe Ser Asn Ile Thr Glu Leu Ala Asp
            500                 505                 510

Lys Ser Ser Ile Val Gly Glu Val Lys Ala Leu Asp Asn Asp Thr Ala
        515                 520                 525

Ser Val Ile Ser Tyr Ser Ile Thr Asn Gly Asn Ile Asp Asp Ala Phe
    530                 535                 540

Met Ile Glu Asn Ser Thr Gly Arg Ile Arg Val Asn Gly Lys Leu Asp
545                 550                 555                 560

Tyr Glu Lys Ile Glu Gln Tyr Asn Leu Thr Val Arg Ala Phe Asp Gly
                565                 570                 575

Ala Phe Glu Asp Phe Ala Ile Val Leu Ile Ser Ile Leu Asn Glu Asn
            580                 585                 590

Asp Glu Pro Pro Val Phe Asp Asp Tyr Ile Arg Glu Ile Gln Ile Lys
        595                 600                 605

Glu Glu Glu Pro Met Ile Ser Gly Cys Val Val Arg Val Thr Ala His
    610                 615                 620

Asp Pro Asp Ile Lys Asp Arg His Ala Asp Gln His Ile Val Tyr Glu
625                 630                 635                 640

Val Ala Lys Glu Gln Lys Asp Phe Leu Thr Val Ser Ala Asp Gly Cys
                645                 650                 655

Val Gln Val Thr Lys Pro Leu Asp Arg Asp Pro Pro Phe Gly Ser Pro
            660                 665                 670

Thr Arg Gln Val Phe Ile Tyr Ala Arg Asp Asn Asp Gly Gly Thr Asn
        675                 680                 685

Ser Leu Leu Ala Thr Ala Glu Ile Glu Ile Ile Leu Ile Asp Ile Asn
    690                 695                 700

Asp Asn Ala Pro Phe Leu Asn Val Thr Glu Ile Val Tyr Tyr Glu Asn
705                 710                 715                 720

Gln Asp Pro Gly Phe Ile Gly Asn Leu Ser Ala Asp Asp Tyr Asp Gly
                725                 730                 735

Pro Asp Asn Gly Pro Pro Phe Ala Phe Arg Leu Ser Asp Thr Ala Ser
            740                 745                 750

Asp Ser Ile Arg Ser Lys Phe Ser Ile Ile Gly Asn Gln Leu Phe Ala
        755                 760                 765

Leu Glu Met Phe Asp Arg Glu Glu Gln Lys Tyr Tyr Asp Ile Ala Ile
    770                 775                 780
```

-continued

```
Asp Ile Thr Asp Ser Gly Val Pro Pro Leu Thr Gly Thr Ser Ile Leu
785                 790                 795                 800

Arg Val Ile Ile Gly Asp Val Asn Asp Asn Pro Ala Thr Asp Gly Asn
                805                 810                 815

Ser Thr Ile Phe Val Tyr Lys Tyr Val Asn Gly Pro Glu Asn Phe Met
            820                 825                 830

Glu Ile Gly Arg Val Tyr Val Thr Asp Leu Asp Asp Trp Asp Leu Asn
        835                 840                 845

Asp Lys Val Phe Val Gln Glu Asp Asn Phe Asp Glu Phe Val Leu Asn
    850                 855                 860

Gln His Asn Asn Gly Met Ile Leu Met Lys Pro Thr Thr Ala Glu Gly
865                 870                 875                 880

Thr Tyr Glu Val His Tyr Arg Val Thr Glu Thr His Glu Pro Thr Ile
                885                 890                 895

His Glu His Thr Val Asn Ala Ile Val Thr Ile Thr Val Lys Val Leu
            900                 905                 910

Pro Glu Glu Ala Val Val Lys Ser Gly Ser Ile Arg Leu Arg Gly Thr
        915                 920                 925

Thr Lys Glu Glu Phe Ile Glu Asn Ser Leu Asn Gly Lys Ser Lys Arg
    930                 935                 940

Asp Ile Leu His Gln Glu Leu Ser Lys Ile Leu Asn Thr Ser Leu Ala
945                 950                 955                 960

Asn Val Asp Val Phe Thr Val Leu Asn Ser Pro His Gln Asn Ser Ser
                965                 970                 975

Phe Val Asp Val Arg Phe Ser Ala His Gly Ser Pro Tyr Tyr Ala Pro
            980                 985                 990

Glu Lys Leu Glu Asn Lys Val Thr  Asp His Gln Met Glu  Leu Glu Gln
        995                 1000                 1005

Lys Leu  Asp Val Glu Phe Tyr  Met Ile Asn Val Asn  Glu Cys Leu
    1010                 1015                 1020

Asn Glu  Thr Thr Cys Gly Ala  Glu Asn Ser Cys Thr  Asn Lys Leu
    1025                 1030                 1035

Asn Ile  Thr Arg Glu Pro Ala  Val Val Phe Thr Asn  Arg Thr Ser
    1040                 1045                 1050

Phe Val  Gly Val Asn Ala Phe  Ile Asp Pro Val Cys  Ala Ala Leu
    1055                 1060                 1065

Pro Arg  Asp Val Met Glu Cys  Phe Asn Gly Gly Val  Leu Ile Glu
    1070                 1075                 1080

Asn Thr  Ala Cys Asn Cys Pro  Ala Gly Phe Glu Gly  Pro His Cys
    1085                 1090                 1095

Glu Ile  Leu Ala Ile Gly Phe  Thr Gly Thr Gly Trp  Ala Met Tyr
    1100                 1105                 1110

Pro Ser  Phe Asp Ala Thr Asn  Arg Thr Glu Ile Ile  Leu His Ile
    1115                 1120                 1125

Leu Ser  Gln Thr Asp Asn Gly  Leu Ile Phe Tyr Asn  Gly Pro Leu
    1130                 1135                 1140

Asn Ile  Arg Gln Thr Ser Leu  Ser Lys Asp Tyr Ile  Ser Leu Glu
    1145                 1150                 1155

Leu Lys  Asp Gly Tyr Pro Leu  Leu Gln Ile Cys Thr  Gly Ser Ser
    1160                 1165                 1170

Thr Gln  Glu Ile Tyr Leu Lys  Glu Arg Ile His Lys  Leu Ser Asp
    1175                 1180                 1185

Gly Ser  Leu His Lys Ile Lys  Ile Gly Ser Gly Phe  Asp Asp Ile
```

```
    1190                1195                1200

Ser Leu  Glu Val Asp Asp Cys  Gly Thr Thr Cys Ser  Ile Trp Thr
    1205                1210                1215

Asn Lys  Leu His Lys Gly Val  Ile Arg Ala Asn Gly  Pro Leu Gln
    1220                1225                1230

Leu Gly  Gly Met Lys Asn Arg  Phe Thr Asp Gln Glu  Phe Lys Arg
    1235                1240                1245

Ile Trp  Asp His Leu Pro Pro  Thr Ala Thr Arg Phe  Ser Gly Cys
    1250                1255                1260

Ile Arg  Asn Leu Thr Tyr Asn  Glu Phe Tyr Tyr Asn  Leu Gly Ala
    1265                1270                1275

Pro Ser  Asp Ala Phe Gln Ala  Tyr Pro Asp Cys Asn  Tyr Ala Val
    1280                1285                1290

Met Gln  Ala Val Thr Phe Gly  Ile Asp Ser Asn Phe  Leu Val Ala
    1295                1300                1305

Ile Leu  Val Cys Val Ala Ile  Leu Ile Ile Leu Leu  Leu Ala Val
    1310                1315                1320

Val Val  His Arg Arg Lys His  Asp Asn Phe Asn Glu  Lys Glu Ile
    1325                1330                1335

Asp Asp  Thr Arg Glu Asn Ile  Ile Asn Tyr Glu Asp  Glu Gly Gly
    1340                1345                1350

Gly Glu  Cys Asp Thr Asn Tyr  Asp Leu Ser Val Phe  His Gln Asn
    1355                1360                1365

Asn Ile  Val Asp Glu Lys Pro  Leu Met Arg Asp Asn  Pro Asp Val
    1370                1375                1380

Pro Ala  Asp Ile Ser Gly Phe  Leu Asp Asn Lys Lys  Asp Asn Cys
    1385                1390                1395

Asp Lys  Asp Pro Asp Asn Leu  Pro Tyr Asp Asp Val  Arg His Tyr
    1400                1405                1410

Ala Tyr  Glu Gly Asp Gly Asn  Ser Thr Gly Ser Leu  Ser Ser Leu
    1415                1420                1425

Ala Ser  Cys Thr Asp Glu Gly  Asp Leu Lys Phe Asn  Tyr Leu Ser
    1430                1435                1440

Ser Phe  Gly Pro Arg Phe Arg  Lys Leu Ala Asp Met  Tyr Gly Glu
    1445                1450                1455

Asp Pro  Ser Asp Glu Asp Ser  His Asp Gly Asn Glu  Glu Ser Trp
    1460                1465                1470

Cys


<210> SEQ ID NO 256
<211> LENGTH: 96
<212> TYPE: PRT
<213> ORGANISM: Diabrotica virgifera

<400> SEQUENCE: 256

Met Pro Phe Cys Gly Pro Lys Leu Ser Leu Cys Gly Leu Ile Ile Ser
1               5                   10                  15

Ala Trp Gly Ile Ile Gln Leu Gly Phe Met Gly Val Phe Tyr Tyr Ile
            20                  25                  30

Gly Ala Val Ala Leu Ala Glu Asp Ile Pro Glu Val Glu Phe Lys Gly
        35                  40                  45

Asp Leu Asp Lys Phe Tyr Ser Asp Val Asn Thr Gly Phe Thr Gln Asn
    50                  55                  60

Ala Tyr Asn Cys Trp Ile Ala Ala Leu Leu Tyr Leu Ile Thr Leu Ala
```

65 70 75 80

Val Ser Ala His Gln Phe Trp Ala Asn Asn Arg Ser Ser Leu Asn Val
85 90 95

<210> SEQ ID NO 257
<211> LENGTH: 179
<212> TYPE: PRT
<213> ORGANISM: Diabrotica virgifera

<400> SEQUENCE: 257

Met Gly Leu Thr Ile Ser Ala Val Phe Asn Arg Leu Phe Ser Lys Lys
1 5 10 15

Pro Met Arg Ile Leu Met Val Gly Leu Asp Ala Ala Gly Lys Thr Thr
20 25 30

Ile Leu Tyr Lys Leu Lys Leu Gly Glu Ile Val Thr Thr Ile Pro Thr
35 40 45

Ile Gly Phe Asn Val Glu Thr Val Glu Tyr Lys Asn Ile Ser Phe Thr
50 55 60

Val Trp Asp Val Gly Gly Gln Thr Arg Ile Arg Lys Leu Trp Arg His
65 70 75 80

Tyr Phe Ala Asn Thr Asp Gly Leu Ile Phe Val Val Asp Ser Asn Asp
85 90 95

Arg Asp Arg Ile Ala Glu Ala Glu Glu Glu Leu His Asn Met Leu Gly
100 105 110

Glu Asp Asp Leu Arg Asp Cys Ile Leu Leu Ile Phe Ala Asn Lys Gln
115 120 125

Asp Leu Pro Asn Ser Met Ser Thr Ala Glu Leu Thr Asp Lys Leu Lys
130 135 140

Leu His Thr Leu Lys Asn Arg Arg Trp Tyr Ile Gln Ala Thr Cys Ala
145 150 155 160

Thr Gln Gly Asn Gly Leu Tyr Glu Gly Leu Asp Trp Leu Ser Asn Glu
165 170 175

Leu Ala Lys

<210> SEQ ID NO 258
<211> LENGTH: 205
<212> TYPE: PRT
<213> ORGANISM: Diabrotica virgifera

<400> SEQUENCE: 258

Met Arg Tyr Thr Leu Ser Tyr Ile Gly Ala Thr Leu Ala Ser Thr Val
1 5 10 15

Thr Leu Ile Phe Ala Leu Tyr Tyr Cys Leu Thr Gly Lys Gly Glu Gln
20 25 30

Val Ser Leu Ala Trp Leu Leu Leu Asn Val Ser Pro His Met Trp Ala
35 40 45

Gly Leu Gly Ile Gly Leu Ala Val Ser Leu Ser Val Val Gly Ala Ala
50 55 60

Ala Gly Ile His Thr Thr Gly Val Ser Ile Val Gly Ala Gly Val Lys
65 70 75 80

Ala Pro Arg Ile Lys Thr Lys Asn Leu Ile Ser Ile Ile Phe Cys Glu
85 90 95

Ala Val Ala Ile Tyr Gly Leu Ile Met Ala Ile Val Leu Cys Gly Ser
100 105 110

Trp Lys Asn Phe Asp Val Asp Leu Phe Asn Leu Lys Thr His Asn Phe
115 120 125

```
Ala Gln Asn His Tyr Gly Ser His Val Ile Phe Gly Ser Gly Leu Thr
    130                 135                 140

Val Gly Phe Val Asn Leu Leu Cys Gly Phe Cys Val Gly Val Val Gly
145                 150                 155                 160

Ser Gly Ala Ala Ile Ser Asp Ala Ala Asn Ser Ser Leu Phe Val Lys
                165                 170                 175

Ile Leu Ile Ile Glu Ile Phe Gly Ser Ala Ile Gly Leu Phe Gly Leu
            180                 185                 190

Ile Val Gly Val Tyr Leu Thr Ser Arg Gly Ser Met Val
        195                 200                 205


<210> SEQ ID NO 259
<211> LENGTH: 1897
<212> TYPE: PRT
<213> ORGANISM: Diabrotica virgifera

<400> SEQUENCE: 259

Met Ala Thr Asn Asp Ser Lys Ala Pro Leu Arg Thr Val Lys Arg Val
1               5                   10                  15

Gln Phe Gly Ile Leu Ser Pro Asp Glu Ile Arg Arg Met Ser Val Thr
            20                  25                  30

Glu Gly Gly Ile Arg Phe Pro Glu Thr Met Glu Ala Gly Arg Pro Lys
        35                  40                  45

Leu Cys Gly Leu Met Asp Pro Arg Gln Gly Val Ile Asp Arg Ser Ser
    50                  55                  60

Arg Cys Gln Thr Cys Ala Gly Asn Met Thr Glu Cys Pro Gly His Phe
65                  70                  75                  80

Gly His Ile Glu Leu Ala Lys Pro Val Phe His Val Gly Phe Val Thr
                85                  90                  95

Lys Thr Ile Lys Ile Leu Arg Cys Val Cys Phe Phe Cys Ser Lys Leu
            100                 105                 110

Leu Val Ser Pro Asn Asn Pro Lys Ile Lys Glu Val Val Met Lys Ser
        115                 120                 125

Lys Gly Gln Pro Arg Lys Arg Leu Ala Phe Val Tyr Asp Leu Cys Lys
    130                 135                 140

Gly Lys Asn Ile Cys Glu Gly Gly Asp Glu Met Asp Val Gly Lys Glu
145                 150                 155                 160

Ser Glu Asp Pro Asn Lys Lys Ala Gly His Gly Gly Cys Gly Arg Tyr
                165                 170                 175

Gln Pro Asn Ile Arg Arg Ala Gly Leu Asp Leu Thr Ala Glu Trp Lys
            180                 185                 190

His Val Asn Glu Asp Thr Gln Glu Lys Lys Ile Ala Leu Ser Ala Glu
        195                 200                 205

Arg Val Trp Glu Ile Leu Lys His Ile Thr Asp Glu Glu Cys Phe Ile
    210                 215                 220

Leu Gly Met Asp Pro Lys Phe Ala Arg Pro Asp Trp Met Ile Val Thr
225                 230                 235                 240

Val Leu Pro Val Pro Pro Leu Ala Val Arg Pro Ala Val Val Met His
                245                 250                 255

Gly Ser Ala Arg Asn Gln Asp Asp Ile Thr His Lys Leu Ala Asp Ile
            260                 265                 270

Ile Lys Ala Asn Asn Glu Leu Gln Lys Asn Glu Ser Ala Gly Ala Ala
        275                 280                 285

Ala His Ile Ile Thr Glu Asn Ile Lys Met Leu Gln Phe His Val Ala
```

```
    290                 295                 300

Thr Leu Val Asp Asn Asp Met Pro Gly Met Pro Arg Ala Met Gln Lys
305                 310                 315                 320

Ser Gly Lys Pro Leu Lys Ala Ile Lys Ala Arg Leu Lys Gly Lys Glu
                325                 330                 335

Gly Arg Ile Arg Gly Asn Leu Met Gly Lys Arg Val Asp Phe Ser Ala
            340                 345                 350

Arg Thr Val Ile Thr Pro Asp Pro Asn Leu Arg Ile Asp Gln Val Gly
        355                 360                 365

Val Pro Arg Ser Ile Ala Gln Asn Met Thr Phe Pro Glu Ile Val Thr
    370                 375                 380

Pro Phe Asn Phe Asp Lys Met Leu Glu Leu Val Gln Arg Gly Asn Ser
385                 390                 395                 400

Gln Tyr Pro Gly Ala Lys Tyr Ile Ile Arg Asp Asn Gly Glu Arg Ile
                405                 410                 415

Asp Leu Arg Phe His Pro Lys Pro Ser Asp Leu His Leu Gln Cys Gly
            420                 425                 430

Tyr Lys Val Glu Arg His Ile Arg Asp Gly Asp Leu Val Ile Phe Asn
        435                 440                 445

Arg Gln Pro Thr Leu His Lys Met Ser Met Met Gly His Arg Val Lys
    450                 455                 460

Val Leu Pro Trp Ser Thr Phe Arg Met Asn Leu Ser Cys Thr Ser Pro
465                 470                 475                 480

Tyr Asn Ala Asp Phe Asp Gly Asp Glu Met Asn Leu His Val Pro Gln
                485                 490                 495

Ser Met Glu Thr Arg Ala Glu Val Glu Asn Leu His Ile Thr Pro Arg
            500                 505                 510

Gln Ile Ile Thr Pro Gln Ala Asn Gln Pro Val Met Gly Ile Val Gln
        515                 520                 525

Asp Thr Leu Thr Ala Val Arg Lys Met Thr Lys Arg Asp Val Phe Ile
    530                 535                 540

Glu Lys Glu Gln Met Met Asn Ile Leu Met Phe Leu Pro Ile Trp Asp
545                 550                 555                 560

Gly Lys Met Pro Arg Pro Ala Ile Leu Lys Pro Lys Pro Leu Trp Thr
                565                 570                 575

Gly Lys Gln Ile Phe Ser Leu Ile Ile Pro Gly Asn Val Asn Met Ile
            580                 585                 590

Arg Thr His Ser Thr His Pro Asp Asp Glu Asp Asp Gly Pro Tyr Lys
        595                 600                 605

Trp Ile Ser Pro Gly Asp Thr Lys Val Met Val Glu His Gly Glu Leu
    610                 615                 620

Val Met Gly Ile Leu Cys Lys Lys Ser Leu Gly Thr Ser Ala Gly Ser
625                 630                 635                 640

Leu Leu His Ile Cys Met Leu Glu Leu Gly His Glu Val Cys Gly Arg
                645                 650                 655

Phe Tyr Gly Asn Ile Gln Thr Val Ile Asn Asn Trp Leu Leu Leu Glu
            660                 665                 670

Gly His Ser Ile Gly Ile Gly Asp Thr Ile Ala Asp Pro Gln Thr Tyr
        675                 680                 685

Thr Glu Ile Gln Arg Ala Ile Arg Lys Ala Lys Glu Asp Val Ile Glu
    690                 695                 700

Val Ile Gln Lys Ala His Asn Met Glu Leu Glu Pro Thr Pro Gly Asn
705                 710                 715                 720
```

-continued

```
Thr Leu Arg Gln Thr Phe Glu Asn Gln Val Asn Arg Ile Leu Asn Asp
                725                 730                 735

Ala Arg Asp Lys Thr Gly Gly Ser Ala Lys Lys Ser Leu Thr Glu Tyr
            740                 745                 750

Asn Asn Leu Lys Ala Met Val Val Ser Gly Ser Lys Gly Ser Asn Ile
        755                 760                 765

Asn Ile Ser Gln Val Ile Ala Cys Val Gly Gln Gln Asn Val Glu Gly
    770                 775                 780

Lys Arg Ile Pro Phe Gly Phe Arg Lys Arg Thr Leu Pro His Phe Ile
785                 790                 795                 800

Lys Asp Asp Tyr Gly Pro Glu Ser Arg Gly Phe Val Glu Asn Ser Tyr
                805                 810                 815

Leu Ala Gly Leu Thr Pro Ser Glu Phe Tyr Phe His Ala Met Gly Gly
            820                 825                 830

Arg Glu Gly Leu Ile Asp Thr Ala Val Lys Thr Ala Glu Thr Gly Tyr
        835                 840                 845

Ile Gln Arg Arg Leu Ile Lys Ala Met Glu Ser Val Met Val His Tyr
    850                 855                 860

Asp Gly Thr Val Arg Asn Ser Val Gly Gln Leu Ile Gln Leu Arg Tyr
865                 870                 875                 880

Gly Glu Asp Gly Leu Cys Gly Glu Met Val Glu Phe Gln Tyr Leu Ala
                885                 890                 895

Thr Val Lys Leu Ser Asn Lys Ala Phe Glu Arg Lys Phe Arg Phe Asp
            900                 905                 910

Pro Ser Asn Glu Arg Tyr Leu Arg Arg Val Phe Asn Glu Glu Val Ile
        915                 920                 925

Lys Gln Leu Met Gly Ser Gly Glu Val Ile Ser Glu Leu Glu Arg Glu
    930                 935                 940

Trp Glu Gln Leu Gln Lys Asp Arg Glu Ala Leu Arg Gln Ile Phe Pro
945                 950                 955                 960

Ser Gly Glu Ser Lys Val Val Leu Pro Cys Asn Leu Gln Arg Met Ile
                965                 970                 975

Trp Asn Val Gln Lys Ile Phe His Ile Asn Lys Arg Ala Pro Thr Asp
            980                 985                 990

Leu Ser Pro Leu Arg Val Ile Gln  Gly Val Arg Glu Leu  Leu Arg Lys
        995                 1000                1005

Cys Val  Ile Val Ala Gly Glu  Asp Arg Leu Ser Lys  Gln Ala Asn
    1010                1015                1020

Glu Asn  Ala Thr Leu Leu Phe  Gln Cys Leu Val Arg  Ser Thr Leu
    1025                1030                1035

Cys Thr  Lys Cys Val Ser Glu  Glu Phe Arg Leu Ser  Thr Glu Ala
    1040                1045                1050

Phe Glu  Trp Leu Ile Gly Glu  Ile Glu Thr Arg Phe  Gln Gln Ala
    1055                1060                1065

Gln Ala  Asn Pro Gly Glu Met  Val Gly Ala Leu Ala  Ala Gln Ser
    1070                1075                1080

Leu Gly  Glu Pro Ala Thr Gln  Met Thr Leu Asn Thr  Phe His Phe
    1085                1090                1095

Ala Gly  Val Ser Ser Lys Asn  Val Thr Leu Gly Val  Pro Arg Leu
    1100                1105                1110

Lys Glu  Ile Ile Asn Ile Ser  Lys Lys Pro Lys Ala  Pro Ser Leu
    1115                1120                1125
```

```
Thr Val  Phe Leu Thr Gly Ala  Ala Ala Arg Asp Ala  Glu Lys Ala
    1130                 1135                 1140

Lys Asn  Val Leu Cys Arg Leu  Glu His Thr Thr Leu  Arg Lys Val
    1145                 1150                 1155

Thr Ala  Asn Thr Ala Ile Tyr  Tyr Asp Pro Asp Pro  Gln Asn Thr
    1160                 1165                 1170

Val Ile  Pro Glu Asp Gln Glu  Phe Val Asn Val Tyr  Tyr Glu Met
    1175                 1180                 1185

Pro Asp  Phe Asp Pro Thr Arg  Ile Ser Pro Trp Leu  Leu Arg Ile
    1190                 1195                 1200

Glu Leu  Asp Arg Lys Arg Met  Thr Asp Lys Lys Leu  Thr Met Glu
    1205                 1210                 1215

Gln Ile  Ala Glu Lys Ile Asn  Ala Gly Phe Gly Asp  Asp Leu Asn
    1220                 1225                 1230

Cys Ile  Phe Asn Asp Asp Asn  Ala Glu Lys Leu Val  Leu Arg Ile
    1235                 1240                 1245

Arg Ile  Met Asn Ser Asp Asp  Gly Lys Phe Gly Glu  Gly Ala Asp
    1250                 1255                 1260

Glu Asp  Val Asp Lys Met Asp  Asp Asp Met Phe Leu  Arg Cys Ile
    1265                 1270                 1275

Glu Ala  Asn Met Leu Ser Asp  Met Thr Leu Gln Gly  Ile Glu Ala
    1280                 1285                 1290

Ile Ser  Lys Val Tyr Met His  Leu Pro Gln Thr Asp  Ser Lys Lys
    1295                 1300                 1305

Arg Ile  Val Ile Thr Glu Thr  Gly Glu Phe Lys Ala  Ile Ala Glu
    1310                 1315                 1320

Trp Leu  Leu Glu Thr Asp Gly  Thr Ser Met Met Lys  Val Leu Ser
    1325                 1330                 1335

Glu Arg  Asp Val Asp Pro Val  Arg Thr Phe Ser Asn  Asp Ile Cys
    1340                 1345                 1350

Glu Ile  Phe Ser Val Leu Gly  Ile Glu Ala Val Arg  Lys Ser Val
    1355                 1360                 1365

Glu Lys  Glu Met Asn Ala Val  Leu Ser Phe Tyr Gly  Leu Tyr Val
    1370                 1375                 1380

Asn Tyr  Arg His Leu Ala Leu  Leu Cys Asp Val Met  Thr Ala Lys
    1385                 1390                 1395

Gly His  Leu Met Ala Ile Thr  Arg His Gly Ile Asn  Arg Gln Asp
    1400                 1405                 1410

Thr Gly  Ala Leu Met Arg Cys  Ser Phe Glu Glu Thr  Val Asp Val
    1415                 1420                 1425

Leu Met  Asp Ala Ala Ser His  Ala Glu Val Asp Pro  Met Arg Gly
    1430                 1435                 1440

Val Ser  Glu Asn Ile Ile Leu  Gly Gln Leu Pro Arg  Met Gly Thr
    1445                 1450                 1455

Gly Cys  Phe Asp Leu Leu Leu  Asp Ala Glu Lys Cys  Lys Met Gly
    1460                 1465                 1470

Ile Ala  Ile Pro Gln Ala His  Ser Ser Asp Leu Met  Ala Ser Gly
    1475                 1480                 1485

Met Phe  Phe Gly Leu Ala Ala  Thr Pro Ser Ser Met  Ser Pro Gly
    1490                 1495                 1500

Gly Ala  Met Thr Pro Trp Asn  Gln Ala Ala Thr Pro  Tyr Val Gly
    1505                 1510                 1515

Ser Ile  Trp Ser Pro Gln Asn  Leu Met Gly Ser Gly  Met Thr Pro
```

```
    1520                1525                1530

Gly Gly  Ala Ala Phe Ser Pro  Ser Ala Ala Ser Asp  Ala Ser Gly
    1535                1540                1545

Met Ser  Pro Ala Tyr Gly Gly  Trp Ser Pro Thr Pro  Gln Ser Pro
    1550                1555                1560

Ala Met  Ser Pro Tyr Met Ala  Ser Pro His Gly Gln  Ser Pro Ser
    1565                1570                1575

Tyr Ser  Pro Ser Ser Pro Ala  Phe Gln Pro Thr Ser  Pro Ser Met
    1580                1585                1590

Thr Pro  Thr Ser Pro Gly Tyr  Ser Pro Ser Ser Pro  Gly Tyr Ser
    1595                1600                1605

Pro Thr  Ser Leu Asn Tyr Ser  Pro Thr Ser Pro Ser  Tyr Ser Pro
    1610                1615                1620

Thr Ser  Gln Ser Tyr Ser Pro  Thr Ser Pro Ser Tyr  Ser Pro Thr
    1625                1630                1635

Ser Pro  Asn Tyr Ser Pro Thr  Ser Pro Ser Tyr Ser  Pro Thr Ser
    1640                1645                1650

Pro Asn  Tyr Ser Pro Thr Ser  Pro Asn Tyr Ser Pro  Thr Ser Pro
    1655                1660                1665

Ser Tyr  Pro Ser Thr Ser Pro  Gly Tyr Ser Pro Thr  Ser Arg Ser
    1670                1675                1680

Tyr Ser  Pro Thr Ser Pro Ser  Tyr Ser Gly Thr Ser  Pro Ser Tyr
    1685                1690                1695

Ser Pro  Thr Ser Pro Ser Tyr  Ser Pro Thr Ser Pro  Ser Tyr Ser
    1700                1705                1710

Pro Ser  Ser Pro Asn Tyr Ser  Pro Thr Ser Pro Asn  Tyr Ser Pro
    1715                1720                1725

Thr Ser  Pro Asn Tyr Ser Pro  Ser Ser Pro Arg Tyr  Thr Pro Gly
    1730                1735                1740

Ser Pro  Ser Phe Ser Pro Ser  Ser Asn Ser Tyr Ser  Pro Thr Ser
    1745                1750                1755

Pro Gln  Tyr Ser Pro Thr Ser  Pro Ser Tyr Ser Pro  Ser Ser Pro
    1760                1765                1770

Lys Tyr  Ser Pro Thr Ser Pro  Asn Tyr Ser Pro Thr  Ser Pro Ser
    1775                1780                1785

Phe Ser  Gly Gly Ser Pro Gln  Tyr Ser Pro Thr Ser  Pro Lys Tyr
    1790                1795                1800

Ser Pro  Thr Ser Pro Asn Tyr  Thr Leu Ser Ser Pro  Gln His Thr
    1805                1810                1815

Pro Thr  Gly Ser Ser Arg Tyr  Ser Pro Ser Thr Ser  Ser Tyr Ser
    1820                1825                1830

Pro Asn  Ser Pro Asn Tyr Ser  Pro Thr Ser Pro Gln  Tyr Ser Ile
    1835                1840                1845

His Ser  Thr Lys Tyr Ser Pro  Ala Ser Pro Thr Phe  Thr Pro Thr
    1850                1855                1860

Ser Pro  Ser Phe Ser Pro Ala  Ser Pro Ala Tyr Ser  Pro Gln Pro
    1865                1870                1875

Met Tyr  Ser Pro Ser Ser Pro  Asn Tyr Ser Pro Thr  Ser Pro Ser
    1880                1885                1890

Gln Asp  Thr Asp
    1895
```

<210> SEQ ID NO 260

<211> LENGTH: 291
<212> TYPE: PRT
<213> ORGANISM: Diabrotica virgifera

<400> SEQUENCE: 260

```
Met Ser Ser Asn Ile Gln Lys Ala Gln Gln Leu Met Ala Asp Ala Glu
1               5                   10                  15

Lys Lys Val Thr Ser Arg Gly Phe Phe Gly Ser Leu Phe Gly Gly Ser
            20                  25                  30

Ser Arg Ile Glu Asp Ala Val Glu Cys Tyr Thr Arg Ala Ala Asn Leu
        35                  40                  45

Phe Lys Met Ala Lys Ser Trp Asp Ala Ala Gly Lys Ala Phe Cys Glu
    50                  55                  60

Ala Ala Asn Leu His Ser Arg Thr Gly Ala Arg His Asp Ala Ala Thr
65                  70                  75                  80

Asn Tyr Ile Asp Ala Ala Asn Cys Tyr Lys Lys Ala Asp Val Phe Glu
                85                  90                  95

Ala Val Asn Cys Phe Ile Lys Ala Ile Asp Ile Tyr Thr Glu Met Gly
            100                 105                 110

Arg Phe Thr Met Ala Ala Lys His His Gln Thr Ile Ala Glu Met Tyr
        115                 120                 125

Glu Thr Asp Ala Val Asp Ile Glu Arg Ala Val Gln His Tyr Glu Gln
    130                 135                 140

Ala Ala Asp Tyr Phe Arg Gly Glu Glu Ser Asn Ala Ser Ala Asn Lys
145                 150                 155                 160

Cys Leu Leu Lys Val Ala Gln Tyr Ala Ala Gln Leu Glu Asn Tyr Glu
                165                 170                 175

Lys Ala Val Gly Ile Tyr Gln Glu Val Ala Tyr Ala Ala Leu Glu Ser
            180                 185                 190

Ser Leu Leu Lys Tyr Ser Ala Lys Glu Tyr Leu Phe Arg Ala Ala Leu
        195                 200                 205

Cys His Leu Cys Val Asp Val Leu Asn Ala Gln His Ala Ile Glu Ser
    210                 215                 220

Tyr Ile Ser Arg Tyr Pro Ala Phe Gln Asp Ser Arg Glu Tyr Lys Leu
225                 230                 235                 240

Leu Lys Thr Leu Ile Glu Asn Ile Glu Glu Gln Asn Val Asp Gly Tyr
                245                 250                 255

Thr Glu Ala Val Lys Asp Tyr Asp Ser Ile Ser Arg Leu Asp Gln Trp
            260                 265                 270

Tyr Thr Thr Ile Leu Leu Arg Ile Lys Lys Gln Val Ser Glu Ser Pro
        275                 280                 285

Asp Leu Arg
    290
```

<210> SEQ ID NO 261
<211> LENGTH: 202
<212> TYPE: PRT
<213> ORGANISM: Diabrotica virgifera

<400> SEQUENCE: 261

```
Met Asn Pro Glu Tyr Asp Tyr Leu Phe Lys Leu Leu Leu Ile Gly Asp
1               5                   10                  15

Ser Gly Val Gly Lys Ser Cys Leu Leu Leu Arg Phe Ala Asp Asp Thr
            20                  25                  30

Tyr Thr Glu Ser Tyr Ile Ser Thr Ile Gly Val Asp Phe Lys Ile Arg
        35                  40                  45
```

Thr Ile Asp Leu Asp Gly Lys Thr Ile Lys Leu Gln Ile Trp Asp Thr
    50                  55                  60

Ala Gly Gln Glu Arg Phe Arg Thr Ile Thr Ser Ser Tyr Tyr Arg Gly
65                  70                  75                  80

Ala His Gly Ile Ile Val Val Tyr Asp Cys Thr Asp Gln Asp Ser Phe
                85                  90                  95

Asn Asn Val Lys Gln Trp Leu Glu Glu Ile Asp Arg Tyr Ala Cys Asp
            100                 105                 110

Asn Val Asn Lys Leu Leu Val Gly Asn Lys Ser Asp Leu Thr Thr Lys
        115                 120                 125

Lys Val Val Asp Phe Thr Thr Ala Lys Glu Tyr Ala Asp Gln Leu Gly
    130                 135                 140

Ile Pro Phe Leu Glu Thr Ser Ala Lys Asn Ala Thr Asn Val Glu Gln
145                 150                 155                 160

Ala Phe Met Thr Met Ala Ala Glu Ile Lys Asn Arg Val Gly Pro Pro
                165                 170                 175

Ser Ser Ala Val Asp Gln Gly Asn Lys Val Arg Phe Asp Gln Ser Arg
            180                 185                 190

Pro Val Glu Thr Thr Lys Ser Gly Cys Cys
        195                 200

<210> SEQ ID NO 262
<211> LENGTH: 262
<212> TYPE: PRT
<213> ORGANISM: Diabrotica virgifera

<400> SEQUENCE: 262

Met Ala Asp Ala Asp Asp Leu Leu Asp Tyr Glu Asp Glu Glu Gln Thr
1               5                   10                  15

Glu Gln Thr Ala Thr Glu Thr Ala Thr Thr Glu Val Gln Lys Lys Gly
            20                  25                  30

Val Lys Gly Thr Tyr Val Ser Ile His Ser Ser Gly Phe Arg Asp Phe
        35                  40                  45

Leu Leu Lys Pro Ala Ile Leu Arg Ala Ile Val Asp Cys Gly Phe Glu
    50                  55                  60

His Pro Ser Glu Val Gln His Glu Cys Ile Pro Gln Ala Val Ile Gly
65                  70                  75                  80

Met Asp Ile Leu Cys Gln Ala Lys Ser Gly Met Gly Lys Thr Ala Val
                85                  90                  95

Phe Val Leu Ala Thr Leu Gln Val Ile Asp Pro Thr Glu Asn Val Val
            100                 105                 110

Tyr Val Leu Val Met Cys His Thr Arg Glu Leu Ala Phe Gln Ile Ser
        115                 120                 125

Lys Glu Tyr Glu Arg Phe Ser Lys Tyr Met Pro Asn Ile Lys Val Gly
    130                 135                 140

Val Phe Phe Gly Gly Leu Pro Ile Gln Lys Asp Glu Glu Thr Leu Lys
145                 150                 155                 160

Asn Asn Cys Pro His Ile Val Val Gly Thr Pro Gly Arg Ile Leu Ala
                165                 170                 175

Leu Val Arg Ser Lys Lys Leu Asn Leu Lys His Leu Lys His Phe Ile
            180                 185                 190

Leu Asp Glu Cys Asp Lys Met Leu Glu Leu Leu Asp Met Arg Arg Asp
        195                 200                 205

Val Gln Glu Ile Tyr Arg Asn Thr Pro His Glu Lys Gln Val Met Met

```
    210                 215                 220

Phe Ser Ala Thr Leu Ser Lys Glu Ile Arg Pro Val Cys Lys Lys Phe
225                 230                 235                 240

Met Gln Asp Val Ile Gln Asn Ser Tyr Asn Thr Gln Phe Cys Asn Asp
                245                 250                 255

Ala Pro Thr Arg Asn Val
            260


<210> SEQ ID NO 263
<211> LENGTH: 245
<212> TYPE: PRT
<213> ORGANISM: Diabrotica virgifera

<400> SEQUENCE: 263

Met Pro Val Ile Asp Gly Tyr Lys Val Leu Tyr Ile Leu Leu His Ser
1               5                   10                  15

Leu Tyr Thr Ile Phe Glu Asn Ile Trp Arg Thr Leu Leu Phe Ile Tyr
            20                  25                  30

Gln Asn Cys Ile Arg Val Ile Asn Pro Glu Ser Thr Phe Asp Asp Ala
        35                  40                  45

Asp Gln Leu Lys Lys Arg Leu Ser Arg Leu Thr Lys Lys Pro Gln His
    50                  55                  60

Leu Thr Ile Ile Ile Gly Val Glu Glu Tyr Ser Leu Val Asp Leu Ala
65                  70                  75                  80

Asn Leu Val Tyr Trp Cys Leu Gly Leu Asn Ile Pro Tyr Val Ser Phe
                85                  90                  95

Tyr Asp Tyr Lys Gly Asn Leu Lys Lys His Glu Glu Lys Leu Gln Gln
            100                 105                 110

Ile Val Glu Ser Arg Lys Ser Glu Asn Ile Asn Ile Ile Trp His Thr
        115                 120                 125

His Ala Glu Gln Arg His Lys Asn Gly Phe Leu Gly Pro Lys Ile His
    130                 135                 140

Val Lys Val Leu Thr His Ala Asp Gly Lys Gln Ser Ile Val Asn Val
145                 150                 155                 160

Thr Lys Lys Leu Ala Leu Asn Lys Glu Lys Asp Ile Ser Lys Glu Lys
                165                 170                 175

Ile Ser Glu Leu Leu Leu Arg Gln Tyr Glu Phe Pro Asp Pro Glu Met
            180                 185                 190

Ala Ile Ile Cys Gly Lys Lys Leu Asn Ile Tyr Asn Tyr Pro Pro Trp
        195                 200                 205

Gln Leu Arg Leu Thr Glu Phe Phe Lys Val Asn Lys Val Asn Asn Ile
    210                 215                 220

Thr Phe Pro Val Phe Val Glu Lys Leu Glu Lys Tyr Ser Lys Cys Glu
225                 230                 235                 240

Gln Arg Val Gly Lys
                245


<210> SEQ ID NO 264
<211> LENGTH: 159
<212> TYPE: PRT
<213> ORGANISM: Diabrotica virgifera

<400> SEQUENCE: 264

Met Thr Asn Ser Lys Gly Tyr Arg Arg Gly Thr Arg Asp Leu Phe Ala
1               5                   10                  15

Arg Lys Phe Lys Lys Arg Gly Val Ile Pro Leu Ser Thr Tyr Leu Arg
```

20 25 30

Val Tyr Lys Val Gly Asp Ile Val Asp Ile Lys Gly Asn Gly Ala Val
35 40 45

Gln Lys Gly Met Pro His Lys Val Tyr His Gly Lys Thr Gly Arg Val
50 55 60

Phe Asn Val Thr Ala His Ala Leu Gly Val Ile Val Asn Lys Arg Val
65 70 75 80

Arg Gly Arg Ile Ile Pro Lys Arg Ile Asn Leu Arg Ile Glu His Val
85 90 95

Asn His Ser Lys Cys Arg Gln Asp Phe Leu Gln Arg Val Lys Ser Asn
100 105 110

Glu Lys Leu Arg Lys Glu Ala Lys Glu Lys Asn Ile Lys Val Glu Leu
115 120 125

Arg Arg Gln Pro Ala Gln Pro Arg Pro Ala His Ile Val Ser Gly Lys
130 135 140

Val Pro Ala Gln Val Leu Ala Pro Ile Pro Tyr Glu Phe Ile Ala
145 150 155

<210> SEQ ID NO 265
<211> LENGTH: 178
<212> TYPE: PRT
<213> ORGANISM: Diabrotica virgifera

<400> SEQUENCE: 265

Met Glu Gly Ile Leu Leu Glu Pro Thr Leu Tyr Thr Ile Lys Gly Ile
1 5 10 15

Ala Ile Leu Asp Tyr Asp Gly Asn Arg Val Leu Ala Lys Tyr Tyr Asp
20 25 30

Lys Asp Ile Phe Pro Thr Ala Lys Glu Gln Lys Ala Phe Glu Lys Asn
35 40 45

Leu Phe Asn Lys Thr His Arg Ala Asp Ala Glu Ile Ile Met Leu Asp
50 55 60

Gly Leu Thr Cys Val Tyr Arg Ser Asn Val Asp Leu Phe Phe Tyr Val
65 70 75 80

Met Gly Ser Ser His Glu Asn Glu Leu Ile Leu Met Ser Val Leu Asn
85 90 95

Cys Leu Tyr Asp Ser Val Ser Gln Ile Leu Lys Lys Asn Met Gln Lys
100 105 110

Arg Ala Val Leu Glu Ser Leu Asp Ile Val Met Leu Ala Met Asp Glu
115 120 125

Ile Val Asp Gly Gly Ile Ile Ile Asp Ser Asp Ser Ser Ser Val Val
130 135 140

Ser Arg Ile Ala Leu Arg Thr Asp Asp Ile Pro Leu Gly Glu Gln Thr
145 150 155 160

Val Ala Gln Val Phe Gln Thr Ala Lys Glu Gln Leu Lys Trp Ser Leu
165 170 175

Leu Lys

<210> SEQ ID NO 266
<211> LENGTH: 149
<212> TYPE: PRT
<213> ORGANISM: Diabrotica virgifera

<400> SEQUENCE: 266

Met Ala Asp Gln Leu Thr Glu Glu Gln Ile Ala Glu Phe Lys Glu Ala
1 5 10 15

Phe Ser Leu Phe Asp Lys Asp Gly Asp Gly Thr Ile Thr Thr Lys Glu
20 25 30

Leu Gly Thr Val Met Arg Ser Leu Gly Gln Asn Pro Thr Glu Ala Glu
35 40 45

Leu Gln Asp Met Ile Asn Glu Val Asp Ala Asp Gly Asn Gly Thr Ile
50 55 60

Asp Phe Pro Glu Phe Leu Thr Met Met Ala Arg Lys Met Lys Asp Thr
65 70 75 80

Asp Ser Glu Glu Glu Ile Arg Glu Ala Phe Arg Val Phe Asp Lys Asp
85 90 95

Gly Asn Gly Phe Ile Ser Ala Ala Glu Leu Arg His Val Met Thr Asn
100 105 110

Leu Gly Glu Lys Leu Thr Asp Glu Glu Val Asp Glu Met Ile Arg Glu
115 120 125

Ala Asp Ile Asp Gly Asp Gly Gln Val Asn Tyr Glu Glu Phe Val Thr
130 135 140

Met Met Thr Ser Lys
145

<210> SEQ ID NO 267
<211> LENGTH: 670
<212> TYPE: PRT
<213> ORGANISM: Diabrotica virgifera

<400> SEQUENCE: 267

Met Met Gln Ala Asn Asn Arg Val Pro Pro Ile Lys Leu Glu Asn Asp
1 5 10 15

Ile Asp Leu Tyr Ala Asp Asp Ile Glu Asp Phe Ala Gln Asp Asp Phe
20 25 30

Gly Gly Glu Asn Val Asp Leu Tyr Asp Asp Val Ile Ser Ala Pro Pro
35 40 45

Gly Asn Asn Asp Asn Pro Gly Asp Ser Asn His His Ala Pro Pro Gly
50 55 60

Ala Gly Glu Asp Gly Gly Gly Asn Phe Val Gly Ser Gly Gly Ala Pro
65 70 75 80

Asn Asn Ile Asn Ser Ser Gly Arg Arg His Gln Leu Tyr Val Gly Asn
85 90 95

Leu Thr Trp Trp Thr Thr Asp Gln Asp Ile Glu Asn Ala Val His Asp
100 105 110

Ile Gly Val Thr Asp Phe His Glu Val Lys Phe Phe Glu His Arg Ala
115 120 125

Asn Gly Gln Ser Lys Gly Phe Cys Val Ile Ser Leu Gly Ser Glu Gly
130 135 140

Ser Met Arg Leu Cys Leu Glu Leu Leu Ser Lys Lys Glu Ile Asn Gly
145 150 155 160

Gln Asn Pro Leu Val Thr Leu Pro Thr Lys Gln Ala Leu Ser Asn Phe
165 170 175

Glu Ser Gln Ser Lys Thr Arg Pro Ser Pro Thr Asn Asn Ser Asn Ser
180 185 190

Arg Pro Pro His Pro Asn Asn Asn Val His Ser Gly Pro Met Gln Asn
195 200 205

Tyr Gly Gly Arg Met Pro Met Asn Pro Ser Met Arg Pro Met Pro Pro
210 215 220

Gly Met Gln Gly Ala Pro Arg Met Gln Gly Pro Pro Gly Phe Asn Gly

-continued

```
225                 230                 235                 240

Pro Pro Asn Met Asn Gln Gln Pro Pro Arg Phe Gln Gly Asn Pro Gln
                245                 250                 255

Trp Asn Gly Pro Arg Pro Asn Gly Pro Gly Pro Asn Met Gly Met Arg
            260                 265                 270

Pro Met Gly Pro Pro His Gly Gln Gln Gly Pro Pro Arg Pro Pro Met
        275                 280                 285

Gln Gly Pro Pro Gln Gln Gly Pro Pro Arg Gly Met Pro Pro Gln Gly
    290                 295                 300

Pro Pro Gln Met Arg Pro Glu Trp Asn Arg Pro Pro Met Gln Gln Gly
305                 310                 315                 320

Tyr Pro Gln Gly Pro Pro His Met Gln Gly Pro Asn Met Gly Pro Arg
                325                 330                 335

Gly Pro Pro Gln Met Gly Pro Pro Gly Ala Pro Gln Gln Gln Gly Pro
            340                 345                 350

Ala Pro His Val Asn Pro Ala Phe Phe Gln Gln Gly Gly Gly Pro Pro
        355                 360                 365

Pro Pro Met Gln His Met Pro Gly Pro Gly Pro Val Met Pro Pro Gln
    370                 375                 380

Gly Pro Pro Gln Gly Pro Pro His Gly Pro Val Gly Pro Pro His Gly
385                 390                 395                 400

Pro Pro Leu Gly Pro Ala Asn Val Pro Pro His Gly Pro Pro His Gly
                405                 410                 415

Tyr Gly Pro Pro Ala Ala Met Pro Gln Pro Pro Tyr Gly Gly Pro Pro
            420                 425                 430

Pro Asp His Arg Ala Glu Ile Pro Gln Leu Thr Glu Gln Glu Phe Glu
        435                 440                 445

Asp Ile Met Ser Arg Asn Arg Thr Val Ser Ser Ser Ala Ile Gly Arg
    450                 455                 460

Ala Val Ser Asp Ala Ala Ala Gly Glu Phe Ala Ser Ala Ile Glu Thr
465                 470                 475                 480

Leu Val Thr Ala Ile Ser Leu Ile Lys Gln Ser Lys Val Ala Asn Asp
                485                 490                 495

Asp Arg Cys Lys Ile Leu Ile Ser Ser Leu Gln Asp Thr Leu Arg Gly
            500                 505                 510

Val Glu Asp Lys Ser Tyr Ser Ser Ser Arg Arg Asp Arg Ser Arg Ser
        515                 520                 525

Arg Asp Arg Ser His Arg Arg Thr Arg Arg Glu Arg Ser Ser Ser Arg
    530                 535                 540

Tyr Arg Asp Arg Ser Arg Glu Arg Glu Arg Glu Arg Asp Arg Asp Arg
545                 550                 555                 560

Asp Arg Glu Arg Asp Arg Tyr Tyr Asp Arg Tyr Ser Glu Arg Glu Arg
                565                 570                 575

Asp Arg Asp Arg Ser Arg Ser Arg Glu Arg Thr Glu Arg Asp Arg Glu
            580                 585                 590

Arg Asp Tyr Arg Asp Arg Glu Pro Glu Glu Thr Asp Lys Glu Lys Ser
        595                 600                 605

Lys Val Ser Arg Val Ser Arg Ser Arg Asn Lys Ser Pro Glu Pro Val
    610                 615                 620

Glu Pro Ser Ser Glu Val Pro Lys Ser Ser Arg Tyr Tyr Glu Asp Arg
625                 630                 635                 640

Tyr Arg Glu Arg Glu Arg Glu Gly Arg Arg Glu Ser Asp Arg Glu Arg
                645                 650                 655
```

```
Glu Arg Asp Arg Arg Gly Glu Asp Ser His Arg Ser Arg His
            660                 665                 670


<210> SEQ ID NO 268
<211> LENGTH: 254
<212> TYPE: PRT
<213> ORGANISM: Diabrotica virgifera

<400> SEQUENCE: 268

Met Ser Ser Ile Gly Thr Gly Tyr Asp Leu Ser Ala Ser Gln Phe Ser
1               5                   10                  15

Pro Asp Gly Arg Val Phe Gln Val Glu Tyr Ala Met Lys Ala Val Glu
            20                  25                  30

Asn Ser Gly Thr Val Ile Gly Leu Arg Gly Thr Asp Gly Ile Val Leu
        35                  40                  45

Ala Ala Glu Lys Leu Ile Met Ser Lys Leu His Glu Pro Ser Thr Asn
    50                  55                  60

Lys Arg Ile Phe Asn Ile Asp Lys His Ile Gly Met Ala Phe Ser Gly
65                  70                  75                  80

Leu Ile Ala Asp Ala Arg Gln Ile Val Glu Ile Ala Arg Lys Glu Ala
                85                  90                  95

Ser Asn Tyr Arg His Gln Tyr Gly Ser Asn Ile Pro Leu Lys Tyr Leu
            100                 105                 110

Asn Asp Arg Val Ser Met Tyr Met His Ala Tyr Thr Leu Tyr Ser Ala
        115                 120                 125

Val Arg Pro Phe Gly Cys Ser Val Ile Leu Ala Ser Tyr Glu Asp Ser
    130                 135                 140

Asp Pro Ser Met Tyr Leu Ile Asp Pro Ser Gly Val Ser Tyr Gly Tyr
145                 150                 155                 160

Phe Gly Cys Ala Thr Gly Lys Ala Lys Gln Ser Ala Lys Thr Glu Ile
                165                 170                 175

Glu Lys Leu Lys Met Gly Asn Leu Thr Cys Lys Glu Leu Val Lys Glu
            180                 185                 190

Ala Ala Lys Ile Ile Tyr Leu Val His Asp Glu Leu Lys Asp Lys Asn
        195                 200                 205

Phe Glu Leu Glu Leu Ser Trp Val Cys Lys Asp Thr Asn Gly Leu His
    210                 215                 220

Thr Lys Val Pro Glu Ser Val Phe Ala Asp Ala Glu Lys Ala Ala Lys
225                 230                 235                 240

Gln Ala Met Glu Ala Asp Ser Glu Ser Asp Thr Glu Asp Met
                245                 250


<210> SEQ ID NO 269
<211> LENGTH: 246
<212> TYPE: PRT
<213> ORGANISM: Diabrotica virgifera

<400> SEQUENCE: 269

Met Ala Ser Lys Asp Arg Leu Met Ile Phe Pro Ser Arg Gly Ala Gln
1               5                   10                  15

Met Met Met Lys Ser Arg Leu Lys Gly Ala Gln Lys Gly His Ser Leu
            20                  25                  30

Leu Lys Lys Lys Ala Asp Ala Leu Gln Met Arg Phe Arg Met Ile Leu
        35                  40                  45

Asn Lys Ile Ile Glu Thr Lys Thr Leu Met Gly Glu Val Met Lys Glu
    50                  55                  60
```

```
Ala Ala Phe Ser Leu Ala Glu Ala Lys Phe Ala Thr Gly Asp Phe Asn
65                  70                  75                  80

Gln Val Val Leu Gln Asn Val Thr Lys Ala Gln Ile Lys Ile Arg Thr
                85                  90                  95

Lys Lys Asp Asn Val Ala Gly Val Thr Leu Pro Val Phe Glu Cys Tyr
            100                 105                 110

Gln Asp Gly Thr Asp Thr Tyr Glu Leu Ala Gly Leu Ala Arg Gly Gly
        115                 120                 125

Gln Gln Leu Thr Lys Leu Lys Lys Asn Tyr Gln Ser Ala Val Lys Leu
    130                 135                 140

Leu Val Glu Leu Ala Ser Leu Gln Thr Ser Phe Val Thr Leu Asp Asp
145                 150                 155                 160

Val Ile Lys Ile Thr Asn Arg Arg Val Asn Ala Ile Glu His Val Ile
                165                 170                 175

Ile Pro Arg Ile Glu Arg Thr Leu Ala Tyr Ile Ile Ser Glu Leu Asp
            180                 185                 190

Glu Leu Glu Arg Glu Glu Phe Tyr Arg Leu Lys Lys Ile Gln Asp Lys
        195                 200                 205

Lys Lys Ile Ser Arg Ala Lys Ala Glu Lys Gln Lys Gln Ala Leu Leu
    210                 215                 220

Gln Ala Gly Leu Leu Lys Glu Ser Gln Ala Asn Met Leu Leu Asp Glu
225                 230                 235                 240

Gly Asp Glu Asp Leu Leu
                245


<210> SEQ ID NO 270
<211> LENGTH: 1605
<212> TYPE: PRT
<213> ORGANISM: Diabrotica virgifera

<400> SEQUENCE: 270

Met Glu Ala Ala Pro Lys Leu Pro Met Leu Ser Phe Glu Leu Asn Thr
1               5                   10                  15

Cys Thr Glu Asn Val His Phe Gly Pro Gln Leu Lys Gln Tyr Ile Ala
            20                  25                  30

Ala Phe Tyr Gly Glu Asp Pro Glu Ser Tyr Ile Thr Glu Ile Ser Asn
        35                  40                  45

Leu Glu Ser Leu Arg Ser Ala Ala Val Arg Pro Ser Thr Asp Val Asn
    50                  55                  60

Gly Val Gln Leu Leu Lys Lys Tyr Phe Cys Gln Leu Arg Phe Leu Lys
65                  70                  75                  80

Ser Arg Phe Pro Met Glu Glu Asn Gln Asp Ala Ala Val Leu Phe Ser
                85                  90                  95

Trp Lys Asn Asn Glu Leu Asp Ile Thr Ser Thr Ser Ser Asp Ile Arg
            100                 105                 110

Tyr Glu Leu Met Val Ile Met Tyr Asn Ile Gly Ala Leu His Thr Phe
        115                 120                 125

Leu Gly Ala Asn Asp Ser Arg Asn Asn Pro Asp Gly Met Lys Met Ala
    130                 135                 140

Cys Thr His Phe Gln Cys Ala Ala Trp Ala Phe Gln Asn Val Lys Glu
145                 150                 155                 160

Lys Tyr His Gln Phe Ile Ser Asn Ile Ser Leu Val Glu Leu Val His
                165                 170                 175

Phe Phe Gln Gln Val Cys Leu Ala Gln Ala Gln Glu Cys Ile Leu Glu
```

```
            180                 185                 190

Lys Ser Met Phe Asp Asn Arg Lys Pro Thr Ile Ile Ala Lys Val Ala
        195                 200                 205

Ile Gln Val Tyr Ser Tyr Tyr Arg Gln Ser Leu Arg Val Leu Glu Ser
    210                 215                 220

Val Asn Glu Ala Tyr Phe Arg Asp Lys Thr Tyr Lys Glu Trp Met Lys
225                 230                 235                 240

Tyr Leu Gln Phe Lys Leu Thr Tyr Tyr Lys Cys Ile Ser Phe Leu Phe
                245                 250                 255

Gln Gly Gln Gln Ala Glu Glu Gln Gln Lys Met Gly Glu Arg Val Ala
            260                 265                 270

Phe Tyr Gln Ala Ala Cys Glu Gln Leu Asp Glu Ala Lys Lys Ile Ala
        275                 280                 285

Ala Thr Leu Lys Asn Gln His His Gln Gln Glu Ile Asn Glu Gly Leu
    290                 295                 300

Ala Phe Thr Thr Asp Val Val Glu Gly Lys Arg Lys Ala Ala Lys Asn
305                 310                 315                 320

Glu Asn Glu Phe Ile Tyr His Glu Ser Val Pro Asp Lys Asp Gln Leu
                325                 330                 335

Pro Glu Val Lys Gly Ala Ser Leu Val Lys Gly Ile Pro Phe Ser Ile
            340                 345                 350

Asn Asp Ile Glu Val Ser Gly Pro Asp Ile Phe Ser Arg Leu Val Pro
        355                 360                 365

Met Glu Ala His Glu Ala Ala Ser Leu Tyr Ser Glu Lys Lys Ala Gln
    370                 375                 380

Arg Leu Arg Gln Ile Gly Glu Leu Ile Glu Asn Lys Asp Gln Thr Leu
385                 390                 395                 400

Ala Glu Phe Met Ser Ser Met Gln Leu Asp Leu Leu Thr Lys Met His
                405                 410                 415

Gln Ala Thr Gly Ile Pro Gln Glu Leu Ile Asp Arg Ala Ala Ala Leu
            420                 425                 430

Ser Ala Lys Pro Asn Ala Ile Gln Asp Leu Ile Ser Ala Met Gly Lys
        435                 440                 445

Leu Ser Asn Ile Tyr Gln Asp Val Glu Ala Ser Leu Asn Glu Ile Asp
    450                 455                 460

Ser Leu Leu Lys Ala Glu Glu Gln Ser Glu Gln Lys Tyr Gln Glu Thr
465                 470                 475                 480

Ile Gly Lys Arg Pro Pro Ser Ile Leu Ala Thr Asp Leu Thr Arg Glu
                485                 490                 495

Ala Ala Lys Tyr Arg Glu Ala His Thr Lys Ala Asn Asp Ser Asn Gln
            500                 505                 510

Thr Leu His Arg Ala Met Met Ala His Val Ala Asn Leu Lys Ile Leu
        515                 520                 525

Gln Gln Pro Leu Lys Gln Leu Gln His Gln Leu Pro Phe Val Glu Phe
    530                 535                 540

Pro Asn Pro Asn Ile Asp Glu Lys Ser Leu Lys Asp Leu Glu Ala Leu
545                 550                 555                 560

Val Ala Lys Val Asp Glu Met Arg Thr Gln Arg Ala Met Leu Trp Ala
                565                 570                 575

Gln Leu Arg Glu Ser Ile His Gln Asp Asp Ile Thr Ser Ser Leu Val
            580                 585                 590

Thr Lys Gln Pro Asn Gln Ser Leu Glu Gln Leu Phe Gln Gln Glu Leu
        595                 600                 605
```

```
Gln Lys His Gln Asn Leu Ile Ser Leu Ile Glu Gln Asn Thr Ser Ala
    610                 615                 620

Gln Glu Asn Ile Lys Ser Ala Leu Val Asp Ser Tyr Ala Tyr Ala Val
625                 630                 635                 640

Asn Ser Arg Lys Tyr Ile Gln Asp Ile Leu Gln Lys Arg Thr Thr Thr
                645                 650                 655

Ile Thr Ser Leu Ile Ala Ser Phe Asp Ser Tyr Glu Asp Leu Leu Ala
            660                 665                 670

Lys Ala Asn Lys Gly Ile Glu Phe Tyr Ser Lys Leu Glu Thr Asn Val
        675                 680                 685

Ser Lys Leu Leu Gln Arg Ile Arg Ser Thr Cys Lys Val Gln Gln Glu
    690                 695                 700

Glu Arg Asp Gln Met Met Ser Thr Ala Gln Val Pro Gln Trp Glu Ser
705                 710                 715                 720

His Thr Ser Leu Ala Ala Pro Lys Leu Lys Asp Tyr Leu Asp Ser Arg
                725                 730                 735

Lys Lys Ser Ala Ala Tyr Ser Glu Pro Ser Val Gln Pro Gln Gln Pro
            740                 745                 750

Thr Leu Ser Tyr Ser Ala Ala Met Asp Leu Pro Pro Gly Ile Arg Pro
        755                 760                 765

Thr Pro Val Gly Ser Glu Ile Thr Asp Val Pro Lys Asn Ile Gln Gly
    770                 775                 780

Glu Pro Gln Gly Tyr Ile Pro Tyr Asn Tyr Gln Gln Pro Ser Val Pro
785                 790                 795                 800

Ala Ser Gln Asn Ile Asp Glu Glu Thr Ile Lys Lys Met Asn Ala Leu
                805                 810                 815

Met Pro Gly Ala Lys Thr Ser Val Pro Ser Gln Tyr Gly Tyr Ser Asn
            820                 825                 830

Tyr Ile Pro Pro Thr Tyr Pro Gln Ser Ala Tyr Gln Pro Gly Asn Gln
        835                 840                 845

Ser Tyr Gly Lys Glu Thr Pro Asp Ile Asn Ser Pro Tyr Asp Pro Thr
    850                 855                 860

Lys Ala Phe Thr Ala Thr Thr Asn Ala Tyr Arg Ser Val Gln Ser Ser
865                 870                 875                 880

Ser Thr Gln Gly Tyr Val Pro Tyr Ala Glu Ser Asn Val Ser Asn Val
                885                 890                 895

Asp Arg Val Gly Tyr Pro Ser Arg Tyr Gln Tyr Gln Gln Val Pro Glu
            900                 905                 910

Ile Ala Thr Thr Pro Ala Asp Pro Asn Ile Asn Ala Tyr Tyr Pro His
        915                 920                 925

Gly Tyr Ser Pro Ser Gln Asn Leu Pro Asn Ala Asn Thr Gln His Ile
    930                 935                 940

Thr Gly Gln Leu Lys Tyr His Ser Val Glu Tyr Ala Ser Ser Val Pro
945                 950                 955                 960

Asn Asn Ile Asn Tyr Asn Ser Ser Thr Tyr Ser Ser Pro Leu Ser Asn
                965                 970                 975

Met Ser Ser Thr Asn Ser Ser Asn Pro Ser Asn Leu Asn Asn Ser Tyr
            980                 985                 990

Glu Tyr Tyr Tyr Asp Pro Asn Thr  Ser Ser Gly Ala Val  Pro Asn Ala
        995                 1000                 1005

Ser Lys  Pro Gln Gln Ser Ser  Ala Ser Ser Ala Asn  Pro Ser Thr
    1010                 1015                 1020
```

```
Ala Met  Asn Asn Tyr Asn Tyr  Tyr Tyr Asn Thr Ser  Thr Ser Gly
    1025                 1030                 1035

Ser Val  Ala Ala Asp Thr Ser  Lys Ile Gln Gln Gln  Gln Gln Tyr
    1040                 1045                 1050

Pro Gly  Thr Gln Met Ser Gln  Ala Gln Tyr Tyr Pro  Ala Asn Ala
    1055                 1060                 1065

Ser Tyr  Tyr Ser Thr Ser Thr  Tyr Asn Thr Asn Val  Gln Gly Gly
    1070                 1075                 1080

Thr Asn  Pro Ser Tyr Ala Thr  Gly Gln Thr Tyr Asn  Gln Val Thr
    1085                 1090                 1095

Pro Val  Thr Ser Gln Asn Val  Ser Gln Asn Tyr Asn  Phe Asn Gln
    1100                 1105                 1110

Val Gly  Ser Gly Ala Gly His  Gln His Gln Tyr Tyr  Ser Ser Ala
    1115                 1120                 1125

Asn Ala  Ala Val Pro Ser Gln  Gln Ala Val Asn Asn  Ser Ser Leu
    1130                 1135                 1140

Pro Asn  Tyr Gly Tyr Asp Gln  Tyr Tyr Gly Asn Asn  Tyr Asn Ser
    1145                 1150                 1155

Ser Gln  Pro Ser Thr Tyr Ser  Ala Asn Gln Ala Pro  Pro Ala Ala
    1160                 1165                 1170

Gln Ala  Ala Pro Ser Asn Ile  Pro Ala Ala Thr Lys  Ser Ser Ser
    1175                 1180                 1185

Asn Val  Asp Leu Leu Ser Gly  Leu Asp Phe Ser Ile  Ser Gln Ala
    1190                 1195                 1200

Pro Leu  Val Pro Gln Gln Asn  Ile Thr Ile Lys Pro  Gln Glu Lys
    1205                 1210                 1215

Glu Thr  Lys Pro Pro Ala Val  Ser Ser Glu Thr Lys  Asn Gln Asp
    1220                 1225                 1230

Pro Thr  Pro Val Thr Thr Pro  Lys Gln Pro Thr Gly  Pro Glu Val
    1235                 1240                 1245

Lys Arg  Leu Tyr Val Lys Ile  Leu Pro Ser Lys Pro  Leu Asn Asn
    1250                 1255                 1260

Asp Asp  Val Lys Lys Leu Phe  Gly Gln Glu Leu Asp  Arg Tyr Glu
    1265                 1270                 1275

Lys Phe  Val Glu Thr Leu Thr  His Lys Thr Leu Ser  Gly Pro Thr
    1280                 1285                 1290

Thr Leu  Asp Ile Lys Trp Lys  Glu Ile Gln Asp Gln  Gln Asp Cys
    1295                 1300                 1305

Glu Pro  Gln Lys Lys Ile Ile  Ser Val Ala Arg Cys  Tyr Pro Met
    1310                 1315                 1320

Lys Asn  Arg Phe Pro Asp Ile  Leu Pro Tyr Asp Phe  Ser Arg Val
    1325                 1330                 1335

Glu Leu  Cys Asp Ser Lys Asp  Asp Tyr Ile Asn Ala  Ser Tyr Ile
    1340                 1345                 1350

Lys Asp  Ile Ser Pro Tyr Ala  Pro Ser Phe Ile Val  Thr Gln Val
    1355                 1360                 1365

Pro Leu  Ser Ser Thr Val Gly  Asp Met Trp Thr Met  Ile Arg Glu
    1370                 1375                 1380

Gln Gln  Val Glu Leu Ile Leu  Cys Leu Val Asn Asp  Asn Glu Ile
    1385                 1390                 1395

Gly Glu  Asp Ile Tyr Trp Pro  Lys Glu Lys Gly Ser  Ser Leu Asn
    1400                 1405                 1410

Ile Leu  Asn Met Val Ile Thr  Leu Gln Asn Val Ile  Val Lys Ser
```

```
    1415                1420                1425

His Trp  Thr Glu Arg Leu Ile  Ala Ile Asn Leu Pro  Glu Lys Arg
    1430                1435                1440

Glu Ser  Arg Val Ile Met His  Leu Gln Phe Thr Ser  Trp Pro Gly
    1445                1450                1455

Ser Leu  Phe Pro Thr Asn Pro  Glu Pro Phe Val Ser  Tyr Thr Leu
    1460                1465                1470

Glu Ser  Ile Asn Leu Tyr Gln  Gln Gln Lys Thr Asn  Thr His Pro
    1475                1480                1485

Val Val  Val His Cys Ser Ser  Gly Ile Gly Arg Ser  Gly Leu Leu
    1490                1495                1500

Cys Leu  Leu Thr Ala Ala Met  Phe Asp Ala Ala Asn  Asn Ala Asn
    1505                1510                1515

Ser Ile  Pro Asp Leu Thr Ala  Leu Ser Ile Lys Leu  Ser Asn Cys
    1520                1525                1530

Arg Lys  Asn Ile Leu Arg Asp  Arg Glu His Leu Lys  Phe Gly Tyr
    1535                1540                1545

Glu Ser  Phe Leu Ala Tyr Ile  Arg His Ile Val Cys  Glu Asp Lys
    1550                1555                1560

Ala Arg  Lys Lys Leu Asn Glu  Ile Gln Pro Lys Val  Lys Glu Glu
    1565                1570                1575

Pro Leu  Glu Pro Pro Val Ile  Val Pro Glu Pro Asn  Ile Asp Pro
    1580                1585                1590

Leu Ser  Thr Leu Asp Pro Phe  Trp Ala Ser Lys Arg
    1595                1600                1605
```

```
<210> SEQ ID NO 271
<211> LENGTH: 744
<212> TYPE: DNA
<213> ORGANISM: Diabrotica barberi

<400> SEQUENCE: 271

atgatgtcga aagtagacaa agatgaagac gcctccttcg caaaattgga aaatcagatt      60

gctgtcatca aatacgtaat actctttacc aacgtcttgc aatgggctct cggtgcagca     120

atcttcgctc tttgcctttg gctacgattc gaggagggca ttcaagaatg gctccagaaa     180

ttggattcag aacaatttta catcggagta tatgtactta tagtcgcttc actgatcgtc     240

atgattgtgt cctttatagg atgtattagt gccctgcagg agagtactac ggccctttta     300

gtgtacatcg gcacccaagt gctcagtttt atattcggtt tatccggttc ggcggttctt     360

ctggataaca gcgccagaga ttcccacttc caaccgagga tccgagagag tatgcgacgt     420

cttatcatga atgctcatca cgaccaatcc agacaaacac tagccatgat tcaggaaaat     480

gttggttgct gcggagctga tggcgcaaca gactacctct ctcttcaaca gccccttcca     540

agtcagtgca gagacaccgt tactggaaac ccattcttcc acggatgtgt agatgaactc     600

acctggttct tcgaagaaaa atgtggctgg atagcaggtt tagctatggc gatatgcatg     660

attaacgtcc ttagtattgt tttatctacg gtactcatcc aggcattgaa aaaagaagaa     720

gaagcatcag attcatacag gaga                                            744


<210> SEQ ID NO 272
<211> LENGTH: 876
<212> TYPE: DNA
<213> ORGANISM: Diabrotica barberi

<400> SEQUENCE: 272
```

atgtcgtcaa atattcaaaa ggcccagcag ttgatggcgg atgcagaaaa gaaagtaaca 60
tctcgaggtt tcttcggatc tctatttggg ggatcaagtc gtattgaaga tgcagtggaa 120
tgttacacaa gagctgcaaa cctttttaaa atggccaaga gctgggatgc tgccggtaaa 180
gccttttgtg aggctgctaa tttgcattca agaactggtg ctcgtcatga cgctgccact 240
aattatatag atgctgcaaa ttgttacaaa aaagccgatg tatttgaggc tgtaaactgc 300
tttataaaag ctatagacat ttataccgaa atgggtcgct ttacaatggc tgcaaaacac 360
catcagacta ttgcagaaat gtatgagact gatgctgtgg acatcgaaag ggctgttcaa 420
cactatgaac aggcggctga ttacttcaga ggagaagaaa gcaatgcttc cgccaataag 480
tgtcttctta aagtggctca atatgcagcc caacttgaaa actatgaaaa agcagtggga 540
atttatcaag aagtggctta cgcagctctg gaaagctctc ttttaaaata cagtgcaaag 600
gaatacttat tcagagctgc cctttgtcac ctttgtgttg atgtactcaa tgcacaacat 660
gctatagaaa gctatatttc aaggtatccc gcatttcaag attcccgcga atacaaactt 720
ttgaaaaccc tcatagaaaa catcgaagag caaaatgtag atggatatac agaagccgtc 780
aaagattacg attcaatttc tcgtcttgat cagtggtata ctacgattct tttacgtatt 840
aagaaacaag taagcgaaag ccctgactta cgttaa 876

<210> SEQ ID NO 273
<211> LENGTH: 552
<212> TYPE: DNA
<213> ORGANISM: Diabrotica barberi

<400> SEQUENCE: 273
atgggtaatg tgtttgcaaa tttattcaaa ggcctctttg gcaaaaaaaa agaaatgagg 60
atattgatgg taggactcga tgcagctggt aaaaccacaa ttttatataa acttaaatta 120
ggagaaattg taacaactat tccaacaatt ggatttaatg tggagactgt agaatataag 180
aacattagtt ttacagtatg ggatgtaggt ggtcaagata aaattaggcc attgtggaga 240
cactatttcc aaaacacaca aggcctaatt ttcgtagtag acagtaacga cagggaacgt 300
atcaccgagg ctaaagatga attaatgcgt atgttggccg aagatgaact tagagatgcc 360
gtacttctca ttttcgccaa caaacaagat ttgcccaatg caatgaacgc tgcagaaatc 420
accgacaaac tcggtctcca ttcactacgc aaccgcaact ggtacattca agctacctgt 480
gcaactagcg gagatggtct ctatgaaggt ctggactggt tgtccaatca attaaagaac 540
gccaatcgct ag 552

<210> SEQ ID NO 274
<211> LENGTH: 744
<212> TYPE: RNA
<213> ORGANISM: Diabrotica barberi

<400> SEQUENCE: 274
augaugucga aaguagacaa agaugaagac gccuccuucg caaaauugga aaaucagauu 60
gcugucauca aauacguaau acucuuuacc aacgucuugc aaugggcucu cggugcagca 120
aucuucgcuc uuugccuuug gcuacgauuc gaggagggca uucaagaaug gcuccagaaa 180
uuggauucag aacaauuuua caucggagua uauguacuua uagucgcuuc acugaucguc 240
augauugugu ccuuuauagg auguauuagu gcccugcagg agaguacuac ggcccuuuua 300
guguacaucg gcacccaagu gcucaguuuu auauucgguu uauccgguuc ggcgguucuu 360

-continued

```
cuggauaaca gcgccagaga uucccacuuc caaccgagga uccgagagag uaugcgacgu    420

cuuaucauga augcucauca cgaccaaucc agacaaacac uagccaugau ucaggaaaau    480

guugguugcu gcggagcuga uggcgcaaca gacuaccucu cucuucaaca gccccuucca    540

agucagugca gagacaccgu uacuggaaac ccauucuucc acggaugugu agaugaacuc    600

accugguucu ucgaagaaaa auguggcugg auagcagguu uagcuauggc gauaugcaug    660

auuaacgucc uuaguauugu uuuaucuacg guacucaucc aggcauugaa aaaagaagaa    720

gaagcaucag auucauacag gaga                                            744
```

```
<210> SEQ ID NO 275
<211> LENGTH: 876
<212> TYPE: RNA
<213> ORGANISM: Diabrotica barberi

<400> SEQUENCE: 275

augucgucaa auauucaaaa ggcccagcag uugauggcgg augcagaaaa gaaaguaaca     60

ucucgagguu ucuucggauc ucuauuuggg ggaucaaguc guauugaaga ugcaguggaa    120

uguuacacaa gagcugcaaa ccuuuuuaaa auggccaaga gcugggaugc ugccgguaaa    180

gccuuuugug aggcugcuaa uuugcauuca agaacuggug cucgucauga cgcugccacu    240

aauuauauag augcugcaaa uuguuacaaa aaagccgaug uauuugaggc uguaaacugc    300

uuuauaaaag cuauagacau uuauaccgaa augggucgcu uuacaauggc ugcaaaacac    360

caucagacua uugcagaaau guaugagacu gaugcugugg acaucgaaag ggcuguucaa    420

cacuaugaac aggcggcuga uuacuucaga ggagaagaaa gcaaugcuuc cgccaauaag    480

ugucuucuua aaguggcuca auaugcagcc caacuugaaa acuaugaaaa agcaguggga    540

auuuaucaag aaguggcuua cgcagcucug gaaagcucuc uuuuaaaaua cagugcaaag    600

gaauacuuau ucagagcugc ccuuugucac cuuuguguug auguacucaa ugcacaacau    660

gcuauagaaa gcuauauuuc aagguauccc gcauuucaag auucccgcga auacaaacuu    720

uugaaaaccc ucauagaaaa caucgaagag caaaauguag auggauauac agaagccguc    780

aaagauuacg auucaauuuc ucgucuugau cagugguaua cuacgauucu uuuacguauu    840

aagaaacaag uaagcgaaag cccugacuua cguuaa                               876
```

```
<210> SEQ ID NO 276
<211> LENGTH: 552
<212> TYPE: RNA
<213> ORGANISM: Diabrotica barberi

<400> SEQUENCE: 276

auggguaaug uguuugcaaa uuuauucaaa ggccucuuug gcaaaaaaaa agaaaugagg     60

auauugaugg uaggacucga ugcagcuggu aaaaccacaa uuuuauauaa acuuaaauua    120

ggagaaauug uaacaacuau uccaacaauu ggauuuaaug uggagacugu agaauauaag    180

aacauuaguu uuacaguaug ggauguaggu ggucaagaua aaauuaggcc auuguggaga    240

cacuauuucc aaaacacaca aggccuaauu uucguaguag acaguaacga cagggaacgu    300

aucaccgagg cuaaagauga auuaaugcgu auguuggccg aagaugaacu uagagaugcc    360

guacuucuca uuuucgccaa caaacaagau uugcccaaug caaugaacgc ugcagaaauc    420

accgacaaac ucggucucca uucacuacgc aaccgcaacu gguacauuca agcuaccugu    480

gcaacuagcg gagauggucu cuaugaaggu cuggacuggu uguccaauca auuaaagaac    540

gccaaucgcu ag                                                         552
```

<210> SEQ ID NO 277
<211> LENGTH: 744
<212> TYPE: DNA
<213> ORGANISM: Diabrotica undecimpunctata

<400> SEQUENCE: 277
atgattggga aagtagacaa agaggaagat gcttccttcg ccaaattaga aaatcagatt 60
gcgatcatca aatacgtaat actatttacc aacgtcttgc agtgggctct cggtgcagca 120
atcttcgctc tttgcctttg gctacgattc gaggagggca ttcaagaatg gctccagaaa 180
ttggattcag aacaatttta catcggagta tatgtactta tagtcgcttc actgatcgtc 240
atgattgtgt cctttatagg atgtattagt gccctgcagg agagtaccat ggccctttta 300
gtgtacatcg gcacccaagt gctcagtttt atattcggtt tatccggttc ggcggttctt 360
ctggataaca gcgccagaga ttcccacttc caaccgagga tccgagagag tatgcgacgt 420
cttatcatga atgctcatca cgaccaatcc agacaaacac tagccatgat tcaggaaaat 480
gttggttgtt gcggagctga tggcgcaaca gactacctac atctccaaca gccccttcca 540
agtcagtgca gagatacagt tactggaaat cctttcttcc acggatgtgt agatgaactc 600
acctggttct tcgaagaaaa atgtggttgg atagcaggtt tggccatggc gatatgtatg 660
attaatgtcc ttagtattgt tttatctacg gtactcatcc aggcattgaa aaaagaagaa 720
gaggcttccg attcatatag aaga 744

<210> SEQ ID NO 278
<211> LENGTH: 876
<212> TYPE: DNA
<213> ORGANISM: Diabrotica undecimpunctata

<400> SEQUENCE: 278
atgtcgtcaa acgttcaaaa ggctcagcag ttgatggcgg atgcagaaaa gaaagtatca 60
tctagaggtt tctttggatc gctatttggg ggatcaagtc gtattgaaga tgcagtggaa 120
tgttacacaa gagctgcaaa cctttttaaa atggccaaga gttgggatgc tgctggcaaa 180
gccttctgtg aggctgctaa tctgcattca agaactggtg ctcgtcatga tgctgccact 240
aattatatag atgctgcaaa ttgttacaaa aaagctgata taatggaggc tgtaaactgc 300
ttcataaaag ctatagacat ttatactgaa atgggtcgct ttacaatggc tgcaaaacac 360
catcagacta ttgcagaaat gtatgagact gatgctgtgg acatcgaaag agctgttcaa 420
cattatgaac aggcggctga ttacttcaga ggagaagaaa gcaatgcttc tgccaataag 480
tgtcttctta aagtggctca atatgcagcc caacttgaaa actatgaaaa agcagtggga 540
atttatcaag aagtagctta tgcagctctg gaaagctctc tgttaaaata cagtgcaaag 600
gaatacttat tcagggctgc cctttgccac ctttgtgttg atgtactcaa tgcacaacat 660
gctatagaaa gctatatttc aaggtatccc gcatttcaag attcccgtga atacaaactt 720
ttgaaaaccc tcatagaaag catcgaagag caaaacgtag atggatatac agaagccgtc 780
aaagattacg attcaatctc tcgtcttgat cagtggtata ctacgattct tttacgtatt 840
aagaaacaag taagcgaaag ccctgactta cgttaa 876

<210> SEQ ID NO 279
<211> LENGTH: 549
<212> TYPE: DNA
<213> ORGANISM: Diabrotica undecimpunctata

<400> SEQUENCE: 279
atgggtaatg tgtttgcaaa cttattcaaa ggcctctttg gcaaaaaaga aatgaggata 60
ttgatggtag gacttgatgc agctggtaaa accacaattt tatataaact taaattagga 120
gaaattgtaa caactattcc aacaattgga tttaatgtgg agactgtaga atataagaac 180
attagcttta cagtatggga tgtaggtggt caagataaaa ttaggccatt gtggagacac 240
tatttccaaa acacacaagg cctaattttc gtagtagaca gtaacgacag ggaacgtatt 300
actgaggcta aagatgaatt aatgcgcatg ttggccgaag atgaacttag agatgccgta 360
cttctcattt tcgccaacaa acaagatttg cccaatgcaa tgaacgctgc agaaatcacc 420
gacaaactcg gtctccattc actacgtaac cgcaactggt acattcaagc tacctgtgca 480
actagcggag atggtctcta tgaaggtctg gactggttgt ccaatcaatt aaagaacgcc 540
aatcgctag 549

<210> SEQ ID NO 280
<211> LENGTH: 744
<212> TYPE: RNA
<213> ORGANISM: Diabrotica undecimpunctata

<400> SEQUENCE: 280
augauuggga aaguagacaa agaggaagau gcuuccuucg ccaaauuaga aaaucagauu 60
gcgaucauca aauacguaau acuauuuacc aacgucuugc agugggcucu cggugcagca 120
aucuucgcuc uuugccuuug gcuacgauuc gaggagggca uucaagaaug gcuccagaaa 180
uuggauucag aacaauuuua caucggagua uauguacuua uagucgcuuc acugaucguc 240
augauugugu ccuuuauagg auguauuagu gcccugcagg agaguaccau ggcccuuuua 300
guguacaucg gcacccaagu gcucaguuuu auauucgguu uauccgguuc ggcgguucuu 360
cuggauaaca gcgccagaga uucccacuuc caaccgagga uccgagagag uaugcgacgu 420
cuuaucauga augcucauca cgaccaaucc agacaaacac uagccaugau ucaggaaaau 480
guugguuguu gcggagcuga uggcgcaaca gacuaccuac aucuccaaca gccccuucca 540
agucagugca gagauacagu uacuggaaau ccuuucuucc acggaugugu agaugaacuc 600
accugguucu ucgaagaaaa augugguugg auagcagguu uggccauggc gauauguaug 660
auuaaugucc uuaguauugu uuuaucuacg guacucaucc aggcauugaa aaaagaagaa 720
gaggcuuccg auucauauag aaga 744

<210> SEQ ID NO 281
<211> LENGTH: 876
<212> TYPE: RNA
<213> ORGANISM: Diabrotica undecimpunctata

<400> SEQUENCE: 281
augucgucaa acguucaaaa ggcucagcag uugauggcgg augcagaaaa gaaaguauca 60
ucuagagguu ucuuuggauc gcuauuuggg ggaucaaguc guauugaaga ugcaguggaa 120
uguuacacaa gagcugcaaa ccuuuuuaaa auggccaaga guugggaugc ugcuggcaaa 180
gccuucugug aggcugcuaa ucugcauuca agaacuggug cucgucauga ugcugccacu 240
aauuauauag augcugcaaa uuguuacaaa aaagcugaua uaauggaggc uguaaacugc 300
uucauaaaag cuauagacau uuauacugaa augggucgcu uuacaauggc ugcaaaacac 360
caucagacua uugcagaaau guaugagacu gaugcugugg acaucgaaag agcuguucaa 420
cauuaugaac aggcggcuga uuacuucaga ggagaagaaa gcaaugcuuc ugccaauaag 480
ugucuucuua aaguggcuca auaugcagcc caacuugaaa acuaugaaaa agcaguggga 540
auuuaucaag aaguagcuua ugcagcucug gaaagcucuc uguuaaaaua cagugcaaag 600
gaauacuuau ucagggcugc ccuuugccac cuuuguguug auguacucaa ugcacaacau 660
gcuauagaaa gcuauauuuc aagguauccc gcauuucaag auucccguga auacaaacuu 720
uugaaaaccc ucauagaaag caucgaagag caaaacguag auggauauac agaagccguc 780
aaagauuacg auucaaucuc ucgucuugau cagugguaua cuacgauucu uuuacguauu 840
aagaaacaag uaagcgaaag cccugacuua cguuaa 876

<210> SEQ ID NO 282
<211> LENGTH: 549
<212> TYPE: RNA
<213> ORGANISM: Diabrotica undecimpunctata

<400> SEQUENCE: 282 augguaaug uguuugcaaa cuuauucaaa ggccucuuug gcaaaaaaga aaugaggaua 60
uugaugguag gacuugaugc agcugguaaa accacaauuu uauauaaacu uaaauuagga 120
gaaauuguaa caacuauucc aacaauugga uuuaaugugg agacuguaga auauaagaac 180
auuagcuuua caguauggga uguaggugu caagauaaaa uuaggccauu guggagacac 240
uauuuccaaa acacacaagg ccuaauuuuc guaguagaca guaacgacag ggaacguauu 300
acugaggcua aagaugaauu aaugcgcaug uuggccgaag augaacuuag agaugccgua 360
cuucucauuu ucgccaacaa acaagauuug cccaaugcaa ugaacgcugc agaaaucacc 420
gacaaacucg gucuccauuc acuacguaac cgcaacuggu acauucaagc uaccugugca 480
acuagcggag auggucucua ugaaggucug gacugguugu ccaaucaauu aaagaacgcc 540
aaucgcuag 549

<210> SEQ ID NO 283
<211> LENGTH: 524
<212> TYPE: DNA
<213> ORGANISM: Diabrotica virgifera

<400> SEQUENCE: 283
tctttgcctt tggctacgat tcgaggaggg cattcaagaa tggctccaga aattggattc 60
agaacaattt tacatcggag tatatgtact tatagtcgct tcactgatcg tcatgattgt 120
gtcctttata ggatgtatta gtgccctgca ggagagtacc atggcccttt tagtgtacat 180
cggcacccaa gtgctcagtt ttatattcgg tttatccggt tcggcggttc ttctggataa 240
cagcgccaga gattcccact tccaaccgag gatccgagag agtatgcgac gtcttatcat 300
gaatgctcat cacgaccaat ccagacaaac actagccatg attcaggaaa atgttggttg 360
ctgcggagct gatggcgcaa cagactacct ctctcttcag cagccccttc caagtcagtg 420
cagagacacc gttactggaa acccattctt ccacggatgt gtagatgaac tcacctggtt 480
cttcgaagaa aaatgtggtt ggatagcagg tttagctatg gcga 524

<210> SEQ ID NO 284
<211> LENGTH: 744
<212> TYPE: DNA
<213> ORGANISM: Diabrotica virgifera

<400> SEQUENCE: 284
atgatgtcca aagcagacac acaggaagat gcctccttcg ccaaattgga aaatcagatt 60

-continued

```
gctatcatca aatacgtaat actctttacc aacgttttgc aatgggctct cggtgcagca    120

atcttcgctc tttgcctttg gctacgattc gaggagggca ttcaagaatg gctccagaaa    180

ttggattcag aacaatttta catcggagta tatgtactta tagtcgcttc actgatcgtc    240

atgattgtgt cctttatagg atgtattagt gccctgcagg agagtaccat ggccctttta    300

gtgtacatcg gcacccaagt gctcagtttt atattcggtt tatccggttc ggcggttctt    360

ctggataaca gcgccagaga ttcccacttc caaccgagga tccgagagag tatgcgacgt    420

cttatcatga atgctcatca cgaccaatcc agacaaacac tagccatgat tcaggaaaat    480

gttggttgct gcggagctga tggcgcaaca gactacctct ctcttcagca gccccttcca    540

agtcagtgca gagacaccgt tactggaaac ccattcttcc acggatgtgt agatgaactc    600

acctggttct tcgaagaaaa atgtggttgg atagcaggtt tagctatggc gatatgcatg    660

attaacgtcc ttagtattgt tttatctacg gtactcatcc aggcattgaa aaaagaagaa    720

gaagcatccg attcatacag gaga                                            744
```

<210> SEQ ID NO 285
<211> LENGTH: 197
<212> TYPE: DNA
<213> ORGANISM: Diabrotica virgifera

<400> SEQUENCE: 285

```
tgatgtccaa agcagacaca caggaagatg cctccttcgc caaattggaa aatcagattg     60

ctatcatcaa atacgtaata ctctttacca acgttttgca atgggctctc ggtgcagcaa    120

tcttcgctct ttgcctttgg ctacgattcg aggagggcat tcaagaatgg ctccagaaat    180

tggattcaga acaattt                                                    197
```

<210> SEQ ID NO 286
<211> LENGTH: 220
<212> TYPE: DNA
<213> ORGANISM: Diabrotica virgifera

<400> SEQUENCE: 286

```
ctacgattcg aggagggcat tcaagaatgg ctccagaaat tggattcaga acaattttac     60

atcggagtat atgtacttat agtcgcttca ctgatcgtca tgattgtgtc ctttatagga    120

tgtattagtg ccctgcagga gagtaccatg gccctttag tgtacatcgg cacccaagtg     180

ctcagtttta tattcggttt atccggttcg gcggttcttc                          220
```

<210> SEQ ID NO 287
<211> LENGTH: 213
<212> TYPE: DNA
<213> ORGANISM: Diabrotica virgifera

<400> SEQUENCE: 287

```
cggcacccaa gtgctcagtt ttatattcgg tttatccggt tcggcggttc ttctggataa     60

cagcgccaga gattcccact tccaaccgag gatccgagag agtatgcgac gtcttatcat    120

gaatgctcat cacgaccaat ccagacaaac actagccatg attcaggaaa atgttggttg    180

ctgcggagct gatggcgcaa cagactacct ctc                                  213
```

<210> SEQ ID NO 288
<211> LENGTH: 198
<212> TYPE: DNA
<213> ORGANISM: Diabrotica virgifera

<400> SEQUENCE: 288
agacaaacac tagccatgat tcaggaaaat gttggttgct gcggagctga tggcgcaaca 60
gactacctct ctcttcagca gccccttcca agtcagtgca gagacaccgt tactggaaac 120
ccattcttcc acggatgtgt agatgaactc acctggttct tcgaagaaaa atgtggttgg 180
atagcaggtt tagctatg 198

<210> SEQ ID NO 289
<211> LENGTH: 169
<212> TYPE: DNA
<213> ORGANISM: Diabrotica virgifera

<400> SEQUENCE: 289
cttccacgga tgtgtagatg aactcacctg gttcttcgaa gaaaaatgtg gttggatagc 60
aggtttagct atggcgatat gcatgattaa cgtccttagt attgttttat ctacggtact 120
catccaggca ttgaaaaaag aagaagaagc atccgattca tacaggaga 169

<210> SEQ ID NO 290
<211> LENGTH: 564
<212> TYPE: DNA
<213> ORGANISM: Diabrotica virgifera

<400> SEQUENCE: 290
cggatctcta tttgggggat caagtcgtat tgaagatgca gtggaatgtt acacaagagc 60
tgcaaacctt tttaaaatgg ccaagagctg ggatgctgcc ggtaaagcct tttgtgaggc 120
tgctaatttg cattccagaa ctggtgctcg tcatgacgct gccactaatt atatagatgc 180
tgcaaattgt tacaaaaaag ccgatgtatt tgaggctgta aactgcttta taaaagctat 240
agacatttat accgaaatgg gtcgctttac aatggctgca aaacaccatc agactattgc 300
agaaatgtat gagactgatg ctgtggacat cgaaagggct gttcaacact atgaacaggc 360
ggctgattac ttcagaggag aagaaagcaa tgcttccgcc aataagtgtc ttcttaaagt 420
ggctcaatat gcagcccaac ttgaaaacta tgaaaaagca gtgggaattt atcaagaagt 480
ggcttatgca gctctggaaa gctctctttt aaaatacagt gcaaaggaat acttattcag 540
agctgccctt tgtcaccttt gtgt 564

<210> SEQ ID NO 291
<211> LENGTH: 873
<212> TYPE: DNA
<213> ORGANISM: Diabrotica virgifera

<400> SEQUENCE: 291
atgtcgtcaa atattcaaaa ggcccagcag ttgatggcgg atgcagaaaa gaaagtaaca 60
tctcgaggtt tcttcggatc tctatttggg ggatcaagtc gtattgaaga tgcagtggaa 120
tgttacacaa gagctgcaaa cctttttaaa atggccaaga gctgggatgc tgccggtaaa 180
gccttttgtg aggctgctaa tttgcattcc agaactggtg ctcgtcatga cgctgccact 240
aattatatag atgctgcaaa ttgttacaaa aaagccgatg tatttgaggc tgtaaactgc 300
tttataaaag ctatagacat ttataccgaa atgggtcgct ttacaatggc tgcaaaacac 360
catcagacta ttgcagaaat gtatgagact gatgctgtgg acatcgaaag ggctgttcaa 420
cactatgaac aggcggctga ttacttcaga ggagaagaaa gcaatgcttc cgccaataag 480
tgtcttctta aagtggctca atatgcagcc caacttgaaa actatgaaaa agcagtggga 540
atttatcaag aagtggctta tgcagctctg gaaagctctc ttttaaaata cagtgcaaag 600

```
gaatacttat tcagagctgc cctttgtcac ctttgtgttg atgtactcaa tgcacaacat    660

gctatagaaa gctatatttc aaggtatccc gcatttcaag attcccgtga atacaaactt    720

ttgaaaaccc tcatagaaaa catcgaagag caaaacgtag atggatatac agaagccgtc    780

aaagattacg attcaatttc tcgtcttgat cagtggtata ctacaattct tttacgtatt    840

aagaaacaag taagcgaaag ccctgactta cgt                                 873


<210> SEQ ID NO 292
<211> LENGTH: 197
<212> TYPE: DNA
<213> ORGANISM: Diabrotica virgifera

<400> SEQUENCE: 292

tcgtcaaata ttcaaaaggc ccagcagttg atggcggatg cagaaaagaa agtaacatct     60

cgaggtttct tcggatctct atttggggga tcaagtcgta ttgaagatgc agtggaatgt    120

tacacaagag ctgcaaacct ttttaaaatg gccaagagct gggatgctgc cggtaaagcc    180

ttttgtgagg ctgctaa                                                   197


<210> SEQ ID NO 293
<211> LENGTH: 236
<212> TYPE: DNA
<213> ORGANISM: Diabrotica virgifera

<400> SEQUENCE: 293

gtggaatgtt acacaagagc tgcaaacctt tttaaaatgg ccaagagctg ggatgctgcc     60

ggtaaagcct tttgtgaggc tgctaatttg cattccagaa ctggtgctcg tcatgacgct    120

gccactaatt atatagatgc tgcaaattgt tacaaaaaag ccgatgtatt tgaggctgta    180

aactgcttta taaaagctat agacatttat accgaaatgg gtcgctttac aatggc        236


<210> SEQ ID NO 294
<211> LENGTH: 197
<212> TYPE: DNA
<213> ORGANISM: Diabrotica virgifera

<400> SEQUENCE: 294

ataaaagcta tagacattta taccgaaatg ggtcgcttta caatggctgc aaaacaccat     60

cagactattg cagaaatgta tgagactgat gctgtggaca tcgaaagggc tgttcaacac    120

tatgaacagg cggctgatta cttcagagga gaagaaagca atgcttccgc caataagtgt    180

cttcttaaag tggctca                                                   197


<210> SEQ ID NO 295
<211> LENGTH: 199
<212> TYPE: DNA
<213> ORGANISM: Diabrotica virgifera

<400> SEQUENCE: 295

ggagaagaaa gcaatgcttc cgccaataag tgtcttctta aagtggctca atatgcagcc     60

caacttgaaa actatgaaaa agcagtggga atttatcaag aagtggctta tgcagctctg    120

gaaagctctc ttttaaaata cagtgcaaag gaatacttat tcagagctgc cctttgtcac    180

ctttgtgttg atgtactca                                                 199


<210> SEQ ID NO 296
<211> LENGTH: 197
<212> TYPE: DNA
<213> ORGANISM: Diabrotica virgifera
```

<400> SEQUENCE: 296
gaatacttat tcagagctgc cctttgtcac ctttgtgttg atgtactcaa tgcacaacat 60
gctatagaaa gctatatttc aaggtatccc gcatttcaag attcccgtga atacaaactt 120
ttgaaaaccc tcatagaaaa catcgaagag caaaacgtag atggatatac agaagccgtc 180
aaagattacg attcaat 197

<210> SEQ ID NO 297
<211> LENGTH: 122
<212> TYPE: DNA
<213> ORGANISM: Diabrotica virgifera

<400> SEQUENCE: 297
caaaacgtag atggatatac agaagccgtc aaagattacg attcaatttc tcgtcttgat 60
cagtggtata ctacaattct tttacgtatt aagaaacaag taagcgaaag ccctgactta 120
cg 122

<210> SEQ ID NO 298
<211> LENGTH: 458
<212> TYPE: DNA
<213> ORGANISM: Diabrotica virgifera

<400> SEQUENCE: 298
ttggcaaaaa ggaaatgagg atattgatgg taggactcga tgcagctggt aaaaccacaa 60
ttttatataa acttaaatta ggagaaattg taacaactat tccaacaatt ggatttaatg 120
tggagactgt agaatataag aacattagtt ttacagtatg ggatgtaggt ggtcaagata 180
aaattaggcc attgtggaga cactatttcc aaaacacaca aggcctaatt ttcgtagtag 240
acagtaacga cagggaacgt atcactgagg ctaaagatga attaatgcgt atgttggccg 300
aagatgaact tagagatgcc gtacttctca ttttcgccaa caaacaagat ttgcccaatg 360
caatgaacgc tgcagaaatc accgacaaac tcggtctcca ttcactacgc aaccgcaact 420
ggtacattca agctacctgt gcaactagcg gagatggt 458

<210> SEQ ID NO 299
<211> LENGTH: 546
<212> TYPE: DNA
<213> ORGANISM: Diabrotica virgifera

<400> SEQUENCE: 299
atgggtaatg tgtttgcaaa tttattcaaa ggcctctttg gcaaaaagga aatgaggata 60
ttgatggtag gactcgatgc agctggtaaa accacaattt tatataaact taaattagga 120
gaaattgtaa caactattcc aacaattgga tttaatgtgg agactgtaga atataagaac 180
attagtttta cagtatggga tgtaggtggt caagataaaa ttaggccatt gtggagacac 240
tatttccaaa acacacaagg cctaattttc gtagtagaca gtaacgacag ggaacgtatc 300
actgaggcta aagatgaatt aatgcgtatg ttggccgaag atgaacttag agatgccgta 360
cttctcattt tcgccaacaa acaagatttg cccaatgcaa tgaacgctgc agaaatcacc 420
gacaaactcg gtctccattc actacgcaac cgcaactggt acattcaagc tacctgtgca 480
actagcggag atggtctcta tgaaggtctg gactggttgt ccaatcaatt aaagaacgcc 540
aatcgc 546

<210> SEQ ID NO 300

<211> LENGTH: 199
<212> TYPE: DNA
<213> ORGANISM: Diabrotica virgifera

<400> SEQUENCE: 300
tgggtaatgt gtttgcaaat ttattcaaag gcctctttgg caaaaaggaa atgaggatat 60
tgatggtagg actcgatgca gctggtaaaa ccacaatttt atataaactt aaattaggag 120
aaattgtaac aactattcca acaattggat ttaatgtgga gactgtagaa tataagaaca 180
ttagttttac agtatggga 199

<210> SEQ ID NO 301
<211> LENGTH: 200
<212> TYPE: DNA
<213> ORGANISM: Diabrotica virgifera

<400> SEQUENCE: 301
tttaatgtgg agactgtaga atataagaac attagtttta cagtatggga tgtaggtggt 60
caagataaaa ttaggccatt gtggagacac tatttccaaa acacacaagg cctaattttc 120
gtagtagaca gtaacgacag ggaacgtatc actgaggcta aagatgaatt aatgcgtatg 180
ttggccgaag atgaacttag 200

<210> SEQ ID NO 302
<211> LENGTH: 198
<212> TYPE: DNA
<213> ORGANISM: Diabrotica virgifera

<400> SEQUENCE: 302
tgaggctaaa gatgaattaa tgcgtatgtt ggccgaagat gaacttagag atgccgtact 60
tctcattttc gccaacaaac aagatttgcc caatgcaatg aacgctgcag aaatcaccga 120
caaactcggt ctccattcac tacgcaaccg caactggtac attcaagcta cctgtgcaac 180
tagcggagat ggtctcta 198

<210> SEQ ID NO 303
<211> LENGTH: 95
<212> TYPE: DNA
<213> ORGANISM: Diabrotica virgifera

<400> SEQUENCE: 303
gcaactggta cattcaagct acctgtgcaa ctagcggaga tggtctctat gaaggtctgg 60
actggttgtc caatcaatta aagaacgcca atcgc 95

<210> SEQ ID NO 304
<211> LENGTH: 524
<212> TYPE: RNA
<213> ORGANISM: Diabrotica virgifera

<400> SEQUENCE: 304
ucuuugccuu uggcuacgau ucgaggaggg cauucaagaa uggcuccaga aauuggauuc 60
agaacaauuu uacaucggag uauauguacu uauagucgcu ucacugaucg ucaugauugu 120
guccuuuaua ggauguauua gugcccugca ggagaguacc auggcccuuu uaguguacau 180
cggcacccaa gugcucaguu uuauauucgg uuuauccggu ucggcgguuc uucuggauaa 240
cagcgccaga gauucccacu uccaaccgag gauccgagag aguaugcgac gucuuaucau 300
gaaugcucau cacgaccaau ccagacaaac acuagccaug auucaggaaa auguuggug 360 cugcggagcu gauggcgcaa cagacuaccu cucucuucag cagccccuuc caagucagug 420
cagagacacc guuacuggaa acccauucuu ccacggaugu guagaugaac ucaccugguu 480
cuucgaagaa aaauguggu ggauagcagg uuuagcuaug gcga 524

<210> SEQ ID NO 305
<211> LENGTH: 744
<212> TYPE: RNA
<213> ORGANISM: Diabrotica virgifera

<400> SEQUENCE: 305
augaugucca aagcagacac acaggaagau gccuccuucg ccaaauugga aaaucagauu 60
gcuaucauca aauacguaau acucuuuacc aacguuuugc aaugggcucu cggugcagca 120
aucuucgcuc uuugccuuug gcuacgauuc gaggagggca uucaagaaug gcuccagaaa 180
uuggauucag aacaauuuua caucggagua uauguacuua uagucgcuuc acugaucguc 240
augauugugu ccuuuauagg auguauuagu gcccugcagg agaguaccau ggcccuuuua 300
guguacaucg gcacccaagu gcucaguuuu auauucgguu uauccgguuc ggcgguucuu 360
cuggauaaca gcgccagaga uucccacuuc caaccgagga uccgagagag uaugcgacgu 420
cuuaucauga augcucauca cgaccaaucc agacaaacac uagccaugau ucaggaaaau 480
guugguugcu gcggagcuga uggcgcaaca gacuaccucu cucuucagca gccccuucca 540
agucagugca gagacaccgu uacuggaaac ccauucuucc acggaugugu agaugaacuc 600
accugguucu ucgaagaaaa augugguugg auagcagguu uagcuauggc gauaugcaug 660
auuaacgucc uuaguauugu uuuaucuacg guacucaucc aggcauugaa aaaagaagaa 720
gaagcauccg auucauacag gaga 744

<210> SEQ ID NO 306
<211> LENGTH: 197
<212> TYPE: RNA
<213> ORGANISM: Diabrotica virgifera

<400> SEQUENCE: 306
ugauguccaa agcagacaca caggaagaug ccuccuucgc caaauuggaa aaucagauug 60
cuaucaucaa auacguaaua cucuuuacca acguuuugca augggcucuc ggugcagcaa 120
ucuucgcucu uugccuuugg cuacgauucg aggagggcau ucaagaaugg cuccagaaau 180
uggauucaga acaauuu 197

<210> SEQ ID NO 307
<211> LENGTH: 220
<212> TYPE: RNA
<213> ORGANISM: Diabrotica virgifera

<400> SEQUENCE: 307
cuacgauucg aggagggcau ucaagaaugg cuccagaaau uggauucaga acaauuuuac 60
aucggaguau auguacuuau agucgcuuca cugaucguca ugauuguguc cuuuauagga 120
uguauuagug cccugcagga gaguaccaug gcccuuuuag uguacaucgg cacccaagug 180
cucaguuuua uauucgguuu auccgguucg gcgguucuuc 220

<210> SEQ ID NO 308
<211> LENGTH: 213
<212> TYPE: RNA
<213> ORGANISM: Diabrotica virgifera

<400> SEQUENCE: 308

```
cggcacccaa gugcucaguu uuauauucgg uuuauccggu ucggcgguuc uucuggauaa     60

cagcgccaga gauucccacu uccaaccgag gauccgagag aguaugcgac gucuuaucau    120

gaaugcucau cacgaccaau ccagacaaac acuagccaug auucaggaaa auguugguug    180

cugcggagcu gauggcgcaa cagacuaccu cuc                                 213


<210> SEQ ID NO 309
<211> LENGTH: 198
<212> TYPE: RNA
<213> ORGANISM: Diabrotica virgifera

<400> SEQUENCE: 309

agacaaacac uagccaugau ucaggaaaau guugguugcu gcggagcuga uggcgcaaca     60

gacuaccucu cucuucagca gccccuucca agucagugca gagacaccgu uacuggaaac    120

ccauucuucc acggaugugu agaugaacuc accugguucu ucgaagaaaa augugguugg    180

auagcagguu uagcuaug                                                  198


<210> SEQ ID NO 310
<211> LENGTH: 169
<212> TYPE: RNA
<213> ORGANISM: Diabrotica virgifera

<400> SEQUENCE: 310

cuuccacgga uguguagaug aacucaccug guucuucgaa gaaaaaugug guuggauagc     60

agguuuagcu auggcgauau gcaugauuaa cguccuuagu auuguuuuau cuacgguacu    120

cauccaggca uugaaaaaag aagaagaagc auccgauuca uacaggaga                169


<210> SEQ ID NO 311
<211> LENGTH: 564
<212> TYPE: RNA
<213> ORGANISM: Diabrotica virgifera

<400> SEQUENCE: 311

cggaucucua uuugggggau caagucguau ugaagaugca guggaauguu acacaagagc     60

ugcaaaccuu uuuaaaaugg ccaagagcug ggaugcugcc gguaaagccu uuugugaggc    120

ugcuaauuug cauuccagaa cuggugcucg ucaugacgcu gccacuaauu auauagaugc    180

ugcaaauugu uacaaaaaag ccgauguauu ugaggcugua aacugcuuua uaaaagcuau    240

agacauuuau accgaaaugg gucgcuuuac aauggcugca aaacaccauc agacuauugc    300

agaaauguau gagacugaug cuguggacau cgaaagggcu guucaacacu augaacaggc    360

ggcugauuac uucagaggag aagaaagcaa ugcuuccgcc aauaaguguc uucuuaaagu    420

ggcucaauau gcagcccaac uugaaaacua ugaaaaagca gugggaauuu aucaagaagu    480

ggcuuaugca gcucuggaaa gcucucuuuu aaaauacagu gcaaaggaau acuuauucag    540

agcugcccuu ugucaccuuu gugu                                           564


<210> SEQ ID NO 312
<211> LENGTH: 873
<212> TYPE: RNA
<213> ORGANISM: Diabrotica virgifera

<400> SEQUENCE: 312

augucgucaa auauucaaaa ggcccagcag uugauggcgg augcagaaaa gaaaguaaca     60

ucucgagguu ucuucggauc ucuauuuggg ggaucaaguc guauugaaga ugcaguggaa    120

uguuacacaa gagcugcaaa ccuuuuuaaa auggccaaga gcugggaugc ugccgguaaa    180
```

gccuuuugug aggcugcuaa uuugcauucc agaacuggug cucgucauga cgcugccacu 240
aauuauauag augcugcaaa uuguuacaaa aaagccgaug uauuugaggc uguaaacugc 300
uuuauaaaag cuauagacau uuauaccgaa augggucgcu uuacaauggc ugcaaaacac 360
caucagacua uugcagaaau guaugagacu gaugcugugg acaucgaaag ggcuguucaa 420
cacuaugaac aggcggcuga uuacuucaga ggagaagaaa gcaaugcuuc cgccaauaag 480
ugucuucuua aaguggcuca auaugcagcc caacuugaaa acuaugaaaa agcaguggga 540
auuuaucaag aaguggcuua ugcagcucug gaaagcucuc uuuuaaaaua cagugcaaag 600
gaauacuuau ucagagcugc ccuuugucac cuuuguguug auguacucaa ugcacaacau 660
gcuauagaaa gcuauauuuc aagguauccc gcauuucaag auucccguga auacaaacuu 720
uugaaaaccc ucauagaaaa caucgaagag caaaacguag auggauauac agaagccguc 780
aaagauuacg auucaauuuc ucgucuugau cagugguaua cuacaauucu uuuacguauu 840
aagaaacaag uaagcgaaag cccugacuua cgu 873

<210> SEQ ID NO 313
<211> LENGTH: 197
<212> TYPE: RNA
<213> ORGANISM: Diabrotica virgifera

<400> SEQUENCE: 313
ucgucaaaua uucaaaaggc ccagcaguug auggcggaug cagaaaagaa aguaacaucu 60
cgagguuucu ucggaucucu auuuggggga ucaagucgua uugaagaugc aguggaaugu 120
uacacaagag cugcaaaccu uuuuaaaaug gccaagagcu gggaugcugc cgguaaagcc 180
uuuugugagg cugcuaa 197

<210> SEQ ID NO 314
<211> LENGTH: 236
<212> TYPE: RNA
<213> ORGANISM: Diabrotica virgifera

<400> SEQUENCE: 314
guggaauguu acacaagagc ugcaaaccuu uuuaaaaugg ccaagagcug ggaugcugcc 60
gguaaagccu uuugugaggc ugcuaauuug cauuccagaa cuggugcucg ucaugacgcu 120
gccacuaauu auauagaugc ugcaaauugu uacaaaaaag ccgauguauu ugaggcugua 180
aacugcuuua uaaaagcuau agacauuuau accgaaaugg gucgcuuuac aauggc 236

<210> SEQ ID NO 315
<211> LENGTH: 197
<212> TYPE: RNA
<213> ORGANISM: Diabrotica virgifera

<400> SEQUENCE: 315
auaaaagcua uagacauuua uaccgaaaug ggucgcuuua caauggcugc aaaacaccau 60
cagacuauug cagaaaugua ugagacugau gcuguggaca ucgaaagggc uguucaacac 120
uaugaacagg cggcugauua cuucagagga gaagaaagca augcuuccgc caauaagugu 180
cuucuuaaag uggcuca 197

<210> SEQ ID NO 316
<211> LENGTH: 199
<212> TYPE: RNA
<213> ORGANISM: Diabrotica virgifera -continued

<400> SEQUENCE: 316
ggagaagaaa gcaaugcuuc cgccaauaag ugucuucuua aaguggcuca auaugcagcc 60
caacuugaaa acuaugaaaa agcaguggga auuuaucaag aaguggcuua ugcagcucug 120
gaaagcucuc uuuuaaaaua cagugcaaag gaauacuuau ucagagcugc ccuuugucac 180
cuuuguguug auguacuca 199

<210> SEQ ID NO 317
<211> LENGTH: 197
<212> TYPE: RNA
<213> ORGANISM: Diabrotica virgifera

<400> SEQUENCE: 317
gaauacuuau ucagagcugc ccuuugucac cuuuguguug auguacucaa ugcacaacau 60
gcuauagaaa gcuauauuuc aagguauccc gcauuucaag auucccguga auacaaacuu 120
uugaaaaccc ucauagaaaa caucgaagag caaaacguag auggauauac agaagccguc 180
aaagauuacg auucaau 197

<210> SEQ ID NO 318
<211> LENGTH: 122
<212> TYPE: RNA
<213> ORGANISM: Diabrotica virgifera

<400> SEQUENCE: 318
caaaacguag auggauauac agaagccguc aaagauuacg auucaauuuc ucgucuugau 60
cagugguaua cuacaauucu uuuacguauu aagaaacaag uaagcgaaag cccugacuua 120
cg 122

<210> SEQ ID NO 319
<211> LENGTH: 458
<212> TYPE: RNA
<213> ORGANISM: Diabrotica virgifera

<400> SEQUENCE: 319
uuggcaaaaa ggaaaugagg auauugaugg uaggacucga ugcagcuggu aaaaccacaa 60
uuuuauauaa acuuaaauua ggagaaauug uaacaacuau uccaacaauu ggauuuaaug 120
uggagacugu agaauauaag aacauuaguu uuacaguaug ggauguaggu ggucaagaua 180
aaauuaggcc auuguggaga cacuauuucc aaaacacaca aggccuaauu uucguaguag 240
acaguaacga cagggaacgu aucacugagg cuaaagauga auuaaugcgu auguuggccg 300
aagaugaacu uagagaugcc guacuucuca uuuucgccaa caaacaagau uugcccaaug 360
caaugaacgc ugcagaaauc accgacaaac ucggucucca uucacuacgc aaccgcaacu 420
gguacauuca agcuaccugu gcaacuagcg gagauggu 458

<210> SEQ ID NO 320
<211> LENGTH: 546
<212> TYPE: RNA
<213> ORGANISM: Diabrotica virgifera

<400> SEQUENCE: 320
auggguaaug uguuugcaaa uuuauucaaa ggccucuuug gcaaaaagga aaugaggaua 60
uugaugguag gacucgaugc agcugguaaa accacaauuu uauauaaacu uaaauuagga 120
gaaauuguaa caacuauucc aacaauugga uuuaaugugg agacuguaga auauaagaac 180
auuaguuuua caguauggga uguagguggu caagauaaaa uuaggccauu guggagacac 240
uauuuccaaa acacacaagg ccuaauuuuc guaguagaca guaacgacag ggaacguauc 300
acugaggcua aagaugaauu aaugcguaug uuggccgaag augaacuuag agaugccgua 360
cuucucauuu ucgccaacaa acaagauuug cccaaugcaa ugaacgcugc agaaaucacc 420
gacaaacucg gucuccauuc acuacgcaac cgcaacuggu acauucaagc uaccugugca 480
acuagcggag auggucucua ugaaggucug gacugguugu ccaaucaauu aaagaacgcc 540
aaucgc 546

<210> SEQ ID NO 321
<211> LENGTH: 199
<212> TYPE: RNA
<213> ORGANISM: Diabrotica virgifera

<400> SEQUENCE: 321 ugggguaaugu guuugcaaau uuauucaaag gccucuuugg caaaaaggaa augaggauau 60
ugaugguagg acucgaugca gcugguaaaa ccacaauuuu auauaaacuu aaauuaggag 120
aaauuguaac aacuauucca acaauuggau uuaaugugga gacuguagaa uauaagaaca 180
uuaguuuuac aguauggga 199

<210> SEQ ID NO 322
<211> LENGTH: 200
<212> TYPE: RNA
<213> ORGANISM: Diabrotica virgifera

<400> SEQUENCE: 322
uuuaaugugg agacuguaga auauaagaac auuaguuuua caguauggga uguaggugu 60 caagauaaaa uuaggccauu guggagacac uauuuccaaa acacacaagg ccuaauuuuc 120
guaguagaca guaacgacag ggaacguauc acugaggcua aagaugaauu aaugcguaug 180
uuggccgaag augaacuuag 200

<210> SEQ ID NO 323
<211> LENGTH: 198
<212> TYPE: RNA
<213> ORGANISM: Diabrotica virgifera

<400> SEQUENCE: 323
ugaggcuaaa gaugaauuaa ugcguauguu ggccgaagau gaacuuagag augccguacu 60
ucucauuuuc gccaacaaac aagauuugcc caaugcaaug aacgcugcag aaaucaccga 120
caaacucggu cuccauucac uacgcaaccg caacugguac auucaagcua ccugugcaac 180
uagcggagau ggucucua 198

<210> SEQ ID NO 324
<211> LENGTH: 95
<212> TYPE: RNA
<213> ORGANISM: Diabrotica virgifera

<400> SEQUENCE: 324
gcaacuggua cauucaagcu accugugcaa cuagcggaga uggucucuau gaaggucugg 60
acugguuguc caaucaauua aagaacgcca aucgc 95

<210> SEQ ID NO 325
<211> LENGTH: 1474
<212> TYPE: DNA
<213> ORGANISM: Artificial Sequence
<220> FEATURE:

<223> OTHER INFORMATION: Derived from Diabrotica virgifera and
Arabidopsis thaliana

<400> SEQUENCE: 325

```
tctttgcctt tggctacgat tcgaggaggg cattcaagaa tggctccaga aattggattc     60
agaacaattt tacatcggag tatatgtact tatagtcgct tcactgatcg tcatgattgt    120
gtcctttata ggatgtatta gtgccctgca ggagagtacc atggcccttt tagtgtacat    180
cggcacccaa gtgctcagtt ttatattcgg tttatccggt tcggcggttc ttctggataa    240
cagcgccaga gattcccact tccaaccgag gttccgagag agtatgcgac gtcttatcat    300
gaatgctcat cacgaccaat ccagacaaac actagccatg attcaggaaa atgttggttg    360
ctgcggagct gatggcgcaa cagactacct ctctcttcag cagccccttc caagtcagtg    420
cagagacacc gttactggaa acccattctt ccacggatgt gtagatgaac tcacctggtt    480
cttcgaagaa aaatgtggtt ggatagcagg tttagctatg gcgaggtacc aagctgcgaa    540
tcttcgtttt tttaaggaat tctcgatctt tatggtgtat aggctctggg ttttctgttt    600
tttgtatctc ttaggatttt gtaaattcca gatctttcta tggccactta gtagtatatt    660
tcaaaaattc tccaatcgag ttcttcattc gcattttcag tcattttctc ttcgacgttg    720
tttttaagcc tgggtattac tcctatttag ttgaactctg cagcaatctt agaaaattag    780
ggttttgagg tttcgatttc tctaggtaac cgatctattg cattcatctg aatttctgca    840
tatatgtctt agatttctga taagcttacg atacgttagg tgtaattgaa gtttattttt    900
caagagtgtt atttttgtt tctgaatttt tcagtcactc catggcctag tcgccatagc    960
taaacctgct atccaaccac atttttcttc gaagaaccag gtgagttcat ctacacatcc   1020
gtggaagaat gggtttccag taacggtgtc tctgcactga cttggaaggg gctgctgaag   1080
agagaggtag tctgttgcgc catcagctcc gcagcaacca acattttcct gaatcatggc   1140
tagtgtttgt ctggattggt cgtgatgagc attcatgata agacgtcgca tactctctcg   1200
gaacctcggt tggaagtggg aatctctggc gctgttatcc agaagaaccg ccgaaccgga   1260
taaaccgaat ataaaactga gcacttgggt gccgatgtac actaaaaggg ccatggtact   1320
ctcctgcagg gcactaatac atcctataaa ggacacaatc atgacgatca gtgaagcgac   1380
tataagtaca tatactccga tgtaaaattg ttctgaatcc aatttctgga gccattcttg   1440
aatgccctcc tcgaatcgta gccaaaggca aaga                               1474
```

<210> SEQ ID NO 326
<211> LENGTH: 820
<212> TYPE: DNA
<213> ORGANISM: Artificial Sequence
<220> FEATURE:
<223> OTHER INFORMATION: Derived from Diabrotica virgifera and
Arabidopsis thaliana

<400> SEQUENCE: 326

```
ataaaagcta tagacattta taccgaaatg ggtcgcttta caatggctgc aaaacaccat     60
cagactattg cagaaatgta tgagactgat gctgtggaca tcgaaagggc tgttcaacac    120
tatgaacagg cggctgatta cttcagagga gaagaaagca atgcttccgc caataagtgt    180
cttcttaaag tggctcaggt accaagctgc gaatcttcgt ttttttaagg aattctcgat    240
ctttatggtg tataggctct gggttttctg ttttttgtat ctcttaggat tttgtaaatt    300
ccagatcttt ctatggccac ttagtagtat atttcaaaaa ttctccaatc gagttcttca    360
ttcgcatttt cagtcatttt ctcttcgacg ttgtttttaa gcctgggtat tactcctatt    420
```

-continued

```
tagttgaact ctgcagcaat cttagaaaat tagggttttg aggtttcgat ttctctaggt    480

aaccgatcta ttgcattcat ctgaatttct gcatatatgt cttagatttc tgataagctt    540

acgatacgtt aggtgtaatt gaagtttatt tttcaagagt gttatttttt gtttctgaat    600

ttttcagtca ctccatggcc tagtgagcca ctttaagaag acacttattg gcggaagcat    660

tgctttcttc tcctctgaag taatcagccg cctgttcata gtgttgaaca gccctttcga    720

tgtccacagc atcagtctca tacatttctg caatagtctg atggtgtttt gcagccattg    780

taaagcgacc catttcggta taaatgtcta tagcttttat                          820
```